(12) United States Patent
Schuler et al.

(10) Patent No.: US 10,441,537 B2
(45) Date of Patent: Oct. 15, 2019

(54) UNIT DOSES, AEROSOLS, KITS, AND METHODS FOR TREATING HEART CONDITIONS BY PULMONARY ADMINISTRATION

(71) Applicant: InCarda Therapeutics, Inc., Newark, CA (US)

(72) Inventors: Carlos Schuler, Kensington, CA (US); Rangachari Narasimhan, Saratoga, CA (US); Luiz Belardinelli, Palo Alto, CA (US); Prashanti Madhavapeddi, Fremont, CA (US)

(73) Assignee: InCarda Therapeutics, Inc., Newark, CA (US)

( * ) Notice: Subject to any disclaimer, the term of this patent is extended or adjusted under 35 U.S.C. 154(b) by 0 days.

(21) Appl. No.: 15/976,516

(22) Filed: May 10, 2018

(65) Prior Publication Data

US 2018/0325818 A1    Nov. 15, 2018

Related U.S. Application Data

(60) Provisional application No. 62/504,292, filed on May 10, 2017.

(51) Int. Cl.
| | |
|---|---|
| *A61K 9/00* | (2006.01) |
| *A61P 9/06* | (2006.01) |
| *A61M 11/00* | (2006.01) |
| *A61K 31/7076* | (2006.01) |
| *A61M 15/00* | (2006.01) |
| *A61K 31/435* | (2006.01) |

(52) U.S. Cl.
CPC ............ *A61K 9/0078* (2013.01); *A61K 9/008* (2013.01); *A61K 31/435* (2013.01); *A61K 31/7076* (2013.01); *A61P 9/06* (2018.01); *A61M 15/00* (2013.01)

(58) Field of Classification Search
None
See application file for complete search history.

(56) References Cited

U.S. PATENT DOCUMENTS

| | | |
|---|---|---|
| 3,991,761 A | 11/1976 | Cocozza |
| 4,069,819 A | 1/1978 | Valentini et al. |
| 4,114,615 A | 9/1978 | Wetterlin |
| 4,247,066 A | 1/1981 | Frost et al. |
| 4,338,931 A | 7/1982 | Cavazza |
| 4,846,876 A | 7/1989 | Draber et al. |
| 4,962,095 A | 10/1990 | Grover et al. |
| 4,995,385 A | 2/1991 | Valentini et al. |
| 5,458,135 A | 10/1995 | Patton et al. |
| 5,619,985 A | 4/1997 | Ohki et al. |
| 5,785,049 A | 7/1998 | Smith et al. |
| 5,855,913 A | 1/1999 | Hanes et al. |
| 5,874,064 A | 2/1999 | Edwards et al. |
| 5,922,675 A | 7/1999 | Baker et al. |
| 5,976,574 A | 11/1999 | Gordon |
| 5,985,248 A | 11/1999 | Gordon et al. |
| 5,985,309 A | 11/1999 | Edwards et al. |
| 6,001,336 A | 12/1999 | Gordon |
| 6,051,256 A | 4/2000 | Platz et al. |
| 6,077,543 A | 6/2000 | Gordon et al. |
| 6,257,233 B1 | 7/2001 | Burr et al. |
| 6,357,490 B1 | 3/2002 | Johnston et al. |
| 6,358,530 B1 | 3/2002 | Eljamal et al. |
| 6,372,258 B1 | 4/2002 | Platz et al. |
| 6,503,480 B1 | 1/2003 | Edwards et al. |
| 6,546,929 B2 | 4/2003 | Burr et al. |
| 7,302,295 B2 | 11/2007 | Stahmann et al. |
| 7,473,433 B2 | 1/2009 | Weickert et al. |
| 8,394,813 B2 * | 3/2013 | Mickle ................ A61K 31/195 514/282 |
| 8,641,631 B2 | 2/2014 | Sierra et al. |
| 8,974,828 B2 | 3/2015 | Schuler et al. |
| 1,001,029 A1 | 7/2018 | Narasimhan et al. |
| 1,004,593 A1 | 8/2018 | Schuler et al. |
| 2002/0017295 A1 | 2/2002 | Weers et al. |
| 2002/0115655 A1 | 8/2002 | Mehanna et al. |
| 2003/0005924 A1 | 1/2003 | Rabinowitz et al. |
| 2003/0079742 A1 | 5/2003 | Giroux |
| 2004/0011358 A1 | 1/2004 | Smaldone et al. |
| 2004/0035413 A1 | 2/2004 | Smaldone et al. |
| 2004/0045546 A1 | 3/2004 | Hirsh et al. |
| 2004/0099269 A1 | 5/2004 | Hale et al. |
| 2004/0105820 A1 | 6/2004 | Weers et al. |

(Continued)

FOREIGN PATENT DOCUMENTS

| | | |
|---|---|---|
| JP | 2002529393 A | 9/2002 |
| WO | WO-9003144 A1 | 4/1990 |

(Continued)

OTHER PUBLICATIONS

"Flecainide" entry in ChemSpider website [online] retrieved on (Dec. 8, 2018) from URL:<http://www.chemspider.com/Chemical-Structure.3239.html>.*
Veldre, Kaspars, Andris Actiņš and Zane Eglīte. "Flecainide acetate acetic acid solvates." Journal of pharmaceutical sciences 100.2 (2011): 604-611.*
Abarbanell, et al. Prehospital management of rapid atrial fibrillation: recommendations for treatment protocols. Am J Emerg Med. Jan. 2001;19(1):6-9.
Barbato, et al. Role of beta2 adrenergic receptors in human atherosclerotic coronary arteries. Circulation. 2005, 111:288-294.
Borlak, et al. Metabolism of verapamil in cultures of rat alveolar epithelial cells and pharmacokinetics after administration by intravenous and inhalation routes. Drug Metab Dispos. Aug. 2005;33(8):1108-14. Epub May 10, 2005.

(Continued)

*Primary Examiner* — John Pak
*Assistant Examiner* — Daniel L Branson
(74) *Attorney, Agent, or Firm* — Wilson Sonsini Goodrich & Rosati

(57) ABSTRACT

Methods of treating a heart condition include administering by inhalation an effective amount of at least one antiarrhythmic pharmaceutical agent to a patient in need thereof. Nebulized drug product and kits are also contemplated.

23 Claims, 72 Drawing Sheets

(56) References Cited

U.S. PATENT DOCUMENTS

| | | |
|---|---|---|
| 2004/0156792 A1 | 8/2004 | Tarara et al. |
| 2004/0167228 A1 | 8/2004 | Rabinowitz et al. |
| 2005/0009776 A1 | 1/2005 | Gadgil et al. |
| 2005/0070552 A1 | 3/2005 | Fedida et al. |
| 2005/0211245 A1 | 9/2005 | Smaldone et al. |
| 2005/0211253 A1 | 9/2005 | Smaldone et al. |
| 2005/0235987 A1 | 10/2005 | Smaldone et al. |
| 2006/0034847 A1 | 2/2006 | Yun et al. |
| 2006/0034906 A1 | 2/2006 | Boni et al. |
| 2006/0052333 A1 | 3/2006 | Belardinelli et al. |
| 2006/0120962 A1 | 6/2006 | Rabinowitz et al. |
| 2007/0122352 A1 | 5/2007 | Kunka et al. |
| 2007/0122353 A1 | 5/2007 | Hale et al. |
| 2008/0038363 A1 | 2/2008 | Zaffaroni et al. |
| 2008/0226736 A1 | 9/2008 | Caponetti et al. |
| 2008/0275036 A1 | 11/2008 | Cross et al. |
| 2010/0086606 A1 | 4/2010 | Ogawa et al. |
| 2012/0003318 A1 | 1/2012 | Schuler et al. |
| 2014/0290647 A1 | 10/2014 | Salvinelli et al. |
| 2015/0313842 A1 | 11/2015 | Schuler et al. |

FOREIGN PATENT DOCUMENTS

| | | |
|---|---|---|
| WO | WO-9524183 A1 | 9/1995 |
| WO | WO-9531479 A1 | 11/1995 |
| WO | WO-9632096 A1 | 10/1996 |
| WO | WO-9632149 A1 | 10/1996 |
| WO | WO-9916419 A1 | 4/1999 |
| WO | WO-9916420 A1 | 4/1999 |
| WO | WO-9916421 A1 | 4/1999 |
| WO | WO-9916422 A1 | 4/1999 |
| WO | WO-0007572 A2 | 2/2000 |
| WO | WO-0027359 A1 | 5/2000 |
| WO | WO-0072904 A1 | 12/2000 |
| WO | WO-0185136 A2 | 11/2001 |
| WO | WO-0185137 A2 | 11/2001 |
| WO | WO-02083220 A2 | 10/2002 |
| WO | WO-2004071368 A2 | 8/2004 |
| WO | WO-2005079897 A1 | 9/2005 |
| WO | WO-2007042467 A1 | 4/2007 |
| WO | WO-2007050347 A1 | 5/2007 |
| WO | WO-2008036247 A1 | 3/2008 |
| WO | WO-2008051621 A2 | 5/2008 |
| WO | WO-2008066745 A1 | 6/2008 |
| WO | WO-2008072190 A2 | 6/2008 |
| WO | WO-2008134630 A1 | 11/2008 |
| WO | WO-2010019914 A2 | 2/2010 |
| WO | WO-2010022259 A1 | 2/2010 |
| WO | WO-2010107964 A1 | 9/2010 |
| WO | WO-2017136421 A1 | 8/2017 |

OTHER PUBLICATIONS

Co-pending U.S. Appl. No. 15/928,851, filed Mar. 22, 2018.
Co-pending U.S. Appl. No. 16/013,165, filed Jun. 20, 2018.
Co-pending U.S. Appl. No. 16/013,178, filed Jun. 20, 2018.
Dell'Orfano, et al. Drugs for Conversion of Atrial Fibrillation. Am. Fam. Physician. 58(2); 471-480, Aug. 1, 1998. 6 pages.
Deneer, et al. Absorption kinetics and pharmacodynamics of two oral dosage forms of flecainide in patients with an episode of paroxysmal atrial fibrillation. Eur J Clin Pharmacol. Dec. 2004;60(10):693-701.
European Office Action dated Nov. 16, 2017 for European Patent Application No. EP10754091.6.
European search report and search opinion dated Jan. 21, 2014 for EP Application No. 10754091.6.
Feldman, et al. Analysis of Coronary Response to Various Doses of Intracoronary Nitroglycerin. Circulation. 1982, 66:321-327.
Gaglione, et al. Is There Coronary Vasoconstriction after Intracoronary Beta-adrenergic Blockade in Patients with Coronary Artery Disease. J Am Coll Cardiol. 1987, 10:299-310.
Harrison, et al. Effect of Single Doses of Inhaled Lignocaine on FEV1 and Bronchial Reactivity in Asthma. Respir Med. Dec. 1992, 12:1359-635.
International Search Report and Written Opinion dated Apr. 18, 2017 for International PCT Patent Application No. PCT/US2017/016018.
International search report and written opinion dated Jul. 12, 2010 for PCT Application No. PCT/US2010/027740.
Lopez-Vidriero, M.T. Issues relating to safety and efficacy in nebulizer use. Eur. Respir. Rev., 2000, 10:72, 210-212.
Noguchi, et al. Effects of Intracoronary Propranolol on Coronary Blood Flow and Regional Myocardial Function in Dogs. Eur J Pharmacol. 1987, 144(2):201-10.
Notice of allowance dated Jan. 21, 2015 for U.S. Appl. No. 13/257,249.
Office action dated Jan. 3, 2013 for U.S. Appl. No. 13/257,249.
Office Action dated Apr. 17, 2017 for U.S. Appl. No. 14/632,252.
Office Action dated Apr. 27, 2016 for U.S. Appl. No. 14/632,252.
Office action dated Jun. 20, 2014 for U.S. Appl. No. 13/257,249.
Office Action dated Jul. 24, 2017 for U.S. Appl. No. 15/422,053.
Office action dated Sep. 9, 2015 for U.S. Appl. No. 14/632,252.
Office action dated Sep. 26, 2013 for U.S. Appl. No. 13/257,249.
Office Action dated Dec. 1, 2016 for U.S. Appl. No. 14/632,252.
PCT/US2018/032092 International Search Report and Written Opinion dated Aug. 1, 2018.
Rabinowitz, et al. Ultra-fast absorption of amorphous pure drug aerosols via deep lung inhalation. J Pharm Sci. Nov. 2006;95(11):2438-51.
U.S. Appl. No. 15/422,053 Notice of Allowance dated Mar. 5, 2018.
Suttorp, et al. The value of class IC antiarrhythmic drugs for acute conversion of paroxysmal atrial fibrillation or flutter to sinus rhythm. J Am Coll Cardiol. Dec. 1990;16(7):1722-7.
Twiss, et al. Efficacy of Calcium Channel Blockers as Maintenance Therapy for Asthma. British J of Clinical Pharmacology. Nov. 2001.
U.S. Appl. No. 14/632,252 Notice of Allowance dated Mar. 29, 2018.
Zalewski, et al. Myocardial Protection during Transient Coronary Artery Occlusion in Man: Beneficial Effects of Regional Beta-adrenergic Blockade. Circulation. 1986, 73:734-73.
Co-pending U.S. Appl. No. 16/172,456, filed Oct. 26, 2018.
Razavi, M. Safe and effective pharmacologic management of arrhythmias. Tex Heart Inst J. 2005;32(2):209-11.
U.S. Appl. No. 15/928,851 Office Action dated Oct. 9, 2018.
U.S. Appl. No. 16/013,165 Office Acton dated Aug. 28, 2018.
U.S. Appl. No. 16/013,178 Office Action dated Sep. 18, 2018.
Juan Tamargo et al., "Narrow therapeutic index drugs: a clinical pharmacological consideration to flecainide", Eur J Clin Pharmacol, vol. 71, 549-567, 2015.
Ikeda, "Effects of Flecainide on the Electrophysiologic Properties of Isolated Canine and Rabbit Myocardial Fibers", JACC, vol. 5, No. 2, pp. 303-310, Feb. 1985.
Kroemer, "Flecainide enantiomers: Disposition i human subjects and electrophysiologic actions in vitro", Clinical Pharmacology & Therapeutics, vol. 46, Issue 5, pp. 584-590, Nov. 1989.
Office Action dated Dec. 28, 2018 for U.S. Appl. No. 16/172,456.
U.S. Appl. No. 16/013,165 Final Office Action dated May 9, 2019.
U.S. Appl. No. 16/013,178 Final Office Action dated May 10, 2019.

* cited by examiner

UNIT DOSES, AEROSOLS, KITS, AND METHODS FOR TREATING HEART CONDITIONS BY PULMONARY ADMINISTRATION

CROSS-REFERENCE

This application claims the benefit of U.S. Provisional Application No. 62/504,292, filed May 10, 2017, which application is incorporated herein by reference in its entirety.

BACKGROUND

1. Field of the Invention

The present invention relates to compositions, unit doses, aerosols, and kits for treating certain heart conditions by pulmonary administration and methods thereof.

2. Background Art

Cardiac arrhythmia (also dysrhythmia) is a term for any of a large and heterogeneous group of conditions in which there is abnormal electrical activity in the heart. The heart beat may be too fast or too slow, and may be regular or irregular.

Atrial arrhythmia therapy is a field with a high level of unmet clinical need. Many drugs used today have been on the market since the early 1980s and 1990s and are mostly inadequate due to either lack of efficacy or a side-effect profile that is often cardiac related, that necessitates extensive monitoring of the patient.

What is needed for fast and safe cardioversion (resolution of arrhythmia) is therapy that:
(a) has little to no risk of acceleration of ventricular rate before cardioversion;
(b) slows atrio-ventribular (AV) conduction so that there is ventricular rate control and cardioversion at the same time;
(c) has minimal to no effect in prolonging the QRS interval above the upper range of normal value (about 120 milliseconds) and should have a low risk of torsade de pointes; and
(d) has minimal to no negative inotropic effect; it should have only mild negative chronotropic effect, without the risk of severe bradycardia when the patient reverts to sinus rhythm.

None of the current approved drug products exhibit these characteristics. High oral and intravenous (IV) doses required to compensate for absorption, metabolism, and dilution result in blood high blood concentrations for an extended period of time that can cause the dangerous adverse cardiac events like pro-arrhythmias, QT prolongation, and torsade de pointes. FELDMAN et al., "Analysis of Coronary Response to Various Doses of Intracoronary Nitroglycerin," Circulation, 66:321-327 (1982); and BARBATO et al., "Adrenergic Receptors in Human Atherosclerotic Coronary Arteries," Circulation, 111:288-294 (2005). Comorbid conditions also limit use of ideal drugs in some patients, for example the case with intravenous adenosine. GAGLIONE et al., "Is There Coronary Vasoconstriction after Intracoronary Beta-adrenergic Blockade in Patients with Coronary Artery Disease," J Am Coll Cardiol, 10:299-310 (1987). Drugs like verapamil and diltiazem injections are second line of therapy requiring close monitoring of patients. NOGUCHI et al., "Effects of Intracoronary Propranolol on Coronary Blood Flow and Regional Myocardial Function in Dogs," Eur J Pharmacol., 144(2):201-10 (1987); and ZALEWSKI et al., "Myocardial Protection during Transient Coronary Artery Occlusion in Man: Beneficial Effects of Regional Beta-adrenergic Blockade," Circulation, 73:734-73 (1986).

Paroxysmal atrial fibrillation (PAF) is a subset of the overall atrial fibrillation (AF) population and is estimated to be 25-30% of the overall AF population. About 2.5 million patients are affected by AF in the United States. The population of PAF patients is estimated to be 900,000 to 1.5 million worldwide.

Paroxysmal supraventricular tachycardia (PSVT) is a type of arrhythmia that affects about 500,000 to 600,000 patients in the United States.

Ablation techniques, e.g., RF ablation, are often used to treat arrhythmias. But ablation is expensive with the cost typically ranging from about $25,000 to $36,000 per procedure. Despite the high expense, ablation may not completely correct the arrhythmia. Often, multiple ablation procedures are required to achieve a satisfactory therapeutic result.

Oral medications, e.g., pills, tend to require high doses and long time for onset of action. The oral dose for heart medications generally tends to be well over 1 mg. High doses increase the likelihood of side effects and drug-drug interactions as these patients typically take multiple medications. The time for onset for oral cardiovascular medications tends to be around 60 minutes. Oral antiarrhythmic medications have been predominantly developed for prevention whereas treatment being given intravenously.

Intravenous injection usually requires a hospital setting for administering a medicine and typically involves a visit to the emergency room (ER). These overheads result in this therapy being expensive compared to therapies where the patients can self-administer their medicines. Intravenous injection requires a dose that is higher than what is actually needed in the heart to compensate for dilution and metabolism. Drug injected by IV passes through the right side of the heart and then the lungs before reaching the left side of the heart. See FIG. 1. The drug remains in the blood stream at a high concentration bathing all the organs and tissues with this drug in a high concentration, until the drug gets excreted through the kidneys or through other metabolic routes (e.g., hepatic). As a result, IV drugs may cause unwanted side effects. Drugs administered via the IV route are significantly diluted in the venous blood volume and lungs before reaching the cardiac circulation.

Injecting a drug to the heart directly is usually a last-resort taken by a cardiologist as a life saving measure in an emergency. The doses of the drugs injected directly into the heart in this manner are usually less than their IV and/or oral doses.

In some cases, an unplanned surgery is necessary to save the patient's life. Of course, unplanned surgeries are expensive and risky to the patient.

Cardiac arrhythmias are associated with disabling symptoms like tightness around the chest, palpitations, feeling tired, shortness of breath, and sometimes chest pain.

In view of the above, arrhythmias frequently result in emergency room (ER) visits, where intravenous drugs are administered, sometimes necessitating an extended stay in the hospital and in some cases also leading to unplanned invasive procedures. Pipeline Insights: Antiarrhythmics, Datamonitor (June 2006); and TWISS et al., "Efficacy of Calcium Channel Blockers as Maintenance Therapy for Asthma," British J of Clinical Pharmacology (November 2001).

There remains, however, a need for improved compositions and methods for treating heart conditions. Accordingly, there also remains a need for methods of making these compositions.

SUMMARY

Accordingly, the present invention provides compositions, unit doses, aerosols, kits, and methods for treating certain heart conditions. Other features and advantages of the present invention will be set forth in the description of invention that follows, and in part will be apparent from the description or may be learned by practice of the invention. The invention will be realized and attained by the compositions and methods particularly pointed out in the written description and claims hereof.

A first embodiment of the present invention is directed to a method of treating atrial arrhythmia. The method comprises administering an effective amount of at least one antiarrhythmic pharmaceutical agent to a patient in need thereof, such that the at least one antiarrhythmic pharmaceutical agent first enters the heart through the pulmonary vein to the left atrium.

In another aspect, the present invention is directed to a method of treating atrial arrhythmia, e.g., tachycardia. The method comprises administering by inhalation (e.g., oral inhalation) an effective amount of at least one antiarrhythmic pharmaceutical agent to a patient in need thereof, wherein an amount of the at least one antiarrhythmic pharmaceutical agent peaks in the coronary circulation of the heart at a time ranging from 10 seconds to 30 minutes from administration (e.g., initiation of the administration or end of the administration). In some cases, coronary circulation can be a coronary artery or a coronary vein, including coronary sinus.

In yet another aspect, the present invention is directed to a method of self-diagnosing and treating atrial arrhythmia. The method comprises self-diagnosing atrial arrhythmia by detecting at least one of shortness of breath, heart palpitations, and above normal heart rate. The method also comprises self-administering by inhalation (e.g., oral inhalation) an effective amount of at least one antiarrhythmic pharmaceutical agent within two hours, one hour, 30 minutes, or 15 minutes of the self-diagnosing.

In another aspect, the present invention is directed to a method of treating atrial arrhythmia, comprising administering by inhalation (e.g., oral inhalation) an effective amount of at least one antiarrhythmic pharmaceutical agent to a patient in need thereof, wherein an electrophysiologic effect is observed, via electrocardiography, at a time ranging from 10 seconds to 30 minutes from the administration.

In still another aspect, the present invention is directed to a method of treating atrial arrhythmia, comprising administering by inhalation (e.g., oral inhalation) an effective amount of at least one antiarrhythmic pharmaceutical agent to a patient in need thereof, wherein a cardiac score from a monitor implementing an arrhythmia detection algorithm shows a transition from an arrhythmic state to normal sinus rhythm in the patient at a time ranging from 10 seconds to 30 minutes from the administration.

In yet another aspect, the present invention is directed to a method of treating atrial arrhythmia, comprising administering by inhalation (e.g., oral inhalation) an effective amount of at least one antiarrhythmic pharmaceutical agent to a patient in need thereof, wherein a short form-36 quality of life score of the patient improves at a time ranging from 10 seconds to 30 minutes from the administration.

In another aspect, the present invention is directed to a unit dose comprising a unit dose receptacle and a composition within the unit dose receptacle. The composition comprises at least one antiarrhythmic pharmaceutical agent in an amount less than or equal to an amount of the same at least one antiarrhythmic pharmaceutical agent administered intravenously in the arm to achieve a minimum effective amount in the coronary circulation, and a pharmaceutically acceptable excipient.

In still another aspect, the present invention is directed to an aerosol comprising particles having a mass median aerodynamic diameter less than 10 μm. The particles comprise at least one antiarrhythmic pharmaceutical agent in an amount less than or equal to an amount of the same at least one antiarrhythmic pharmaceutical agent administered intravenously in the arm to achieve a minimum effective amount in the coronary circulation, and a pharmaceutically acceptable excipient.

Yet another aspect of the present invention is directed to a kit. The kit comprises a container containing at least one antiarrhythmic pharmaceutical agent and an aerosolization device.

In another aspect, the present invention is directed to a method of treating atrial arrhythmia, comprising: administering an effective amount of at least one antiarrhythmic pharmaceutical agent to a patient in need thereof, such that the at least one antiarrhythmic pharmaceutical agent first enters the heart through the pulmonary vein to the left atrium. In some cases, an amount of the at least one antiarrhythmic pharmaceutical agent peaks in the coronary circulation of the heart at a time ranging from 10 seconds to 30 minutes from the administration.

In some cases, the amount of the at least one antiarrhythmic pharmaceutical agent in the coronary circulation of the heart peaks at a time ranging from 2 minutes to 8 minutes from the administration. In some cases, the amount of the at least one antiarrhythmic pharmaceutical agent in the coronary circulation of the heart ranges from 0.1 mg/L to 60 mg/L at 2.5 minutes after the administration. In some cases, the amount of the at least one antiarrhythmic pharmaceutical agent in the coronary circulation of the heart is less than 0.1 mg/L at 30 minutes after the administration. In some cases, the effective amount is an effective amount for only one pass through the heart. In some cases, 10% to 60% of the nominal dose of the administered at least one antiarrhythmic pharmaceutical agent reaches the coronary circulation. In some cases, an amount of administered antiarrhythmic pharmaceutical agent entering the patient ranges from 0.1 mg to 200 mg. In some cases, a nominal amount of the at least one antiarrhythmic pharmaceutical agent administered via inhalation (e.g., oral inhalation) is less than or equal to an amount of the same antiarrhythmic pharmaceutical agent administered intravenously in the arm to achieve the same amount in the coronary circulation. In some cases, the administering comprises 1 to 6 inhalations.

In some cases, the at least one antiarrhythmic pharmaceutical agent comprises at least one member selected from class Ia, class Ib, class Ic, class II, class III, class IV, and class V antiarrhythmics. In some cases, the at least one antiarrhythmic pharmaceutical agent comprises at least one class Ia antiarrhythmic. In some cases, the at least one antiarrhythmic pharmaceutical agent comprises at least one class Ia antiarrhythmic selected from quinidine, procainamide, and disopyramide. In some cases, the at least one antiarrhythmic pharmaceutical agent comprises at least one class Ib antiarrhythmic. In some cases, the at least one antiarrhythmic pharmaceutical agent comprises at least one class Ib antiarrhythmic selected from lidocaine, tocainide, phenytoin, moricizine, and mexiletine. In some cases, the at least one antiarrhythmic pharmaceutical agent comprises at least one class Ic antiarrhythmic. In some cases, the at least one antiarrhythmic pharmaceutical agent comprises at least one class Ic antiarrhythmic selected from flecainide, propafenone, and moricizine. In some cases, the at least one antiarrhythmic pharmaceutical agent comprises at least one class II antiarrhythmic. In some cases, the at least one antiarrhythmic pharmaceutical agent comprises at least one class II antiarrhythmic selected from propranolol, acebutolol, soltalol, esmolol, timolol, metoprolol, and atenolol. In some cases, the at least one antiarrhythmic pharmaceutical agent comprises at least one class III antiarrhythmic. In some cases, the at least one antiarrhythmic pharmaceutical agent comprises at least one class III antiarrhythmic selected from amiodarone, sotalol, bretylium, ibutilide, methanesulfonamide, vernakalant, and dofetilide. In some cases, the at least one antiarrhythmic pharmaceutical agent comprises at least one class IV antiarrhythmic. In some cases, the at least one antiarrhythmic pharmaceutical agent comprises at least one class IV antiarrhythmic selected from bepridil, nitrendipine, amlodipine, isradipine, nifedipine, nicardipine, verapamil, and diltiazem. In some cases, the at least one antiarrhythmic pharmaceutical agent comprises at least one class V antiarrhythmic. In some cases, the at least one antiarrhythmic pharmaceutical agent comprises at least one class V antiarrhythmic selected from digoxin and adenosine.

In some cases, the atrial arrhythmia comprises tachycardia. In some cases, the atrial arrhythmia comprises supraventricular tachycardia. In some cases, the atrial arrhythmia comprises paroxysmal supraventricular tachycardia. In some cases, the atrial arrhythmia comprises atrial fibrillation. In some cases, the atrial arrhythmia comprises paroxysmal atrial fibrillation. In some cases, the atrial arrhythmia comprises of acute episodes in persistent and permanent atrial fibrillation. In some cases, the atrial arrhythmia comprises atrial flutter. In some cases, the atrial arrhythmia comprises paroxysmal atrial flutter. In some cases, the atrial arrhythmia comprises lone atrial fibrillation. In some cases, the administering comprises administering a liquid comprising the at least one antiarrhythmic pharmaceutical agent. In some cases, the administering comprises administering a powder comprising the at least one antiarrhythmic pharmaceutical agent. In some cases, the administering comprises administering a condensation aerosol comprising the at least one antiarrhythmic pharmaceutical agent. In some cases, the administering comprises administering a composition compnslng the at least one antiarrhythmic pharmaceutical agent, wherein the composition is not a condensation aerosol.

In some cases, the pulmonary administration comprises nebulizing a solution comprising the at least one antiarrhythmic pharmaceutical agent. In some cases, the nebulizing comprises nebulizing with a vibrating mesh nebulizer. In some cases, the nebulizing comprises nebulizing with a jet nebulizer. In some cases, the nebulizing comprises nebulizing with a breach-activated nebulizer. In some cases, the nebulizing comprises forming droplets having a mass median aerodynamic diameter of less than 10 itm. In some cases, the pulmonary administration comprises administering a dry powder comprising the at least one antiarrhythmic pharmaceutical agent. In some cases, the dry powder comprises particles having a mass median aerodynamic diameter of less than 10 itm. In some cases, the dry powder is administered via an active dry powder inhaler. In some cases, the dry powder is administered via a passive dry powder inhaler.

In some cases, the pulmonary administration comprises administering the at least one antiarrhythmic pharmaceutical agent via a metered dose inhaler. In some cases, the metered dose inhaler forms particles having a mass median aerodynamic diameter of less than 10 μm. In some cases, the metered dose inhaler contains the at least one antiarrhythmic pharmaceutical agent formulated in a carrier selected from hydrofluoroalkane and chlorofluorocarbon. In some cases, the treating comprises acute treatment after detection of atrial arrhythmia. In some cases, the patient has normal sinus rhythm within 10 minutes of initiating the administering.

In another aspect, the present invention is directed to a method of treating atrial arrhythmia, comprising: administering by inhalation (e.g., oral inhalation) an effective amount of at least one antiarrhythmic pharmaceutical agent to a patient in need thereof, wherein an amount of the at least one antiarrhythmic pharmaceutical agent peaks in the coronary circulation of the heart at a time ranging from 10 seconds to 30 minutes from the administration. In some cases, the amount of the at least one antiarrhythmic pharmaceutical agent in the coronary circulation of the heart peaks at a time ranging from 2 minutes to 8 minutes from the administration. In some cases, the amount of the at least one antiarrhythmic pharmaceutical agent in the coronary circulation of the heart ranges from 0.1 mg/L to 60 mg/L at 2.5 minutes after the administration.

In some cases, the amount of the at least one antiarrhythmic pharmaceutical agent in the coronary circulation of the heart is less than 0.1 mg/L at 30 minutes after the administration. In some cases, the effective amount is an effective amount for only one pass through the heart. In some cases, 10% to 60% of the nominal dose of the administered at least one antiarrhythmic pharmaceutical agent reaches the coronary circulation. In some cases, an amount of administered antiarrhythmic pharmaceutical agent entering the patient ranges from 0.1 mg to 200 mg. In some cases, a nominal amount of the at least one antiarrhythmic pharmaceutical agent administered via inhalation (e.g., oral inhalation) is less than or equal to an amount of the same antiarrhythmic pharmaceutical agent administered intravenously in the arm to achieve the same amount in the coronary circulation. In some cases, the administering comprises 1 to 6 inhalations.

In some cases, the at least one antiarrhythmic pharmaceutical agent comprises at least one member selected from class Ia, class Ib, class Ic, class II, class III, class IV, and class V antiarrhythmics. In some cases, the at least one antiarrhythmic pharmaceutical agent comprises at least one class Ia antiarrhythmic. In some cases, the at least one antiarrhythmic pharmaceutical agent comprises at least one class Ia antiarrhythmic selected from quinidine, procainamide, and disopyramide. In some cases, the at least one antiarrhythmic pharmaceutical agent comprises at least one class Ib antiarrhythmic. In some cases, the at least one antiarrhythmic pharmaceutical agent comprises at least one class Ib antiarrhythmic selected from lidocaine, tocainide, phenytoin, moricizine, and mexiletine. In some cases, the at least one antiarrhythmic pharmaceutical agent comprises at least one class Ic antiarrhythmic. In some cases, the at least one antiarrhythmic pharmaceutical agent comprises at least one class Ic antiarrhythmic selected from flecainide, propafenone, and moricizine. In some cases, the at least one antiarrhythmic pharmaceutical agent comprises at least one class II antiarrhythmic. In some cases, the at least one antiarrhythmic pharmaceutical agent comprises at least one class II antiarrhythmic selected from propranolol, acebutolol, soltalol, esmolol, timolol, metoprolol, and atenolol. In some cases, the at least one antiarrhythmic pharmaceutical agent comprises at least one class III antiarrhythmic. In some cases, the at least one antiarrhythmic pharmaceutical agent comprises at least one class III antiarrhythmic selected from amiodarone, sotalol, bretylium, ibutilide, methanesulfonamide, vernakalant, and dofetilide. In some cases, the at least one antiarrhythmic pharmaceutical agent comprises at least one class IV antiarrhythmic. In some cases, the at least one antiarrhythmic pharmaceutical agent comprises at least one class IV antiarrhythmic selected from bepridil, nitrendipine, amlodipine, isradipine, nifedipine, nicardipine, verapamil, and diltiazem. In some cases, the at least one antiarrhythmic pharmaceutical agent comprises at least one class V antiarrhythmic. In some cases, the at least one antiarrhythmic pharmaceutical agent comprises at least one class V antiarrhythmic selected from digoxin and adenosine.

In some cases, the atrial arrhythmia comprises tachycardia. In some cases, the atrial arrhythmia comprises supraventricular tachycardia. In some cases, the atrial arrhythmia comprises paroxysmal supraventricular tachycardia. In some cases, the atrial arrhythmia comprises atrial fibrillation. In some cases, the atrial arrhythmia comprises paroxysmal atrial fibrillation. In some cases, the atrial arrhythmia comprises of acute episodes in persistent and permanent atrial fibrillation. In some cases, the atrial arrhythmia comprises atrial flutter. In some cases, the atrial arrhythmia comprises paroxysmal atrial flutter. In some cases, the atrial arrhythmia comprises lone atrial fibrillation.

In some cases, the administering comprises administering a liquid comprising the at least one antiarrhythmic pharmaceutical agent. In some cases, the administering comprises administering a powder comprising the at least one antiarrhythmic pharmaceutical agent. In some cases, the administering comprises administering a condensation aerosol comprising the at least one antiarrhythmic pharmaceutical agent. In some cases, the administering comprises administering a composition comprising the at least one antiarrhythmic pharmaceutical agent, wherein the composition is not a condensation aerosol. In some cases, the pulmonary administration comprises nebulizing a solution comprising the at least one antiarrhythmic pharmaceutical agent. In some cases, the nebulizing comprises nebulizing with a vibrating mesh nebulizer. In some cases, the nebulizing comprises nebulizing with a jet nebulizer. In some cases, the nebulizing comprises forming droplets having a mass median aerodynamic diameter of less than 10 µm. In some cases, the pulmonary administration comprises administering a dry powder comprising the at least one antiarrhythmic pharmaceutical agent. In some cases, the dry powder comprises particles having a mass median aerodynamic diameter of less than 10 µm. In some cases, the dry powder is administered via an active dry powder inhaler. In some cases, the dry powder is administered via a passive dry powder inhaler. In some cases, the pulmonary administration comprises administering the at least one antiarrhythmic pharmaceutical agent via a metered dose inhaler. In some cases, the metered dose inhaler forms particles having a mass median aerodynamic diameter of less than 10 µm. In some cases, the metered dose inhaler contains the at least one antiarrhythmic pharmaceutical agent formulated in a carrier selected from hydrofluroalkane and chlorofluorocarbon.

In some cases, the treating comprises acute treatment after detection of atrial arrhythmia. In some cases, the patient has normal sinus rhythm within 30 minutes of initiating the administration. In some cases, the patient has normal sinus rhythm within 10 minutes of initiating the administration.

In another aspect, the present invention is directed to a method of self-diagnosing and treating atrial arrhythmia, comprising: self-diagnosing atrial arrhythmia by detecting at least one of shortness of breath, heart palpitations, and above normal heart rate; and self-administering by inhalation (e.g., oral inhalation) an effective amount of at least one antiarrhythmic pharmaceutical agent within two hours of the self-diagnosing. In some cases, the self-administering occurs within one hour of the self-diagnosing. In some cases, the self-administering occurs within 30 minutes of the self-diagnosing. In some cases, the self-administering occurs within 15 minutes of the self-diagnosing. In some cases, the self-administering continues until the patient no longer detects the at least one of shortness of breath, heart palpitations, and above normal heart rate.

In another aspect, the present invention is directed to a method of treating atrial arrhythmia, comprising: administering by inhalation (e.g., oral inhalation) an effective amount of at least one antiarrhythmic pharmaceutical agent to a patient in need thereof, wherein an electrophysiologic effect is observed, via electrocardiography, at a time ranging from 10 seconds to 30 minutes from the administration. In some cases, the electrophysiologic effect comprises a transition from arrhythmia to a normal sinus rhythm. In some cases, the electro physiologic effect comprises a transition from an absence of a P wave to a presence of a P wave.

In another aspect, the present invention is directed to a method of treating atrial arrhythmia, comprising: administering by inhalation (e.g., oral inhalation) an effective amount of at least one antiarrhythmic pharmaceutical agent to a patient in need thereof, wherein a cardiac score from a monitor implementing an arrhythmia detection algorithm shows a transition from an arrhythmic state to normal sinus rhythm in the patient at a time ranging from 10 seconds to 30 minutes from the administration. In some cases, the monitor comprises a Holter monitor, telemetry, and mobile ECG.

In another aspect, the present invention is directed to a method of treating atrial arrhythmia, comprising: administering by inhalation (e.g., oral inhalation) an effective amount of at least one antiarrhythmic pharmaceutical agent to a patient in need thereof, wherein a short form-36 quality of life score of the patient improves at a time ranging from 10 seconds to 30 minutes from the administration.

In another aspect, the present invention is directed to a unit dose comprising: a unit dose receptacle; a composition within the unit dose receptacle, the composition comprising: at least one antiarrhythmic pharmaceutical agent in an amount less than or equal to an amount of the same at least one antiarrhythmic pharmaceutical agent administered intravenously in the arm to achieve a minimum effective amount in the coronary circulation; and a pharmaceutically acceptable excipient. In some cases, the composition comprises a solution. In some cases, the composition comprises a solution having a tonicity that ranges from isotonic to physiologic isotonicity. In some cases, the composition comprises an aqueous solution. In some cases, the composition comprises a non-aqueous solution. In some cases, the composition further comprises a pH buffer. In some cases, the composition further comprises a pH buffer selected from citrate, phosphate, phthalate, and lactate. In some cases, the composition consists essentially of the at least one antiarrhythmic pharmaceutical agent and water. In some cases, the composition consists essentially of the at least one antiarrhythmic pharmaceutical agent, water, and a pH buffer. In some cases, the composition has a pH ranging from 3.5 to 8.0.

In some cases, the pharmaceutically acceptable excipient comprises hydrofluroalkane. In some cases, the pharmaceutically acceptable excipient comprises chlorofluoroalkane. In some cases, the composition is substantially preservative-free. In some cases, the at least one antiarrhythmic pharmaceutical agent comprises at least one member selected from class Ia, class Ib, class Ic, class II, class III, class IV, and class V antiarrhythmics. In some cases, the at least one antiarrhythmic pharmaceutical agent comprises at least one class Ia antiarrhythmic. In some cases, the at least one antiarrhythmic pharmaceutical agent comprises at least one class Ia antiarrhythmic selected from quinidine, procainamide, and disopyramide, and pharmaceutically acceptable salts thereof. In some cases, the at least one antiarrhythmic pharmaceutical agent comprises at least one class Ib antiarrhythmic. In some cases, the at least one antiarrhythmic pharmaceutical agent comprises at least one class Ib antiarrhythmic selected from lidocaine, tocainide, phenytoin, moricizine, and mexiletine, and pharmaceutically acceptable salts thereof. In some cases, the at least one antiarrhythmic pharmaceutical agent comprises at least one class Ic antiarrhythmic. In some cases, the at least one antiarrhythmic pharmaceutical agent comprises at least one class Ic antiarrhythmic selected from flecainide, propafenone, and moricizine, and pharmaceutically acceptable salts thereof. In some cases, the at least one antiarrhythmic pharmaceutical agent comprises at least one class II antiarrhythmic. In some cases, the at least one antiarrhythmic pharmaceutical agent comprises at least one class II antiarrhythmic selected from propranolol, acebutolol, soltalol, esmolol, timolol, metoprolol, and atenolol, and pharmaceutically acceptable salts thereof. In some cases, the at least one antiarrhythmic pharmaceutical agent comprises at least one class III antiarrhythmic. In some cases, the at least one antiarrhythmic pharmaceutical agent comprises at least one class III antiarrhythmic selected from amiodarone, sotalol, bretylium, ibutilide, methanesulfonamide, vernakalant, and dofetilide, and pharmaceutically acceptable salts thereof. In some cases, the at least one antiarrhythmic pharmaceutical agent comprises at least one class IV antiarrhythmic. In some cases, the at least one antiarrhythmic pharmaceutical agent comprises at least one class IV antiarrhythmic selected from bepridil, nimodipine, nisoldipine, nitrendipine, amlodipine, isradipine, nifedipine, nicardipine, verapamil, and diltiazem, and pharmaceutically acceptable salts thereof. In some cases, the at least one antiarrhythmic pharmaceutical agent comprises at least one class V antiarrhythmic. In some cases, the at least one antiarrhythmic pharmaceutical agent comprises at least one class V antiarrhythmic selected from digoxin and adenosine, and pharmaceutically acceptable salts thereof. In some cases, the receptacle comprises 0.1 mg to 200 mg of the at least one antiarrhythmic pharmaceutical agent. In some cases, the unit dose is substantially tasteless.

In another aspect, the present invention is directed to an aerosol comprising particles having a mass median aerodynamic diameter less than 10 μm, wherein the particles comprise: at least one antiarrhythmic pharmaceutical agent in an amount less than or equal to an amount of the same at least one antiarrhythmic pharmaceutical agent administered intravenously in the arm to achieve a minimum effective amount in the coronary circulation; and a pharmaceutically acceptable excipient.

In some cases, the particles comprise a nebulized solution. In some cases, the particles comprise a nebulized aqueous solution. In some cases, the particles further comprise a pH buffer. In some cases, the particles further comprise a pH buffer selected from citrate, phosphate, phthalate, and lactate. In some cases, the particles consist essentially of the at least one antiarrhythmic pharmaceutical agent and water. In some cases, the particles consist essentially of the at least one antiarrhythmic pharmaceutical agent, water, and a pH buffer. In some cases, the particles have a pH ranging from 3.5 to 8.0. In some cases, the particles are substantially preservative-free.

In some cases, the at least one antiarrhythmic pharmaceutical agent comprises at least one member selected from class Ia, class 1b, class 1c, class II, class III, class IV, and class V antiarrhythmics. In some cases, the at least one antiarrhythmic pharmaceutical agent comprises at least one class Ia antiarrhythmic. In some cases, the at least one antiarrhythmic pharmaceutical agent comprises at least one class Ia antiarrhythmic selected from quinidine, procainamide, and disopyramide. In some cases, the at least one antiarrhythmic pharmaceutical agent comprises at least one class Ib antiarrhythmic. In some cases, the at least one antiarrhythmic pharmaceutical agent comprises at least one class Ib antiarrhythmic selected from lidocaine, tocainide, phenytoin, moricizine, and mexiletine. In some cases, the at least one antiarrhythmic pharmaceutical agent comprises at least one class Ic antiarrhythmic. In some cases, the at least one antiarrhythmic pharmaceutical agent comprises at least one class Ic antiarrhythmic selected from flecainide, propafenone, and moricizine. In some cases, the at least one antiarrhythmic pharmaceutical agent comprises at least one class II antiarrhythmic. In some cases, the at least one antiarrhythmic pharmaceutical agent comprises at least one class II antiarrhythmic selected from propranolol, acebutolol, soltalol, esmolol, timolol, metoprolol, and atenolol. In some cases, the at least one antiarrhythmic pharmaceutical agent comprises at least one class III antiarrhythmic. In some cases, the at least one antiarrhythmic pharmaceutical agent comprises at least one class III antiarrhythmic selected from amiodarone, sotalol, bretylium, ibutilide, methanesulfonamide, vernakalant, and dofetilide. In some cases, the at least one antiarrhythmic pharmaceutical agent comprises at least one class IV antiarrhythmic. In some cases, the at least one antiarrhythmic pharmaceutical agent comprises at least one class IV antiarrhythmic selected from bepridil, nimodipine, nisoldipine, nitrendipine, amlodipine, isradipine, nifedipine, nicardipine, verapamil, and diltiazem. In some cases, the at least one antiarrhythmic pharmaceutical agent comprises at least one class V antiarrhythmic. In some cases, the at least one antiarrhythmic pharmaceutical agent comprises at least one class V antiarrhythmic selected from digoxin and adenosine. In some cases, the aerosol is substantially tasteless.

In another aspect, the present invention is directed to a kit, comprising: a container containing at least one antiarrhythmic pharmaceutical agent; and an aerosolization device. In some cases, the aerosolization device comprises a nebulizer. In some cases, the aerosolization device comprises a vibrating mesh nebulizer. In some cases, the aerosolization device comprises a jet nebulizer. In some cases, the aerosolization device comprises a dry powder inhaler. In some cases, the aerosolization device comprises an active dry powder inhaler. In some cases, the aerosolization device comprises a passive dry powder inhaler. In some cases, the aerosolization device comprises a metered dose inhaler. In some cases, an amount of the at least one antiarrhythmic pharmaceutical agent is sufficient to produce an electrophysiologic effect with a minimum of one pass through the heart. In some cases, the effective amount of the at least one antiarrhythmic pharmaceutical agent is sub-therapeutic when diluted by overall blood volume.

In another aspect, the present invention is directed to a method of treating atrial arrhythmia, comprising: administering to one or more pulmonary veins through pulmonary airways and through use of an aerosolization device an effective amount of at least one antiarrhythmic pharmaceutical agent selected from a group consisting of class I, class II, class III, and class IV antiarrhythmics, to a patient in need thereof, wherein the effective amount of the at least one antiarrhythmic pharmaceutical agent is a total amount from 0.1 mg to 200 mg administered over multiple inhalations, wherein the at least one antiarrhythmic pharmaceutical agent level peaks in a coronary circulation of the heart at a time between 30 seconds and 20 minutes from the pulmonary administration, and wherein the patient's sinus rhythm is restored to normal within 30 minutes of initiating the administration.

In some cases, the concentration of the at least one antiarrhythmic pharmaceutical agent in the coronary circulation of the heart ranges between 0.1 mg/L and 60 mg/L at 2.5 minutes after pulmonary administration, and the concentration of the at least one antiarrhythmic pharmaceutical agent in the coronary circulation of the heart is less than 0.1 mg/L at 30 minutes after pulmonary administration, or wherein 10% to 60% of a nominal dose of the administered at least one antiarrhythmic pharmaceutical agent reaches the coronary circulation. In some cases, the concentration of the at least one antiarrhythmic pharmaceutical agent in the coronary circulation of the heart is between 0.1 mg/L and 20 mg/L at 2.5 minutes after pulmonary administration, and the concentration of the at least one antiarrhythmic pharmaceutical agent in the coronary circulation of the heart is less than 0.1 mg/L at 30 minutes after pulmonary administration, or wherein between 5% and 60% of a nominal dose of the administered at least one antiarrhythmic pharmaceutical agent reaches the coronary circulation. In some cases, the method comprises pulmonary administration of the at least one antiarrhythmic in up to 6 inhalations. In some cases, the atrial arrhythmia comprises tachycardia. In some cases, the tachycardia comprises supraventricular tachycardia, paroxysmal supraventricular tachycardia, atrial fibrillation, paroxysmal atrial fibrillation, acute episodes in persistent and permanent atrial fibrillation, atrial flutter, paroxysmal atrial flutter or lone atrial fibrillation. In some cases, the method comprises administering a liquid, dry powder, or nebulized droplets comprising the at least one antiarrhythmic pharmaceutical agent, wherein the powder or nebulized droplets have a mass median aerodynamic diameter of less than 10 µm.

In some cases, the antiarrhythmic pharmaceutical agent is a class I antiarrhythmic. In some cases, the class I antiarrhythmic is a class Ia, Ib, or Ic antiarrhythmic. In some cases, the antiarrhythmic pharmaceutical agent is a class II antiarrhythmic. In some cases, the class II antiarrhythmic is esmolol HCl. In some cases, dosage of the esmolol HCl is between 0.5 and 0.75 mg/kg body weight. In some cases, the antiarrhythmic pharmaceutical agent is a class IV antiarrhythmic. In some cases, the class IV antiarrhythmic is diltiazem. In some cases, dosage of the diltiazem is 0.25 mg/kg body weight. In some cases, the at least one antiarrhythmic pharmaceutical agent level peaks in the coronary circulation of the heart at a time between 1 minute and 10 minutes. In some cases, the aerosolization device is a nebulizer configured to administer the at least one antiarrhythmic pharmaceutical agent in a liquid pharmaceutical formulation, wherein the aerosolization occurs at room temperature. In some cases, the at least one antiarrhythmic pharmaceutical agent is self-administered by the patient.

In another aspect, the present invention is directed to a method of treating atrial arrhythmia, comprising: administering to one or more pulmonary veins through pulmonary airways and through use of an aerosolization device an effective amount of at least one antiarrhythmic pharmaceutical agent selected from a group consisting of class I, class II, class III, and class IV antiarrhythmics, to a patient in need thereof, wherein the patient self-administers and self-titrates an effective inhaled dose of at least one antiarrhythmic pharmaceutical agent for a conversion of atrial arrhythmia to normal sinus rhythm, wherein the at least one antiarrhythmic pharmaceutical agent level peaks in a coronary circulation of the heart at a time between 30 seconds and 20 minutes from the pulmonary administration, and wherein the patient's sinus rhythm is restored to normal within 30 minutes of initiating the administration.

In some cases, the concentration of the at least one antiarrhythmic pharmaceutical agent in the coronary circulation of the heart ranges between 0.1 mg/L and 60 mg/L at 2.5 minutes after pulmonary administration, and the concentration of the at least one antiarrhythmic pharmaceutical agent in the coronary circulation of the heart is less than 0.1 mg/L at 30 minutes after pulmonary administration, or wherein 10% to 60% of the nominal dose of the administered at least one antiarrhythmic pharmaceutical agent reaches the coronary circulation.

In some cases, the concentration of the at least one antiarrhythmic pharmaceutical agent in the coronary circulation of the heart is between 0.1 mg/L and 20 mg/L at 2.5 minutes after pulmonary administration, and the concentration of the at least one antiarrhythmic pharmaceutical agent in the coronary circulation of the heart is less than 0.1 mg/L at 30 minutes after pulmonary administration, or wherein between 5% and 60% of the nominal dose of the administered at least one antiarrhythmic pharmaceutical agent reaches the coronary circulation. In some cases, the method comprises pulmonary administration of the at least one antiarrhythmic in up to 6 inhalations.

In some cases, the atrial arrhythmia comprises tachycardia. In some cases, the tachycardia comprises supraventricular tachycardia, paroxysmal supraventricular tachycardia, atrial fibrillation, paroxysmal atrial fibrillation, acute episodes in persistent and permanent atrial fibrillation, atrial flutter, paroxysmal atrial flutter or lone atrial fibrillation. In some cases, the method comprises administering a liquid, dry powder, or nebulized droplets comprising the at least one antiarrhythmic pharmaceutical agent, wherein the dry powder or nebulized droplets have a mass median aerodynamic diameter of less than 10 µm.

In some cases, the antiarrhythmic pharmaceutical agent is a class I antiarrhythmic. In some cases, the class I antiarrhythmic is a class Ia, Ib, or Ic antiarrhythmic. In some cases, the antiarrhythmic pharmaceutical agent is a class II antiarrhythmic. In some cases, the class II antiarrhythmic is esmolol HCl. In some cases, the effective inhaled dose of the esmolol HCl is between 0.5 and 0.75 mg/kg body weight. In some cases, the antiarrhythmic pharmaceutical agent is a class IV antiarrhythmic. In some cases, the class IV antiarrhythmic is diltiazem. In some cases, the effective inhaled dose of the diltiazem is 0.25 mg/kg body weight. In some cases, the at least one antiarrhythmic pharmaceutical agent level peaks in the coronary circulation of the heart at a time between 1 minute and 10 minutes. In some cases, the aerosolization device is a nebulizer configured to administer the at least one antiarrhythmic pharmaceutical agent in a liquid pharmaceutical formulation, wherein the aerosolization occurs at room temperature.

In another aspect, the present invention is directed to a method of treating atrial arrhythmia, comprising: administering to one or more pulmonary veins through pulmonary airways by inhalation (e.g., oral inhalation) an effective amount of at least one antiarrhythmic pharmaceutical agent selected from a group consisting of class I, class II, class III, and class IV antiarrhythmics, to a subject in need thereof, wherein the effective amount of the at least one antiarrhythmic pharmaceutical agent is a total amount from 0.1 mg to 200 mg and has: i) a $T_{max}$ of from about 0.1 minute to about 30 minutes; ii) a $C_{max}$ of from about 10 ng/mL to about 5000 ng/mL; iii) an $AUC_{Last}$ of from about 100 hr*ng/mL to about 10000 hr*ng/mL; iv) a distribution $t_{1/2}$ of from about 0.1 minute to about 15 minutes; v) an elimination $t_{1/2}$ of from about 1 hour to about 25 hours; vi) a ΔQRS of from about 0.01 msec to about 100 msec; or any combination thereof.

In some cases, the at least one antiarrhythmic pharmaceutical agent is administered over multiple inhalations. In some cases, the at least one antiarrhythmic pharmaceutical agent is administered in up to 6 inhalations. In some cases, the subject's sinus rhythm is restored to normal within 30 minutes of initiating the administration. In some cases, the at least one antiarrhythmic pharmaceutical agent level peaks in a coronary circulation of the heart at a time between 30 seconds and 20 minutes from the administration. In some cases, concentration of the at least one antiarrhythmic pharmaceutical agent in the coronary circulation of the heart ranges between 0.1 mg/L and 60 mg/L at 2.5 minutes after the administration. In some cases, concentration of the at least one antiarrhythmic pharmaceutical agent in the coronary circulation of the heart is less than 0.1 mg/L at 30 minutes after the administration. In some cases, 5% to 60% of a nominal dose of the administered at least one antiarrhythmic pharmaceutical agent reaches the coronary circulation. In some cases, the effective amount of the at least one antiarrhythmic pharmaceutical agent has a $T_{max}$ of from about 0.1 minute to about 30 minutes. In some cases, the effective amount of the at least one antiarrhythmic pharmaceutical agent has a $T_{max}$ of from about 1 minute to about 5 minutes. In some cases, the effective amount of the at least one antiarrhythmic pharmaceutical agent has a $T_{max}$ of from about 0.1 minute to about 3 minutes. In some cases, the effective amount of the at least one antiarrhythmic pharmaceutical agent has a $T_{max}$ of from about 0.2 minute to about 5 minutes. In some cases, the effective amount of the at least one antiarrhythmic pharmaceutical agent has a $C_{max}$ of from about 50 ng/mL to about 500 ng/mL. In some cases, the effective amount of the at least one antiarrhythmic pharmaceutical agent has a $C_{max}$ of from about 100 ng/mL to about 250 ng/mL. In some cases, the effective amount of the at least one antiarrhythmic pharmaceutical agent has an $AUC_{Last}$ of from about 100 hr*ng/mL to about 10000 hr*ng/mL. In some cases, the effective amount of the at least one antiarrhythmic pharmaceutical agent has an $AUC_{Last}$ of from about 200 ng/mL to about 2000 hr*ng/mL. In some cases, the effective amount of the at least one antiarrhythmic pharmaceutical agent has an $AUC_{Last}$ of from about 500 ng/mL to about 800 hr*ng/mL. In some cases, the effective amount of the at least one antiarrhythmic pharmaceutical agent has an $AUC_{Last}$ of from about 400 ng/mL to about 600 hr*ng/mL. In some cases, the effective amount of the at least one antiarrhythmic pharmaceutical agent has a distribution $t_{1/2}$ of from about 0.1 minute to about 15 minutes. In some cases, the effective amount of the at least one antiarrhythmic pharmaceutical agent has a distribution $t_{1/2}$ of from about 3 minute to about 4 minutes. In some cases, the effective amount of the at least one antiarrhythmic pharmaceutical agent has a distribution $t_{1/2}$ of from about 3 minute to about 5 minutes. In some cases, the effective amount of the at least one antiarrhythmic pharmaceutical agent has an elimination $t_{1/2}$ of from about 1 hour to about 25 hours. In some cases, the effective amount of the at least one antiarrhythmic pharmaceutical agent has an elimination $t_{1/2}$ of from about 8.5 hour to about 10.5 hours. In some cases, the effective amount of the at least one antiarrhythmic pharmaceutical agent has a ΔQRS of from about 0.01 msec to about 100 msec. In some cases, the effective amount of the at least one antiarrhythmic pharmaceutical agent has a ΔQRS of from about 1 msec to about 10 msec. In some cases, the effective amount of the at least one antiarrhythmic pharmaceutical agent has a ΔQRS of from about 5 msec to about 20 msec. In some cases, the effective amount of the at least one antiarrhythmic pharmaceutical agent delivered through the pulmonary airways by inhalation has a higher ratio of the maximum ΔQRS to the $C_{max}$ as compared to that provided by intravenous delivery of an effective amount of the at least one antiarrhythmic pharmaceutical agent. In some cases, the ratio of the maximum ΔQRS to the $C_{max}$ provided by the effective amount of the at least one antiarrhythmic pharmaceutical agent delivered through the pulmonary airways by inhalation is at least 2 folds greater than that provided by intravenous delivery of an effective amount of the at least one antiarrhythmic pharmaceutical agent. In some cases, the atrial arrhythmia comprises tachycardia. In some cases, the tachycardia comprises supraventricular tachycardia, paroxysmal supraventricular tachycardia, atrial fibrillation, paroxysmal atrial fibrillation, acute episodes in persistent and permanent atrial fibrillation, atrial flutter, paroxysmal atrial flutter, or lone atrial fibrillation. In some cases, the method comprises administering a liquid, dry powder, extruded droplets, or nebulized droplets comprising the at least one antiarrhythmic pharmaceutical agent, wherein the powder or nebulized droplets have a mass median aerodynamic diameter of less than 10 μm. In some cases, the antiarrhythmic pharmaceutical agent is a class I antiarrhythmic. In some cases, the class I antiarrhythmic is a class Ia, Ib, or Ic antiarrhythmic. In some cases, the class Ic antiarrhythmic is flecainide. In some cases, the antiarrhythmic pharmaceutical agent is a class II antiarrhythmic. In some cases, the class II antiarrhythmic is esmolol HCl. In some cases, dosage of the esmolol HCl is between 0.5 and 0.75 mg/kg body weight. In some cases, the antiarrhythmic pharmaceutical agent is a class IV antiarrhythmic. In some cases, the class IV antiarrhythmic is diltiazem. In some cases, dosage of the diltiazem is 0.25 mg/kg body weight. In some cases, the at least one antiarrhythmic pharmaceutical agent is aerosolized in a nebulizer. In some cases, the nebulizer is a breath-activated nebulizer. In some cases, the nebulizer is a breath-actuated nebulizer. In some cases, the nebulizer is configured to administer a liquid pharmaceutical formulation of the at least one antiarrhythmic pharmaceutical agent. In some cases, the aerosolization occurs at room temperature. In some cases, the at least one antiarrhythmic pharmaceutical agent is self-administered by the subject. In some cases, the Tax, the $C_{max}$, the $AUC_{Last}$, the distribution $t_{1/2}$, the elimination $t_{1/2}$, or the maximum ΔQRS of the effective amount of the at least one antiarrhythmic agent is measured in a human PK/PD study. In some cases, the human PK/PD study is a single-dose PK/PD study. In some cases, the human PK/PD study is a multi-dose (e.g., escalating dose) PK/PD study.

In another aspect, disclosed herein is a method of treating a heart condition, comprising administering a pharmaceutically effective amount of an antiarrhythmic pharmaceutical agent via inhalation to a patient in need thereof, wherein $T_{max}$ of the pharmaceutically effective amount of the antiarrhythmic pharmaceutical agent after inhalation is from about 0.1 minute to about 30 minutes; $C_{max}$ of the pharmaceutically effective amount of the antiarrhythmic pharmaceutical agent after inhalation is from about 10 ng/mL to about 5000 ng/mL; or $AUC_{Last}$ of the pharmaceutically effective amount of the antiarrhythmic pharmaceutical agent after inhalation is from about 100 hr*ng/mL to about 10000 hr*ng/mL. In some cases, the Tax is from about 0.1 minute to about 5 minutes, the $C_{max}$ is from about 50 ng/mL to about 500 ng/mL, or the $AUC_{Last}$ is from about 200 hr*ng/mL to about 2000 hr*ng/mL. In some cases, the $T_{max}$ is from about 0.1 minute to about 5 minutes and the $C_{max}$ is from about 50 ng/mL to about 500 ng/mL. In some cases, the $T_{max}$ is from about 0.1 minute to about 5 minutes and the $AUC_{Last}$ is from about 200 hr*ng/mL to about 2000 hr*ng/mL. In some cases, the $C_{max}$ is from about 50 ng/mL to about 500 ng/mL, and the $AUC_{Last}$t is from about 200 hr*ng/mL to about 2000 hr*ng/mL. In some cases, the antiarrhythmic pharmaceutical agent is a class I, class II, class III, or class IV antiarrhythmic. In some cases, the antiarrhythmic pharmaceutical agent comprises a class Ic antiarrhythmic. In some cases, the antiarrhythmic pharmaceutical agent comprises flecainide or a pharmaceutically acceptable salt thereof. In some cases, the method comprises administering 20 mg to 100 mg of flecainide or a pharmaceutically acceptable salt thereof via inhalation to the patient in need thereof. In some cases, the method comprises administering 0.25 mg/kg body weight to 1.5 mg/kg body weight of flecainide or a pharmaceutically acceptable salt thereof via inhalation to the patient in need thereof. In some cases, the antiarrhythmic pharmaceutical agent is delivered over two or more inhalations. In some cases, time between the two or more inhalations is from about 0.1 to 10 minutes.

In another aspect, disclosed herein is a nebulized drug product, comprising a pharmaceutically effective amount of an antiarrhythmic pharmaceutical agent, wherein $T_{max}$ of the pharmaceutically effective amount of the antiarrhythmic pharmaceutical agent after inhalation is from about 0.1 minute to about 30 minutes; $C_{max}$ of the pharmaceutically effective amount of the antiarrhythmic pharmaceutical agent after inhalation is from about 10 ng/mL to about 5000 ng/mL; or $AUC_{Last}$ of the pharmaceutically effective amount of the antiarrhythmic pharmaceutical agent after inhalation is from about 100 hr*ng/mL to about 10000 hr*ng/mL. In some cases, the $T_{max}$ is from about 0.1 minute to about 5 minutes, the $C_{max}$ is from about 50 ng/mL to about 500 ng/mL, or the $AUC_{Last}$ is from about 200 hr*ng/mL to about 2000 hr*ng/mL. In some cases, the $T_{max}$ is from about 0.1 minute to about 5 minutes and the $C_{max}$ is from about 50 ng/mL to about 500 ng/mL. In some cases, the $T_{max}$ is from about 0.1 minute to about 5 minutes and the $AUC_{Las}$t is from about 200 hr*ng/mL to about 2000 hr*ng/mL. In some cases, the $C_{max}$ is from about 50 ng/mL to about 500 ng/mL, and the $AUC_{Las}$t is from about 200 hr*ng/mL to about 2000 hr*ng/mL. In some cases, the antiarrhythmic pharmaceutical agent is a class I, class II, class III, or class IV antiarrhythmic. In some cases, the antiarrhythmic pharmaceutical agent comprises a class Ic antiarrhythmic. In some cases, the antiarrhythmic pharmaceutical agent comprises flecainide or a pharmaceutically acceptable salt thereof. In some cases, the nebulized drug product comprises 20 mg to 100 mg of flecainide or a pharmaceutically acceptable salt thereof.

In another aspect, disclosed herein is a method of manufacturing a formulation for the treatment of a heart condition, comprising a pharmaceutically effective amount of an antiarrhythmic pharmaceutical agent, wherein $T_{max}$ of the pharmaceutically effective amount of the antiarrhythmic pharmaceutical agent after nebulization and inhalation of the formulation by a patient in need thereof is from about 0.1 minute to about 30 minutes; $C_{max}$ of the pharmaceutically effective amount of the antiarrhythmic pharmaceutical agent after nebulization and inhalation of the formulation by a patient in need thereof is from about 10 ng/mL to about 5000 ng/mL; or $AUC_{Last}$ of the pharmaceutically effective amount of the antiarrhythmic pharmaceutical agent after nebulization and inhalation of the formulation by a patient in need thereof is from about 100 hr*ng/mL to about 10000 hr*ng/mL. In some cases, the $T_{max}$ is from about 0.1 minute to about 5 minutes, the $C_{max}$ is from about 50 ng/mL to about 500 ng/mL, or the $AUC_{Last}$ is from about 200 hr*ng/mL to about 2000 hr*ng/mL. In some cases, the $T_{max}$ is from about 0.1 minute to about 5 minutes and the $C_{max}$ is from about 50 ng/mL to about 500 ng/mL. In some cases, the $T_{max}$ is from about 0.1 minute to about 5 minutes and the $AUC_{Last}$ is from about 200 hr*ng/mL to about 2000 hr*ng/mL. In some cases, the $C_{max}$ is from about 50 ng/mL to about 500 ng/mL, and the $AUC_{Last}$ is from about 200 hr*ng/mL to about 2000 hr*ng/mL. In some cases, the antiarrhythmic pharmaceutical agent is a class I, class II, class III, or class IV antiarrhythmic. In some cases, the antiarrhythmic pharmaceutical agent comprises a class Ic antiarrhythmic. In some cases, the antiarrhythmic pharmaceutical agent comprises flecainide or a pharmaceutically acceptable salt thereof. In some cases, the antiarrhythmic pharmaceutical agent is delivered over two or more inhalations. In some cases, time between the two or more inhalations is from about 0.1 to 10 minutes.

In another aspect, disclosed herein is a nebulized drug product, comprising a pharmaceutically effective amount of an antiarrhythmic pharmaceutical agent for use in treating a heart condition, wherein $T_{max}$ of the pharmaceutically effective amount of the antiarrhythmic pharmaceutical agent after inhalation is from about 0.1 minute to about 30 minutes; $C_{max}$ of the pharmaceutically effective amount of the antiarrhythmic pharmaceutical agent after inhalation is from about 10 ng/mL to about 5000 ng/mL; or $AUC_{Last}$ of the pharmaceutically effective amount of the antiarrhythmic pharmaceutical agent after inhalation is from about 100 hr*ng/mL to about 10000 hr*ng/mL. In some cases, the $T_{max}$ is from about 0.1 minute to about 5 minutes, the $C_{max}$ is from about 50 ng/mL to about 500 ng/mL, or the $AUC_{Las}$t is from about 200 hr*ng/mL to about 2000 hr*ng/mL. In some cases, the $T_{max}$ is from about 0.1 minute to about 5 minutes and the $C_{max}$ is from about 50 ng/mL to about 500 ng/mL. In some cases, the $T_{max}$ is from about 0.1 minute to about 5 minutes and the $AUC_{Las}$t is from about 200 hr*ng/mL to about 2000 hr*ng/mL. In some cases, the $C_{max}$ is from about 50 ng/mL to about 500 ng/mL, and the $AUC_{Last}$ is from about 200 hr*ng/mL to about 2000 hr*ng/mL. In some cases, the antiarrhythmic pharmaceutical agent is a class I, class II, class III, or class IV antiarrhythmic. In some cases, the antiarrhythmic pharmaceutical agent comprises a class Ic antiarrhythmic. In some cases, the antiarrhythmic pharmaceutical agent comprises flecainide or a pharmaceutically acceptable salt thereof. In some cases, the nebulized drug product comprises 20 mg to 100 mg of flecainide or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The present invention is further described in the description of invention that follows, in reference to the noted plurality of non-limiting drawings, wherein:

FIGS. 39-67 refer to data obtained in pigs. FIG. 39 shows flecainide venous and left ventricular chamber (LV) plasma levels at different time points following intravenous administration of 2.0 mg/kg over 2 min.

FIG. 40 shows flecainide venous and LV plasma levels at different time points following intratracheal instillation of 0.75 mg/kg.

FIG. 41 shows flecainide venous and LV plasma levels at different time points following intratracheal instillation of 1.5 mg/kg.

FIG. 42 shows the effects of intravenous administration of flecainide (2.0 mg/kg) on heart rate (primary vertical axis) and LV plasma levels (secondary vertical axis) at different time points.

FIG. 43 shows the effects of intravenous administration of flecainide (2.0 mg/kg) on mean arterial blood pressure (MAP; primary vertical axis) and LV plasma levels (secondary vertical axis) at different time points.

FIG. 44 shows the effects of intravenous administration of flecainide (2.0 mg/kg) on the PR interval duration (primary vertical axis) and LV plasma levels (secondary vertical axis) at different time points.

FIG. 45 shows the effects of intravenous administration of flecainide (2.0 mg/kg) on QRS interval duration (primary vertical axis) and LV plasma levels (secondary vertical axis) at different time points.

FIG. 46 shows the effects of intravenous administration of flecainide (2.0 mg/kg) on the QTc interval duration (primary vertical axis) and LV plasma levels (secondary vertical axis) at different time points.

FIG. 47 shows the effects of intravenous administration of flecainide (2.0 mg/kg) on the JTc interval duration (primary vertical axis) and LV plasma levels (secondary vertical axis) at different time points.

FIG. 48 shows the effects of intratracheal instillation of the lower dose of flecainide (0.75 mg/kg) on heart rate (primary vertical axis) and LV plasma levels (secondary vertical axis) at different time points.

FIG. 49 shows the effects of intratracheal instillation of the lower dose of flecainide (0.75 mg/kg) on MAP (primary vertical axis) and LV plasma levels (secondary vertical axis) at different time points.

FIG. 50 shows the effects of intratracheal instillation of the lower dose of flecainide (0.75 mg/kg) on the PR interval (primary vertical axis) and LV plasma levels (secondary vertical axis) at different time points.

FIG. 51 shows the effects of intratracheal instillation of the lower dose of flecainide (0.75 mg/kg) on QRS interval duration (primary vertical axis) and LV plasma levels (secondary vertical axis) at different time points.

FIG. 52 shows the effects of intratracheal instillation of the lower dose of flecainide (0.75 mg/kg) on the QTc interval (primary vertical axis) and LV plasma levels (secondary vertical axis) at different time points.

FIG. 53 shows the effects of intratracheal instillation of the lower dose of flecainide (0.75 mg/kg) on the JTc interval (primary vertical axis) and LV plasma level (secondary vertical axis) at different time points.

FIG. 54 shows the effects of intratracheal instillation of the higher dose of flecainide (1.5 mg/kg) on heart rate (primary vertical axis) and LV plasma levels (secondary vertical axis) at different time points.

FIG. 55 shows the effects of intratracheal instillation of the higher dose of flecainide (1.5 mg/kg) on MAP (primary vertical axis) and LV plasma levels (secondary vertical axis) at different time points.

FIG. 56 shows the effects of intratracheal instillation of the higher dose of flecainide (1.5 mg/kg) on the PR interval (primary vertical axis) and LV plasma levels (secondary vertical axis) at different time points.

FIG. 57 shows the effects of intratracheal instillation of the higher dose of flecainide (1.5 mg/kg) on QRS interval duration (primary vertical axis) and LV plasma levels (secondary vertical axis) at different time points.

FIG. 58 shows the effects of intratracheal instillation of the higher dose of flecainide (1.5 mg/kg) on the QTc interval (primary vertical axis) and LV plasma levels (secondary vertical axis) at different time points.

FIG. 59 shows the effects of intratracheal instillation of the higher dose of flecainide (1.5 mg/kg) on the JTc interval (primary vertical axis) and LV plasma levels (secondary vertical axis) at different time points.

FIG. 60 shows the protocol and a representative example of induction of atrial fibrillation (AF) to test conversion by IT flecainide.

FIG. 61 shows a summary of the data from experiments evaluating the effects of intratracheal instillation of flecainide (1.5 mg/kg) on AF duration (n=3).

FIG. 63 shows catheter placement in anesthetized Yorkshire pigs.

FIG. 64 shows AF duration was correlated with IT flecainide dose.

FIG. 65 shows representative electrograms demonstrating AF conversion at 5 min after IT flecainide (1.5 mg/kg) (lower panel) compared to no conversion by 10 min after no drug (upper panel).

FIG. 67 shows the reduction in the dominant frequency of AF by IT flecainide (0.75 mg/kg and 1.5 mg/kg).

FIGS. 68A-71 refer to data obtained in dogs. FIG. 68A shows a representative ECG demonstrating AF prior to dosing.

FIG. 69 shows a summary of the changes in blood pressure, ventricular rate, and LV dP/dTax (the maximal rate of rise of LV pressure) upon conversion of AF to NSR following administration of flecainide via IV or IT.

FIG. 70 shows the variations in plasma concentrations of flecainide in the left ventricular chamber (LV), pulmonary artery (PA), and femoral vein (VEN) based on the route of delivery (IT and IV) of flecainide. Note that following IV infusion, the concentrations of flecainide in the PA were transiently higher (2.1- to 3.5-fold)* than those in the LV. After IT instillation of flecainide, its concentrations were transiently higher (1.4- to 3.2-fold)* in the LV chamber than in the PA (*between 1 to 3 min after administration of flecainide).

FIG. 71 shows the time course of the ratios of the plasma concentrations of flecainide in the pulmonary artery (PA) and left ventricular chamber (LV) following IV or IT administration.

FIGS. 72-87B refer to data obtained in human subjects. FIG. 72 shows the effects of postural changes and inhalation of flecainide or placebo (n=3) on heart rate (HR) at different time points.

FIG. 73 shows the effects of intravenously delivered (IV) flecainide on systolic blood pressure and heart rate in 6 subjects at different time points.

FIG. 74 shows the effects of inhaled flecainide on systolic blood pressure and heart rate in 6 subjects at different time points.

FIG. 78 shows venous plasma concentration-time curve following flecainide IV infusion (normalized to 30 mg eTLD dose) and oral inhalation.

FIG. 79 shows time course of changes in QRS interval duration with flecainide or placebo.

FIG. 81 shows time course of changes in PR interval duration with flecainide or placebo.

FIG. 83 shows relationship between peak venous plasma concentrations of flecainide ($C_{max}$) and the magnitude of maximal QRS prolongation.

FIG. 85 shows non-steady state relationships between plasma concentration of flecainide and QRS duration following flecainide IV infusion and oral inhalation, respectively.

FIG. 86 shows non-steady state relationships between plasma concentrations of flecainide and QRS duration following flecainide IV infusion and oral inhalation in subjects with near-equal Δ QRS values.

FIG. 87B shows baseline (pre-dose) values of QRS complexes and PR intervals in Periods 1 and 2 of 6 subjects in Part B study.

DETAILED DESCRIPTION

Figure 1:
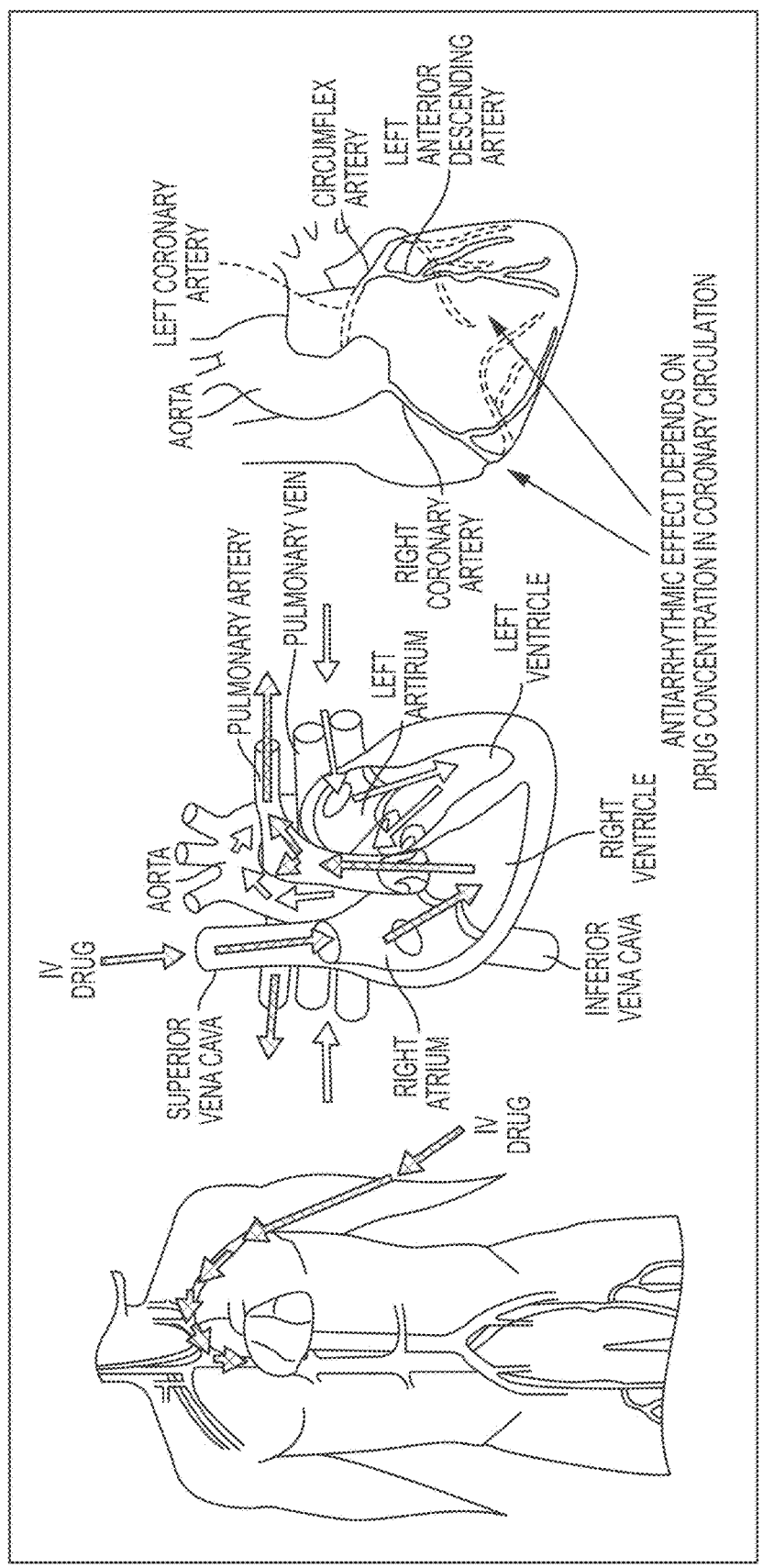
FIG. 1 shows how prior art intravenous drug passes through the heart and lungs before reaching coronary arteries, hence coronary circulation.
Figure 2A:
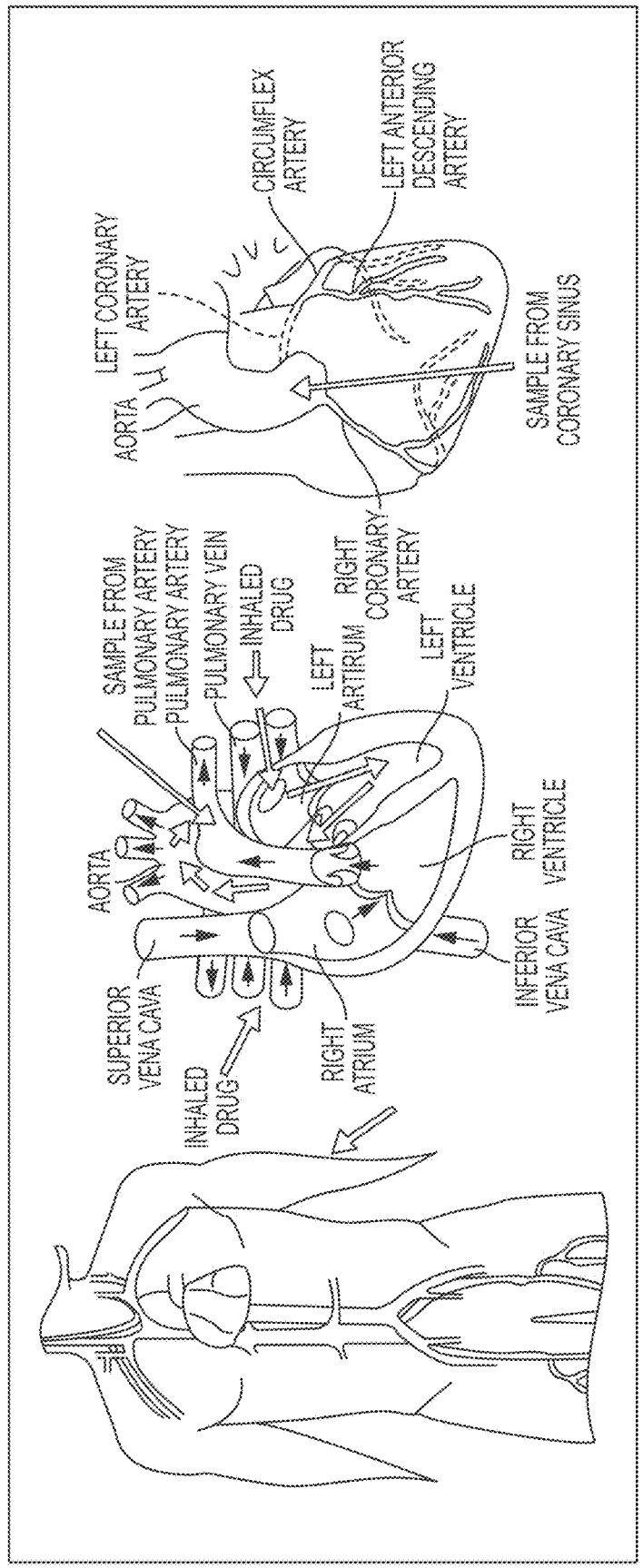
FIG. 2A shows how inhaled drug of the present invention passes through directly from the lungs to the left atrium, left ventricle and then into the coronary arteries.
Figure 2B:
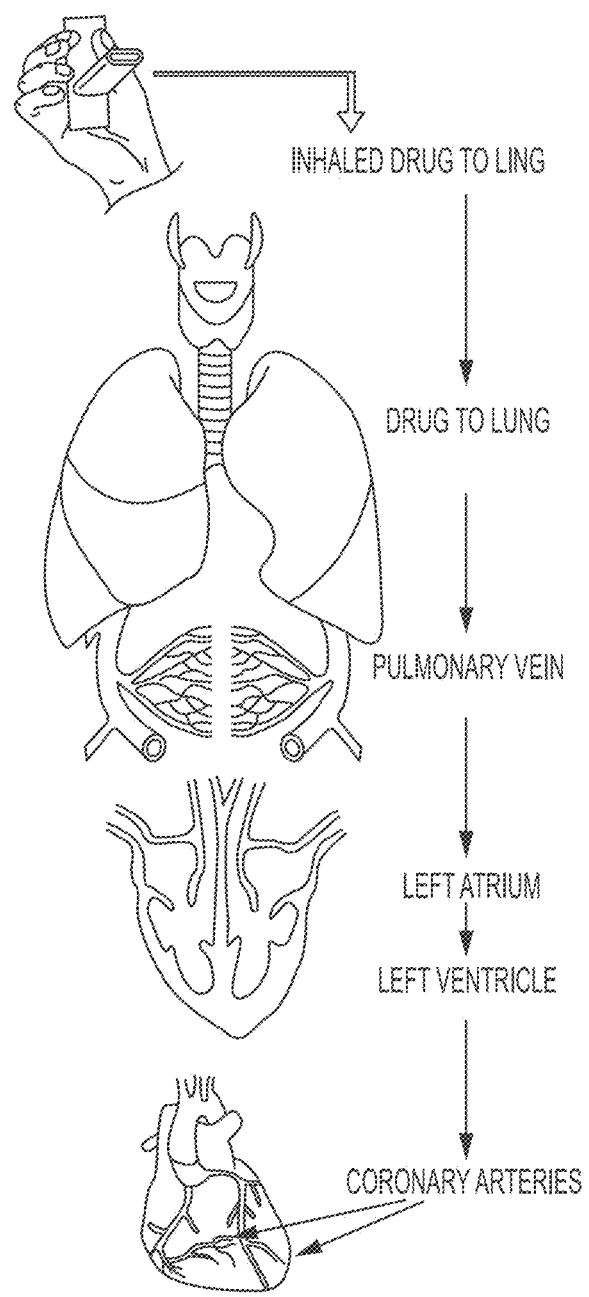
FIG. 2B shows how inhaled drug of the present invention passes through the pulmonary vein to the left atrium.
Figure 3:
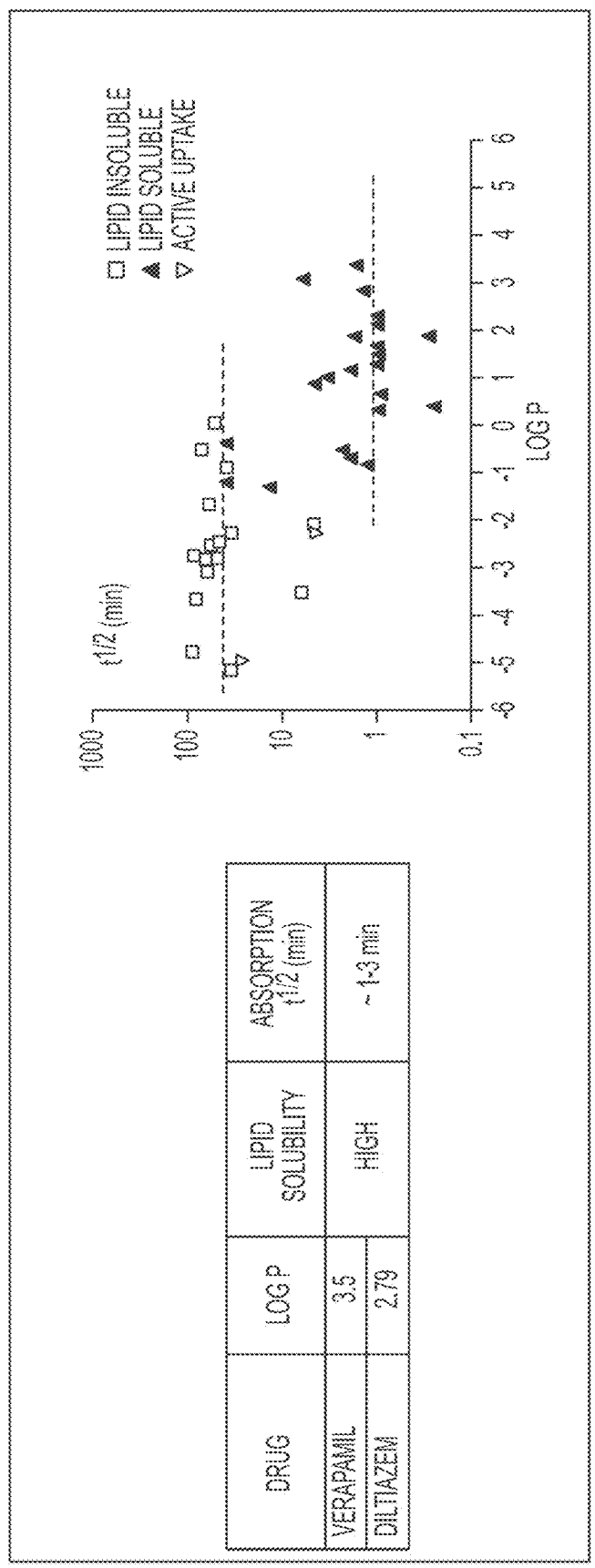
FIG. 3 shows that molecules with high Log-P values and those that have high lipid solubility are likely to exhibit faster absorption through the lung.

It is to be understood that unless otherwise indicated the present invention is not limited to specific formulation components, drug delivery systems, manufacturing techniques, administration steps, or the like, as such may vary. In this regard, unless otherwise stated, a reference to a compound or component includes the compound or component by itself, as well as the compound or component in combination with other compounds or components, such as mixtures of compounds.

Before further discussion, a definition of the following terms will aid in the understanding of the present invention.

As used herein, the singular forms "a," "an," and "the" include plural referents unless the context clearly dictates otherwise. Thus, for example, reference to "an antiarrhythmic pharmaceutical agent" includes not only a single active agent but also a combination or mixture of two or more different active agents.

Reference herein to "one embodiment," "one version," or "one aspect" shall include one or more such embodiments, versions or aspects, unless otherwise clear from the context.

As used herein, the term "solvate" is intended to include, but not be limited to, pharmaceutically acceptable solvates.

As used herein, the term "pharmaceutically acceptable solvate" is intended to mean a solvate that retains one or more of the biological activities and/or properties of the antiarrhythmic pharmaceutical agent and that is not biologically or otherwise undesirable.

Examples of pharmaceutically acceptable solvates include, but are not limited to, antiarrhythmic pharmaceutical agents in combination with water, isopropanol, ethanol, methanol, DMSO, ethyl acetate, acetic acid, ethanolamine, or combinations thereof.

As used herein, the term "salt" is intended to include, but not be limited to, pharmaceutically acceptable salts.

As used herein, the term "pharmaceutically acceptable salt" is intended to mean those salts that retain one or more of the biological activities and properties of the free acids and bases and that are not biologically or otherwise undesirable. Illustrative examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, di nitrobenzoates, hydroxybenzoates, methoxybenzoates, phthalates, sulfonates, xylenesulfonates, phenylacetates, phenyipropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

If the antiarrhythmic pharmaceutical agent is a base, the desired salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such as p-toluenesulfonic acid and ethanesulfonic acid, or the like.

If the antiarrhythmic pharmaceutical agent is an acid, the desired salt may be prepared by any suitable method known in the art, including treatment of the free acid with an inorganic or organic base, such as an amine (primary, secondary or tertiary), an alkali metal or alkaline earth metal hydroxide, or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

The term "about" in relation to a reference numerical value can include a range of values plus or minus 10% from that value. For example, the amount "about 10" includes amounts from 9 to 11, including the reference numbers of 9, 10, and 11. The term "about" in relation to a reference numerical value can also include a range of values plus or minus 10%, 9%, 8%, 7%, 6%, 5%, 4%, 3%, 2%, or 1% from that value.

As used herein, "atrial arrhythmia" can mean an arrhythmia that affects at least one atrium and does not include bradycardia. For instance, atrial arrhythmia may originate in and affect at least one atrium.

As used herein, "tachycardia" can mean an arrhythmia in which the heart beat is too fast, e.g., faster than normal. For instance, tachycardia may involve a resting heart rate of over 100 beats per minute, such as greater than 110, greater than 120, or greater than 130 beats minute.

As used herein, the phrase "heart rhythm arrhythmia" can mean an arrhythmia in which the heart beat is irregular.

As used herein, the "amount of the at least one antiarrhythmic pharmaceutical agent in blood in the coronary circulation of the heart" may be measured by extracting a sample from any vascular region of the coronary circulation of the heart (e.g., arteries, veins, including coronary sinus) by using a cannula. The amount of antiarrhythmic pharmaceutical agent in the sample may then be determined by known means, such as bioanalytical techniques that employ analytical equipment such as LC-MS/MS. Thus, the amount of antiarrhythmic pharmaceutical agent in the blood in the heart may be measured for any particular time.

As used herein, the terms "treating" and "treatment" can refer to reduction in severity and/or frequency of symptoms, elimination of symptoms and/or underlying cause, reduction in likelihood of the occurrence of symptoms and/or underlying cause, and/or remediation of damage. Thus, "treating" a patient with an active agent as provided herein includes prevention of a particular condition, disease, or disorder in a susceptible individual as well as treatment of a clinically symptomatic individual.

As used herein, "nominal amount" can refer to the amount contained within the unit dose receptacle(s) that are administered.

As used herein, "effective amount" can refer to an amount covering both therapeutically effective amounts and prophylactically effective amounts.

As used herein, a "therapeutically effective amount" of an active agent refers to an amount that is effective to achieve a desired therapeutic result. A therapeutically effective amount of a given active agent will typically vary with respect to factors such as the type and severity of the disorder or disease being treated and the age, gender, and weight of the patient. In some cases, "inhalation" (e.g., "oral inhalation") can refer to inhalation delivery of a therapeutically effective amount of a pharmaceutical agent contained in one unit dose receptacle, which, in some instance, can require one or more breaths, like 1, 2, 3, 4, 5, 6, 7, 8, 9, or more breaths. For example, if the effective amount is 90 mg, and each unit dose receptacle contains 30 mg, the delivery of the effective amount can require 3 inhalations.

Unless otherwise specified, the term "therapeutically effective amount" can include a "prophylactically effective amount," e.g., an amount of active agent that is effective to prevent the onset or recurrence of a particular condition, disease, or disorder in a susceptible individual.

As used herein, the phrase "minimum effective amount" can mean the minimum amount of a pharmaceutical agent necessary to achieve an effective amount.

As used herein, "mass median diameter" or "MMD" can refer to the median diameter of a plurality of particles, typically in a polydisperse particle population, e.g., consisting of a range of particle sizes. MMD values as reported herein are determined by laser diffraction (Sympatec Helos, Clausthal-Zellerfeld, Germany), unless the context indicates otherwise. For instance, for powders the samples are added directly to the feeder funnel of the Sympatec RODOS dry powder dispersion unit. This can be achieved manually or by agitating mechanically from the end of a VIBRI vibratory feeder element. Samples are dispersed to primary particles via application of pressurized air (2 to 3 bar), with vacuum depression (suction) maximized for a given dispersion pressure. Dispersed particles are probed with a 632.8 nm laser beam that intersects the dispersed particles' trajectory at right angles. Laser light scattered from the ensemble of particles is imaged onto a concentric array of photomultiplier detector elements using a reverse-Fourier lens assembly. Scattered light is acquired in time-slices of 5 ms. Particle size distributions are back-calculated from the scattered light spatial/intensity distribution using a proprietary algorithm.

As used herein, "geometric diameter" can refer to the diameter of a single particle, as determined by microscopy, unless the context indicates otherwise.

As used herein, "mass median aerodynamic diameter" or "MMAD" can refer to the median aerodynamic size of a plurality of particles or particles, typically in a polydisperse population. The "aerodynamic diameter" can be the diameter of a unit density sphere having the same settling velocity, generally in air, as a powder and is therefore a useful way to characterize an aerosolized powder or other dispersed particle or particle formulation in terms of its settling behavior. The aerodynamic diameter encompasses particle or particle shape, density, and physical size of the particle or particle. As used herein, MMAD refers to the median of the aerodynamic particle or particle size distribution of aerosolized particles determined by cascade impaction, unless the context indicates otherwise.

As used herein, the term "emitted dose" or "ED" can refer to an indication of the delivery of particles from an aerosolization device after an actuation or dispersion event from a unit dose receptacle or reservoir. ED is defined as the ratio of the dose delivered by an inhaler device to the nominal dose (e.g., the mass of powder or liquid per unit dose placed into a suitable inhaler device prior to firing). The ED is an experimentally determined amount, and may be determined using an in vitro system that mimics patient dosing. For instance, to determine an ED value for a dry powder, a nominal dose of dry powder is placed into a Turbospin® DPI device (PH&T, Italy), described in U.S. Pat. Nos. 4,069,819 and 4,995,385, which are incorporated herein by reference in their entireties. The Turbospin® DPI is actuated, dispersing the powder. The resulting aerosol cloud is then drawn from the device by vacuum (30 L/min) for 2.5 seconds after actuation, at which point it is captured on a tared glass fiber filter (Gelman, 47 mm diameter) attached to the device mouthpiece. The amount of powder that reaches the filter constitutes the delivered dose. For example, for a capsule containing 5 mg of dry powder, capture of 4 mg of powder on the tared filter would indicate an ED of 80% (=4 mg (delivered dose)/5 mg (nominal dose)).

As used herein, "passive dry powder inhaler" can refer to an inhalation device that relies upon a patient's inspiratory effort to disperse and aerosolize a pharmaceutical composition contained within the device in a reservoir or in a unit dose form and does not include inhaler devices which comprise a means for providing energy, such as pressurized gas and vibrating or rotating elements, to disperse and aerosolize the drug composition.

As used herein, "active dry powder inhaler" can refer to an inhalation device that does not rely solely on a patient's inspiratory effort to disperse and aerosolize a pharmaceutical composition contained within the device in a reservoir or in a unit dose form and does include inhaler devices that comprise a means for providing energy to disperse and aerosolize the drug composition, such as pressurized gas and vibrating or rotating elements.

By a "pharmaceutically acceptable" component is meant a component that is not biologically or otherwise undesirable, e.g., the component may be incorporated into a pharmaceutical formulation of the invention and administered to a patient as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

As used herein, "P wave" can represent the wave generated by the electrical depolarization of the atria (right and left), and is usually 0.08 to 0.1 seconds (80-100 ms) in duration.

As used herein, "short form-36 quality of life" can mean the Short Form 36 (SF-36) survey of patient health (updated August 2005). The SF-36 consists of eight scaled scores, which are the sums of the questions in their section. Each scale is directly transformed into a 0-100 scale on the assumption that each question carries equal weight. The eight sections are: (1) vitality; (2) physical functioning; (3) bodily pain; (4) general health perceptions; (5) physical role functioning; (6) emotional role functioning; (7) social role functioning; and (8) mental health. It can also refer to any Quality of Life questionnaire for AF symptoms.

As used herein, "preservative" can mean cresols and benzoates. Thus, "substantially preservative-free" can mean that a composition does not include a substantial amount of any cresols and/or benzoates. For instance, "substantially preservative-free" compositions can comprise less than 1 wt %, such as less than 0.5 wt %, less than 0.4 wt %, less than 0.3 wt %, less than 0.2 wt %, or less than 0.1 wt %, of preservative. Of course, "preservative-free" can mean that no preservative is present.

As used herein, "substantially tasteless" can mean a composition that has substantially little to no taste upon initial ingestion.

As an overview, the present invention relates to methods of treating atrial arrhythmia. The methods may comprise administering an effective amount of at least one antiarrhythmic pharmaceutical agent to a patient in need thereof, such that the at least one antiarrhythmic pharmaceutical agent first enters the heart through the pulmonary veins to the left atrium.

In one aspect, a method of treating atrial arrhythmia comprises administering by inhalation an effective amount of at least one antiarrhythmic pharmaceutical agent to a patient in need thereof, wherein an amount of the at least one antiarrhythmic pharmaceutical agent peaks in the coronary circulation of the heart at a time ranging from 10 seconds to 30 minutes from the administration.

In yet another aspect, the present invention is directed to a method of self-diagnosing and treating atrial arrhythmia. The method comprises self-diagnosing atrial arrhythmia by detecting at least one of shortness of breath, heart palpitations, and above normal heart rate. The method also comprises self-administering by inhalation an effective amount of at least one antiarrhythmic pharmaceutical agent within two hours, one hour, 30 minutes, or 15 minutes of the self-diagnosing. In some cases, the method comprises self-administering by inhalation an effective amount of at least one antiarrhythmic pharmaceutical agent within 15 minutes of the self-diagnosing.

In another aspect, a method of treating atrial arrhythmia comprises administering by inhalation an effective amount of at least one antiarrhythmic pharmaceutical agent to a patient in need thereof, wherein an electrophysiologic effect is observed, via electrocardiography, at a time ranging from 10 seconds to 30 minutes from the administration.

In still another aspect, a method of treating atrial arrhythmia comprises administering by inhalation an effective amount of at least one antiarrhythmic pharmaceutical agent to a patient in need thereof, wherein a cardiac score from a monitor implementing an arrhythmia detection algorithm shows a transition from an arrhythmic state to normal sinus rhythm in the patient at a time ranging from 10 seconds to 30 minutes from the administration.

In yet another aspect, a method of treating atrial arrhythmia comprises administering by inhalation an effective amount of at least one antiarrhythmic pharmaceutical agent to a patient in need thereof, wherein a short form-36 quality of life score of the patient improves at a time ranging from 10 seconds to 30 minutes from the administration.

In another aspect, a unit dose comprises a unit dose receptacle and a composition within the unit dose receptacle. The composition comprises at least one antiarrhythmic pharmaceutical agent in an amount less than or equal to an amount of the same at least one antiarrhythmic pharmaceutical agent administered intravenously in the arm to achieve a minimum effective amount in the coronary circulation, and a pharmaceutically acceptable excipient.

In still another aspect, an aerosol comprises particles having a mass median aerodynamic diameter less than 10 µm. The particles comprise at least one antiarrhythmic pharmaceutical agent in an amount less than or equal to an amount of the same at least one antiarrhythmic pharmaceutical agent administered intravenously in the arm to achieve a minimum effective amount in the coronary circulation, and a pharmaceutically acceptable excipient.

In yet another aspect, a kit comprises a container containing at least one antiarrhythmic pharmaceutical agent and an aerosolization device.

In certain embodiments, the present invention includes "pharmaco-rescue-therapies" to provide fast cardioversion in patients with atrial arrhythmias like Paroxysmal Ventricular Tachycardia (PSVT), and Paroxysmal Atrial Fibrillation (PAF). The pharmaco-rescue-therapies are usually intended for self-administration of the medicine by inhalation.

Inhalation is the shortest route for a drug to reach the heart, next only to intracardiac injection, as shown in FIGS. 2A and 2B. Drugs delivered by inhalation generally exhibit "pulsatile pharmacokinetics" of transient high drug concentrations, followed by dilution to sub-therapeutic levels.

Thus, in some embodiments, the present invention involves a rapid acting inhaled product with a fast onset of action compared to oral medicine. The product is expected to be at least as fast as intravenous medicine. In some embodiments, an amount of the at least one antiarrhythmic pharmaceutical agent peaks in the coronary circulation of the heart at a time ranging from 10 seconds to 30 minutes, such as 30 seconds to 20 minutes, 1 minute to 10 minutes, 2 minutes to 8 minutes, or 2.5 minutes to 5 minutes, from the administration. In certain embodiments, an electrophysiologic effect is observed, via electrocardiography, at a time ranging from 10 seconds to 30 minutes, such as 30 seconds to 20 minutes, 1 minute to 10 minutes, 2 minutes to 8 minutes, or 2.5 minutes to 5 minutes, from the administration. In some embodiments, a cardiac score from a device with an arrhythmia detection algorithm shows a transition from an arrhythmic state to normal sinus rhythm in the patient at a time ranging from 10 seconds to 30 minutes, such as 30 seconds to 20 minutes, 1 minute to 10 minutes, 2 minutes to 8 minutes, or 2.5 minutes to 5 minutes, from the administration. In some embodiments, a short form-36 quality of life score of the patient improves at a time ranging from 10 seconds to 30 minutes, such as 30 seconds to 20 minutes, 1 minute to 10 minutes, 2 minutes to 8 minutes, or 2.5 minutes to 5 minutes, from the administration. In certain embodiments, the patient has normal sinus rhythm within 30 minutes, such as within 10 minutes, of initiating the administering.

In some aspects, the present invention involves low doses that are safe and effective. Other aspects typically involve low premature metabolism and low drug-drug interaction.

The present invention includes non-invasive drug delivery to the heart. The lung is shortest route for drug to heart with minimal dilution next to intra-cardiac injection. Drugs delivered via the lung have a fast onset action compared to those delivered via the oral route. Pipeline Insights: Antiarrhythmics, Datamonitor (June 2006). Pulmonary drug delivery to the heart is at least equivalent to a portable intravenous injection. Inhaled drugs (e.g., verapamil, diltiazem, lidocaine, ibutilide, procainamide, and propafenone) are expected to exhibit "pulsatile pharmacokinetics" of transient high drug concentrations, followed by dilution to sub-therapeutic levels.

Existing cardiovascular drugs tend to be small molecules with high lipid solubility. These lipid soluble molecules (e.g., diltiazem, verapamil, ibutilide, propafenone) are expected to have a high pulmonary bioavailability and fast rate of pulmonary absorption. This ensures that they reach the heart through the pulmonary veins.

The pulsatile pharmacokinetic behavior of the drugs show that the drug is diluted within a few seconds of reaching effective concentrations in the heart and is diluted to sub-therapeutic levels in the volume of the blood. This characteristic will minimize drug-drug interactions that produce significant toxicological responses normally seen at steady state.

Thus, in certain embodiments, the present invention relates to achieving transient high drug concentrations in the heart that effect rate and rhythm changes in the heart within a short period of time allowing for treatment of episodic arrhythmias such as paroxysmal atrial arrhythmias.

The results of the invention are surprising and unexpected. In this regard, the antiarrhythmic pharmaceutical agents pass through the lungs quickly. For instance, verapamil and diltiazem will ionize if in salt form, so the base will pass through the lungs quickly. In some aspects, the methods of the present invention take advantage of fast onset of action, high drug bioavailability, and fast absorption through the lung. Most cardiovascular drugs are small molecules that have high lipid solubility and are therefore expected to have high pulmonary bioavailability and a fast rate of absorption. FIG. 3 shows the log-p values and lipid solubility of exemplary cardiovascular molecules along with their expected high pulmonary bioavailability.

Another reason why the results of the present invention are surprising and unexpected involves the rate at which the antiarrhythmic pharmaceutical agents pass through the heart. While a skilled artisan might expect the rate to be too fast, modeling indicates that the drug will not pass through the heart too fast. Thus, a therapeutic effect is achieved despite fast pass-through and despite only one pass-through at therapeutic levels.

In view of the above, in one or more embodiments of the invention, a composition comprises an antiarrhythmic pharmaceutical agent. Examples of antiarrhythmic pharmaceutical agents include, but are not limited to, class Ia (sodium channel blockers, intermediate association/dissociation), class Ib (sodium channel blockers, fast association/dissociation), class Ic (sodium channel blocker, slow association/dissociation), class II (beta blockers), class III (potassium channel blockers), class IV (calcium channel blockers), and class V (unknown mechanisms) antiarrhythmics.

Class Ia antiarrhythmics include, but are not limited to, quinidine, procainamide, and disopyramide, and pharmaceutically acceptable salts thereof. Class Ib antiarrhythmics include, but are not limited to, lidocaine, tocainide, phenytoin, moricizine, and mexiletine, and pharmaceutically acceptable salts thereof. Class Ic antiarrhythmics include, but are not limited to, flecainide, propafenone, and moricizine, and pharmaceutically acceptable salts thereof. Class II antiarrhythmics include, but are not limited to, propranolol, acebutolol, soltalol, esmolol, timolol, metoprolol, and atenolol, and pharmaceutically acceptable salts thereof. Class III antiarrhythmics include, but are not limited to, amiodarone, sotalol, bretylium, ibutilide, E-4031 (methanesulfonamide), vernakalant, and dofetilide, and pharmaceutically acceptable salts thereof. Class IV antiarrhythmics include, but are not limited to, bepridil, nitrendipine, amlodipine, isradipine, nifedipine, nicardipine, verapamil, and diltiazem, and pharmaceutically acceptable salts thereof. Class V antiarrhythmics include, but are not limited to, digoxin and adenosine, and pharmaceutically acceptable salts thereof.

The present invention also includes derivatives of the above antiarrhythmic pharmaceutical agents such as solvates, salts, solvated salts, esters, amides, hydrazides, N-alkyls, and/or N-amino acyls. The derivatives of the antiarrhythmic pharmaceutical agents can be pharmaceutically acceptable derivatives. Examples of ester derivatives include, but are not limited to, methyl esters, choline esters, and dimethylaminopropyl esters. Examples of amide derivatives include, but are not limited to, primary, secondary, and tertiary amides. Examples of hydrazide derivatives include, but are not limited to, N-methylpiperazine hydrazides. Examples of N-alkyl derivatives include, but are not limited to, N',N',N'-trimethyl and N',N'-dimethylaminopropyl succininimidyl derivatives of antiarrhythmic pharmaceutical agent methyl esters. Examples of N-aminoacyl derivatives include, but are not limited to, N-omithyl-, N-diaminopropionyl-, N-lysil-, N-hexamethyllysil-, and N-piperdine-propionyl- or N',N'-methyl-1-piperazine-propionyl-antiarrhythmic pharmaceutical agent methyl esters.

The antiarrhythmic pharmaceutical agents may exist as single stereoisomers, racemates, and/or mixtures of enantiomers, and/or diastereomers. All such single stereoisomers, racemates, and mixtures thereof are intended to be within the scope of the present invention. These various forms of the compounds may be isolated/prepared by methods known in the art.

The antiarrhythmic pharmaceutical agents of the present invention may be prepared in a racemic mixture (e.g., mixture of isomers) that contains more than 50%, preferably at least 75%, and more preferably at least 90% of the desired isomer (e.g., 80% enantiomeric or diastereomeric excess). According to particularly preferred embodiments, the compounds of the present invention are prepared in a form that contains at least 95% (90% e.e. or d.e.), even more preferably at least 97.5% (95% e.e. or d.e.), and most preferably at least 99% (98% e.e. or d.e.) of the desired isomer. Compounds identified herein as single stereoisomers are meant to describe compounds used in a form that contains more than 50% of a single isomer. By using known techniques, these compounds may be isolated in any of such forms by slightly varying the method of purification and/or isolation from the solvents used in the synthetic preparation of such compounds.

The pharmaceutical composition according to one or more embodiments of the invention may comprise one or more antiarrhythmic pharmaceutical agents and, optionally, one or more other active ingredients and, optionally, one or more pharmaceutically acceptable excipients. For example, the pharmaceutical composition may comprise neat particles of antiarrhythmic pharmaceutical agent (e.g., particles containing only the antiarrhythmic pharmaceutical agent), may comprise neat particles of antiarrhythmic pharmaceutical agent together with other particles, and/or may comprise particles comprising antiarrhythmic pharmaceutical agent and one or more active ingredients and/or one or more pharmaceutically acceptable excipients.

Thus, the pharmaceutical composition according to one or more embodiments of the invention may, if desired, contain a combination of antiarrhythmic pharmaceutical agent and one or more additional active agents. Examples of additional active agents include, but are not limited to, agents that may be delivered through the lungs.

Additional active agents may comprise, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, additional anti-infectives (antivirals, antifungals, vaccines) antiarthritics, antimalarials, antiemetics, anepileptics, cytokines, growth factors, anti-cancer agents, antithrombotic agents, antihypertensives, cardiovascular drugs, antiarrhythmics, antioxidants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The additional active agent, when administered by inhalation, may act locally or systemically.

The additional active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of additional active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., monoacylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFFR) gene, deoxyribonuclease (DNase), bactericidal/permeability increasing protein (BPI), anti-CMV antibody, 13-cis retinoic acid, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments, derivatives, and analogs thereof.

Additional active agents for use in the invention can further include nucleic acids, as bare nucleic acid molecules, vectors, associated viral particles, plasmid DNA or RNA or other nucleic acid constructs of a type suitable for transfection or transformation of cells, e.g., suitable for gene therapy including antisense. Further, an active agent may comprise live attenuated or killed viruses suitable for use as vaccines. Other useful drugs include those listed within the Physician's Desk Reference (most recent edition), which is incorporated herein by reference in its entirety.

When a combination of active agents is used, the agents may be provided in combination in a single species of pharmaceutical composition or individually in separate species of pharmaceutical compositions.

The amount of antiarrhythmic pharmaceutical agent in the pharmaceutical composition may vary. The amount of antiarrhythmic pharmaceutical agent(s) is typically at least about 5 wt %, such as at least about 10 wt %, at least about 20 wt %, at least about 30 wt %, at least about 40 wt %, at least about 50 wt %, at least about 60 wt %, at least about 70 wt %, or at least about 80 wt %, of the total amount of the pharmaceutical composition. The amount of antiarrhythmic pharmaceutical agent(s) generally varies between about 0.1 wt % to 100 wt %, such as about 5 wt % to about 95 wt %, about 10 wt % to about 90 wt %, about 30 wt % to about 80 wt %, about 40 wt % to about 70 wt %, or about 50 wt % to about 60 wt %.

As noted above, the pharmaceutical composition may include one or more pharmaceutically acceptable excipient. Examples of pharmaceutically acceptable excipients include, but are not limited to, lipids, metal ions, surfactants, amino acids, carbohydrates, buffers, salts, polymers, and the like, and combinations thereof.

Examples of lipids include, but are not limited to, phospholipids, glycolipids, ganglioside GM1, sphingomyelin, phosphatidic acid, cardiolipin; lipids bearing polymer chains such as polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate.

In one or more embodiments, the phospholipid comprises a saturated phospholipid, such as one or more phosphatidylcholines. Exemplary acyl chain lengths are 16:0 and 18:0 (e.g., palmitoyl and stearoyl). The phospholipid content may be determined by the active agent activity, the mode of delivery, and other factors.

Phospholipids from both natural and synthetic sources may be used in varying amounts. When phospholipids are present, the amount is typically sufficient to coat the active agent(s) with at least a single molecular layer of phospholipid. In general, the phospholipid content ranges from about 5 wt % to about 99.9 wt %, such as about 20 wt % to about 80 wt %.

Generally, compatible phospholipids can comprise those that have a gel to liquid crystal phase transition greater than about 40° C., such as greater than about 60° C., or greater than about 80° C. The incorporated phospholipids may be relatively long chain (e.g., $C_{16}$-$C_{22}$) saturated lipids. Exemplary phospholipids useful in the present invention include, but are not limited to, phosphoglycerides such as dipalmitoylphosphatidylcholine, distearoylphosphatidylcholine, diarachidoylphosphatidylcholine, dibehenoylphosphatidylcholine, diphosphatidyl glycerols, short-chain phosphatidylcholines, hydrogenated phosphatidylcholine, E-100-3 (available from Lipoid KG, Ludwigshafen, Germany), long-chain saturated phosphatidylethanolamines, long-chain saturated phosphatidylserines, long-chain saturated phosphatidylglycerols, long-chain saturated phosphatidylinositols, phosphatidic acid, phosphatidylinositol, and sphingomyelin.

Examples of metal ions include, but are not limited to, divalent cations, including calcium, magnesium, zinc, iron, and the like. For instance, when phospholipids are used, the pharmaceutical composition may also comprise a polyvalent cation, as disclosed in WO 01/85136 and WO 01/85137, which are incorporated herein by reference in their entireties. The polyvalent cation may be present in an amount effective to increase the melting temperature ($T_m$) of the phospholipid such that the pharmaceutical composition exhibits a $T_m$ which is greater than its storage temperature ($T_m$) by at least about 20° C., such as at least about 40° C.

The molar ratio of polyvalent cation to phospholipid may be at least about 0.05:1, such as about 0.05:1 to about 2.0:1 or about 0.25:1 to about 1.0:1. An example of the molar ratio of polyvalent cation:phospholipid is about 0.50:1. When the polyvalent cation is calcium, it may be in the form of calcium chloride. Although metal ion, such as calcium, is often included with phospholipid, none is required.

As noted above, the pharmaceutical composition may include one or more surfactants. For instance, one or more surfactants may be in the liquid phase with one or more being associated with solid particles or particles of the composition. By "associated with" it is meant that the pharmaceutical compositions may incorporate, adsorb, absorb, be coated with, or be formed by the surfactant. Surfactants include, but are not limited to, fluorinated and nonfluorinated compounds, such as saturated and unsaturated lipids, nonionic detergents, nonionic block copolymers, ionic surfactants, and combinations thereof. It should be emphasized that, in addition to the aforementioned surfactants, suitable fluorinated surfactants are compatible with the teachings herein and may be used to provide the desired preparations.

Examples of nonionic detergents include, but are not limited to, sorbitan esters including sorbitan trioleate (Span™ 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents can be easily identified using McCutcheon's Emulsifiers and Detergents (McPublishing Co., Glen Rock, N.J.), which is incorporated herein by reference in its entirety.

Examples of block copolymers include, but are not limited to, diblock and triblock copolymers of polyoxyethylene and polyoxypropylene, including poloxamer 188 (Pluronic™ F-68), poloxamer 407 (Pluronic™ F-127), and poloxamer 338.

Examples of ionic surfactants include, but are not limited to, sodium sulfosuccinate, and fatty acid soaps.

Examples of amino acids include, but are not limited to hydrophobic amino acids. Use of amino acids as pharmaceutically acceptable excipients is known in the art as disclosed in WO 95/31479, WO 96/32096, and WO 96/32149, which are incorporated herein by reference in their entireties.

Examples of carbohydrates include, but are not limited to, monosaccharides, disaccharides, and polysaccharides. For example, monosaccharides such as dextrose (anhydrous and monohydrate), galactose, mannitol, D-mannose, sorbitol, sorbose and the like; disaccharides such as lactose, maltose, sucrose, trehalose, and the like; trisaccharides such as raffinose and the like; and other carbohydrates such as starches (hydroxyethylstarch), cyclodextrins, and maltodextrins.

Examples of buffers include, but are not limited to, tris or citrate.

Examples of acids include, but are not limited to, carboxylic acids.

Examples of salts include, but are not limited to, sodium chloride, salts of carboxylic acids, (e.g., sodium citrate, sodium ascorbate, magnesium gluconate, sodium gluconate, tromethamine hydrochloride, etc.), ammonium carbonate, ammonium acetate, ammonium chloride, and the like.

Examples of organic solids include, but are not limited to, camphor, and the like.

The pharmaceutical composition of one or more embodiments of the present invention may also include a biocompatible, such as biodegradable polymer, copolymer, or blend or other combination thereof. In this respect useful polymers comprise polylactides, polylactide-glycolides, cyclodextrins, polyacrylates, methylcellulose, carboxymethylcellulose, polyvinyl alcohols, polyanhydrides, polylactams, polyvinyl pyrrolidones, polysaccharides (dextrans, starches, chitin, chitosan, etc.), hyaluronic acid, proteins, (albumin, collagen, gelatin, etc.). Those skilled in the art will appreciate that, by selecting the appropriate polymers, the delivery efficiency of the composition and/or the stability of the dispersions may be tailored to optimize the effectiveness of the antiarrhythmic pharmaceutical agent(s).

For solutions, the compositions may include one or more osmolality adjuster, such as sodium chloride. For instance, sodium chloride may be added to solutions to adjust the osmolality of the solution. In one or more embodiments, an aqueous composition consists essentially of the antiarrhythmic pharmaceutical agent, the osmolality adjuster, and water.

Solutions may also comprise a buffer or a pH adjusting agent, typically a salt prepared from an organic acid or base. Representative buffers comprise organic acid salts of citric acid, lactic acid, ascorbic acid, gluconic acid, carbonic acid, tartaric acid, succinic acid, acetic acid, or phthalic acid, Tris, tromethamine hydrochloride, or phosphate buffers. Thus, the buffers include citrates, phosphates, phthalates, and lactates.

Besides the above mentioned pharmaceutically acceptable excipients, it may be desirable to add other pharmaceutically acceptable excipients to the pharmaceutical composition to improve particle rigidity, production yield, emitted dose and deposition, shelf-life, and patient acceptance. Such optional pharmaceutically acceptable excipients include, but are not limited to: coloring agents, taste masking agents, buffers, hygroscopic agents, antioxidants, and chemical stabilizers. Further, various pharmaceutically acceptable excipients may be used to provide structure and form to the particle compositions (e.g., latex particles). In this regard, it will be appreciated that the rigidifying components can be removed using a post-production technique such as selective solvent extraction.

The pharmaceutical compositions of one or more embodiments of the present invention can lack taste. In this regard, although taste masking agents are optionally included within the composition, the compositions often do not include a taste masking agent and lack taste even without a taste masking agent.

The pharmaceutical compositions may also include mixtures of pharmaceutically acceptable excipients. For instance, mixtures of carbohydrates and amino acids are within the scope of the present invention.

The compositions of one or more embodiments of the present invention may take various forms, such as solutions, dry powders, reconstituted powders, suspensions, or dispersions comprising a non-aqueous phase, such as propellants (e.g., chlorofluorocarbon, hydrofluoroalkane).

The solutions of the present invention are typically clear. In this regard, many of the antiarrhythmic pharmaceutical agents of the present invention are water soluble.

In some embodiments, the isotonicity of the solution ranges from isotonic to physiologic isotonicity. Physiologic isotonicity is the isotonicity of physiological fluids.

The compositions typically have a pH ranging from 3.5 to 8.0, such as from 4.0 to 7.5, or 4.5 to 7.0, or 5.0 to 6.5.

For dry powders, the moisture content is typically less than about 15 wt %, such as less than about 10 wt %, less than about 5 wt %, less than about 2 wt %, less than about 1 wt %, or less than about 0.5 wt %. Such powders are described in WO 95/24183, WO 96/32149, WO 99/16419, WO 99/16420, and WO 99/16422, which are incorporated herein by reference in their entireties.

In one version, the pharmaceutical composition comprises antiarrhythmic pharmaceutical agent incorporated into a phospholipid matrix. The pharmaceutical composition may comprise phospholipid matrices that incorporate the active agent and that are in the form of particles that are hollow and/or porous microstructures, as described in the aforementioned WO 99/16419, WO 99/16420, WO 99/16422, WO 01/85136, and WO 01/85137, which are incorporated herein by reference in their entireties. The hollow and/or porous microstructures are useful in delivering the antiarrhythmic pharmaceutical agent to the lungs because the density, size, and aerodynamic qualities of the hollow and/or porous microstructures facilitate transport into the deep lungs during a user's inhalation. In addition, the phospholipid-based hollow and/or porous microstructures reduce the attraction forces between particles, making the pharmaceutical composition easier to deagglomerate during aerosolization and improving the flow properties of the pharmaceutical composition making it easier to process.

In one version, the pharmaceutical composition is composed of hollow and/or porous microstructures having a bulk density less than about 1.0 g/cm$^3$, less than about 0.5 g/cm$^3$, less than about 0.3 g/cm$^3$, less than about 0.2 g/cm$^3$, or less than about 0.1 g/cm$^3$. By providing low bulk density particles or particles, the minimum powder mass that can be filled into a unit dose container is reduced, which eliminates the need for carrier particles. That is, the relatively low density of the powders of one or more embodiments of the present invention provides for the reproducible administration of relatively low dose pharmaceutical compounds. Moreover, the elimination of carrier particles will potentially reduce throat deposition and any "gag" effect or coughing, since large carrier particles, e.g., lactose particles, will impact the throat and upper airways due to their size.

In some aspects, the present invention involves high rugosity particles. For instance, the particles may have a rugosity of greater than 2, such as greater than 3, or greater than 4, and the rugosity may range from 2 to 15, such as 3 to 10.

In one version, the pharmaceutical composition is in dry powder form and is contained within a unit dose receptacle which may be inserted into or near the aerosolization apparatus to aerosolize the unit dose of the pharmaceutical composition. This version is useful in that the dry powder form may be stably stored in its unit dose receptacle for a long period of time. In some examples, pharmaceutical compositions of one or more embodiments of the present invention may be stable for at least 2 years. In some versions, no refrigeration is required to obtain stability. In other versions, reduced temperatures, e.g., at 2-8° C., may be used to prolong stable storage. In many versions, the storage stability allows aerosolization with an external power source.

It will be appreciated that the pharmaceutical compositions disclosed herein may comprise a structural matrix that exhibits, defines or comprises voids, pores, defects, hollows, spaces, interstitial spaces, apertures, perforations or holes. The absolute shape (as opposed to the morphology) of the perforated microstructure is generally not critical and any overall configuration that provides the desired characteristics is contemplated as being within the scope of the invention. Accordingly, some embodiments comprise approximately spherical shapes. However, collapsed, deformed or fractured particles are also compatible.

In one version, the antiarrhythmic pharmaceutical agent is incorporated in a matrix that forms a discrete particle, and the pharmaceutical composition comprises a plurality of the discrete particles. The discrete particles may be sized so that they are effectively administered and/or so that they are available where needed. For example, for an aerosolizable pharmaceutical composition, the particles are of a size that allows the particles to be aerosolized and delivered to a user's respiratory tract during the user's inhalation.

The matrix material may comprise a hydrophobic or a partially hydrophobic material. For example, the matrix material may comprise a lipid, such as a phospholipid, and/or a hydrophobic amino acid, such as leucine or trileucine. Examples of phospholipid matrices are described in WO 99/16419, WO 99/16420, WO 99/16422, WO 01/85136, and WO 01/85137 and in U.S. Pat. Nos. 5,874,064; 5,855,913; 5,985,309; 6,503,480; and 7,473,433, and in U.S. Published App. No. 20040156792, all of which are incorporated herein by reference in their entireties. Examples of hydrophobic amino acid matrices are described in U.S. Pat. Nos. 6,372,258; 6,358,530; and 7,473,433, which are incorporated herein by reference in their entireties.

When phospholipids are utilized as the matrix material, the pharmaceutical composition may also comprise a polyvalent cation, as disclosed in WO 01/85136 and WO 01/85137, which are incorporated herein by reference in their entireties.

According to another embodiment, release kinetics of the composition containing antiarrhythmic pharmaceutical agent(s) is controlled. According to one or more embodiments, the compositions of the present invention provide immediate release of the antiarrhythmic pharmaceutical agent(s). Alternatively, the compositions of other embodiments of the present invention may be provided as non-homogeneous mixtures of active agent incorporated into a matrix material and unincorporated active agent in order to provide desirable release rates of antiarrhythmic pharmaceutical agent According to this embodiment, antiarrhythmic pharmaceutical agents formulated using the emulsion-based manufacturing process of one or more embodiments of the present invention have utility in immediate release applications when administered to the respiratory tract. Rapid release is facilitated by: (a) the high specific surface area of the low density porous powders; (b) the small size of the drug crystals that are incorporated therein, and; (c) the low surface energy of the particles.

Alternatively, it may be desirable to engineer the particle matrix so that extended release of the active agent(s) is effected. This may be particularly desirable when the active agent(s) is rapidly cleared from the lungs or when sustained release is desired. For example, the nature of the phase behavior of phospholipid molecules is influenced by the nature of their chemical structure and/or preparation methods in spray-drying feedstock and drying conditions and other composition components utilized. In the case of spray-drying of active agent(s) solubilized within a small unilamellar vesicle (SUV) or multilamellar vesicle (MLV), the active agent(s) are encapsulated within multiple bilayers and are released over an extended time.

In contrast, spray-drying of a feedstock comprised of emulsion droplets and dispersed or dissolved active agent(s) in accordance with the teachings herein leads to a phospholipid matrix with less long-range order, thereby facilitating rapid release. While not being bound to any particular theory, it is believed that this is due in part to the fact that the active agent(s) are never formally encapsulated in the phospholipid, and the fact that the phospholipid is initially present on the surface of the emulsion droplets as a monolayer (not a bilayer as in the case of liposomes). The spray-dried particles prepared by the emulsion-based manufacturing process of one or more embodiments of the present invention often have a high degree of disorder. Also, the spray-dried particles typically have low surface energies, where values as low as 20 mN/m have been observed for spray-dried DSPC particles (determined by inverse gas chromatography). Small angle X-ray scattering (SAXS) studies conducted with spray-dried phospholipid particles have also shown a high degree of disorder for the lipid, with scattering peaks smeared out, and length scales extending in some instances only beyond a few nearest neighbors.

It should be noted that a matrix having a high gel to liquid crystal phase transition temperature is not sufficient in itself to achieve sustained release of the active agent(s). Having sufficient order for the bilayer structures is also important for achieving sustained release. To facilitate rapid release, an emulsion-system of high porosity (high surface area), and minimal interaction between the drug substance and phospholipid may be used. The pharmaceutical composition formation process may also include the additions of other composition components (e.g., small polymers such as Pluronic F-68; carbohydrates, salts, hydrotropes) to break the bilayer structure are also contemplated.

To achieve a sustained release, incorporation of the phospholipid in bilayer form may be used, especially if the active agent is encapsulated therein. In this case increasing the $T_m$ of the phospholipid may provide benefit via incorporation of divalent counterions or cholesterol. As well, increasing the interaction between the phospholipid and drug substance via the formation of ion-pairs (negatively charged active+steayl-amine, positively charged active+phosphatidylglycerol) would tend to decrease the dissolution rate. If the active is amphiphilic, surfactant/surfactant interactions may also slow active dissolution.

The addition of divalent counterions (e.g., calcium or magnesium ions) to long-chain saturated phosphatidylcholines results in an interaction between the negatively charged phosphate portion of the zwitterionic headgroup and the positively charged metal ion. This results in a displacement of water of hydration and a condensation of the packing of the phospholipid lipid headgroup and acyl chains. Further, this results in an increase in the Tm of the phospholipid. The decrease in headgroup hydration can have profound effects on the spreading properties of spray-dried phospholipid particles on contact with water. A fully hydrated phosphatidylcholine molecule will diffuse very slowly to a dispersed crystal via molecular diffusion through the water phase. The process is exceedingly slow because the solubility of the phospholipid in water is very low (about $10^{-10}$ mol/L for DPPC). Prior art attempts to overcome this phenomenon include homogenizing the crystals in the presence of the phospholipid. In this case, the high degree of shear and radius of curvature of the homogenized crystals facilitates coating of the phospholipid on the crystals. In contrast, "dry" phospholipid powders according to one or more embodiments of this invention can spread rapidly when contacted with an aqueous phase, thereby coating dispersed crystals without the need to apply high energies.

For example, upon reconstitution, the surface tension of spray-dried DSPC/Ca mixtures at the air/water interface decreases to equilibrium values (about 20 mN/m) as fast as a measurement can be taken. In contrast, liposomes of DSPC decrease the surface tension (about 50 mN/m) very little over a period of hours, and it is likely that this reduction is due to the presence of hydrolysis degradation products such as free fatty acids in the phospholipid. Single-tailed fatty acids can diffuse much more rapidly to the air/water interface than can the hydrophobic parent compound. Hence, the addition of calcium ions to phosphatidylcholines can facilitate the rapid encapsulation of crystalline drugs more rapidly and with lower applied energy.

In another version, the pharmaceutical composition comprises low density particles achieved by co-spray-drying nanocrystals with a perfluorocarbon-in-water emulsion. The nanocrystals may be formed by precipitation and may, e.g., range in size from about 45 m to about 80 m. Examples of perfluorocarbons include, but are not limited to, perfluorohexane, perfluorooctyl bromide, perfluorooctyl ethane, perfluorodecalin, perfluorobutyl ethane.

In accordance with the teachings herein the particles may be provided in a "dry" state. That is, in one or more embodiments, the particles will possess a moisture content that allows the powder to remain chemically and physically stable during storage at ambient or reduced temperature and remain dispersible. In this regard, there is little or no change in primary particle size, content, purity, and aerodynamic particle size distribution.

As such, the moisture content of the particles is typically less than about 10 wt %, such as less than about 6 wt %, less than about 3 wt %, or less than about 1 wt %. The moisture content is, at least in part, dictated by the composition and is controlled by the process conditions employed, e.g., inlet temperature, feed concentration, pump rate, and blowing agent type, concentration and post drying. Reduction in bound water leads to significant improvements in the dispersibility and flowability of phospholipid based powders, leading to the potential for highly efficient delivery of powdered lung surfactants or particle composition comprising active agent dispersed in the phospholipid. The improved dispersibility allows simple passive DPI devices to be used to effectively deliver these powders.

Yet another version of the pharmaceutical composition includes particle compositions that may comprise, or may be partially or completely coated with, charged species that prolong residence time at the point of contact or enhance penetration through mucosae. For example, anionic charges are known to favor mucoadhesion while cationic charges may be used to associate the formed particle with negatively charged bioactive agents such as genetic material. The charges may be imparted through the association or incorporation of polyanionic or polycationic materials such as polyacrylic acids, polylysine, polylactic acid, and chitosan.

In some versions, the pharmaceutical composition comprises particles having a mass median diameter less than about 20 m, such as less than about 10 m, less than about 7 μm, or less than about 5 μm. The particles may have a mass median aerodynamic diameter ranging from about 1 m to about 6 m, such as about 1.5 m to about 5 μm, or about 2 m to about 4 μm. If the particles are too large, a larger percentage of the particles may not reach the lungs. If the particles are too small, a larger percentage of the particles may be exhaled.

Unit doses of the pharmaceutical compositions may be placed in a container. Examples of containers include, but are not limited to, syringes, capsules, blow fill seal, blisters, vials, ampoules, or container closure systems made of metal, polymer (e.g., plastic, elastomer), glass, or the like. For instance, the vial may be a colorless Type I borosilicate glass ISO 6R 10 mL vial with a chlorobutyl rubber siliconized stopper, and rip-off type aluminum cap with colored plastic cover.

The container may be inserted into an aerosolization device. The container may be of a suitable shape, size, and material to contain the pharmaceutical composition and to provide the pharmaceutical composition in a usable condition. For example, the capsule or blister may comprise a wall which comprises a material that does not adversely react with the pharmaceutical composition. In addition, the wall may comprise a material that allows the capsule to be opened to allow the pharmaceutical composition to be aerosolized. In one version, the wall comprises one or more of gelatin, hydroxypropyl methylcellulose (HPMC), polyethyleneglycol-compounded HPMC, hydroxyproplycellulose, agar, aluminum foil, or the like. In one version, the capsule may comprise telescopically adjoining sections, as described for example in U.S. Pat. No. 4,247,066 which is incorporated herein by reference in its entirety. The size of the capsule may be selected to adequately contain the dose of the pharmaceutical composition. The sizes generally range from size 5 to size 000 with the outer diameters ranging from about 4.91 mm to 9.97 mm, the heights ranging from about 11.10 mm to about 26.14 mm, and the volumes ranging from about 0.13 mL to about 1.37 mL, respectively. Suitable capsules are available commercially from, for example, Shionogi Qualicaps Co. in Nara, Japan and Capsugel in Greenwood, S.C. After filling, a top portion may be placed over the bottom portion to form a capsule shape and to contain the powder within the capsule, as described in U.S. Pat. Nos. 4,846,876 and 6,357,490, and in WO 00/07572, which are incorporated herein by reference in their entireties. After the top portion is placed over the bottom portion, the capsule can optionally be banded.

For solutions, the amount of the composition in the unit dose typically ranges from about 0.5 ml to about 15 ml, such as about 2 ml to about 15 ml, from about 3 ml to about 10 ml, about 4 ml to about 8 ml, or about 5 ml to about 6 ml.

The compositions of the present invention may be made by any of the various methods and techniques known and available to those skilled in the art.

For instance, a solution of antiarrhythmic pharmaceutical agent may be made using the following procedure. Typically, manufacturing equipment is sterilized before use. A portion of the final volume, e.g., 70%, of solvent, e.g., water for injection, may be added into a suitable container. Antiarrhythmic pharmaceutical agent may then be added. The antiarrhythmic pharmaceutical agent may be mixed until dissolved. Additional solvent may be added to make up the final batch volume. The batch may be filtered, e.g., through a 0.2 m filter into a sterilized receiving vessel. Filling components may be sterilized before use in filling the batch into vials, e.g., 10 ml vials.

As an example, the above-noted sterilizing may include the following. A 5 liter type 1 glass bottle and lid may be placed in an autoclave bag and sterilized at elevated temperature, e.g., 121° C. for 15 minutes, using an autoclave. Similarly, vials may be placed into suitable racks, inserted into an autoclave bag, and sterilized at elevated temperature, e.g., 121° C. for 15 minutes, using an autoclave. Also similarly, stoppers may be placed in an autoclave bag and sterilized at elevated temperature, e.g., 121° C. for 15 minutes, using an autoclave. Before sterilization, sterilizing filters may be attached to tubing, e.g., a 2 mm length of 7 mm×13 mm silicone tubing. A filling line may be prepared by placed in an autoclave bag and sterilized at elevated temperature, e.g., 121° C. for 15 minutes, using an autoclave.

The above-noted filtration may involve filtration into a laminar flow work area. The receiving bottle and filters may be set up in the laminar flow work area.

The above-noted filling may also be conducted under laminar flow protection. The filling line may be unwrapped and placed into the receiving bottle. The sterilized vials and stoppers may be unwrapped under laminar flow protection. Each vial may be filled, e.g., to a target fill of 5 g, and stoppered. A flip off collar may be applied to each vial. The sealed vials may be inspected for vial leakage, correct overseals, and cracks.

In certain cases, the antiarrhythmic pharmaceutical agent may be in a solution. In particular examples, the solution is an aqueous solution. In other examples, the antiarrhythmic pharmaceutical agent can be present at a concentration from about 1 mg/mL to about 60 mg/mL, such as 1 mg/mL to 5 mg/mL, 1 mg/ml to 10 mg/mL, 1 mg/ml to 15 mg/mL, 1 mg/mL to 20 mg/mL, 1 mg/mL to 25 mg/mL, 1 mg/mL to 30 mg/mL, 1 mg/mL to 35 mg/mL, 1mg/mL to 40 mg/mL, 1 mg/mL to 45 mg/mL, 1 mg/mL to 50 mg/mL, 1 mg/mL to 55 mg/mL, 5 mg/ml to 10 mg/mL, 5 mg/ml to 15 mg/mL, 5 mg/mL to 20 mg/mL, 5 mg/mL to 25 mg/mL, 5 mg/mL to 30 mg/mL, 5 mg/mL to 35 mg/mL, 5 mg/mL to 40 mg/mL, 5 mg/mL to 45 mg/mL, 5 mg/mL to 50 mg/mL, 5 mg/mL to 55 mg/mL, 5 mg/mL to 60 mg/mL; 10 mg/ml to 15 mg/mL, 10 mg/mL to 20 mg/mL, 10 mg/mL to 25 mg/mL, 10 mg/mL to 30 mg/mL, 10 mg/mL to 35 mg/mL, 10 mg/mL to 40 mg/mL, 10 mg/mL to 45 mg/mL, 10 mg/mL to 50 mg/mL, 10 mg/mL to 55 mg/mL, 10 mg/mL to 60 mg/mL, 15 mg/mL to 20 mg/mL, 15 mg/mL to 25 mg/mL, 15 mg/mL to 30 mg/mL, 15 mg/mL to 35 mg/mL, 15 mg/mL to 40 mg/mL, 15 mg/mL to 45 mg/mL, 15 mg/mL to 50 mg/mL, 15 mg/mL to 55 mg/mL, 15 mg/mL to 60 mg/mL, 20 mg/mL to 25 mg/mL, 20 mg/mL to 30 mg/mL, 20 mg/mL to 35 mg/mL, 20 mg/mL to 40 mg/mL, 20 mg/mL to 45 mg/mL, 20 mg/mL to 50 mg/mL, 20 mg/mL to 55 mg/mL, 20 mg/mL to 60 mg/mL, 25 mg/mL to 30 mg/mL, 25 mg/mL to 35 mg/mL, 25 mg/mL to 40 mg/mL, 25 mg/mL to 45 mg/mL, 25 mg/mL to 50 mg/mL, 25 mg/mL to 55 mg/mL, 25 mg/mL to 60 mg/mL, 30 mg/mL to 35 mg/mL, 30 mg/mL to 40 mg/mL, 30 mg/mL to 45 mg/mL, 30 mg/mL to 50 mg/mL, 30 mg/mL to 55 mg/mL, 30 mg/mL to 60 mg/mL, 35 mg/mL to 40 mg/mL, 35 mg/mL to 45 mg/mL, 35 mg/mL to 50 mg/mL, 35 mg/mL to 55 mg/mL, 35 mg/mL to 60 mg/mL, 40 mg/mL to 45 mg/mL, 40 mg/mL to 50 mg/mL, 40 mg/mL to 55 mg/mL, 40 mg/mL to 60 mg/mL, 45 mg/mL to 50 mg/mL, 45 mg/mL to 55 mg/mL, 45 mg/mL to 60 mg/mL, 50 mg/mL to 55 mg/mL, 50 mg/mL to 60 mg/mL, or 55 mg/mL to 60 mg/mL. In yet other embodiments, the antiarrhythmic pharmaceutical agent is be present at about 30 mg/mL, 31 mg/mL, 32 mg/mL, 33 mg/mL, 34 mg/mL, 35 mg/mL, 36 mg/mL, 37 mg/ml, 38 mg/mL, 39 mg/mL, 40 mg/mL, 41 mg/mL, 42 mg/mL, 43 mg/mL, 44 mg/mL, 45 mg/mL, 46 mg/mL, 47 mg/mL, 48 mg/mL, 49 mg/mL, 50 mg/mL, 51 mg/mL, 52 mg/mL, 53 mg/mL, 54 mg/mL, or 55 mg/mL.

As another example, an antiarrhythmic may be prepared by lyophilizing the antiarrhythmic to form a powder for storage. The powder is then reconstituted prior to use. This technique may be used when the antiarrhythmic is unstable in solution.

In some cases, the lyophilized powder can be reconstituted in a suitable solvent such that the antiarrhythmic pharmaceutical agent is present at a concentration from about 1 mg/mL to about 60 mg/mL, such as 1 mg/mL to 5 mg/mL, 1 mg/ml to 10 mg/mL, 1 mg/ml to 15 mg/mL, 1 mg/mL to 20 mg/mL, 1 mg/mL to 25 mg/mL, 1 mg/mL to 30 mg/mL, 1 mg/mL to 35 mg/mL, 1mg/mL to 40 mg/mL, 1 mg/mL to 45 mg/mL, 1 mg/mL to 50 mg/mL, 1 mg/mL to 55 mg/mL, 5 mg/ml to 10 mg/mL, 5 mg/mL to 15 mg/mL, 5 mg/mL to 20 mg/mL, 5 mg/mL to 25 mg/mL, 5 mg/mL to 30 mg/mL, 5 mg/mL to 35 mg/mL, 5 mg/mL to 40 mg/mL, 5 mg/mL to 45 mg/mL, 5 mg/mL to 50 mg/mL, 5 mg/mL to 55 mg/mL, 5 mg/mL to 60 mg/mL; 10 mg/ml to 15 mg/mL, 10 mg/mL to 20 mg/mL, 10 mg/mL to 25 mg/mL, 10 mg/mL to 30 mg/mL, 10 mg/mL to 35 mg/mL, 10 mg/mL to 40 mg/mL, 10 mg/mL to 45 mg/mL, 10 mg/mL to 50 mg/mL, 10 mg/mL to 55 mg/mL, 10 mg/mL to 60 mg/mL, 15 mg/mL to 20 mg/mL, 15 mg/mL to 25 mg/mL, 15 mg/mL to 30 mg/mL, 15 mg/mL to 35 mg/mL, 15 mg/mL to 40 mg/mL, 15 mg/mL to 45 mg/mL, 15 mg/mL to 50 mg/mL, 15 mg/mL to 55 mg/mL, 15 mg/mL to 60 mg/mL, 20 mg/mL to 25 mg/mL, 20 mg/mL to 30 mg/mL, 20 mg/mL to 35 mg/mL, 20 mg/mL to 40 mg/mL, 20 mg/mL to 45 mg/mL, 20 mg/mL to 50 mg/mL, 20 mg/mL to 55 mg/mL, 20 mg/mL to 60 mg/mL, 25 mg/mL to 30 mg/mL, 25 mg/mL to 35 mg/mL, 25 mg/mL to 40 mg/mL, 25 mg/mL to 45 mg/mL, 25 mg/mL to 50 mg/mL, 25 mg/mL to 55 mg/mL, 25 mg/mL to 60 mg/mL, 30 mg/mL to 35 mg/mL, 30 mg/mL to 40 mg/mL, 30 mg/mL to 45 mg/mL, 30 mg/mL to 50 mg/mL, 30 mg/mL to 55 mg/mL, 30 mg/mL to 60 mg/mL, 35 mg/mL to 40 mg/mL, 35 mg/mL to 45 mg/mL, 35 mg/mL to 50 mg/mL, 35 mg/mL to 55 mg/mL, 35 mg/mL to 60 mg/mL, 40 mg/mL to 45 mg/mL, 40 mg/mL to 50 mg/mL, 40 mg/mL to 55 mg/mL, 40 mg/mL to 60 mg/mL, 45 mg/mL to 50 mg/mL, 45 mg/mL to 55 mg/mL, 45 mg/mL to 60 mg/mL, 50 mg/mL to 55 mg/mL, 50 mg/mL to 60 mg/mL, or 55 mg/mL to 60 mg/mL. In yet other embodiments, after reconstitution of a lyophilized powder the antiarrhythmic pharmaceutical agent is present at about 30 mg/mL, 31 mg/mL, 32 mg/mL, 33 mg/mL, 34 mg/mL, 35 mg/mL, 36 mg/mL, 37 mg/ml, 38 mg/mL, 39 mg/mL, 40 mg/mL, 41 mg/mL, 42 mg/mL, 43 mg/mL, 44 mg/mL, 45 mg/mL, 46 mg/mL, 47 mg/mL, 48 mg/mL, 49 mg/mL, 50 mg/mL, 51 mg/mL, 52 mg/mL, 53 mg/mL, 54 mg/mL, or 55 mg/mL.

The solvent for the solution to be lyophilized may comprise water. The solution may be excipient-free. For instance, the solution may be cryoprotectant-free.

In one or more embodiments, a suitable amount (e.g., 120 g per liter of final solution) of drug substance may be dissolved, e.g., in about the 75% of the theoretical total amount of water for injection under nitrogen bubbling. The dissolution time may be recorded and appearance may be evaluated.

Then, the dilution to the final volume with WFI may be carried out. Final volume may be checked. Density, pH, endotoxin, bioburden, and content by UV may be measured both before and after sterile filtration.

The solution may be filtered before lyophilizing. For instance, a double 0.22 µm filtration may be performed before filling. The filters may be tested for integrity and bubble point before and after the filtration.

Pre-washed and autoclaved vials may be aseptically filled using an automatic filling line to a target of 5 ml per vial and then partially stoppered. In process check for fill volumes may be done by checking the fill weight every 15 minutes.

The lyophilizing is generally conducted within about 72 hours, such as within about 8 hours, or within about 4 hours, of the dissolving.

In one or more embodiments, the lyophilizing comprises freezing the solution to form a frozen solution. The frozen solution is typically held at an initial temperature ranging from about −40° C. to about −50° C., such as about −45° C. During the initial temperature period, the pressure around the frozen solution is typically atmospheric pressure. The initial temperature period typically ranges from about 1 hour to about 4 hours, such about 1.5 hours to about 3 hours, or about 2 hours.

The lyophilizing may further comprise raising a temperature of the frozen solution to a first predetermined temperature, which may range from about 10° C. to about 20° C., such as about 15° C. The time for the heat ramp from the initial temperature to the first predetermined temperature generally ranges from about 6 hours to about 10 hours, such as about 7 hours to about 9 hours.

During the first predetermined temperature period, the pressure around the solution typically ranges from about 100 µbar to about 250 µbar, such as about 150 µbar to about 225 µbar. The solution may be held at the first predetermined temperature for a period ranging from about 20 hours to about 30 hours, such as from about 24 hours.

The lyophilizing may still further comprise raising a temperature of the solution to a second predetermined temperature, which may range from about 25° C. to about 35° C., such as about 30° C. During the second predetermined temperature period, the pressure around the frozen solution typically ranges from about 100 µbar to about 250 µbar, such as about 150 µbar to about 225 µbar. The solution may be held at the second predetermined temperature for a period ranging from about 10 hours to about 20 hours.

In view of the above, the lyophilization cycle may comprise a freezing ramp, e.g., from 20° C. to −45° C. in 65 minutes, followed by a freeze soak, e.g., at −45° C. for 2 hours. Primary drying may be accomplished with a heating ramp, e.g., from −45° C. to 15° C. in 8 hours, followed by a temperature hold, e.g., at 15° C. for 24 hours at a pressure of 200 µbar. Secondary drying may be accomplished with a heating ramp, e.g., from 15° C. to 30° C. in 15 minutes, followed by a temperature hold at 30° C. for 15 hours at a pressure of 200 µbar. At the end of the lyophilization cycle, the vacuum may be broken with sterile nitrogen, and the vials may be automatically stoppered.

The water content of the lyophilized powder is typically less than about 7 wt %, such as less than about 5 wt %, less than about 4 wt %, less than about 3 wt %, less than about 2 wt %, or less than about 1 wt %.

The powder is capable of being reconstituted with water at 25° C. and 1.0 atmosphere and with manual agitation, in less than about 60 seconds, such as less than about 30 seconds, less than about 15 seconds, or less than about 10 seconds.

The powder typically has a large specific surface area that facilitates reconstitution. The specific surface area typically ranges from about 5 $m^2/g$ to about 20 $m^2/g$, such as about 8 $m^2/g$ to 15 $m^2/g$, or about 10 $m^2/g$ to 12 $m^2/g$.

Upon reconstitution with water, the antiarrhythmic pharmaceutical agent solution typically has a pH that ranges from about 2.5 to about 7, such as about 3 to about 6.

For dry powders, the composition may be formed by spray drying, lyophilization, milling (e.g., wet milling, dry milling), and the like.

In spray drying, the preparation to be spray dried or feedstock can be any solution, coarse suspension, slurry, colloidal dispersion, or paste that may be atomized using the selected spray drying apparatus. In the case of insoluble agents, the feedstock may comprise a suspension as described above. Alternatively, a dilute solution and/or one or more solvents may be utilized in the feedstock. In one or more embodiments, the feed stock will comprise a colloidal system such as an emulsion, reverse emulsion microemulsion, multiple emulsion, particle dispersion, or slurry.

In one version, the antiarrhythmic pharmaceutical agent and the matrix material are added to an aqueous feedstock to form a feedstock solution, suspension, or emulsion. The feedstock is then spray dried to produce dried particles comprising the matrix material and the antiarrhythmic pharmaceutical agent. Suitable spray-drying processes are known in the art, for example as disclosed in WO 99/16419 and U.S. Pat. Nos. 6,077,543; 6,051,256; 6,001,336; 5,985,248; and 5,976,574, which are incorporated herein by reference in their entireties.

Whatever components are selected, the first step in particle production typically comprises feedstock preparation. If a phospholipids-based particle is intended to act as a carrier for the antiarrhythmic pharmaceutical agent, the selected active agent(s) may be introduced into a liquid, such as water, to produce a concentrated suspension. The concentration of antiarrhythmic pharmaceutical agent and optional active agents typically depends on the amount of agent required in the final powder and the performance of the delivery device employed (e.g., the fine particle dose for a metered dose inhaler (MDI) or a dry powder inhaler (DPI)).

Any additional active agent(s) may be incorporated in a single feedstock preparation and spray dried to provide a single pharmaceutical composition species comprising a plurality of active agents. Conversely, individual active agents could be added to separate stocks and spray dried separately to provide a plurality of pharmaceutical composition species with different compositions. These individual species could be added to the suspension medium or dry powder dispensing compartment in any desired proportion and placed in the aerosol delivery system as described below.

Polyvalent cation may be combined with the antiarrhythmic pharmaceutical agent suspension, combined with the phospholipid emulsion, or combined with an oil-in-water emulsion formed in a separate vessel. The antiarrhythmic pharmaceutical agent may also be dispersed directly in the emulsion.

For example, polyvalent cation and phospholipid may be homogenized in hot distilled water (e.g., 70° C.) using a suitable high shear mechanical mixer (e.g., Ultra-Turrax model T-25 mixer) at 8000 rpm for 2 to 5 min. Typically, 5 to 25 g of fluorocarbon is added dropwise to the dispersed surfactant solution while mixing. The resulting polyvalent cation-containing perfluorocarbon in water emulsion may then be processed using a high pressure homogenizer to reduce the particle size. Typically, the emulsion is processed for five discrete passes at 12,000 to 18,000 PSI and kept at about 50° C. to about 80° C.

When the polyvalent cation is combined with an oil-in-water emulsion, the dispersion stability and dispersibility of the spray dried pharmaceutical composition can be improved by using a blowing agent, as described in WO 99/16419, which is incorporated herein by reference in its entirety. This process forms an emulsion, optionally stabilized by an incorporated surfactant, typically comprising submicron droplets of water immiscible blowing agent dispersed in an aqueous continuous phase. The blowing agent may be a fluorinated compound (e.g., perfluorohexane, perfluorooctyl bromide, perfluorooctyl ethane, perfluorodecalin, perfluorobutyl ethane) which vaporizes during the spray-drying process, leaving behind generally hollow, porous aerodynamically light particles. Other suitable liquid blowing agents include nonfluorinated oils, chloroform, Freon® fluorocarbons, ethyl acetate, alcohols, hydrocarbons, nitrogen, and carbon dioxide gases. The blowing agent may be emulsified with a phospholipid.

Although the pharmaceutical compositions may be formed using a blowing agent as described above, it will be appreciated that, in some instances, no additional blowing agent is required and an aqueous dispersion of the antiarrhythmic pharmaceutical agent and/or pharmaceutically acceptable excipients and surfactant(s) are spray dried directly. In such cases, the pharmaceutical composition may possess certain physicochemical properties (e.g., high crystallinity, elevated melting temperature, surface activity, etc.) that make it particularly suitable for use in such techniques.

As needed, cosurfactants such as poloxamer 188 or span 80 may be dispersed into this annex solution. Additionally, pharmaceutically acceptable excipients such as sugars and starches can also be added.

The feedstock(s) may then be fed into a spray dryer. Typically, the feedstock is sprayed into a current of warm filtered air that evaporates the solvent and conveys the dried product to a collector. The spent air is then exhausted with the solvent. Commercial spray dryers manufactured by Buchi Ltd. or Niro Corp. may be modified for use to produce the pharmaceutical composition. Examples of spray drying methods and systems suitable for making the dry powders of one or more embodiments of the present invention are disclosed in U.S. Pat. Nos. 6,077,543; 6,051,256; 6,001,336; 5,985,248; and 5,976,574, which are incorporated herein by reference in their entireties.

Operating conditions of the spray dryer such as inlet and outlet temperature, feed rate, atomization pressure, flow rate of the drying air, and nozzle configuration can be adjusted in order to produce the required particle size, and production yield of the resulting dry particles.

The selection of appropriate apparatus and processing conditions are within the purview of a skilled artisan in view of the teachings herein and may be accomplished without undue experimentation. Exemplary settings are as follows: an air inlet temperature between about 60° C. and about 170° C.; an air outlet between about 40° C. to about 120° C.; a feed rate between about 3 mL/min to about 15 mL/min; an aspiration air flow of about 300 L/min; and an atomization air flow rate between about 25/min and about 50 L/min. The settings will, of course, vary depending on the type of equipment used. In any event, the use of these and similar methods allow formation of aerodynamically light particles with diameters appropriate for aerosol deposition into the lung.

Hollow and/or porous microstructures may be formed by spray drying, as disclosed in WO 99/16419, which is incorporated herein by reference. The spray-drying process can result in the formation of a pharmaceutical composition comprising particles having a relatively thin porous wall defining a large internal void. The spray-drying process is also often advantageous over other processes in that the particles formed are less likely to rupture during processing or during deagglomeration.

Pharmaceutical compositions useful in one or more embodiments of the present invention may alternatively be formed by lyophilization. Lyophilization is a freeze-drying process in which water is sublimed from the composition after it is frozen. The lyophilization process is often used because biologics and pharmaceuticals that are relatively unstable in an aqueous solution may be dried without exposure to elevated temperatures, and then stored in a dry state where there are fewer stability problems. With respect to one or more embodiments of the instant invention, such techniques are particularly compatible with the incorporation of peptides, proteins, genetic material and other natural and synthetic macromolecules in pharmaceutical compositions without compromising physiological activity. Lyophilized cake containing a fine foam-like structure can be micronized using techniques known in the art to provide particles of the desired size.

The compositions of one or more embodiments of the present invention may be administered by inhalation.

Moreover, the doses of composition that are inhaled are typically much less than those administered by other routes and required to obtain similar effects, due to the efficient targeting of the inhaled composition to the heart.

In one or more embodiments of the invention, a pharmaceutical composition comprising antiarrhythmic pharmaceutical agent is administered to the lungs of a patient in need thereof. For example, the patient may have been diagnosed with an arrhythmia. Examples of arrhythmias include, but are not limited to, tachycardia, supraventricular tachycardia (SVT), paroxysmal supraventricular tachycardia (PSVT), atrial fibrillation (AF), paroxysmal atrial fibrillation (PAF), persistent atrial fibrillation, permanent atrial fibrillation, atrial flutter, paroxysmal atrial flutter, and lone atrial fibrillation.

Thus, the pharmaceutical compositions of one or more embodiments of the present invention can be used to treat and/or provide prophylaxis for a broad range of patients. A suitable patient for, receiving treatment and/or prophylaxis as described herein is any mammalian patient in need thereof, preferably such mammal is a human. Examples of patients include, but are not limited to, pediatric patients, adult patients, and geriatric patients. In some embodiments, the composition is intended only as a treatment for rapid resolution of symptoms and restoration of normal sinus rhythm, and is not taken as a preventative, e.g., when the patient is well, there is no need for drug—this can increase the benefit-risk ratio of the therapy and overall safety due to the sporadic or intermittent dosing, and the focus on reducing disabling symptoms and restoring sinus rhythm only when needed.

The dosage necessary and the frequency of dosing of the antiarrhythmic pharmaceutical agent depend on the composition and concentration of the antiarrhythmic pharmaceutical agent within the composition. In some cases, the dose is less than about 10%, 20%, 30%, 40%, 50%, 60%, 70%, 80%, 90%, or 95% of its normal intravenous dose. In some cases, the dose is about 5% to about 10%, is about 10% to about 20%, is about 20% to about 30%, is about 30% to about 40%, is about 50% to about 60%, is about 60% to about 70%, is about 70% to about 80%, is about 80% to about 90%, or is about 90% to about 95% of the intravenous dose. The pulmonary dose is similar to intracardiac doses. Inhalation avoids dilution of drug in the body as compared to intravenous or oral dosing.

In some cases, the effective dosage administered intravenously can be calculated based on the weight of the subject. For example, in some cases, the effective dose administered intravenously to a subject weighing 70 kg is 2 mg/kg (i.e., 140 mg).

Inhalation also avoids metabolism, such as hepatic metabolism. For instance, calcium channel blockers, such as diltiazem, undergo significant hepatic metabolism when taken orally. Inhalation allows rapid delivery of the parent diltiazem compound to the heart as a bolus. Surprisingly, administration by inhalation of diltiazem via the inhalation route according to the present invention converted atrial fibrillation to normal sinus rhythm and reduced heart rate. Thus, administration by inhalation of diltiazem can be useful for treating both atrial fibrillation and supraventricular tachycardia (SVT). In contrast, administration by IV of diltiazem is typically only used for converting SVT to normal sinus rhythm and in atrial fibrillation to reduce heart rate (not for converting to normal sinus rhythm).

Inhalation also avoids red blood cell metabolism. For instance, the reduced dilution and short route associated with inhalation reduces red blood cell metabolism of esmolol.

Inhalation may also avoid reduced blood pressure and fainting. For instance, IV administration of beta blockers, such as esmolol, may reduce mean arterial blood pressure (MAP). Inhalation allows rapid delivery of esmolol without reducing MAP. As a result, inhalation of beta blockers may result in an MAP of 10 mm Hg to 20 mm Hg greater than the MAP resulting from IV administration of the same beta blocker.

With inhaled cardiotherapy the drug is directed to the heart from the lungs as a bolus. So, the heart sees a high concentration. The drug is rapidly diluted as it passes through the heart, but the exposure time is sufficient for the desired pharmacological action. Once the drug passes through the heart, the concentration of the drug in the systemic circulation (e.g., peripheral venous blood) is below the therapeutic concentration and is considered ineffective. The therapeutic window is the range of dosage of a drug or of its concentration in a bodily system that provides safe effective therapy. Anything below the minimum amount is sub-therapeutic and hence ineffective in that concentration. In view of the dilution, unwanted side effects are minimized.

In one version, the antiarrhythmic may be administered daily. In this version, the daily dosage of antiarrhythmic pharmaceutical agent ranges from about 0.1 mg to about 600 mg, such as about 0.5 mg to about 500 mg, about 1 mg to about 400 mg, about 2 mg to about 300 mg, and about 3 mg to about 200 mg. The amount of antiarrhythmic pharmaceutical agent for the treatment of arrhythmia can be at least about 0.1 mg, such as at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 30, 35, 40, 45, 50, 60, 70, 80, 90, 100, 110, 120, 130, 140, 150, 200, 250, 300, 350, 400, 450, or 500 mg. The amount of antiarrhythmic pharmaceutical agent for the treatment of arrhythmia can range about 0.01-500 mg, such as about 0.1-500, 0.1-450, 0.1-400, 0.1-350, 0.1-300, 0.1-250, 0.1-200, 0.1-150, 0.1-130, 0.1-110, 0.1-90, 0.1-70, 0.1-50, 0.1-30, 0.1-10, 0.1-5, 0.1-1.0, 0.1-0.5, 1-500, 1-450, 1-400, 1-350, 1-300, 1-250, 1-200, 1-150, 1-130, 1-110, 1-90, 1-70, 1-50, 1-30, 1-10, 1-5, 5-500, 5-450, 5-400, 5-350, 5-300, 5-250, 5-200, 5-150, 5-130, 5-110, 5-90, 5-70, 5-50, 5-30, 5-10, 10-500, 10-450, 10-400, 10-350, 10-300, 10-250, 10-200, 10-150, 10-130, 10-110, 10-90, 10-70, 10-50, 10-30, 30-500, 30-450, 30-400, 30-350, 30-300, 30-250, 30-200, 30-150, 30-130, 30-110, 30-90, 30-70, 30-50, 50-500, 50-450, 50-400, 50-350, 50-300, 50-250, 50-200, 50-150, 50-130, 50-110, 50-90, 50-70, 70-500, 70-450, 70-400, 70-350, 70-300, 70-250, 70-200, 70-150, 70-130, 70-110, 70-90, 90-500, 90-450, 90-400, 90-350, 90-300, 90-250, 90-200, 90-150, 90-130, 90-110, 110-500, 110-450, 110-400, 110-350, 110-300, 110-250, 110-200, 110-150, 110-130, 130-500, 130-450, 130-400, 130-350, 130-300, 130-250, 130-200, 130-150, 150-500, 150-450, 150-400, 150-350, 150-300, 150-250, 150-200, 200-500, 200-450, 200-400, 200-350, 200-300, 200-250, 250-500, 250-450, 250-400, 250-350, 250-300, 300-500, 300-450, 300-400, 300-350, 350-500, 350-450, 350-400, 400-500, 400-450, or 450-500 mg. For example, the amount of antiarrhythmic pharmaceutical agent for the treatment of arrhythmia can range about from 0.1 to about 5 mg.

The dose may be administered during a single inhalation or may be administered during several inhalations. The fluctuations of antiarrhythmic pharmaceutical agent concentration can be reduced by administering the pharmaceutical composition more often or may be increased by administering the pharmaceutical composition less often. Therefore, the pharmaceutical composition of one or more embodiments of the present invention may be administered from about four times daily to about once a month, such as about once daily to about once every two weeks, about once every two days to about once a week, and about once per week. The pharmaceutical composition can also be administered to the patient on an as-needed basis.

For treating a patient suffering from an arrhythmia, the amount per dose of antiarrhythmic pharmaceutical agent administered may be an amount that is effective to treat the arrhythmia. The amount of antiarrhythmic pharmaceutical agent for the treatment of arrhythmia will generally be higher than that used for prevention, and will typically range from about 0.001 mg/kg to 6 mg/kg, such as from about 0.002 mg/kg to about 5 mg/kg, or from about 0.005 mg/kg to about 4 mg/kg. In one exemplary treatment regimen, the formulation in accordance with one or more embodiments of the invention may be administered about 1 to about 4 times daily, such as from about 2 to about 3 times daily. Generally, the dose of antiarrhythmic pharmaceutical agent delivered to a patient will range from about 0.1 mg to about 600 mg, such as from about 0.2 mg to 500 mg daily, depending on the condition being treated, the age and weight of the patient, and the like.

In some cases, the amount of antiarrhythmic pharmaceutical agent for the treatment of arrhythmia can be at least about 0.001 mg/kg, such as at least about 0.001 mg/kg, 0.002 mg/kg, 0.003 mg/kg, 0.004 mg/kg, 0.005 mg/kg, 0.01 mg/kg, 0.02 mg/kg, 0.04 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 6 mg/kg, 7 mg/kg, 8 mg/kg, 9 mg/kg, 10 mg/kg, 15 mg/kg, or 20 mg/kg. The amount of antiarrhythmic pharmaceutical agent for the treatment of arrhythmia can range from about 0.001 mg/kg to 20 mg/kg, such as from about 0.001 mg/kg to about 0.01 mg/kg, from about 0.01 mg/kg to about 0.05 mg/kg, from about 0.05 mg/kg to about 0.1 mg/kg, from about 0.1 mg/kg to about 0.2 mg/kg, from about 0.5 mg/kg to from about 0.1 mg/kg to about 1 mg/kg, from about 0.1 mg/kg to about 2 mg/kg, from about 0.1 mg/kg to about 3 mg/kg, from about 0.3 mg/kg to about 1 mg/kg, from about 0.3 mg/kg to about 2 mg/kg, from about 0.3 mg/kg to about 3 mg/kg, from about 0.5 mg/kg to about 1 mg/kg, from about 0.5 mg/kg to about 2 mg/kg, from about 0.5 mg/kg to about 3 mg/kg, from about 0.5 mg/kg to about 6 mg/kg, from about 0.7 mg/kg to about 1 mg/kg, from about 0.7 mg/kg to about 2 mg/kg, from about 0.7 mg/kg to about 4 mg/kg, from about 0.7 mg/kg to about 6 mg/kg, from about 1 mg/kg to about 2 mg/kg, from about 1 mg/kg to about 4 mg/kg, from about 1 mg/kg to about 6 mg/kg, from about 1 mg/kg to about 8 mg/kg, from about 1 mg/kg to about 10 mg/kg, from about 1 mg/kg to about 15 mg/kg, from about 1 mg/kg to about 20 mg/kg, from about 2 mg/kg to about 3 mg/kg, from about 2 mg/kg to about 4 mg/kg, from about 2 mg/kg to about 6 mg/kg, from about 2 mg/kg to about 8 mg/kg, from about 2 mg/kg to about 10 mg/kg, from about 2 mg/kg to about 15 mg/kg, from about 2 mg/kg to about 20 mg/kg, from about 3 mg/kg to about 4 mg/kg, from about 3 mg/kg to about 5 mg/kg, from about 3 mg/kg to about 6 mg/kg, from about 3 mg/kg to about 8 mg/kg, from about 3 mg/kg to about 10 mg/kg, from about 3 mg/kg to about 15 mg/kg, from about 3 mg/kg to about 20 mg/kg, from about 4 mg/kg to about 5 mg/kg, from about 4 mg/kg to about 6 mg/kg, from about 4 mg/kg to about 8 mg/kg, from about 4 mg/kg to about 10 mg/kg, from about 4 mg/kg to about 15 mg/kg, from about 4 mg/kg to about 20 mg/kg, from about 6 mg/kg to about 8 mg/kg, from about 6 mg/kg to about 10 mg/kg, from about 6 mg/kg to about 15 mg/kg, from about 6 mg/kg to about 20 mg/kg, from about 8 mg/kg to about 10 mg/kg, from about 8 mg/kg to about 15 mg/kg, from about 8 mg/kg to about 20 mg/kg, from about 10 mg/kg to about 15 mg/kg, from about 10 mg/kg to about 20 mg/kg, or from about 15 mg/kg to about 20 mg/kg.

For instance, the present invention may involve a follow-up inhalation if no cardioversion occurs after an initial inhalation. Typically, if no cardioversion occurs within 30 minutes of the initial inhalation, the follow-up dosage is higher or the same as the initial dosage.

The dosing may be guided by how the patient feels. Also or alternatively, dosing may be guided by using a portable/mobile ECG device. For instance, the dosing may be guided by using a Holter monitor.

In another version, the pharmaceutical composition is administered prophylactically to a patient who is likely to develop an arrhythmia. For example, a patient who has a history of arrhythmias can be prophylactically treated with a pharmaceutical composition comprising antiarrhythmic pharmaceutical agent to reduce the likelihood of developing an arrhythmia.

The pharmaceutical composition may be administered to a patient in any regimen which is effective to prevent an arrhythmia. Illustrative prophylactic regimes include administering an antiarrhythmic pharmaceutical agent as described herein 1 to 21 times per week.

While not wishing to be bound by theory, by providing the antiarrhythmic pharmaceutical agent in accordance with one or more embodiments of the invention, the systemic exposure of the antiarrhythmic pharmaceutical agent can be reduced by avoiding initial dilution. As noted above, the antiarrhythmic pharmaceutical agent undergoes dilution as and after it passes through the heart. Thus, the administration via inhalation of antiarrhythmic pharmaceutical agent is believed to be safer than intravenous delivery.

In another aspect, a method of administering comprises administering to free breathing patients by way of an aerosol generator device and/or system for administration of aerosolized medicaments such as those disclosed in U.S. Published Application Nos. 20050235987, 20050211253, 20050211245, 20040035413, and 20040011358, the disclosures of which are incorporated herein by reference in their entireties.

In one version, the pharmaceutical composition may be delivered to the lungs of a patient in the form of a dry powder. Accordingly, the pharmaceutical composition comprises a dry powder that may be effectively delivered to the deep lungs or to another target site. This pharmaceutical composition is in the form of a dry powder comprising particles having a size selected to permit penetration into the alveoli of the lungs. In one version, the pharmaceutical composition may be delivered by extruding a liquid through micron or submicron-sized holes with subsequent Rayleigh break-up into fine droplets.

In some instances, it is desirable to deliver a unit dose, such as doses of 0.1 mg or 100 mg or greater of an antiarrhythmic pharmaceutical agent to the lung in a single inhalation. The above described phospholipid hollow and/or porous dry powder particles allow for doses of about 5 mg or greater, often greater than about 10 mg, sometimes greater than about 15 mg, sometimes greater than about 20 mg, sometimes greater than about 25 mg, and sometimes greater than about 30 mg, to be delivered in a single inhalation and in an advantageous manner. Alternatively, a dosage may be delivered over two or more inhalations, such as 1 to 6, 1 to 5, or 1 to 4, inhalations. For example, a 10 mg dosage may be delivered by providing two unit doses of 5 mg each, and the two unit doses may be separately inhaled. In certain embodiments, the overall dose of the antiarrhythmic pharmaceutical agent ranges from 0.1 mg to 200 mg, such as 0.5 mg to 150 mg, or 1 mg to 100 mg.

In some cases, a dosage may be delivered over two or more inhalations, such as at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 inhalations. A dosage may also be delivered over 1 to 100 inhalations, such as 1-3, 1-4, 1-5, 1-6, 1-10, 1-20, 1-50, 1-80, 1-100, 2-5, 2-6, 2-10, 2-20, 2-50, 2-100, 5-10, 5-20, 5-50, 5-100, 10-20, 10-50, 10-100, 20-50, 20-100, or 50-100 inhalations. For example, a 10 mg dosage may be delivered by providing two unit doses of 5 mg each, and the two unit doses may be separately inhaled. In certain embodiments, the overall dose of the antiarrhythmic pharmaceutical agent ranges from about 0.01-500 mg, such as about 0.1-500, 0.1-450, 0.1-400, 0.1-350, 0.1-300, 0.1-250, 0.1-200, 0.1-150, 0.1-130, 0.1-110, 0.1-90, 0.1-70, 0.1-50, 0.1-30, 0.1-10, 0.1-5, 0.1-1.0, 0.1-0.5, 1-500, 1-450, 1-400, 1-350, 1-300, 1-250, 1-200, 1-150, 1-130, 1-110, 1-90, 1-70, 1-50, 1-30, 1-10, 1-5, 5-500, 5-450, 5-400, 5-350, 5-300, 5-250, 5-200, 5-150, 5-130, 5-110, 5-90, 5-70, 5-50, 5-30, 5-10, 10-500, 10-450, 10-400, 10-350, 10-300, 10-250, 10-200, 10-150, 10-130, 10-110, 10-90, 10-70, 10-50, 10-30, 30-500, 30-450, 30-400, 30-350, 30-300, 30-250, 30-200, 30-150, 30-130, 30-110, 30-90, 30-70, 30-50, 50-500, 50-450, 50-400, 50-350, 50-300, 50-250, 50-200, 50-150, 50-130, 50-110, 50-90, 50-70, 70-500, 70-450, 70-400, 70-350, 70-300, 70-250, 70-200, 70-150, 70-130, 70-110, 70-90, 90-500, 90-450, 90-400, 90-350, 90-300, 90-250, 90-200, 90-150, 90-130, 90-110, 110-500, 110-450, 110-400, 110-350, 110-300, 110-250, 110-200, 110-150, 110-130, 130-500, 130-450, 130-400, 130-350, 130-300, 130-250, 130-200, 130-150, 150-500, 150-450, 150-400, 150-350, 150-300, 150-250, 150-200, 200-500, 200-450, 200-400, 200-350, 200-300, 200-250, 250-500, 250-450, 250-400, 250-350, 250-300, 300-500, 300-450, 300-400, 300-350, 350-500, 350-450, 350-400, 400-500, 400-450, or 450-500 mg. For example, the amount of antiarrhythmic pharmaceutical agent for the treatment of arrhythmia can range about from 0.1 to about 5 mg. In some instances the antiarrhythmic agent can be administered as-needed titrating the dosage to effect.

The time for dosing is typically short. For nebulizers the dosing time usually ranges from 1 minute to 20 minutes, such as from 2 minutes to 15 minutes, or from 3 minutes to 10 minutes. Regarding dry powders, for a single capsule, the total dosing time is normally less than about 1 minute. Thus, the time for dosing may be less than about 5 min, such as less than about 4 min, less than about 3 min, less than about 2 min, or less than about 1 min.

In certain embodiments, the present invention is directed to a method of diagnosis by a health care provider followed by treatment of atrial arrhythmia. In certain embodiments, the present invention is directed to a method of self-diagnosing and treating atrial arrhythmia. The method comprises diagnosing or self-diagnosing atrial arrhythmia by detecting at least one of shortness of breath, heart palpitations, and above normal heart rate. The method also comprises self-administering by inhalation an effective amount of at least one antiarrhythmic pharmaceutical agent within two hours, such as within one hour, 30 minutes, or within 15 minutes, of the self-diagnosing.

In certain embodiments, the patient can self-titrate. For example, the patient can self-administer, e.g., by using a nebulizer, until disabling symptoms disappear. In some cases, the self-administering continues until the patient no longer feels heart palpitations, or until the patient detects the restoration of normal sinus rhythm using a portable/mobile ECG device (which can be worn by the patient, such as a watch; or otherwise carried by the patient, such as an over the skin patch or an implantable device connected to a smart phone or watch).

The time for onset of action is also typically short. For instance, the patient may have normal sinus rhythm within 20 minutes of initiating the administering, such as within 15 minutes, within 10 minutes, or within 5 minutes of initiating the administering. The rapid onset of action is advantageous because the longer a patient has had arrhythmia, the longer it typically takes to convert the patient to normal sinus rhythm.

In some embodiments, the method of the present invention allows the patient to avoid other therapies, such as ablation and/or electrical cardioversion. In other embodiments, the method of the present invention is used in combination with other therapies, such as before or after electrical cardioversion and/or ablation therapy.

The dispersions or powder pharmaceutical compositions may be administered using an aerosolization device. The aerosolization device may be a nebulizer, a metered dose inhaler, a liquid dose instillation device, or a dry powder inhaler. The aerosolization device may comprise the extrusion of the pharmaceutical preparation through micron or submicron-sized holes with subsequent Rayleigh break-up into fine droplets. The pharmaceutical composition may be delivered by a nebulizer as described in WO 99/16420, by a metered dose inhaler as described in WO 99/16422, by a liquid dose instillation apparatus as described in WO 99/16421, and by a dry powder inhaler as described in U.S. Published Application Nos. 20020017295 and 20040105820, WO 99/16419, WO 02/83220, and U.S. Pat. No. 6,546,929, which are incorporated herein by reference in their entireties. As such, an inhaler may comprise a canister containing the particles or particles and propellant, and wherein the inhaler comprises a metering valve in communication with an interior of the canister. The propellant may be a hydrofluoroalkane.

The formulations of the present invention may be administered with nebulizers, such as that disclosed in PCT WO 99/16420, the disclosure of which is hereby incorporated in its entirety by reference, in order to provide an aerosolized medicament that may be administered to the pulmonary air passages of a patient in need thereof. Nebulizers are known in the art and could easily be employed for administration of the claimed formulations without undue experimentation. Breath activated or breath-actuated nebulizers, as well as those comprising other types of improvements which have been, or will be, developed are also compatible with the formulations of the present invention and are contemplated as being within the scope thereof.

In some cases, the nebulizer is a breath activated or breath-actuated nebulizer. In some cases, the nebulizer is a hand-held inhaler device (e.g., AeroEclipse® II Breath Actuated Nebulizer (BAN)). In some cases, the nebulizer has a compressed air source. In some cases, the nebulizer converts liquid medication into an aerosol. In some cases, the nebulizer converts liquid medication into an aerosol by extruding the pharmaceutical preparation through micron or submicron-sized holes. In some cases, the nebulizer converts liquid medication into an aerosol so it can be inhaled into the lungs. In some cases, the nebulizer is a small volume nebulizer. In some cases, the nebulizer is a small volume jet nebulizer. In some cases, aerosolized medication is only produced when inhaled through the device. In some cases, the medication is contained in the cup between breaths or during breaks in treatment. In some cases, the medication is contained in the cup until ready to be inhaled.

Nebulizers impart energy into a liquid pharmaceutical formulation to aerosolize the liquid, and to allow delivery to the pulmonary system, e.g., the lungs, of a patient. A nebulizer comprises a liquid delivery system, such as a container having a reservoir that contains a liquid pharmaceutical formulation. The liquid pharmaceutical formulation generally comprises an active agent that is either in solution or suspended within a liquid medium.

In one type of nebulizer, generally referred to as a jet nebulizer, compressed gas is forced through an orifice in the container. The compressed gas forces liquid to be withdrawn through a nozzle, and the withdrawn liquid mixes with the flowing gas to form aerosol droplets. A cloud of droplets is then administered to the patients respiratory tract.

In another type of nebulizer, generally referred to as a vibrating mesh nebulizer, energy, such as mechanical energy, vibrates a mesh. This vibration of the mesh aerosolizes the liquid pharmaceutical formulation to create an aerosol cloud that is administered to the patient's lungs. In another type of nebulizer the nebulizing comprises extrusion through micron or submicron-sized holes followed by Rayleigh break-up into fine droplets.

Alternatively or additionally, the pharmaceutical formulation may be in a liquid form and may be aerosolized using a nebulizer as described in WO 2004/071368, which is herein incorporated by reference in its entirety, as well as U.S. Published application Nos. 2004/0011358 and 2004/0035413, which are both herein incorporated by reference in their entireties. Other examples of nebulizers include, but are not limited to, the Aeroneb® Go or Aeroneb® Pro nebulizers, available from Aerogen Ltd. of Galway, Ireland; the PARI eFlow and other PARI nebulizers available from PARI Respiratory Equipment, Inc. of Midlothian, Va.; the Lumiscope® Nebulizer 6600 or 6610 available from Lumiscope Company, Inc. of East Brunswick, N.J.; and the Omron NE-U22 available from Omron Healthcare, Inc. of Kyoto, Japan. Other examples of nebulizers include devices produced by Medspray (Enschede, The Netherlands).

It has been found that a nebulizer of the vibrating mesh type, such as one that that forms droplets without the use of compressed gas, such as the Aeroneb® Pro provides unexpected improvement in dosing efficiency and consistency. By generating fine droplets by using a vibrating perforated or unperforated membrane, rather than by introducing compressed air, the aerosolized pharmaceutical formulation can be introduced without substantially affecting the flow characteristics. In addition, the generated droplets when using a nebulizer of this type are introduced at a low velocity, thereby decreasing the likelihood of the droplets being driven to an undesired region. It has been found that when using a nebulizer of the extrusion/Rayleigh jet breakup type, the generated droplets are also introduced at a low velocity, thereby decreasing the likelihood of the droplets being driven to an undesired region.

In some cases, the nebulizer can be of the vibrating mesh type. In some cases, the nebulizer can be of the pressurized jet type. In some cases, the nebulizer can be of the extrusion/Rayleigh breakup type. In some cases, the nebulizer is lightweight (at most 60 g, at most 100 g, at most 200 g, at most 250 g) and nearly silent. In some cases, the nebulizer has a sound level less than 35 A-weighted decibels (dBA) at 1 meter. In some cases, the nebulizer has a medication cup capacity of 6 mL. In some cases, the nebulizer has a residual volume of less than 0.3 mL. In some cases, the nebulizer generates an average flow rate of 0.4 mL/min. In some cases, the nebulizer generates an average flow rate of 0.5 mL/min. In some cases, the nebulizer generates an average flow rate of 0.6 mL/min. In some cases, the nebulizer generates an average flow rate of 0.7 mL/min. In some cases, the nebulizer generates an average flow rate of 0.8 mL/min. In some cases, the nebulizer generates an average flow rate of 0.9 mL/min. In some cases, the nebulizer generates an average flow rate of 1.0 mL/min. In some cases, the nebulizer generates an average flow rate of 1.1 mL/min. In some cases, the nebulizer generates an average flow rate of 1.2 mL/min. In some cases, the nebulizer generates an average particle size of 3.0 μm MMAD. In some cases, the nebulizer generates an average particle size between 3.0 μm MMAD and 4.0 μm MMAD. In some cases, the nebulizer generates an average particle size of 3.0 μm MMAD. In some cases, the nebulizer generates an average particle size between 3.0 μm MMAD and 5.0 μm MMAD. In some cases, the nebulizer generates an average particle size of 3.0 μm MMAD. In some cases, the nebulizer generates an average particle size between 3.0 μm MMAD and 6.0 μm MMAD.

In still another type of nebulizer, ultrasonic waves are generated to directly vibrate and aerosolize the pharmaceutical formulation.

As noted above, the present invention may also involve a dry powder inhaler. A specific version of a dry powder aerosolization apparatus is described in U.S. Pat. Nos. 4,069,819 and 4,995,385, which are incorporated herein by reference in their entireties. Another useful device, which has a chamber that is sized and shaped to receive a capsule so that the capsule is orthogonal to the inhalation direction, is described in U.S. Pat. No. 3,991,761, which is incorporated herein by reference in its entirety. As also described in U.S. Pat. No. 3,991,761, a puncturing mechanism may puncture both ends of the capsule. In another version, a chamber may receive a capsule in a manner where air flows through the capsule as described for example in U.S. Pat. Nos. 4,338,931 and 5,619,985, which are incorporated herein by reference in their entireties. In another version, the aerosolization of the pharmaceutical composition may be accomplished by pressurized gas flowing through the inlets, as described for example in U.S. Pat. Nos. 5,458,135; 5,785,049; and 6,257,233, or propellant, as described in WO 00/72904 and U.S. Pat. No. 4,114,615, which are incorporated herein by reference. These types of dry powder inhalers are generally referred to as active dry powder inhalers.

Other dry powder inhalers include those available from Boehringer Ingelheim (e.g., Respimat inhaler), Hovione (e.g., FlowCaps inhaler), Plastiape (e.g., Osmohaler inhaler), and MicroDose. The present invention may also utilize condensation aerosol devices, available from Alexza, Mountain View, Calif. Yet another useful inhaler is disclosed in WO 2008/051621, which is incorporated herein by reference in its entirety.

The pharmaceutical formulations disclosed herein may also be administered to the lungs of a patient via aerosolization, such as with a metered dose inhaler. The use of such formulations provides for superior dose reproducibility and improved lung deposition as disclosed in WO 99/16422, hereby incorporated in its entirety by reference. MDIs are known in the art and could easily be employed for administration of the claimed dispersions without undue experimentation.

Breath-activated or breath-actuated MDIs and pressurized MDIs (pMDIs), as well as those comprising other types of improvements which have been, or will be, developed are also compatible with the formulations of the present invention and, as such, are contemplated as being within the scope thereof.

Along with DPIs, MDIs and nebulizers, it will be appreciated that the formulations of one or more embodiments of the present invention may be used in conjunction with liquid dose installation or LDI techniques as disclosed in, for example, WO 99/16421, which is incorporated herein by reference in its entirety. Liquid dose installation involves the direct administration of a formulation to the lung. With respect to LDI the formulations are preferably used in conjunction with partial liquid ventilation or total liquid ventilation. Moreover, one or more embodiments of the present invention may further comprise introducing a therapeutically beneficial amount of a physiologically acceptable gas (such as nitric oxide or oxygen) into the pharmaceutical microdispersion prior to, during or following administration.

The pharmaceutical composition of one or more embodiments of the present invention typically has improved emitted dose efficiency. Accordingly, high doses of the pharmaceutical composition may be delivered using a variety of aerosolization devices and techniques.

The emitted dose (ED) of the particles of the present invention may be greater than about 30%, such as greater than about 40%, greater than about 50%, greater than about 60%, or greater than about 70%.

One or more embodiments are directed to kits. For instance, the kit may include an aerosolization device and a container, e.g., unit dose receptacle, containing aerosolizable antiarrhythmic pharmaceutical agent, e.g., liquid or dry powder.

The kit may further comprise a package, such as a bag, that contains the aerosolization device and the container.

In view of the above, the present invention involves methods to treat acute episodes of and/or chronic arrhythmias. In certain embodiments, the treating comprises acute treatment after detection of atrial arrhythmia.

This method of treatment results in a pulsatile pharmacokinetic profile and transient pharmacodynamic effect mimicking the effect of an IV. This method delivers high drug concentrations that are safe and effective to the heart, while the distribution to the rest of the body results in the drug being diluted to sub-therapeutic levels. This method is the shortest route of delivery to the heart next to intra-cardial injection. This provides the convenience of self-administration like the "pill-in-the-pocket" approach, but the effectiveness and fast onset of action of an IV. Although the delivery of medications through the lung for systemic effect is not new, it was thought it wouldn't be effective to the heart, because of the fast passage of drug through it. The animal and human PK/PD data in this study show that the drug exposure is sufficient for therapeutic effect at a much lower dose compared to other routes of administration. This method ensures dug concentrations in overall plasma are much lower than what is achieved by oral/IV hence minimizing drug-drug interactions and side effects.

In some cases, the $T_{max}$ of the antiarrhythmic pharmaceutical agent administered via inhalation can be from about 0.1 minute to about 30 minutes, such as 0.1-0.5, 0.1-1, 0.1-1.5, 0.1-2, 0.1-2.5, 0.1-3, 0.1-3.5, 0.1-4, 0.1-4.5, 0.1-5, 0.1-6, 0.1-8, 0.1-10, 0.1-15, 0.1-20, 0.1-25, 0.1-30, 0.2-0.5, 0.2-1, 0.2-1.5, 0.2-2, 0.2-2.5, 0.2-3, 0.2-3.5, 0.2-4, 0.2-4.5, 0.2-5, 0.2-6, 0.2-8, 0.2-10, 0.2-15, 0.2-20, 0.2-25, 0.2-30, 0.3-0.5, 0.3-1, 0.3-1.5, 0.3-2, 0.3-2.5, 0.3-3, 0.3-3.5, 0.3-4, 0.3-4.5, 0.3-5, 0.3-6, 0.3-8, 0.3-10, 0.3-15, 0.3-20, 0.3-25, 0.3-30, 0.5-1, 0.5-1.5, 0.5-2, 0.5-2.5, 0.5-3, 0.5-3.5, 0.5-4, 0.5-4.5, 0.5-5, 0.5-6, 0.5-8, 0.5-10, 0.5-15, 0.5-20, 0.5-25, 0.5-30, 1-1.5, 1-2, 1-2.5, 1-3, 1-3.5, 1-4, 1-4.5, 1-5, 1-6, 1-8, 1-10, 1-15, 1-20, 1-25, 1-30, 1.5-2, 1.5-2.5, 1.5-3, 1.5-3.5, 1.5-4, 1.5-4.5, 1.5-5, 1.5-6, 1.5-8, 1.5-10, 1.5-15, 1.5-20, 1.5-25, 1.5-30, 2-2.5, 2-3, 2-3.5, 2-4, 2-4.5, 2-5, 2-6, 2-8, 2-10, 2-15, 2-20, 2-25, 2-30, 2.5-3, 2.5-3.5, 2.5-4, 2.5-4.5, 2.5-5, 2.5-6, 2.5-8, 2.5-10, 2.5-15, 2.5-20, 2.5-25, 2.5-30, 3-3.5, 3-4, 3-4.5, 3-5, 3-6, 3-8, 3-10, 3-15, 3-20, 3-25, 3-30, 3.5-4, 3.5-4.5, 3.5-5, 3.5-6, 3.5-8, 3.5-10, 3.5-15, 3.5-20, 3.5-25, 3.5-30, 4-4.5, 4-5, 4-6, 4-8, 4-10, 4-15, 4-20, 4-25, 4-30, 4.5-5, 4.5-6, 4.5-8, 4.5-10, 4.5-15, 4.5-20, 4.5-25, 4.5-30, 5-6, 5-8, 5-10, 5-15, 5-20, 5-25, 5-30, 5.5-6, 5.5-8, 5.5-10, 5.5-15, 5.5-20, 5.5-25, 5.5-30, 6-8, 6-10, 6-15, 6-20, 6-25, 6-30, 8-10, 8-15, 8-20, 8-25, 8-30, 10-15, 10-20, 10-25, 10-30, 15-20, 15-25, 15-30, 20-25, 20-30, or 25-30 min. A range given out in the present disclosure can be a range between two accurate numerical values, in some cases, a range in the present disclosure can also refer to a range between two approximate numerical values. For instance, "1-10" can refer to "from 1 to 10" in some cases, while in other case, "1-10" can refer to "from about 1 to about 10". In some cases, the $T_{max}$ of the antiarrhythmic pharmaceutical agent administered via inhalation can be 0.01-5, 0.02-5, 0.03-5, 0.04-5, 0.05-5, 0.06-5, 0.07-5, 0.08-5, 0.09-5, 0.12-5, 0.14-5, 0.15-5, 0.16-5, 0.18-5, 0.2-5, 0.24-5, 0.26-5, 0.28-5, 0.3-5, 0.35-5, 0.4-5, 0.5-5, 0.6-5, 0.7-5, 0.8-5, 0.9-5, or 1-5 min. In some cases, the $T_{max}$ of the antiarrhythmic pharmaceutical agent administered via inhalation can be from about 0.1 to about 3 min. In some cases, the $T_{max}$ of the antiarrhythmic pharmaceutical agent administered via inhalation can be from about 0.1 to about 5 min. In some cases, the $T_{max}$ of the antiarrhythmic pharmaceutical agent (e.g., flecainide) administered via inhalation can be from about 0.2 to about 5 min. In one or more embodiments, the antiarrhythmic pharmaceutical agent is a class I, class II, class III, or class IV antiarrhythmic. In some embodiments, the antiarrhythmic pharmaceutical agent is a class Ic, antiarrhythmic. In other embodiments, the antiarrhythmic pharmaceutical agent is flecainide or a pharmaceutically acceptable salt thereof.

In some cases, the $T_{max}$ can be calculated as the amount of time at which the maximum plasma concentration of the antiarrhythmic pharmaceutical agent is observed. In some cases, the $T_{max}$ can be calculated as the amount of time after administration of the antiarrhythmic pharmaceutical agent when the maximum plasma concentration is reached. In some cases, the $T_{max}$ can be calculated as the amount of time after the initiation of the administration of the antiarrhythmic pharmaceutical agent when the maximum plasma concentration is reached. In some cases, the $T_{max}$ can be calculated as the amount of time after the completion of the administration of the antiarrhythmic pharmaceutical agent when the maximum plasma concentration is reached. In some cases, the Tax can be calculated from plasma concentration of the antiarrhythmic pharmaceutical agent measured in the left ventricular chamber. In some cases, the $T_{max}$ can be calculated from plasma concentration of the antiarrhythmic pharmaceutical agent measured in the pulmonary artery. In some cases, the $T_{max}$ can be calculated from plasma concentration of the antiarrhythmic pharmaceutical agent measured in the vein (e.g., femoral vein). In some cases, the $T_{max}$ can be measured in a human PK/PD study. The term "human PK/PD study" as used herein can refer to any settings where a human subject receives administration of a single dose of the antiarrhythmic agent as provided herein and a pharmacokinetic (PK) or pharmacodynamic (PD) parameter is measured from the human subject after the administration of the antiarrhythmic agent. In some cases, a human PK/PD study as provided herein can refer to a clinical study performed in a clinic or hospital settings. In some cases, the human PK/PD study can be a single center or multi-center study. A human PK/PD study can be performed on healthy human subjects or human cardiovascular patients. In some cases, the patients with cardiovascular disease experience arrhythmia as described herein. In some cases, a human PK/PD study can be a single-dose study, in other cases, a human PK/PD study can be a multi-dose (e.g. escalating doses) study.

In some cases, the $C_{max}$ of the antiarrhythmic pharmaceutical agent administered via inhalation can be from about 10 ng/mL to about 5000 ng/mL, such as from about 10-30, 10-50, 10-70, 10-80, 10-90, 10-100, 10-110, 10-120, 10-130, 10-140, 10-150, 10-160, 10-170, 10-180, 10-190, 10-200, 10-250, 10-300, 10-350, 10-400, 10-450, 10-500, 10-550, 10-600, 10-650, 10-700, 10-800, 10-900, 10-1000, 10-1500, 10-2000, 10-3000, 10-4000, 10-5000, 20-30, 20-50, 20-70, 20-80, 20-90, 20-100, 20-110, 20-120, 20-130, 20-140, 20-150, 20-160, 20-170, 20-180, 20-190, 20-200, 20-250, 20-300, 20-350, 20-400, 20-450, 20-500, 20-550, 20-600, 20-650, 20-700, 20-800, 20-900, 20-1000, 20-1500, 20-2000, 20-3000, 20-4000, 20-5000, 30-50, 30-70, 30-80, 30-90, 30-100, 30-110, 30-120, 30-130, 30-140, 30-150, 30-160, 30-170, 30-180, 30-190, 30-200, 30-250, 30-300, 30-350, 30-400, 30-450, 30-500, 30-550, 30-600, 30-650, 30-700, 30-800, 30-900, 30-1000, 30-1500, 30-2000, 30-3000, 30-4000, 30-5000, 50-70, 50-80, 50-90, 50-100, 50-110, 50-120, 50-130, 50-140, 50-150, 50-160, 50-170, 50-180, 50-190, 50-200, 50-250, 50-300, 50-350, 50-400, 50-450, 50-500, 50-550, 50-600, 50-650, 50-700, 50-800, 50-900, 50-1000, 50-1500, 50-2000, 50-3000, 50-4000, 50-5000, 70-80, 70-90, 70-100, 70-110, 70-120, 70-130, 70-140, 70-150, 70-160, 70-170, 70-180, 70-190, 70-200, 70-250, 70-300, 70-350, 70-400, 70-450, 70-500, 70-550, 70-600, 70-650, 70-700, 70-800, 70-900, 70-1000, 70-1500, 70-2000, 70-3000, 70-4000, 70-5000, 80-90, 80-100, 80-110, 80-120, 80-130, 80-140, 80-150, 80-160, 80-170, 80-180, 80-190, 80-200, 80-250, 80-300, 80-350, 80-400, 80-450, 80-500, 80-550, 80-600, 80-650, 80-700, 80-800, 80-900, 80-1000, 80-1500, 80-2000, 80-3000, 80-4000, 80-5000, 90-100, 90-110, 90-120, 90-130, 90-140, 90-150, 90-160, 90-170, 90-180, 90-190, 90-200, 90-250, 90-300, 90-350, 90-400, 90-450, 90-500, 90-550, 90-600, 90-650, 90-700, 90-800, 90-900, 90-1000, 90-1500, 90-2000, 90-3000, 90-4000, 90-5000, 100-110, 100-120, 100-130, 100-140, 100-150, 100-160, 100-170, 100-180, 100-190, 100-200, 100-250, 100-300, 100-350, 100-400, 100-450, 100-500, 100-550, 100-600, 100-650, 100-700, 100-800, 100-900, 100-1000, 100-1500, 100-2000, 100-3000, 100-4000, 100-5000, 110-120, 110-130, 110-140, 110-150, 110-160, 110-170, 110-180, 110-190, 110-200, 110-250, 110-300, 110-350, 110-400, 110-450, 110-500, 110-550, 110-600, 110-650, 110-700, 110-800, 110-900, 110-1000, 110-1500, 110-2000, 110-3000, 110-4000, 110-5000, 120-130, 120-140, 120-150, 120-160, 120-170, 120-180, 120-190, 120-200, 120-250, 120-300, 120-350, 120-400, 120-450, 120-500, 120-550, 120-600, 120-650, 120-700, 120-800, 120-900, 120-1000, 120-1500, 120-2000, 120-3000, 120-4000, 120-5000, 130-140, 130-150, 130-160, 130-170, 130-180, 130-190, 130-200, 130-250, 130-300, 130-350, 130-400, 130-450, 130-500, 130-550, 130-600, 130-650, 130-700, 130-800, 130-900, 130-1000, 130-1500, 130-2000, 130-3000, 130-4000, 130-5000, 140-150, 140-160, 140-170, 140-180, 140-190, 140-200, 140-250, 140-300, 140-350, 140-400, 140-450, 140-500, 140-550, 140-600, 140-650, 140-700, 140-800, 140-900, 140-1000, 140-1500, 140-2000, 140-3000, 140-4000, 140-5000, 150-160, 150-170, 150-180, 150-190, 150-200, 150-250, 150-300, 150-350, 150-400, 150-450, 150-500, 150-550, 150-600, 150-650, 150-700, 150-800, 150-900, 150-1000, 150-1500, 150-2000, 150-3000, 150-4000, 150-5000, 160-170, 160-180, 160-190, 160-200, 160-250, 160-300, 160-350, 160-400, 160-450, 160-500, 160-550, 160-600, 160-650, 160-700, 160-800, 160-900, 160-1000, 160-1500, 160-2000, 160-3000, 160-4000, 160-5000, 170-180, 170-190, 170-200, 170-250, 170-300, 170-350, 170-400, 170-450, 170-500, 170-550, 170-600, 170-650, 170-700, 170-800, 170-900, 170-1000, 170-1500, 170-2000, 170-3000, 170-4000, 170-5000, 180-190, 180-200, 180-250, 180-300, 180-350, 180-400, 180-450, 180-500, 180-550, 180-600, 180-650, 180-700, 180-800, 180-900, 180-1000, 180-1500, 180-2000, 180-3000, 180-4000, 180-5000, 190-200, 190-250, 190-300, 190-350, 190-400, 190-450, 190-500, 190-550, 190-600, 190-650, 190-700, 190-800, 190-900, 190-1000, 190-1500, 190-2000, 190-3000, 190-4000, 190-5000, 200-250, 200-300, 200-350, 200-400, 200-450, 200-500, 200-550, 200-600, 200-650, 200-700, 200-800, 200-900, 200-1000, 200-1500, 200-2000, 200-3000, 200-4000, 200-5000, 250-300, 250-350, 250-400, 250-450, 250-500, 250-550, 250-600, 250-650, 250-700, 250-800, 250-900, 250-1000, 250-1500, 250-2000, 250-3000, 250-4000, 250-5000, 300-350, 300-400, 300-450, 300-500, 300-550, 300-600, 300-650, 300-700, 300-800, 300-900, 300-1000, 300-1500, 300-2000, 300-3000, 300-4000, 300-5000, 350-400, 350-450, 350-500, 350-550, 350-600, 350-650, 350-700, 350-800, 350-900, 350-1000, 350-1500, 350-2000, 350-3000, 350-4000, 350-5000, 400-450, 400-500, 400-550, 400-600, 400-650, 400-700, 400-800, 400-900, 400-1000, 400-1500, 400-2000, 400-3000, 400-4000, 400-5000, 450-500, 450-550, 450-600, 450-650, 450-700, 450-800, 450-900, 450-1000, 450-1500, 450-2000, 450-3000, 450-4000, 450-5000, 500-550, 500-600, 500-650, 500-700, 500-800, 500-900, 500-1000, 500-1500, 500-2000, 500-3000, 500-4000, 500-5000, 550-600, 550-650, 550-700, 550-800, 550-900, 550-1000, 550-1500, 550-2000, 550-3000, 550-4000, 550-5000, 600-650, 600-700, 600-800, 600-900, 600-1000, 600-1500, 600-2000, 600-3000, 600-4000, 600-5000, 650-700, 650-800, 650-900, 650-1000, 650-1500, 650-2000, 650-3000, 650-4000, 650-5000, 700-800, 700-900, 700-1000, 700-1500, 700-2000, 700-3000, 700-4000, 700-5000, 800-900, 800-1000, 800-1500, 800-2000, 800-3000, 800-4000, 800-5000, 900-1000, 900-1500, 900-2000, 900-3000, 900-4000, 900-5000, 1000-1500, 1000-2000, 1000-3000, 1000-4000, 1000-5000, 1500-2000, 1500-3000, 1500-4000, 1500-5000, 2000-3000, 2000-4000, 2000-5000, 3000-4000, 3000-5000, or 4000-5000 ng/mL. In some cases, the $C_{max}$ of the antiarrhythmic pharmaceutical agent administered via inhalation can be from about 20 ng/mL to about 500 ng/mL, such as 20-500, 30-500, 40-500, 50-500, 60-500, 70-500, 80-500, 90-500, 100-500, 150-500, 200-500, or 250-500 ng/mL. In some cases, the $C_{max}$ of the antiarrhythmic pharmaceutical agent administered via inhalation can be from about 50 to about 500 ng/mL. In some cases, the $C_{max}$ of the antiarrhythmic pharmaceutical agent administered via inhalation can be from about 100 to about 250 ng/mL. In one or more embodiments antiarrhythmic pharmaceutical agent is a class I, class II, class III, or class IV antiarrhythmic. In some embodiments, the antiarrhythmic pharmaceutical agent is a class Ic, antiarrhythmic. In other embodiments, the antiarrhythmic pharmaceutical agent is flecainide or a pharmaceutically acceptable salt thereof.

In some cases, the $C_{max}$ can be calculated as the maximum plasma concentration of the antiarrhythmic pharmaceutical agent observed. In some cases, the $C_{max}$ can be calculated as the peak plasma concentration that the antiarrhythmic pharmaceutical agent achieves after the drug has been administrated. In some cases, the $C_{max}$ can be calculated from plasma concentration of the antiarrhythmic pharmaceutical agent measured in the left ventricular chamber. In some cases, the $C_{mx}$ can be calculated from plasma concentration of the antiarrhythmic pharmaceutical agent measured in the pulmonary artery. In some cases, the $C_{max}$ can be calculated from plasma concentration of the antiarrhythmic pharmaceutical agent measured in the vein (e.g., femoral vein). In some cases, the $C_{max}$ can be measured in a human PK/PD study.

In some cases, the $AUC_{Last}$ of the antiarrhythmic pharmaceutical agent administered via inhalation can be from about 100 hr*ng/mL to about 10000 hr*ng/mL, such as from 100-200, 100-300, 100-400, 100-420, 100-440, 100-460, 100-480, 100-500, 100-520, 100-540, 100-560, 100-580, 100-600, 100-620, 100-640, 100-660, 100-680, 100-700, 100-800, 100-900, 100-1000, 100-1500, 100-2000, 100-3000, 100-3500, 100-4000, 100-4500, 100-5000, 100-5500, 100-6000, 100-6500, 100-7000, 100-8000, 100-9000, 100-10000, 200-300, 200-400, 200-420, 200-440, 200-460, 200-480, 200-500, 200-520, 200-540, 200-560, 200-580, 200-600, 200-620, 200-640, 200-660, 200-680, 200-700, 200-800, 200-900, 200-1000, 200-1500, 200-2000, 200-3000, 200-3500, 200-4000, 200-4500, 200-5000, 200-5500, 200-6000, 200-6500, 200-7000, 200-8000, 200-9000, 200-10000, 300-400, 300-420, 300-440, 300-460, 300-480, 300-500, 300-520, 300-540, 300-560, 300-580, 300-600, 300-620, 300-640, 300-660, 300-680, 300-700, 300-800, 300-900, 300-1000, 300-1500, 300-2000, 300-3000, 300-3500, 300-4000, 300-4500, 300-5000, 300-5500, 300-6000, 300-6500, 300-7000, 300-8000, 300-9000, 300-10000, 400-420, 400-440, 400-460, 400-480, 400-500, 400-520, 400-540, 400-560, 400-580, 400-600, 400-620, 400-640, 400-660, 400-680, 400-700, 400-800, 400-900, 400-1000, 400-1500, 400-2000, 400-3000, 400-3500, 400-4000, 400-4500, 400-5000, 400-5500, 400-6000, 400-6500, 400-7000, 400-8000, 400-9000, 400-10000, 420-440, 420-460, 420-480, 420-500, 420-520, 420-540, 420-560, 420-580, 420-600, 420-620, 420-640, 420-660, 420-680, 420-700, 420-800, 420-900, 420-1000, 420-1500, 420-2000, 420-3000, 420-3500, 420-4000, 420-4500, 420-5000, 420-5500, 420-6000, 420-6500, 420-7000, 420-8000, 420-9000, 420-10000, 440-460, 440-480, 440-500, 440-520, 440-540, 440-560, 440-580, 440-600, 440-620, 440-640, 440-660, 440-680, 440-700, 440-800, 440-900, 440-1000, 440-1500, 440-2000, 440-3000, 440-3500, 440-4000, 440-4500, 440-5000, 440-5500, 440-6000, 440-6500, 440-7000, 440-8000, 440-9000, 440-10000, 460-480, 460-500, 460-520, 460-540, 460-560, 460-580, 460-600, 460-620, 460-640, 460-660, 460-680, 460-700, 460-800, 460-900, 460-1000, 460-1500, 460-2000, 460-3000, 460-3500, 460-4000, 460-4500, 460-5000, 460-5500, 460-6000, 460-6500, 460-7000, 460-8000, 460-9000, 460-10000, 480-500, 480-520, 480-540, 480-560, 480-580, 480-600, 480-620, 480-640, 480-660, 480-680, 480-700, 480-800, 480-900, 480-1000, 480-1500, 480-2000, 480-3000, 480-3500, 480-4000, 480-4500, 480-5000, 480-5500, 480-6000, 480-6500, 480-7000, 480-8000, 480-9000, 480-10000, 500-520, 500-540, 500-560, 500-580, 500-600, 500-620, 500-640, 500-660, 500-680, 500-700, 500-800, 500-900, 500-1000, 500-1500, 500-2000, 500-3000, 500-3500, 500-4000, 500-4500, 500-5000, 500-5500, 500-6000, 500-6500, 500-7000, 500-8000, 500-9000, 500-10000, 520-540, 520-560, 520-580, 520-600, 520-620, 520-640, 520-660, 520-680, 520-700, 520-800, 520-900, 520-1000, 520-1500, 520-2000, 520-3000, 520-3500, 520-4000, 520-4500, 520-5000, 520-5500, 520-6000, 520-6500, 520-7000, 520-8000, 520-9000, 520-10000, 540-560, 540-580, 540-600, 540-620, 540-640, 540-660, 540-680, 540-700, 540-800, 540-900, 540-1000, 540-1500, 540-2000, 540-3000, 540-3500, 540-4000, 540-4500, 540-5000, 540-5500, 540-6000, 540-6500, 540-7000, 540-8000, 540-9000, 540-10000, 560-580, 560-600, 560-620, 560-640, 560-660, 560-680, 560-700, 560-800, 560-900, 560-1000, 560-1500, 560-2000, 560-3000, 560-3500, 560-4000, 560-4500, 560-5000, 560-5500, 560-6000, 560-6500, 560-7000, 560-8000, 560-9000, 560-10000, 580-600, 580-620, 580-640, 580-660, 580-680, 580-700, 580-800, 580-900, 580-1000, 580-1500, 580-2000, 580-3000, 580-3500, 580-4000, 580-4500, 580-5000, 580-5500, 580-6000, 580-6500, 580-7000, 580-8000, 580-9000, 580-10000, 600-620, 600-640, 600-660, 600-680, 600-700, 600-800, 600-900, 600-1000, 600-1500, 600-2000, 600-3000, 600-3500, 600-4000, 600-4500, 600-5000, 600-5500, 600-6000, 600-6500, 600-7000, 600-8000, 600-9000, 600-10000, 620-640, 620-660, 620-680, 620-700, 620-800, 620-900, 620-1000, 620-1500, 620-2000, 620-3000, 620-3500, 620-4000, 620-4500, 620-5000, 620-5500, 620-6000, 620-6500, 620-7000, 620-8000, 620-9000, 620-10000, 640-660, 640-680, 640-700, 640-800, 640-900, 640-1000, 640-1500, 640-2000, 640-3000, 640-3500, 640-4000, 640-4500, 640-5000, 640-5500, 640-6000, 640-6500, 640-7000, 640-8000, 640-9000, 640-10000, 660-680, 660-700, 660-800, 660-900, 660-1000, 660-1500, 660-2000, 660-3000, 660-3500, 660-4000, 660-4500, 660-5000, 660-5500, 660-6000, 660-6500, 660-7000, 660-8000, 660-9000, 660-10000, 680-700, 680-800, 680-900, 680-1000, 680-1500, 680-2000, 680-3000, 680-3500, 680-4000, 680-4500, 680-5000, 680-5500, 680-6000, 680-6500, 680-7000, 680-8000, 680-9000, 680-10000, 700-800, 700-900, 700-1000, 700-1500, 700-2000, 700-3000, 700-3500, 700-4000, 700-4500, 700-5000, 700-5500, 700-6000, 700-6500, 700-7000, 700-8000, 700-9000, 700-10000, 800-900, 800-1000, 800-1500, 800-2000, 800-3000, 800-3500, 800-4000, 800-4500, 800-5000, 800-5500, 800-6000, 800-6500, 800-7000, 800-8000, 800-9000, 800-10000, 900-1000, 900-1500, 900-2000, 900-3000, 900-3500, 900-4000, 900-4500, 900-5000, 900-5500, 900-6000, 900-6500, 900-7000, 900-8000, 900-9000, 900-10000, 1000-1500, 1000-2000, 1000-3000, 1000-3500, 1000-4000, 1000-4500, 1000-5000, 1000-5500, 1000-6000, 1000-6500, 1000-7000, 1000-8000, 1000-9000, 1000-10000, 1500-2000, 1500-3000, 1500-3500, 1500-4000, 1500-4500, 1500-5000, 1500-5500, 1500-6000, 1500-6500, 1500-7000, 1500-8000, 1500-9000, 1500-10000, 2000-3000, 2000-3500, 2000-4000, 2000-4500, 2000-5000, 2000-5500, 2000-6000, 2000-6500, 2000-7000, 2000-8000, 2000-9000, 2000-10000, 2500-3000, 2500-3500, 2500-4000, 2500-4500, 2500-5000, 2500-5500, 2500-6000, 2500-6500, 2500-7000, 2500-8000, 2500-9000, 2500-10000, 3000-3500, 3000-4000, 3000-4500, 3000-5000, 3000-5500, 3000-6000, 3000-

6500, 3000-7000, 3000-8000, 3000-9000, 3000-10000, 3500-4000, 3500-4500, 3500-5000, 3500-5500, 3500-6000, 3500-6500, 3500-7000, 3500-8000, 3500-9000, 3500-10000, 4000-4500, 4000-5000, 4000-5500, 4000-6000, 4000-6500, 4000-7000, 4000-8000, 4000-9000, 4000-10000, 4500-5000, 4500-5500, 4500-6000, 4500-6500, 4500-7000, 4500-8000, 4500-9000, 4500-10000, 5000-5500, 5000-6000, 5000-6500, 5000-7000, 5000-8000, 5000-9000, 5000-10000, 5500-6000, 5500-6500, 5500-7000, 5500-8000, 5500-9000, 5500-10000, 6000-6500, 6000-7000, 6000-8000, 6000-9000, 6000-10000, 6500-7000, 6500-8000, 6500-9000, 6500-10000, 7000-8000, 7000-9000, 7000-10000, 8000-9000, 8000-10000, or 9000-10000 hr*ng/mL. In some cases, the $AUC_{Last}$ of the antiarrhythmic pharmaceutical agent administered via inhalation can be from about 200 to about 2000 hr*ng/mL. In some cases, the $AUC_{Last}$ of the antiarrhythmic pharmaceutical agent administered via inhalation can be from about 500 to about 800 hr*ng/mL. In some cases, the $AUC_{Last}$ of the antiarrhythmic pharmaceutical agent administered via inhalation can be from about 400 to about 600 hr*ng/mL. In one or more embodiments antiarrhythmic pharmaceutical agent is a class I, class II, class III, or class IV antiarrhythmic. In some embodiments, the antiarrhythmic pharmaceutical agent is a class Ic, antiarrhythmic. In other embodiments, the antiarrhythmic pharmaceutical agent is flecainide or a pharmaceutically acceptable salt thereof.

In some cases, the $AUC_{Last}$ can be calculated as the area under the concentration-time curve up to the last measurable concentration. In some cases, the $AUC_{Last}$ can be calculated as the total drug exposure over time. In some cases, the $AUC_{Last}$ can be calculated from plasma concentration of the antiarrhythmic pharmaceutical agent measured in the left ventricular chamber. In some cases, the $AUC_{Last}$ can be calculated from plasma concentration of the antiarrhythmic pharmaceutical agent measured in the pulmonary artery. In some cases, the $AUC_{Last}$ can be calculated from plasma concentration of the antiarrhythmic pharmaceutical agent measured in the vein (e.g., femoral vein). In some cases, the $AUC_{Last}$ can be measured in a human PK/PD study.

In some cases, the distribution $t_{1/2}$ of the antiarrhythmic pharmaceutical agent administered via inhalation can be from about 0.1 minute to about 15 minutes, such as from about 0.1-0.5, 0.1-1, 0.1-1.5, 0.1-2, 0.1-2.5, 0.1-2.6, 0.1-2.7, 0.1-2.8, 0.1-2.9, 0.1-3, 0.1-3.1, 0.1-3.2, 0.1-3.3, 0.1-3.4, 0.1-3.5, 0.1-3.6, 0.1-3.7, 0.1-3.8, 0.1-3.9, 0.1-4, 0.1-4.1, 0.1-4.2, 0.1-4.3, 0.1-4.4, 0.1-4.5, 0.1-5, 0.1-5.5, 0.1-6, 0.1-7, 0.1-8, 0.1-9, 0.1-10, 0.1-11, 0.1-12, 0.1-13, 0.1-14, 0.1-15, 0.5-1, 0.5-1.5, 0.5-2, 0.5-2.5, 0.5-2.6, 0.5-2.7, 0.5-2.8, 0.5-2.9, 0.5-3, 0.5-3.1, 0.5-3.2, 0.5-3.3, 0.5-3.4, 0.5-3.5, 0.5-3.6, 0.5-3.7, 0.5-3.8, 0.5-3.9, 0.5-4, 0.5-4.1, 0.5-4.2, 0.5-4.3, 0.5-4.4, 0.5-4.5, 0.5-5, 0.5-5.5, 0.5-6, 0.5-7, 0.5-8, 0.5-9, 0.5-10, 0.5-11, 0.5-12, 0.5-13, 0.5-14, 0.5-15, 1-1.5, 1-2, 1-2.5, 1-2.6, 1-2.7, 1-2.8, 1-2.9, 1-3, 1-3.1, 1-3.2, 1-3.3, 1-3.4, 1-3.5, 1-3.6, 1-3.7, 1-3.8, 1-3.9, 1-4, 1-4.1, 1-4.2, 1-4.3, 1-4.4, 1-4.5, 1-5, 1-5.5, 1-6, 1-7, 1-8, 1-9, 1-10, 1-11, 1-12, 1-13, 1-14, 1-15, 1.5-2, 1.5-2.5, 1.5-2.6, 1.5-2.7, 1.5-2.8, 1.5-2.9, 1.5-3, 1.5-3.1, 1.5-3.2, 1.5-3.3, 1.5-3.4, 1.5-3.5, 1.5-3.6, 1.5-3.7, 1.5-3.8, 1.5-3.9, 1.5-4, 1.5-4.1, 1.5-4.2, 1.5-4.3, 1.5-4.4, 1.5-4.5, 1.5-5, 1.5-5.5, 1.5-6, 1.5-7, 1.5-8, 1.5-9, 1.5-10, 1.5-11, 1.5-12, 1.5-13, 1.5-14, 1.5-15, 2-2.5, 2-2.6, 2-2.7, 2-2.8, 2-2.9, 2-3, 2-3.1, 2-3.2, 2-3.3, 2-3.4, 2-3.5, 2-3.6, 2-3.7, 2-3.8, 2-3.9, 2-4, 2-4.1, 2-4.2, 2-4.3, 2-4.4, 2-4.5, 2-5, 2-5.5, 2-6, 2-7, 2-8, 2-9, 2-10, 2-11, 2-12, 2-13, 2-14, 2-15, 2.5-2.6, 2.5-2.7, 2.5-2.8, 2.5-2.9, 2.5-3, 2.5-3.1, 2.5-3.2, 2.5-3.3, 2.5-3.4, 2.5-3.5, 2.5-3.6, 2.5-3.7, 2.5-3.8, 2.5-3.9, 2.5-4, 2.5-4.1, 2.5-4.2, 2.5-4.3, 2.5-4.4, 2.5-4.5, 2.5-5, 2.5-5.5, 2.5-6, 2.5-7, 2.5-8, 2.5-9, 2.5-10, 2.5-11, 2.5-12, 2.5-13, 2.5-14, 2.5-15, 2.6-2.7, 2.6-2.8, 2.6-2.9, 2.6-3, 2.6-3.1, 2.6-3.2, 2.6-3.3, 2.6-3.4, 2.6-3.5, 2.6-3.6, 2.6-3.7, 2.6-3.8, 2.6-3.9, 2.6-4, 2.6-4.1, 2.6-4.2, 2.6-4.3, 2.6-4.4, 2.6-4.5, 2.6-5, 2.6-5.5, 2.6-6, 2.6-7, 2.6-8, 2.6-9, 2.6-10, 2.6-11, 2.6-12, 2.6-13, 2.6-14, 2.6-15, 2.7-2.8, 2.7-2.9, 2.7-3, 2.7-3.1, 2.7-3.2, 2.7-3.3, 2.7-3.4, 2.7-3.5, 2.7-3.6, 2.7-3.7, 2.7-3.8, 2.7-3.9, 2.7-4, 2.7-4.1, 2.7-4.2, 2.7-4.3, 2.7-4.4, 2.7-4.5, 2.7-5, 2.7-5.5, 2.7-6, 2.7-7, 2.7-8, 2.7-9, 2.7-10, 2.7-11, 2.7-12, 2.7-13, 2.7-14, 2.7-15, 2.8-2.9, 2.8-3, 2.8-3.1, 2.8-3.2, 2.8-3.3, 2.8-3.4, 2.8-3.5, 2.8-3.6, 2.8-3.7, 2.8-3.8, 2.8-3.9, 2.8-4, 2.8-4.1, 2.8-4.2, 2.8-4.3, 2.8-4.4, 2.8-4.5, 2.8-5, 2.8-5.5, 2.8-6, 2.8-7, 2.8-8, 2.8-9, 2.8-10, 2.8-11, 2.8-12, 2.8-13, 2.8-14, 2.8-15, 2.9-3, 2.9-3.1, 2.9-3.2, 2.9-3.3, 2.9-3.4, 2.9-3.5, 2.9-3.6, 2.9-3.7, 2.9-3.8, 2.9-3.9, 2.9-4, 2.9-4.1, 2.9-4.2, 2.9-4.3, 2.9-4.4, 2.9-4.5, 2.9-5, 2.9-5.5, 2.9-6, 2.9-7, 2.9-8, 2.9-9, 2.9-10, 2.9-11, 2.9-12, 2.9-13, 2.9-14, 2.9-15, 3-3.1, 3-3.2, 3-3.3, 3-3.4, 3-3.5, 3-3.6, 3-3.7, 3-3.8, 3-3.9, 3-4, 3-4.1, 3-4.2, 3-4.3, 3-4.4, 3-4.5, 3-5, 3-5.5, 3-6, 3-7, 3-8, 3-9, 3-10, 3-11, 3-12, 3-13, 3-14, 3-15, 3.1-3.2, 3.1-3.3, 3.1-3.4, 3.1-3.5, 3.1-3.6, 3.1-3.7, 3.1-3.8, 3.1-3.9, 3.1-4, 3.1-4.1, 3.1-4.2, 3.1-4.3, 3.1-4.4, 3.1-4.5, 3.1-5, 3.1-5.5, 3.1-6, 3.1-7, 3.1-8, 3.1-9, 3.1-10, 3.1-11, 3.1-12, 3.1-13, 3.1-14, 3.1-15, 3.2-3.3, 3.2-3.4, 3.2-3.5, 3.2-3.6, 3.2-3.7, 3.2-3.8, 3.2-3.9, 3.2-4, 3.2-4.1, 3.2-4.2, 3.2-4.3, 3.2-4.4, 3.2-4.5, 3.2-5, 3.2-5.5, 3.2-6, 3.2-7, 3.2-8, 3.2-9, 3.2-10, 3.2-11, 3.2-12, 3.2-13, 3.2-14, 3.2-15, 3.3-3.4, 3.3-3.5, 3.3-3.6, 3.3-3.7, 3.3-3.8, 3.3-3.9, 3.3-4, 3.3-4.1, 3.3-4.2, 3.3-4.3, 3.3-4.4, 3.3-4.5, 3.3-5, 3.3-5.5, 3.3-6, 3.3-7, 3.3-8, 3.3-9, 3.3-10, 3.3-11, 3.3-12, 3.3-13, 3.3-14, 3.3-15, 3.4-3.5, 3.4-3.6, 3.4-3.7, 3.4-3.8, 3.4-3.9, 3.4-4, 3.4-4.1, 3.4-4.2, 3.4-4.3, 3.4-4.4, 3.4-4.5, 3.4-5, 3.4-5.5, 3.4-6, 3.4-7, 3.4-8, 3.4-9, 3.4-10, 3.4-11, 3.4-12, 3.4-13, 3.4-14, 3.4-15, 3.5-3.6, 3.5-3.7, 3.5-3.8, 3.5-3.9, 3.5-4, 3.5-4.1, 3.5-4.2, 3.5-4.3, 3.5-4.4, 3.5-4.5, 3.5-5, 3.5-5.5, 3.5-6, 3.5-7, 3.5-8, 3.5-9, 3.5-10, 3.5-11, 3.5-12, 3.5-13, 3.5-14, 3.5-15, 3.6-3.7, 3.6-3.8, 3.6-3.9, 3.6-4, 3.6-4.1, 3.6-4.2, 3.6-4.3, 3.6-4.4, 3.6-4.5, 3.6-5, 3.6-5.5, 3.6-6, 3.6-7, 3.6-8, 3.6-9, 3.6-10, 3.6-11, 3.6-12, 3.6-13, 3.6-14, 3.6-15, 3.7-3.8, 3.8-3.9, 3.8-4, 3.8-4.1, 3.8-4.2, 3.8-4.3, 3.8-4.4, 3.8-4.5, 3.8-5, 3.8-5.5, 3.8-6, 3.8-7, 3.8-8, 3.8-9, 3.8-10, 3.8-11, 3.8-12, 3.8-13, 3.8-14, 3.8-15, 3.9-4, 3.9-4.1, 3.9-4.2, 3.9-4.3, 3.9-4.4, 3.9-4.5, 3.9-5, 3.9-5.5, 3.9-6, 3.9-7, 3.9-8, 3.9-9, 3.9-10, 3.9-11, 3.9-12, 3.9-13, 3.9-14, 3.9-15, 4-4.1, 4-4.2, 4-4.3, 4-4.4, 4-4.5, 4-5, 4-5.5, 4-6, 4-7, 4-8, 4-9, 4-10, 4-11, 4-12, 4-13, 4-14, 4-15, 4.1-4.2, 4.1-4.3, 4.1-4.4, 4.1-4.5, 4.1-5, 4.1-5.5, 4.1-6, 4.1-7, 4.1-8, 4.1-9, 4.1-10, 4.1-11, 4.1-12, 4.1-13, 4.1-14, 4.1-15, 4.2-4.3, 4.2-4.4, 4.2-4.5, 4.2-5, 4.2-5.5, 4.2-6, 4.2-7, 4.2-8, 4.2-9, 4.2-10, 4.2-11, 4.2-12, 4.2-13, 4.2-14, 4.2-15, 4.3-4.4, 4.3-4.5, 4.3-5, 4.3-5.5, 4.3-6, 4.3-7, 4.3-8, 4.3-9, 4.3-10, 4.3-11, 4.3-12, 4.3-13, 4.3-14, 4.3-15, 4.4-4.5, 4.4-5, 4.4-5.5, 4.4-6, 4.4-7, 4.4-8, 4.4-9, 4.4-10, 4.4-11, 4.4-12, 4.4-13, 4.4-14, 4.4-15, 4.5-5, 4.5-5.5, 4.5-6, 4.5-7, 4.5-8, 4.5-9, 4.5-10, 4.5-11, 4.5-12, 4.5-13, 4.5-14, 4.5-15, 5-5.5, 5-6, 5-7, 5-8, 5-9, 5-10, 5-11, 5-12, 5-13, 5-14, 5-15, 5.5-6, 5.5-7, 5.5-8, 5.5-9, 5.5-10, 5.5-11, 5.5-12, 5.5-13, 5.5-14, 5.5-15, 6-7, 6-8, 6-9, 6-10, 6-11, 6-12, 6-13, 6-14, 6-15, 7-8, 7-9, 7-10, 7-11, 7-12, 7-13, 7-14, 7-15, 8-9, 8-10, 8-11, 8-12, 8-13, 8-14, 8-15, 9-10, 9-11, 9-12, 9-13, 9-14, 9-15, 10-11, 10-12, 10-13, 10-14, 10-15, 11-12, 11-13, 11-14, 11-15, 12-13, 12-14, 12-15, 13-14, 13-15, or 14-15 min. In some cases, the distribution $t_{1/2}$ of the antiarrhythmic pharmaceutical agent administered via inhalation can be from about 3 to about 5 minutes. In one or more embodiments antiarrhythmic pharmaceutical agent is a class I, class II, class III, or class IV antiarrhythmic. In some embodiments, the antiarrhythmic pharmaceutical agent is a class Ic, antiarrhythmic. In other embodiments, the antiarrhythmic pharmaceutical agent is flecainide or a pharmaceutically acceptable salt thereof.

In some cases, the distribution $t_{1/2}$ can be calculated as the time at which the antiarrhythmic pharmaceutical agent plasma levels decreased to half of what they were at equilibrium due to distribution to tissues throughout the body. In some cases, the distribution $t_{1/2}$ can be calculated as the time it takes for an antiarrhythmic pharmaceutical agent to lose half of its pharmacologic activity. In some cases, the distribution $t_{1/2}$ can be calculated from plasma concentration of the antiarrhythmic pharmaceutical agent measured in the left ventricular chamber. In some cases, the distribution $t_{1/2}$ can be calculated from plasma concentration of the antiarrhythmic pharmaceutical agent measured in the pulmonary artery. In some cases, the distribution $t_{1/2}$ can be calculated from plasma concentration of the antiarrhythmic pharmaceutical agent measured in the vein (e.g., femoral vein). In some cases, the distribution $t_{1/2}$ can be measured in a human PK/PD study.

In some cases, the elimination $t_{1/2}$ of the antiarrhythmic pharmaceutical agent administered via inhalation can be from about 1 hour to about 25 hours, such as from about 1-3, 1-5, 1-7, 1-7.5, 1-8, 1-8.5, 1-8.7, 1-8.9, 1-9.1, 1-9.3, 1-9.5, 1-9.7, 1-9.9, 1-10.1, 1-10.3, 1-10.5, 1-10.7, 1-10.9, 1-11.1, 1-11.3, 1-11.5, 1-11.7, 1-11.9, 1-12.1, 1-12.5, 1-13, 1-13.5, 1-14, 1-15, 1-16, 1-17, 1-18, 1-19, 1-20, 1-25, 3-5, 3-7, 3-7.5, 3-8, 3-8.5, 3-8.7, 3-8.9, 3-9.1, 3-9.3, 3-9.5, 3-9.7, 3-9.9, 3-10.1, 3-10.3, 3-10.5, 3-10.7, 3-10.9, 3-11.1, 3-11.3, 3-11.5, 3-11.7, 3-11.9, 3-12.1, 3-12.5, 3-13, 3-13.5, 3-14, 3-15, 3-16, 3-17, 3-18, 3-19, 3-20, 3-25, 5-7, 5-7.5, 5-8, 5-8.5, 5-8.7, 5-8.9, 5-9.1, 5-9.3, 5-9.5, 5-9.7, 5-9.9, 5-10.1, 5-10.3, 5-10.5, 5-10.7, 5-10.9, 5-11.1, 5-11.3, 5-11.5, 5-11.7, 5-11.9, 5-12.1, 5-12.5, 5-13, 5-13.5, 5-14, 5-15, 5-16, 5-17, 5-18, 5-19, 5-20, 5-25, 7-7.5, 7-8, 7-8.5, 7-8.7, 7-8.9, 7-9.1, 7-9.3, 7-9.5, 7-9.7, 7-9.9, 7-10.1, 7-10.3, 7-10.5, 7-10.7, 7-10.9, 7-11.1, 7-11.3, 7-11.5, 7-11.7, 7-11.9, 7-12.1, 7-12.5, 7-13, 7-13.5, 7-14, 7-15, 7-16, 7-17, 7-18, 7-19, 7-20, 7-25, 7.5-8, 7.5-8.5, 7.5-8.7, 7.5-8.9, 7.5-9.1, 7.5-9.3, 7.5-9.5, 7.5-9.7, 7.5-9.9, 7.5-10.1, 7.5-10.3, 7.5-10.5, 7.5-10.7, 7.5-10.9, 7.5-11.1, 7.5-11.3, 7.5-11.5, 7.5-11.7, 7.5-11.9, 7.5-12.1, 7.5-12.5, 7.5-13, 7.5-13.5, 7.5-14, 7.5-15, 7.5-16, 7.5-17, 7.5-18, 7.5-19, 7.5-20, 7.5-25, 8-8.5, 8-8.7, 8-8.9, 8-9.1, 8-9.3, 8-9.5, 8-9.7, 8-9.9, 8-10.1, 8-10.3, 8-10.5, 8-10.7, 8-10.9, 8-11.1, 8-11.3, 8-11.5, 8-11.7, 8-11.9, 8-12.1, 8-12.5, 8-13, 8-13.5, 8-14, 8-15, 8-16, 8-17, 8-18, 8-19, 8-20, 8-25, 8.5-8.7, 8.5-8.9, 8.5-9.1, 8.5-9.3, 8.5-9.5, 8.5-9.7, 8.5-9.9, 8.5-10.1, 8.5-10.3, 8.5-10.5, 8.5-10.7, 8.5-10.9, 8.5-11.1, 8.5-11.3, 8.5-11.5, 8.5-11.7, 8.5-11.9, 8.5-12.1, 8.5-12.5, 8.5-13, 8.5-13.5, 8.5-14, 8.5-15, 8.5-16, 8.5-17, 8.5-18, 8.5-19, 8.5-20, 8.5-25, 8.7-8.9, 8.7-9.1, 8.7-9.3, 8.7-9.5, 8.7-9.7, 8.7-9.9, 8.7-10.1, 8.7-10.3, 8.7-10.5, 8.7-10.7, 8.7-10.9, 8.7-11.1, 8.7-11.3, 8.7-11.5, 8.7-11.7, 8.7-11.9, 8.7-12.1, 8.7-12.5, 8.7-13, 8.7-13.5, 8.7-14, 8.7-15, 8.7-16, 8.7-17, 8.7-18, 8.7-19, 8.7-20, 8.7-25, 8.9-9.1, 8.9-9.3, 8.9-9.5, 8.9-9.7, 8.9-9.9, 8.9-10.1, 8.9-10.3, 8.9-10.5, 8.9-10.7, 8.9-10.9, 8.9-11.1, 8.9-11.3, 8.9-11.5, 8.9-11.7, 8.9-11.9, 8.9-12.1, 8.9-12.5, 8.9-13, 8.9-13.5, 8.9-14, 8.9-15, 8.9-16, 8.9-17, 8.9-18, 8.9-19, 8.9-20, 8.9-25, 9.1-9.3, 9.1-9.5, 9.1-9.7, 9.1-9.9, 9.1-10.1, 9.1-10.3, 9.1-10.5, 9.1-10.7, 9.1-10.9, 9.1-11.1, 9.1-11.3, 9.1-11.5, 9.1-11.7, 9.1-11.9, 9.1-12.1, 9.1-12.5, 9.1-13, 9.1-13.5, 9.1-14, 9.1-15, 9.1-16, 9.1-17, 9.1-18, 9.1-19, 9.1-20, 9.1-25, 9.3-9.5, 9.3-9.7, 9.3-9.9, 9.3-10.1, 9.3-10.3, 9.3-10.5, 9.3-10.7, 9.3-10.9, 9.3-11.1, 9.3-11.3, 9.3-11.5, 9.3-11.7, 9.3-11.9, 9.3-12.1, 9.3-12.5, 9.3-13, 9.3-13.5, 9.3-14, 9.3-15, 9.3-16, 9.3-17, 9.3-18, 9.3-19, 9.3-20, 9.3-25, 9.5-9.7, 9.5-9.9, 9.5-10.1, 9.5-10.3, 9.5-10.5, 9.5-10.7, 9.5-10.9, 9.5-11.1, 9.5-11.3, 9.5-11.5, 9.5-11.7, 9.5-11.9, 9.5-12.1, 9.5-12.5, 9.5-13, 9.5-13.5, 9.5-14, 9.5-15, 9.5-16, 9.5-17, 9.5-18, 9.5-19, 9.5-20, 9.5-25, 9.7-9.9, 9.7-10.1, 9.7-10.3, 9.7-10.5, 9.7-10.7, 9.7-10.9, 9.7-11.1, 9.7-11.3, 9.7-11.5, 9.7-11.7, 9.7-11.9, 9.7-12.1, 9.7-12.5, 9.7-13, 9.7-13.5, 9.7-14, 9.7-15, 9.7-16, 9.7-17, 9.7-18, 9.7-19, 9.7-20, 9.7-25, 9.9-10.1, 9.9-10.3, 9.9-10.5, 9.9-10.7, 9.9-10.9, 9.9-11.1, 9.9-11.3, 9.9-11.5, 9.9-11.7, 9.9-11.9, 9.9-12.1, 9.9-12.5, 9.9-13, 9.9-13.5, 9.9-14, 9.9-15, 9.9-16, 9.9-17, 9.9-18, 9.9-19, 9.9-20, 9.9-25, 10.1-10.3, 10.1-10.5, 10.1-10.7, 10.1-10.9, 10.1-11.1, 10.1-11.3, 10.1-11.5, 10.1-11.7, 10.1-11.9, 10.1-12.1, 10.1-12.5, 10.1-13, 10.1-13.5, 10.1-14, 10.1-15, 10.1-16, 10.1-17, 10.1-18, 10.1-19, 10.1-20, 10.1-25, 10.3-10.5, 10.3-10.7, 10.3-10.9, 10.3-11.1, 10.3-11.3, 10.3-11.5, 10.3-11.7, 10.3-11.9, 10.3-12.1, 10.3-12.5, 10.3-13, 10.3-13.5, 10.3-14, 10.3-15, 10.3-16, 10.3-17, 10.3-18, 10.3-19, 10.3-20, 10.3-25, 10.5-10.7, 10.5-10.9, 10.5-11.1, 10.5-11.3, 10.5-11.5, 10.5-11.7, 10.5-11.9, 10.5-12.1, 10.5-12.5, 10.5-13, 10.5-13.5, 10.5-14, 10.5-15, 10.5-16, 10.5-17, 10.5-18, 10.5-19, 10.5-20, 10.5-25, 10.7-10.9, 10.7-11.1, 10.7-11.3, 10.7-11.5, 10.7-11.7, 10.7-11.9, 10.7-12.1, 10.7-12.5, 10.7-13, 10.7-13.5, 10.7-14, 10.7-15, 10.7-16, 10.7-17, 10.7-18, 10.7-19, 10.7-20, 10.7-25, 10.9-11.1, 10.9-11.3, 10.9-11.5, 10.9-11.7, 10.9-11.9, 10.9-12.1, 10.9-12.5, 10.9-13, 10.9-13.5, 10.9-14, 10.9-15, 10.9-16, 10.9-17, 10.9-18, 10.9-19, 10.9-20, 10.9-25, 11.1-11.3, 11.1-11.5, 11.1-11.7, 11.1-11.9, 11.1-12.1, 11.1-12.5, 11.1-13, 11.1-13.5, 11.1-14, 11.1-15, 11.1-16, 11.1-17, 11.1-18, 11.1-19, 11.1-20, 11.1-25, 11.3-11.5, 11.3-11.7, 11.3-11.9, 11.3-12.1, 11.3-12.5, 11.3-13, 11.3-13.5, 11.3-14, 11.3-15, 11.3-16, 11.3-17, 11.3-18, 11.3-19, 11.3-20, 11.3-25, 11.5-11.7, 11.5-11.9, 11.5-12.1, 11.5-12.5, 11.5-13, 11.5-13.5, 11.5-14, 11.5-15, 11.5-16, 11.5-17, 11.5-18, 11.5-19, 11.5-20, 11.5-25, 11.7-11.9, 11.7-12.1, 11.7-12.5, 11.7-13, 11.7-13.5, 11.7-14, 11.7-15, 11.7-16, 11.7-17, 11.7-18, 11.7-19, 11.7-20, 11.7-25, 11.9-12.1, 11.9-12.5, 11.9-13, 11.9-13.5, 11.9-14, 11.9-15, 11.9-16, 11.9-17, 11.9-18, 11.9-19, 11.9-20, 11.9-25, 12.1-12.5, 12.1-13, 12.1-13.5, 12.1-14, 12.1-15, 12.1-16, 12.1-17, 12.1-18, 12.1-19, 12.1-20, 12.1-25, 12.5-13, 12.5-13.5, 12.5-14, 12.5-15, 12.5-16, 12.5-17, 12.5-18, 12.5-19, 12.5-20, 12.5-25, 13-13.5, 13-14, 13-15, 13-16, 13-17, 13-18, 13-19, 13-20, 13-25, 13.5-14, 13.5-15, 13.5-16, 13.5-17, 13.5-18, 13.5-19, 13.5-20, 13.5-25, 14-15, 14-16, 14-17, 14-18, 14-19, 14-20, 14-25, 15-16, 15-17, 15-18, 15-19, 15-20, 15-25, 16-17, 16-18, 16-19, 16-20, 16-25, 17-18, 17-19, 17-20, 17-25, 18-19, 18-20, 18-25, 19-20, 19-25, or 20-25 hours. In some cases, the elimination $t_{1/2}$ of the antiarrhythmic pharmaceutical agent administered via inhalation can be from about 8.5 to about 10.5 hours. In one or more embodiments antiarrhythmic pharmaceutical agent is a class I, class II, class III, or class IV antiarrhythmic. In some embodiments, the antiarrhythmic pharmaceutical agent is a class Ic, antiarrhythmic. In other embodiments, the antiarrhythmic pharmaceutical agent is flecainide or a pharmaceutically acceptable salt thereof.

In some cases, the elimination $t_{1/2}$ can be calculated as the time at which the antiarrhythmic pharmaceutical agent plasma levels decreased to half of what they were at equilibrium due to metabolism and elimination. In some cases, the elimination $t_{1/2}$ can be calculated from plasma concentration of the antiarrhythmic pharmaceutical agent measured in the left ventricular chamber. In some cases, the elimination $t_{1/2}$ can be calculated from plasma concentration of the antiarrhythmic pharmaceutical agent measured in the pulmonary artery. In some cases, the elimination $t_{1/2}$ can be calculated from plasma concentration of the antiarrhythmic pharmaceutical agent measured in the vein (e.g., femoral vein). In some cases, the elimination $t_{1/2}$ can be measured in a human PK/PD study.

In some cases, the maximum change in QRS interval duration (ΔQRS) following the antiarrhythmic pharmaceutical agent administered via inhalation can be from about 0.01 msec to about 100 msec, such as from about 0.01-0.1, 0.01-0.5, 0.01-1, 0.01-1.5, 0.01-2, 0.01-2.5, 0.01-3, 0.01-3.5, 0.01-4, 0.01-4.5, 0.01-5, 0.01-5.5, 0.01-6, 0.01-8, 0.01-10, 0.01-15, 0.01-20, 0.01-25, 0.01-30, 0.01-40, 0.01-50, 0.01-60, 0.01-70, 0.01-80, 0.01-90, 0.01-100, 0.1-0.5, 0.1-1, 0.1-1.5, 0.1-2, 0.1-2.5, 0.1-3, 0.1-3.5, 0.1-4, 0.1-4.5, 0.1-5, 0.1-5.5, 0.1-6, 0.1-8, 0.1-10, 0.1-15, 0.1-20, 0.1-25, 0.1-30, 0.1-40, 0.1-50, 0.1-60, 0.1-70, 0.1-80, 0.1-90, 0.1-100, 0.5-1, 0.5-1.5, 0.5-2, 0.5-2.5, 0.5-3, 0.5-3.5, 0.5-4, 0.5-4.5, 0.5-5, 0.5-5.5, 0.5-6, 0.5-8, 0.5-10, 0.5-15, 0.5-20, 0.5-25, 0.5-30, 0.5-40, 0.5-50, 0.5-60, 0.5-70, 0.5-80, 0.5-90, 0.5-100, 1-1.5, 1-2, 1-2.5, 1-3, 1-3.5, 1-4, 1-4.5, 1-5, 1-5.5, 1-6, 1-8, 1-10, 1-15, 1-20, 1-25, 1-30, 1-40, 1-50, 1-60, 1-70, 1-80, 1-90, 1-100, 1.5-2, 1.5-2.5, 1.5-3, 1.5-3.5, 1.5-4, 1.5-4.5, 1.5-5, 1.5-5.5, 1.5-6, 1.5-8, 1.5-10, 1.5-15, 1.5-20, 1.5-25, 1.5-30, 1.5-40, 1.5-50, 1.5-60, 1.5-70, 1.5-80, 1.5-90, 1.5-100, 2-2.5, 2-3, 2-3.5, 2-4, 2-4.5, 2-5, 2-5.5, 2-6, 2-8, 2-10, 2-15, 2-20, 2-25, 2-30, 2-40, 2-50, 2-60, 2-70, 2-80, 2-90, 2-100, 2.5-3, 2.5-3.5, 2.5-4, 2.5-4.5, 2.5-5, 2.5-5.5, 2.5-6, 2.5-8, 2.5-10, 2.5-15, 2.5-20, 2.5-25, 2.5-30, 2.5-40, 2.5-50, 2.5-60, 2.5-70, 2.5-80, 2.5-90, 2.5-100, 3-3.5, 3-4, 3-4.5, 3-5, 3-5.5, 3-6, 3-8, 3-10, 3-15, 3-20, 3-25, 3-30, 3-40, 3-50, 3-60, 3-70, 3-80, 3-90, 3-100, 3.5-4, 3.5-4.5, 3.5-5, 3.5-5.5, 3.5-6, 3.5-8, 3.5-10, 3.5-15, 3.5-3.20, 3.5-3.25, 3.5-3.30, 3.5-40, 3.5-50, 3.5-60, 3.5-70, 3.5-80, 3.5-90, 3.5-100, 4-4.5, 4-5, 4-5.5, 4-6, 4-8, 4-10, 4-15, 4-20, 4-25, 4-30, 4-40, 4-50, 4-60, 4-70, 4-80, 4-90, 4-100, 4.5-5, 4.5-5.5, 4.5-6, 4.5-8, 4.5-10, 4.5-15, 4.5-20, 4.5-25, 4.5-30, 4.5-4.50, 4.5-50, 4.5-60, 4.5-70, 4.5-80, 4.5-90, 4.5-100, 5-5.5, 5-6, 5-8, 5-10, 5-15, 5-20, 5-25, 5-30, 5-40, 5-50, 5-60, 5-70, 5-80, 5-90, 5-100, 5.5-6, 5.5-8, 5.5-10, 5.5-15, 5.5-20, 5.5-25, 5.5-30, 5.5-40, 5.5-50, 5.5-60, 5.5-70, 5.5-80, 5.5-90, 5.5-100, 6-8, 6-10, 6-15, 6-20, 6-25, 6-30, 6-40, 6-50, 6-60, 6-70, 6-80, 6-90, 6-100, 8-10, 8-15, 8-20, 8-25, 8-30, 8-40, 8-50, 8-60, 8-70, 8-80, 8-90, 8-100, 10-15, 10-20, 10-25, 10-30, 10-40, 10-50, 10-60, 10-70, 10-80, 10-90, 10-100, 15-20, 15-25, 15-30, 15-40, 15-50, 15-60, 15-70, 15-80, 15-90, 15-100, 20-25, 20-30, 20-40, 20-50, 20-60, 20-70, 20-80, 20-90, 20-100, 25-30, 25-40, 25-50, 25-60, 25-70, 25-80, 25-90, 25-100, 30-40, 30-50, 30-60, 30-70, 30-80, 30-90, 30-100, 40-50, 40-60, 40-70, 40-80, 40-90, 40-100, 50-60, 50-70, 50-80, 50-90, 50-100, 60-70, 60-80, 60-90, 60-100, 70-80, 70-90, 70-100, 80-90, 80-100, or 90-100 msec. In some cases, the maximum change in QRS interval duration (ΔQRS) following the antiarrhythmic pharmaceutical agent administered via inhalation can be from about 1 to about 10 msec. In some cases, the maximum change in QRS interval duration (ΔQRS) following the antiarrhythmic pharmaceutical agent administered via inhalation can be from about 5 to about 20 msec. In some cases, the ΔQRS can be measured in a human PK/PD study. In the present disclosure, the term "ΔQRS", if not referred to with reference to time post-administration of the antiarrhythmic agent, can be used interchangeably with the term "maximum ΔQRS", e.g. meaning the maximum change in QRS following administration of the antiarrhythmic agent as provided herein. In one or more embodiments antiarrhythmic pharmaceutical agent is a class I, class II, class III, or class IV antiarrhythmic. In some embodiments, the antiarrhythmic pharmaceutical agent is a class Ic, antiarrhythmic. In other embodiments, the antiarrhythmic pharmaceutical agent is flecainide or a pharmaceutically acceptable salt thereof.

In some cases, the time point at which the QRS interval is measured following the antiarrhythmic pharmaceutical agent administration via inhalation to determine the ΔQRS relative to pre-dose can be from about 0.1 minute to about 450 minutes, such as from about 0.1-1, 0.1-3, 0.1-5, 0.1-10, 0.1-15, 0.1-30, 0.1-45, 0.1-60, 0.1-90, 0.1-120, 0.1-150, 0.1-180, 0.1-210, 0.1-240, 0.1-270, 0.1-300, 0.1-330, 0.1-360, 0.1-390, 0.1-410, 0.1-450, 1-3, 1-5, 1-10, 1-15, 1-30, 1-45, 1-60, 1-90, 1-120, 1-150, 1-180, 1-210, 1-240, 1-270, 1-300, 1-330, 1-360, 1-390, 1-410, 1-450, 3-5, 3-10, 3-15, 3-30, 3-45, 3-60, 3-90, 3-120, 3-150, 3-180, 3-210, 3-240, 3-270, 3-300, 3-330, 3-360, 3-390, 3-410, 3-450, 5-10, 5-15, 5-30, 5-45, 5-60, 5-90, 5-120, 5-150, 5-180, 5-210, 5-240, 5-270, 5-300, 5-330, 5-360, 5-390, 5-410, 5-450, 10-15, 10-30, 10-45, 10-60, 10-90, 10-120, 10-150, 10-180, 10-210, 10-240, 10-270, 10-300, 10-330, 10-360, 10-390, 10-410, 10-450, 15-30, 15-45, 15-60, 15-90, 15-120, 15-150, 15-180, 15-210, 15-240, 15-270, 15-300, 15-330, 15-360, 15-390, 15-410, 15-450, 30-45, 30-60, 30-90, 30-120, 30-150, 30-180, 30-210, 30-240, 30-270, 30-300, 30-330, 30-360, 30-390, 30-410, 30-450, 45-60, 45-90, 45-120, 45-150, 45-180, 45-210, 45-240, 45-270, 45-300, 45-330, 45-360, 45-390, 45-410, 45-450, 60-90, 60-120, 60-150, 60-180, 60-210, 60-240, 60-270, 60-300, 60-330, 60-360, 60-390, 60-410, 60-450, 90-120, 90-150, 90-180, 90-210, 90-240, 90-270, 90-300, 90-330, 90-360, 90-390, 90-410, 90-450, 120-150, 120-180, 120-210, 120-240, 120-270, 120-300, 120-330, 120-360, 120-390, 120-410, 120-450, 150-180, 150-210, 150-240, 150-270, 150-300, 150-330, 150-360, 150-390, 150-410, 150-450, 180-210, 180-240, 180-270, 180-300, 180-330, 180-360, 180-390, 180-410, 180-450, 210-240, 210-270, 210-300, 210-330, 210-360, 210-390, 210-410, 210-450, 240-270, 240-300, 240-330, 240-360, 240-390, 240-410, 240-450, 270-300, 270-330, 270-360, 270-390, 270-410, 270-450, 300-330, 300-360, 300-390, 300-410, 300-450, 330-360, 330-390, 330-410, 330-450, 360-390, 360-410, 360-450, 390-410, 390-450, or 410-450 min.

The antiarrhythmic activity of pharmaceutical agent can be correlated with QRS interval duration. In some examples, the antiarrhythmic pharmaceutical agent administered via inhalation can have higher antiarrhythmic activity as compared to the antiarrhythmic pharmaceutical agent administered by intravenous delivery (e.g., intravenous infusion). In some cases, such a higher antiarrhythmic activity is reflected by a higher ratio of maximum ΔQRS to $C_{max}$. For example, given the same $C_{max}$, e.g., peak plasma concentration of the antiarrhythmic pharmaceutic agent, inhalation delivery of the antiarrhythmic agent as provided herein can have a higher maximum ΔQRS as compared to intravenous delivery of the same agent. In some cases, the comparison may not be made between corresponding doses via the two different administration routes, for example, inhalation of a first dose of the agent can have a first $C_{max}$($C_{max1}$) and a first maximum ΔQRS (ΔQRS$_{max1}$), and intravenous administration of a second dose of the agent can have a second $C_{max}$ ($C_{max2}$) and a second maximum ΔQRS (ΔQRS$_{max2}$). In some cases, $C_{max1}$ and $C_{max2}$ can be similar. In other case, $C_{max1}$ and $C_{max2}$ can be dissimilar. In some examples of the present disclosure, the ratio of ΔQRS$_{max1}$ versus $C_{max}$ can be higher than ΔQRS$_{max2}$ versus $C_{max2}$, i.e., ΔQRS$_{max1}$/$C_{max1}$>ΔQRS$_{max2}$/$C_{max2}$. In some cases, ΔQRS$_{max1}$/$C_{max1}$ is at least 1.1 folds, at least 1.2 folds, at least 1.3 folds, at least 1.4 folds, at least 1.5 folds, at least 1.6 folds, at least 1.7 folds, at least 1.8 folds, at least 1.9 folds, at least 2.0 folds, at least 2.1 folds, at least 2.2 folds, at least 2.3 folds, at least 2.4 folds, at least 2.5 folds, at least 2.6 folds, at least 2.7 folds, at least 2.8 folds, at least 2.9 folds, at least 3.0 folds, at least 3.1 folds, at least 3.2 folds, at least 3.3 folds, at least 3.4 folds, at least 3.5 folds, at least 3.6 folds, at least 3.7 folds, at least 3.8 folds, at least 3.9 folds, at least 4.0 folds, at least 4.2 folds, at least 4.4 folds, at least 4.6 folds, at least 4.8 folds, at least 5.0 folds, at least 5.5 folds, at least 6 folds, at least 7 folds, at least 8 folds, at least 9 folds, at least 10 folds, at least 12 folds, at least 15 folds, at least 20 folds, at least 25 folds, or at least 50 folds greater than $\Delta QRS_{max2}/C_{max2}$. In some cases, $\Delta QRS_{max1}/C_{max1}$ is at least 2 folds greater than $\Delta QRS_{max2}/C_{max2}$. In one or more embodiments antiarrhythmic pharmaceutical agent is a class I, class II, class III, or class IV antiarrhythmic. In some embodiments, the antiarrhythmic pharmaceutical agent is a class Ic, antiarrhythmic. In other embodiments, the antiarrhythmic pharmaceutical agent is flecainide or a pharmaceutically acceptable salt thereof.

The present invention will be further illustrated by way of the following Examples. These examples are non-limiting and do not restrict the scope of the invention. Unless stated otherwise, all percentages, parts, etc. presented in the examples are by weight.

EXAMPLES

Example 1

Prophetic Analytical Model Involving Verapamil and Lidocaine

Figure 4:
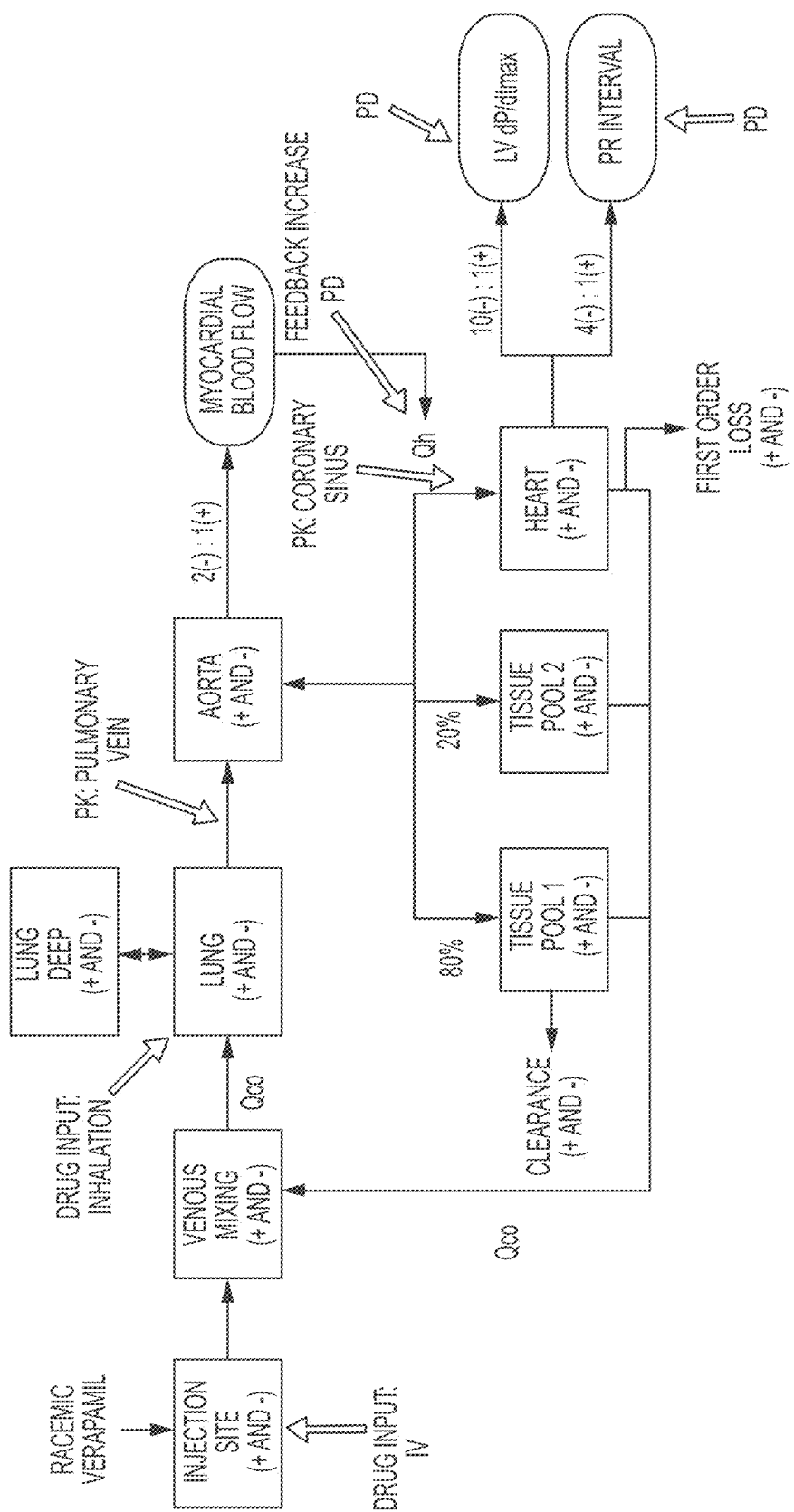
FIG. 4 shows a six compartment PK-PD model to compare intravenous and pulmonary delivery.

Published pharmacokinetic and pharmacodynamic models (FIG. 4) show relationships between drug concentration in coronary blood and desired coronary effect. IV drug information was used from published literature. HARRISON et al., "Effect of Single Doses of Inhaled Lignocaine on FEV1 and Bronchial Reactivity in Asthma," Respir Med., 12:1359-635 (December 1992). Inhaled drug information was simulated based on known properties of pulmonary small molecule absorption.

Figure 5:
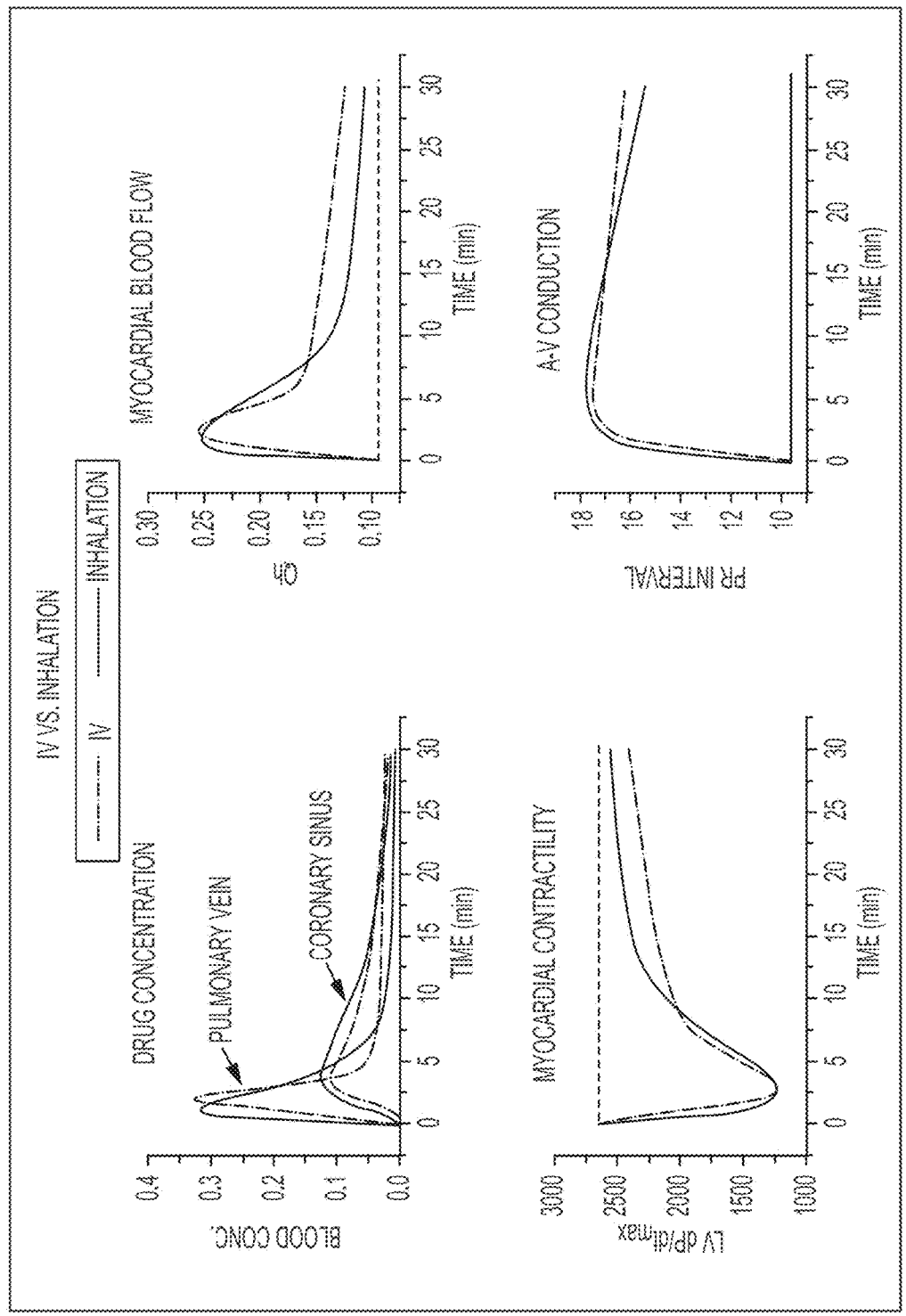
FIG. 5 shows the results of a simulation comparing intravenous and pulmonary delivery of verapamil.

FIG. 5 shows the different time concentration profiles of drug administered via the IV and inhalation routes. Verapamil was selected as an example heart drug as it possesses both cardiac rate and rhythm control properties and is often used to rescue acute arrhythmia episodes (e.g., PSVT, paroxysmal supraventricular tachycardia).

Figure 6:
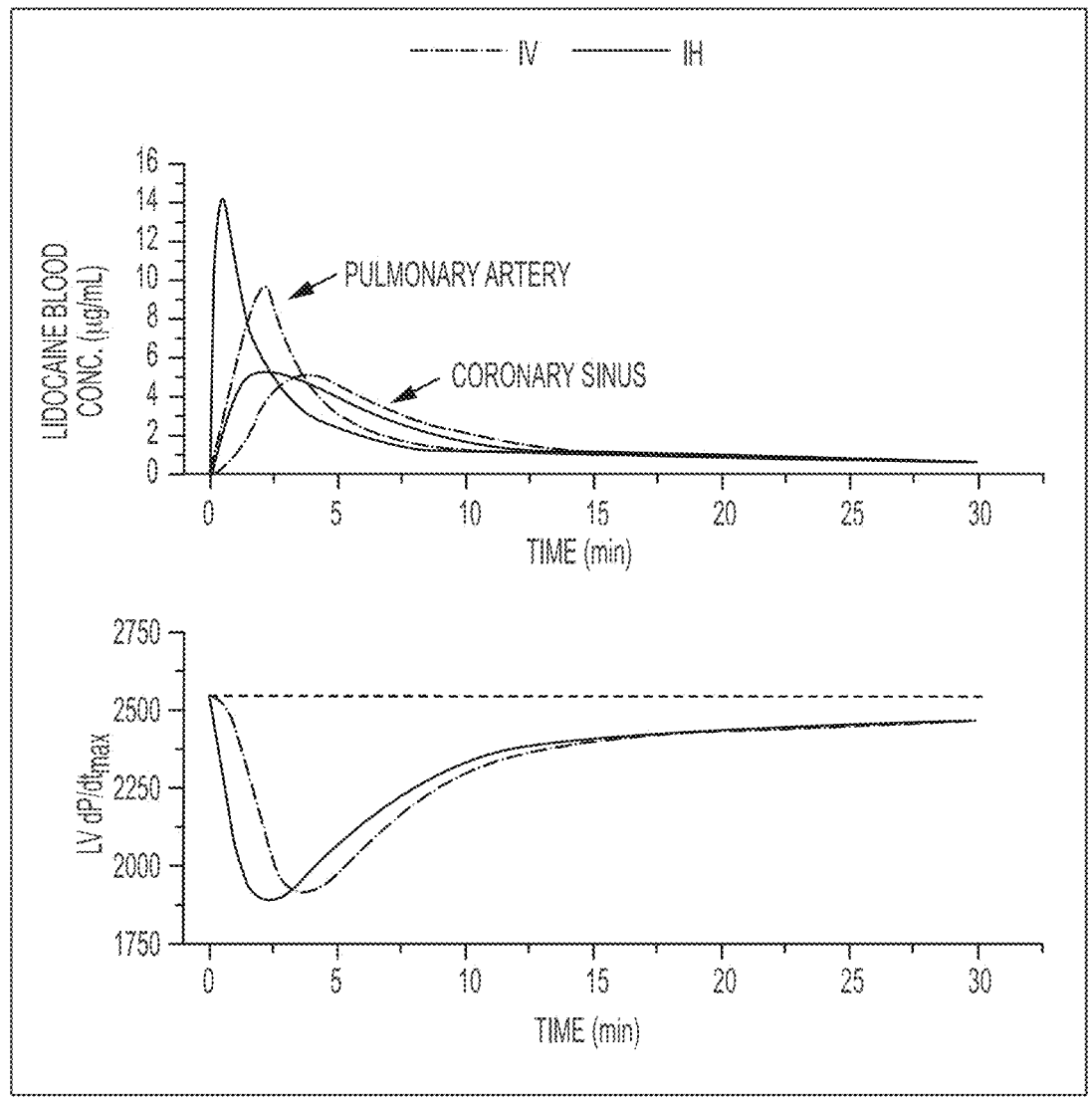
FIG. 6 shows the results of a simulation comparing intravenous and pulmonary delivery of lidocaine.

FIG. 6 also shows different time concentration profiles of drug administered via the IV and inhalation routes. Lidocaine was selected as an example heart drug. This PK/PD modeling with lidocaine shows same high feasibility.

Example 2

Effects of Intratracheal (IT) Administration of Anti-Arrhythmic Compounds on the Ventricular Response of Dogs with Induced Atrial Fibrillation and Supraventricular Tachycardia (SVT)

Objective:
To evaluate the effects/efficacy of common antiarrhythmic drugs when given via the pulmonary route, on the electrophysiological response of anesthetized dogs with induced atrial fibrillation and supraventricular tachycardia.

Animal Models Used
Atrial Fibrillation Model:
Anesthesia/Surgical Preparation:
A venous catheter was placed in a peripheral vessel (i.e., cephalic) for administration of anesthetic. For anesthesia induction, all animals were given morphine sulfate (~2 mg/kg) and a bolus of alpha chloralose (~100 mg/kg) intravenously through the venous catheter. Anesthesia was sustained with alpha chloralose (35-75 mg/kg/hour IV), until completion of the study (<2 hours). Following induction, animals were endotracheally intubated and mechanically ventilated (~12 breaths/minute with a tidal volume of 200-300 mL). Subsequently, a cut-down on a jugular vein permitted introduction of a pacing lead into the right atrium. Transthoracic electrodes forming ECG lead II were placed. For test/vehicle article delivery, a 4F catheter was introduced through the trachea and wedged into a small airway, and a venous catheter was placed in a peripheral vessel (i.e., cephalic).

Experiments

Following instrumentation and hemodynamic stabilization (for at least 15 minutes), phenylephrine was continuously infused (2 ug/kg/min IV) to elevate the systemic arterial pressure and increase vagal (parasympathetic) efferent activity for the duration of the study. Approximately 5 min after administration of this parasympathomimetic was started; the following experiments were performed:

First, the right atrium was paced (20 V, 40 Hz, 4 ms pulse) for 15 minutes, and following pacing discontinuation, atrial fibrillation ensued. Approximately 3 minutes after pacing was stopped and atrial fibrillation was observed, the animals were given vehicle (~3 mL) intra-tracheally (IT); the duration between dosing and, (if observed) the return to sinus rhythm and/or the ventricular rate was noted. Observations were made for up to 10 minutes.

Figure 7:
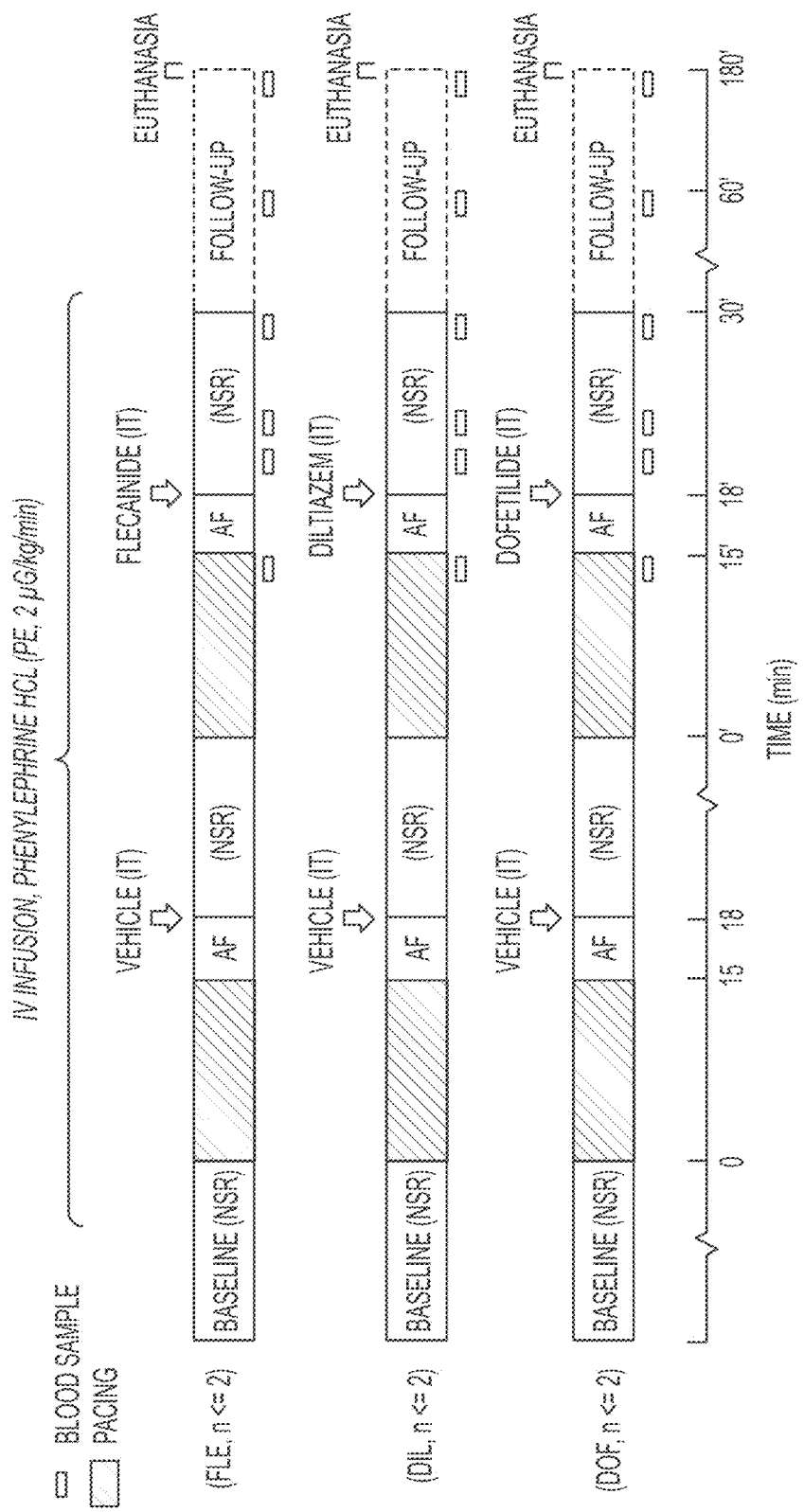
FIG. 7 shows a representative study outline: effects of flecainide (FLE, n=2), diltiazem (DIL, n=2), and dofetilide (DOF, n=2) on induced atrial-fibrillation. NSR: normal sinus rhythm.

Subsequently, atrial fibrillation was re-established via 15-minute pacing cycle(s), as described above. Once pacing was discontinued and atrial fibrillation was observed/stable for 3 minutes, the animals were administered the vehicle or one of the test articles, delivered as a bolus (~3 mL) directly into a small airway through the intratracheal catheter. Vehicle was only water. In the case of flecainide as the test article, the concentration was 15 mg of flecainide/3 ml of water. Following dosing, the duration between cessation of administration and, if observed, return to sinus rhythm and/or ventricular rate were noted; observations were made for up to 10 minutes. Overall, three groups/test-articles were studied, and up to two animals were assigned to each group (n=2/group): one group received flecainide acetate (2-4 mg/kg, FLE), while the others received diltiazem (0.25-0.50 mg/kg, DIL) or dofetilide (20-60 ug/kg, DOF); only one test article was administered per animal. The experimental protocol(s) are summarized in FIG. 7.

Supraventricular Tachycardia Model:
Anesthesia/Surgical Preparation:
A venous catheter was placed in a peripheral vessel (i.e., cephalic) for administration of anesthetic(s). For anesthesia induction, all animals were given a combination of diazepam (~0.5 mg/kg) and ketamine (~10 mg/kg) intravenously through this venous catheter. Anesthesia was sustained until completion of the study with an intravenous infusion of pentobarbital (5-15 mg/kg/hr). Following induction, animals were endotracheally intubated and mechanically ventilated (~12 breaths/min with a tidal volume of 200-300 mL).

Subsequently, a cut-down on a jugular vein permitted the introduction of a pacing lead into the right atrium. Similarly, for arterial pressure monitoring, a solid-state micromanometer catheter (Millar Instruments) was advanced into the aortic root via a cut-down over an artery (e.g., femoral, carotid). Transthoracic electrodes forming ECG lead II was placed. For vehicle/test article delivery, a 4F catheter was introduced through the trachea and wedged into a small airway, and a venous catheter was placed in a peripheral vessel (i.e., cephalic).

Experiments

Following instrumentation/hemodynamic stabilization (for at least 15 minutes), right atrial pacing (5-10 V, 40 Hz, 2 ms pulses) was established in order to induce supraventricular tachycardia (SVT); pacing and SVT was sustained throughout the duration of the experiments. Approximately 5 minutes after onset of SVT and while monitoring ECG/ arterial pressure continuously, the animals were administered three escalating doses (one at a time) of a test article; each dose was delivered as a bolus (~3 mL) directly into a small airway through the intratracheal catheter (IT). Following dosing, the heart-rate (HR) and arterial pressure response were monitored for 15 minutes.

Subsequently (once the response to three IT doses had been recorded), hemodynamic recovery was allowed for approximately 30 minutes, and the electrocardiographic/ hemodynamic response to the highest test-article dose was re-evaluated; however, for comparison purposes, this dose was delivered intravenously (IV).

Figure 8:
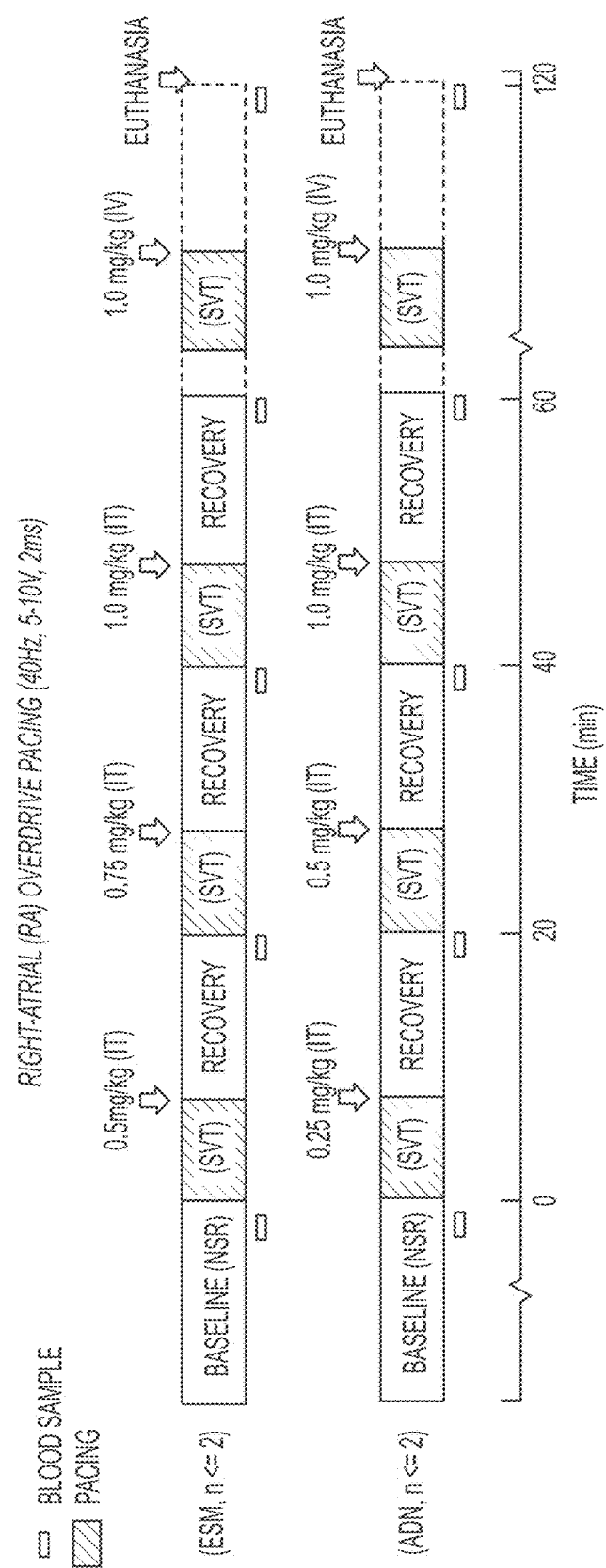
FIG. 8 shows a representative study outline: dose-response of intratracheal (IT) esmolol HCL (ESM, n<=2) or adenosine (ADN, n<=2) on induced supra-ventricular tachycardia (SVT). NSR: normal sinus rhythm. IV: intravenous

Overall, two groups/test-articles were studied, and up to two animals were assigned to each group (n=2/group): one group received esmolol HCL (0.5-1.0 mg/kg, ESM), while the other received adenosine (0.25-1.0 mg/kg, ADN); only one test article was administered to per animal. The experimental protocol(s) are summarized in FIG. 8.

Observations:

Atrial Fibrillation:

Among the three test articles (flecainide, diltiazem and dofetilide) studied, both flecainide and diltiazem rapidly converted the Atrial Fibrillation to normal sinus rhythm, while dofetilide marginally slowed the ventricular rate.

Figure 9:
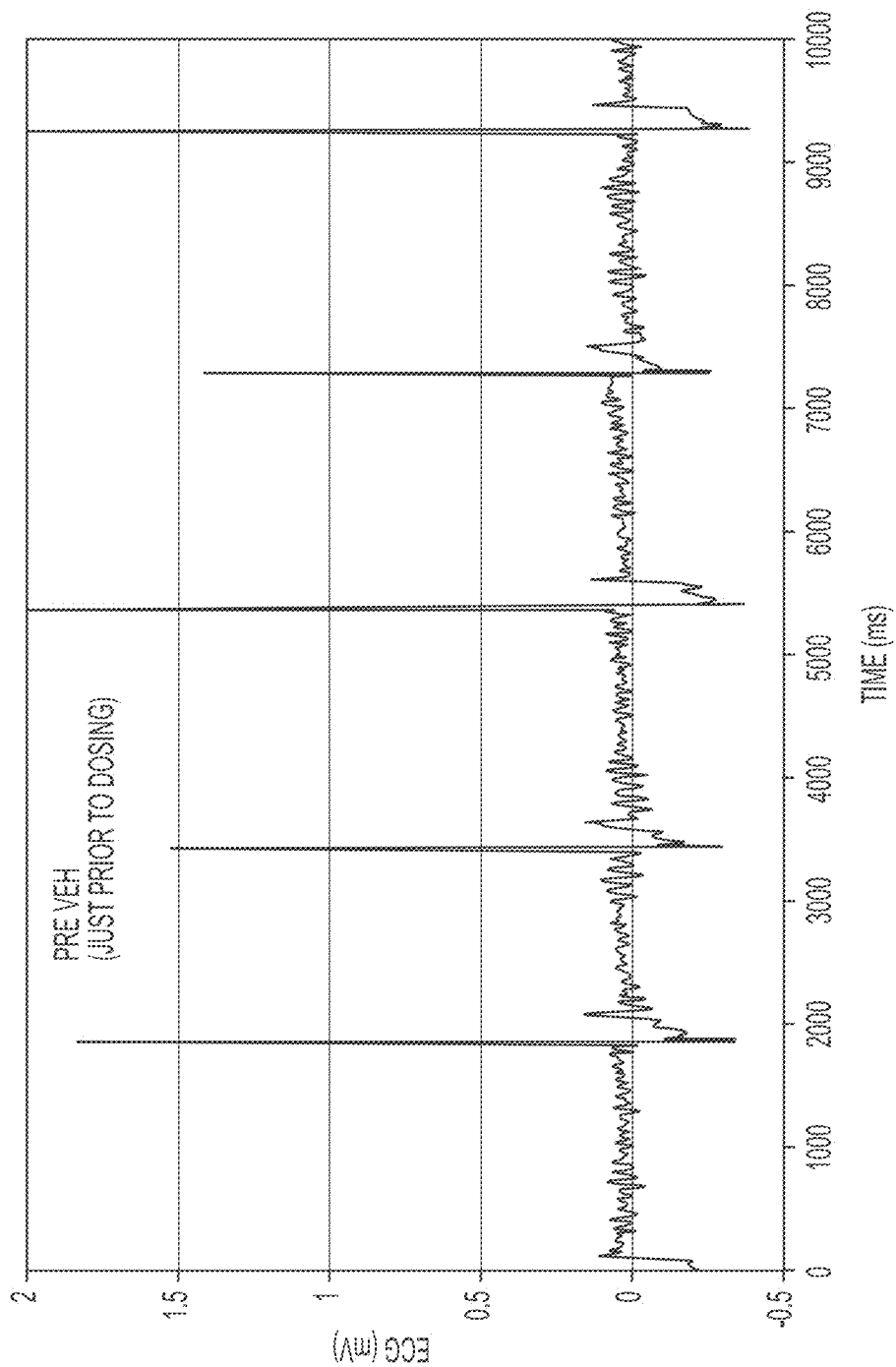
FIG. 9 shows an ECG trace showing Dog in Afib prior to dosing of either vehicle or test article.
Figure 10:
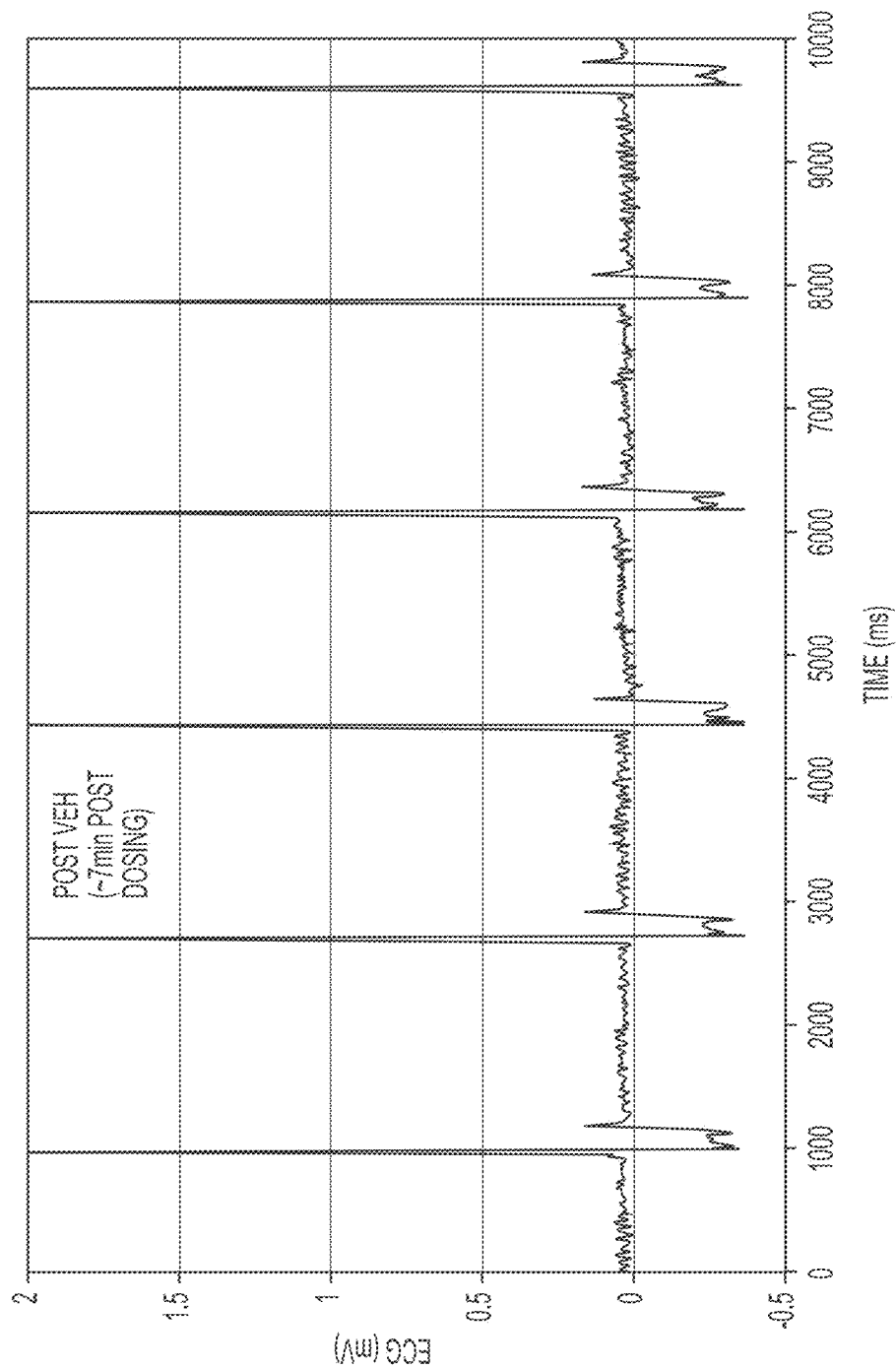
FIG. 10 shows an ECG trace showing Dog continues to be in Afib after pulmonary administration of vehicle (water, 3 ml).

Vehicle:

FIG. 9 shows a representative example of a dog in atrial fibrillation prior to administration of either vehicle or test article. FIG. 10 shows an example of the vehicle having no effect on the arrhythmia. Vehicle administered in same volumes as the test articles had no effect on the arrhythmia.

Figure 11:
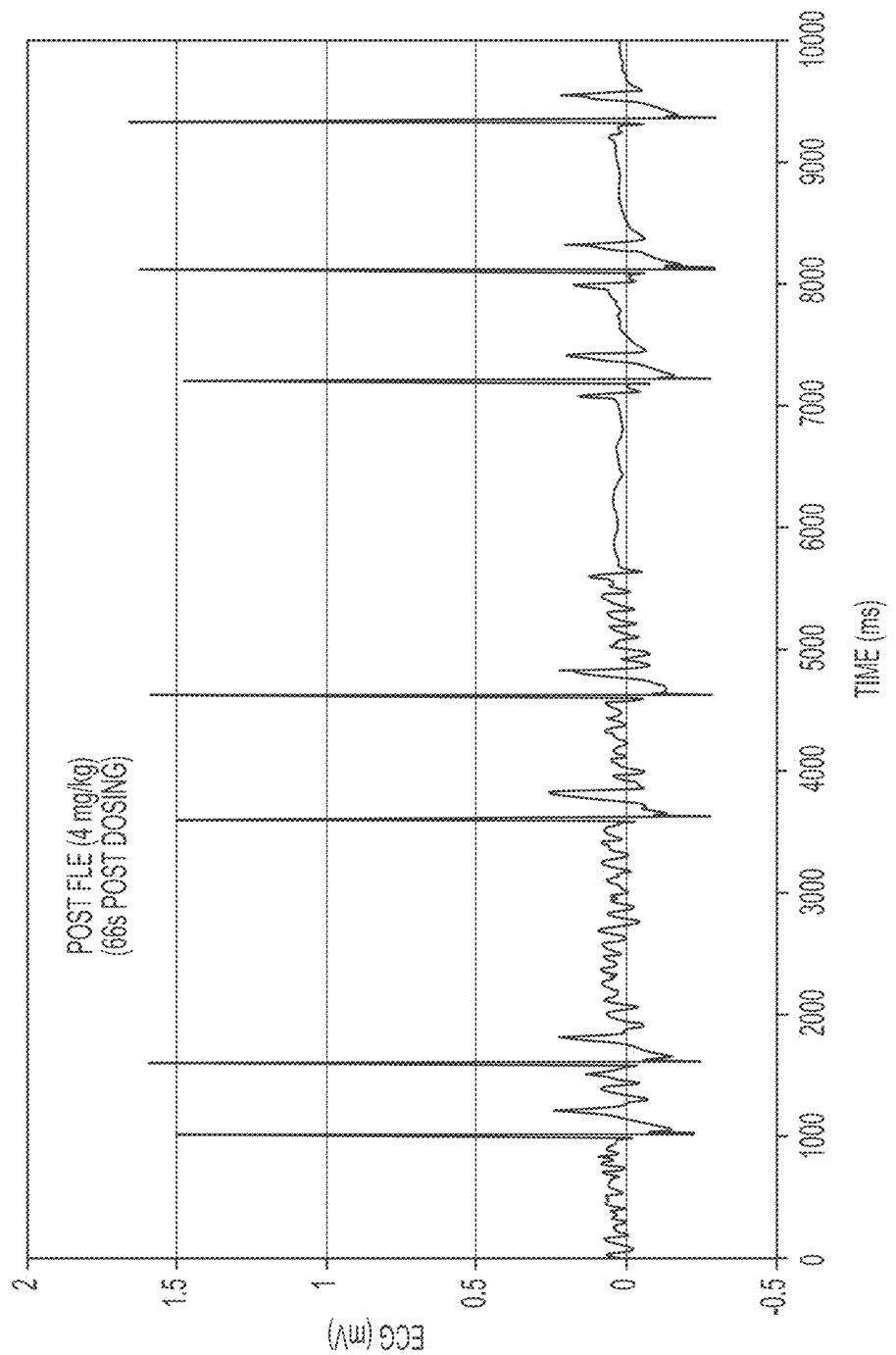
FIG. 11 shows an ECG trace showing the Afib converting into normal sinus rhythm when a dog was administered 4 mg/kg body weight of Flecainide acetate by intra-tracheal instillation.
Figure 12:
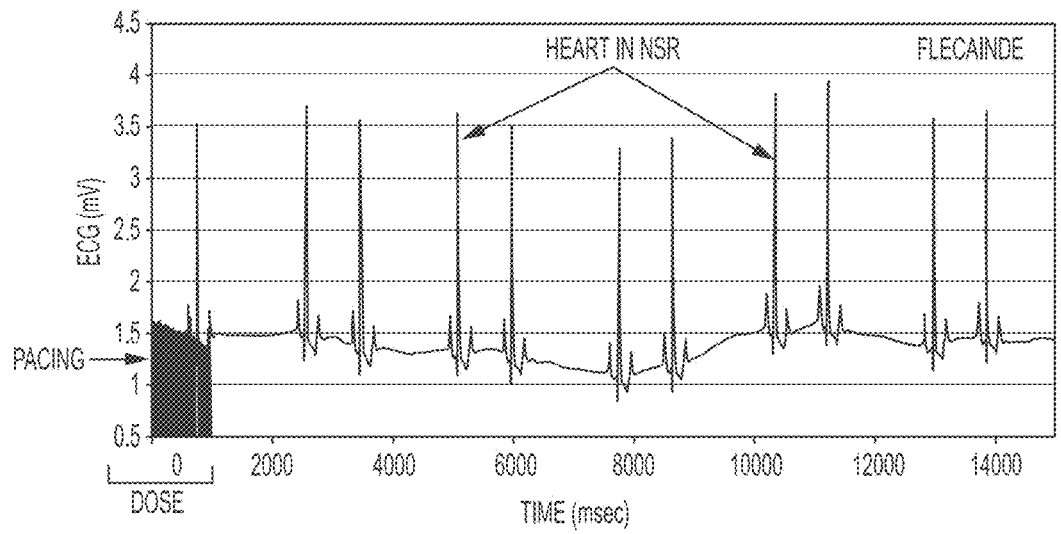
FIG. 12 shows an ECG trace showing Afib converting as soon as dosing occurred at 2 mg/kg body weight of flecainide acetate.

Flecainide:

At pulmonary dose between 2-4 mg/kg body weight, flecainide converted the induced atrial fibrillation to normal sinus rhythm. Large doses of the drug also resulted in slower ventricular rates. None to minimal drop in mean arterial pressure was noted. Neither dogs exhibited any known adverse events such as proarrhythmia. See FIGS. 11 and 12.

Diltiazem:

At pulmonary doses of 0.25 mg/kg body weight, diltiazem converted the induced atrial fibrillation to normal sinus rhythm and also prolonged the PQ interval. Heart rate also slowed down but marginally. There was however a notable drop in mean arterial blood pressure (MAP).

Figure 13:
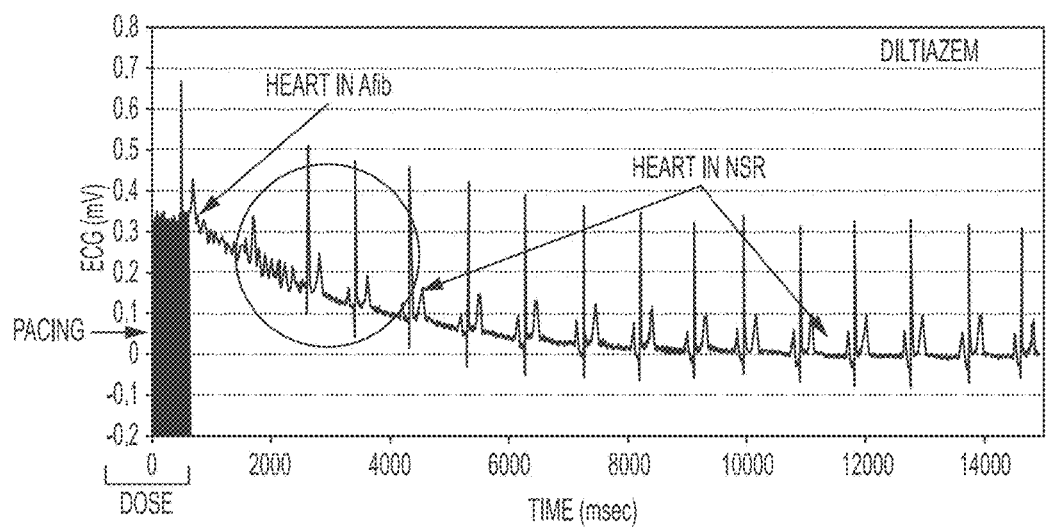
FIG. 13 shows an ECG trace showing Afib converting after administration of diltiazem HCl at 0.25 mg/kg body weight.

See FIG. 13.

Dofetilide:

At escalating pulmonary doses of 10-40 mcg/kg body weight, dofetilide caused minor reduction in heart rate.

Figure 14:
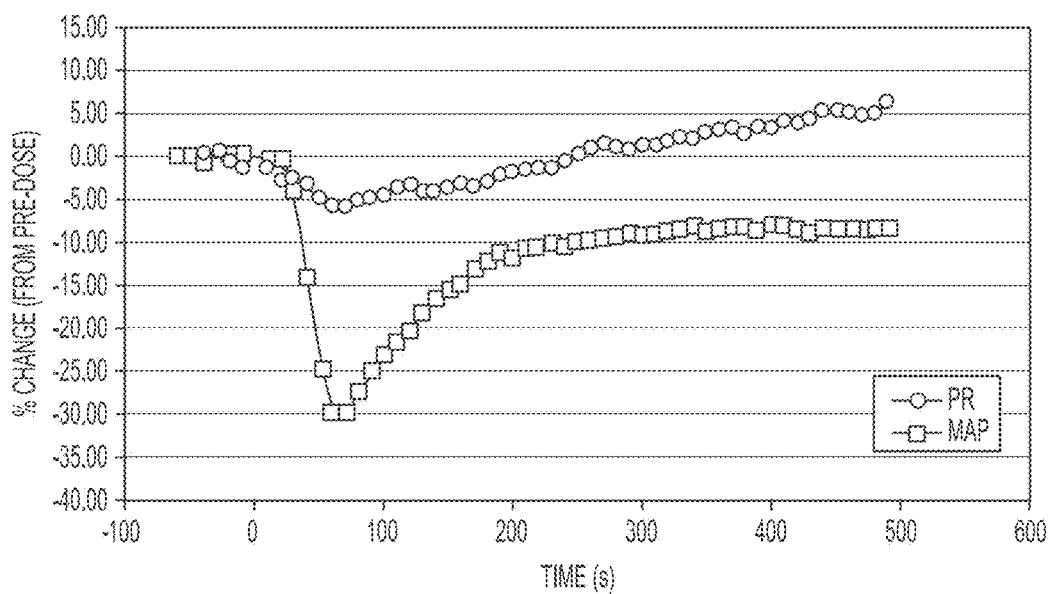
FIG. 14 shows results from a supraventricular tachycardia model in which PR interval and Mean Arterial blood pressure (MAP) change in time after pulmonary administration of pulmonary diltiazem 0.25 mg/kg.
Figure 15:
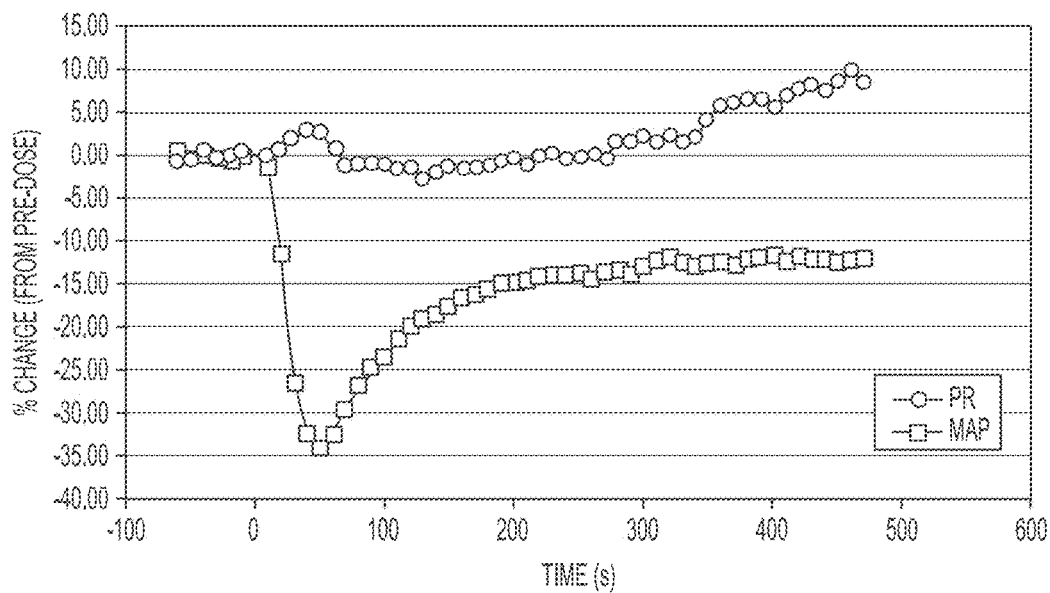
FIG. 15 shows results from the supraventricular tachycardia model in which PR interval and Mean Arterial blood pressure (MAP) change in time after intravenous administration of pulmonary diltiazem 0.25 mg/kg.
Figure 16:
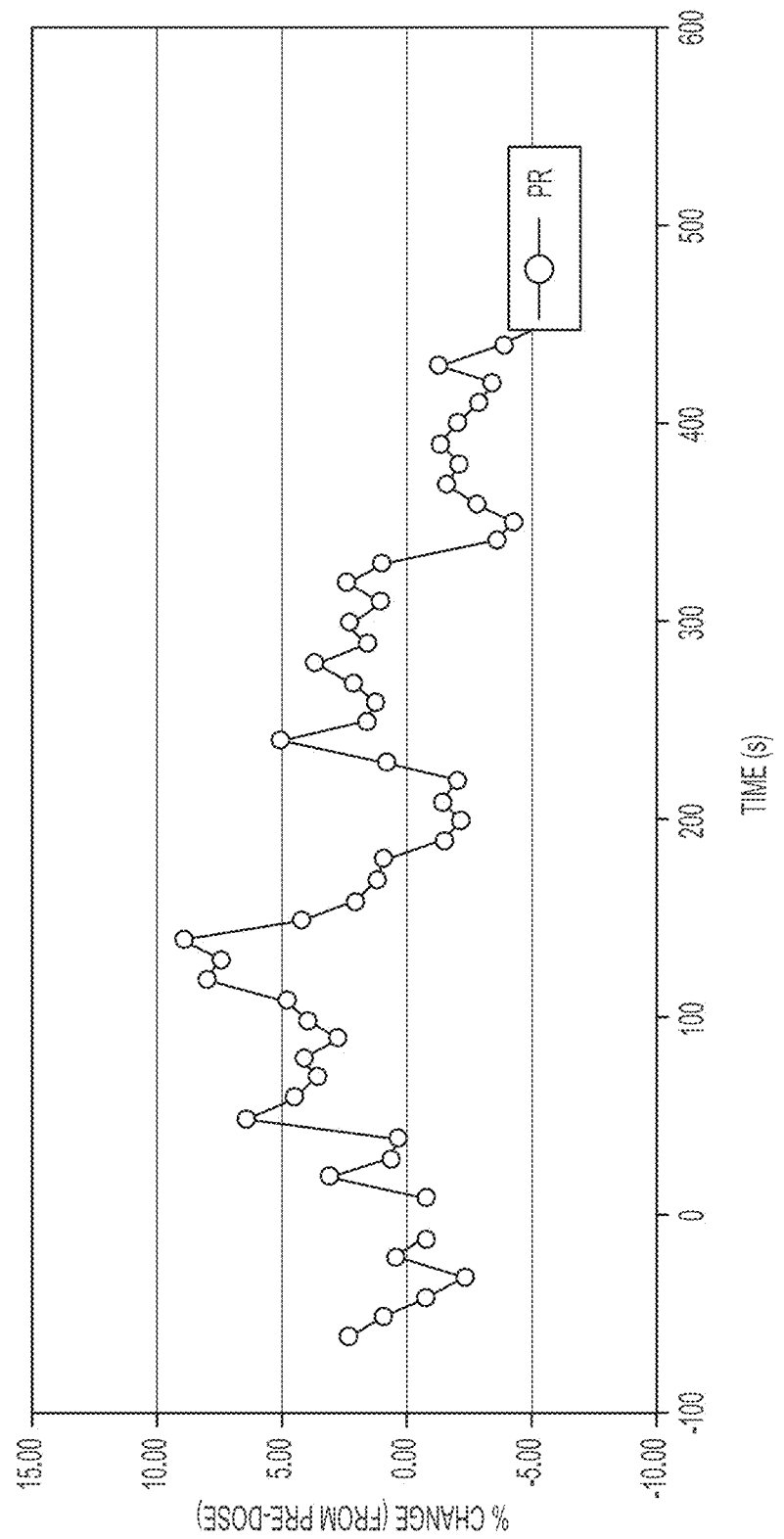
FIG. 16 shows results from the supraventricular tachycardia model showing effect on PR interval over time of 0.5 mg/kg body weight of esmolol HCl administered via the lung (IT).
Figure 17:
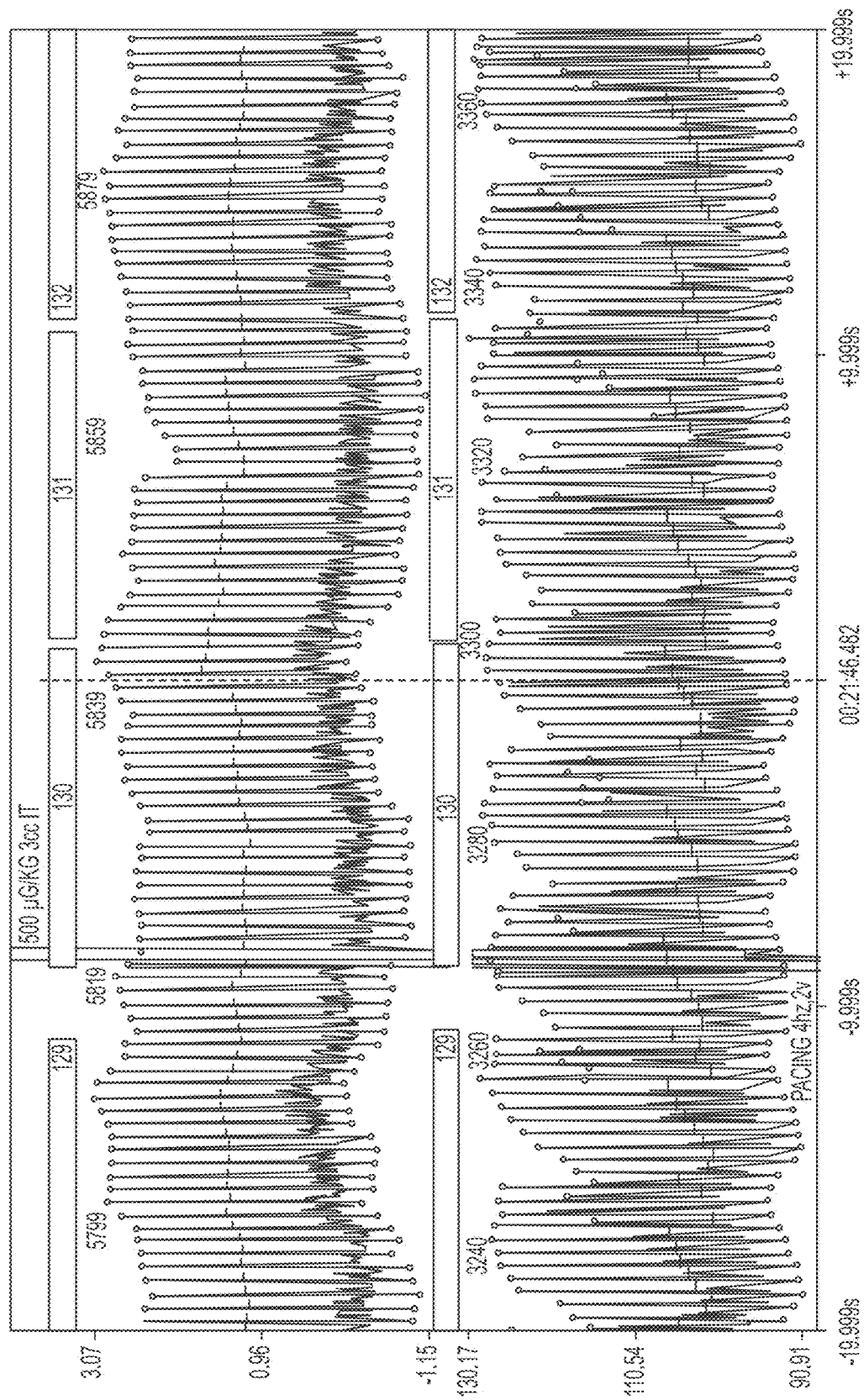
FIG. 17 shows results from the supraventricular tachycardia model showing period of AV block induced by esmolol 0.5 mg/kg administered via the lung.
Figure 18:
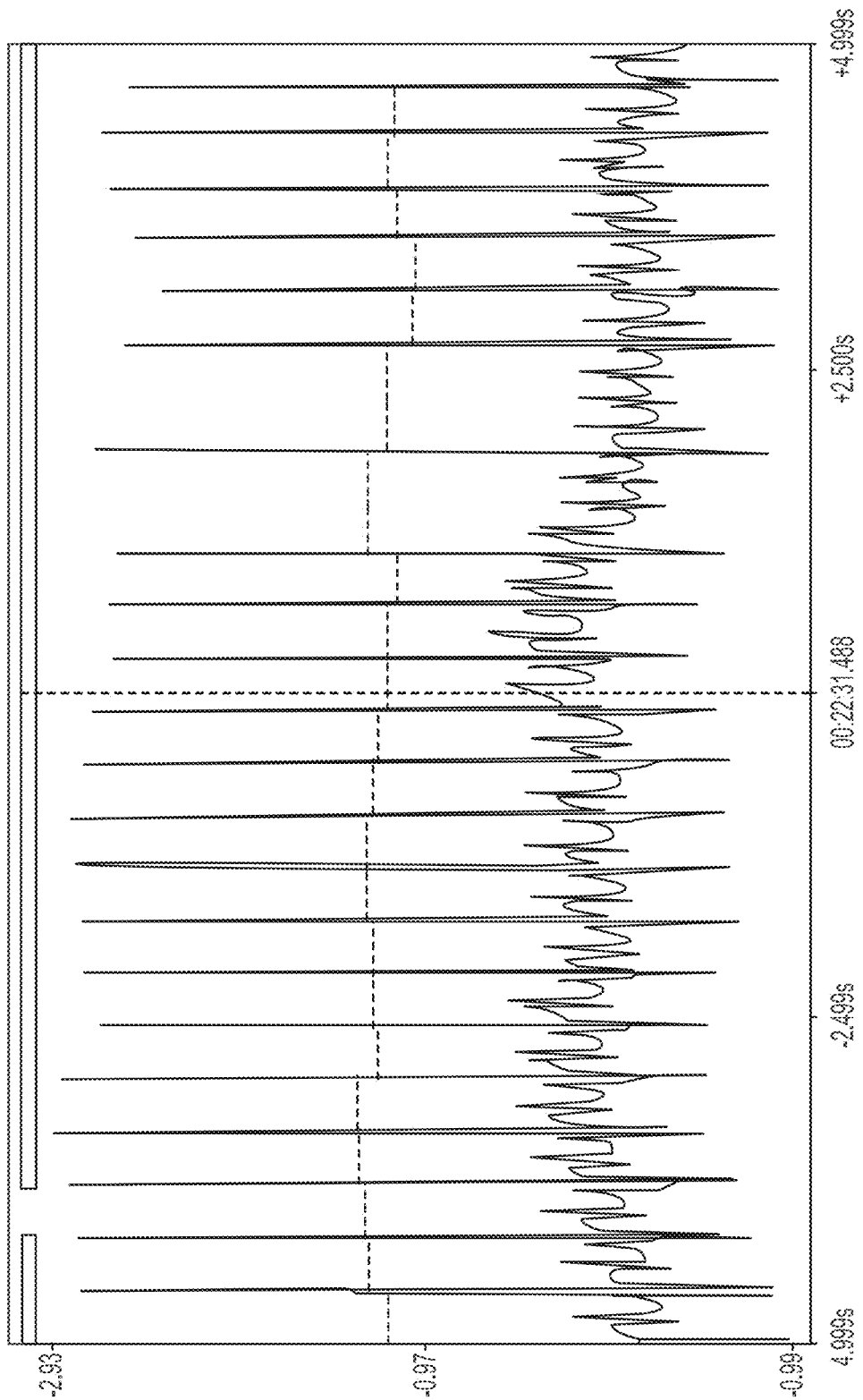
FIG. 18 shows results from the supraventricular tachycardia model showing period of AV block induced by esmolol 0.5 mg/kg administered via the lung.
Figure 19:
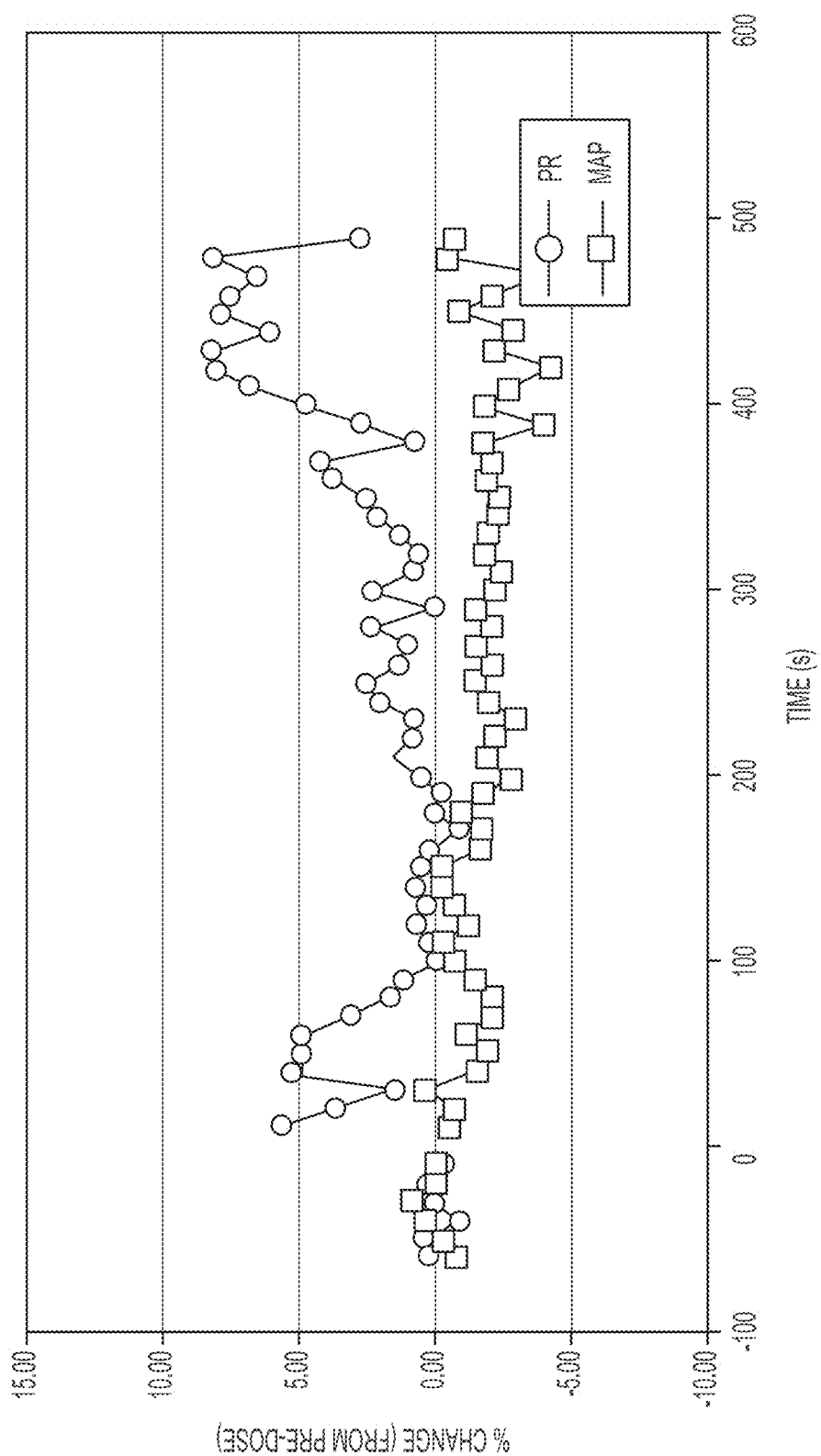
FIG. 19 shows results from the supraventricular tachycardia model showing effect on PR interval over time of 0.5 mg/kg body weight of esmolol HCl administered via the lung (IT).
Figure 20:
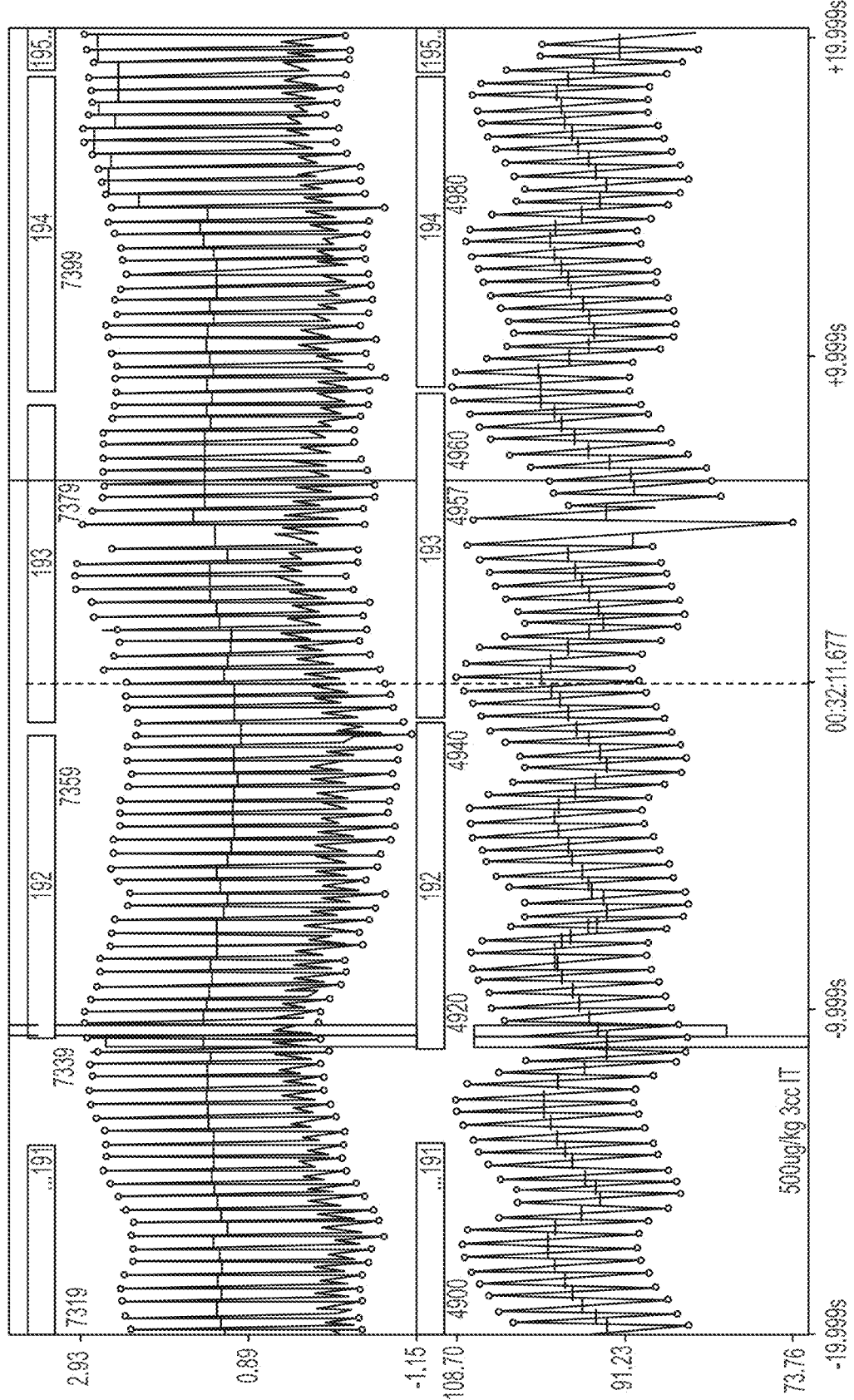
FIG. 20 shows results from the supraventricular tachycardia model showing period of AV block induced by esmolol 0.75 mg/kg administered via the lung.

Supraventricular Tachycardia (SVT):

Diltiazem:

The diltiazem delivered via the pulmonary and IV routes were comparable in all aspects. The Mean Arterial Pressure (MAP) dropped significantly in both cases, attributed directly to the dose of the drug. Diltiazem also prolonged the PR interval indicating that the drug delivered by either IV or pulmonary routes has the potential to convert the SVT to normal sinus rhythm. The timing of the electrophysiological change was comparable between IV and pulmonary. See FIGS. 14 and 15.

Esmolol:

Elevating doses of esmolol were shown to produce $2^{nd}$ degree AV block at lower doses and also prolonging the PR intervals in the ECG traces. See FIGS. 16-20.

However, higher doses of esmolol at 1.0 mg/kg did not produce the same electrophysiological effects. It is noteworthy that esmolol delivered via the lung did not cause a drop in MAP in any of the doses.

Adenosine:

Adenosine administered via the lung did not have any effect on the heart. Adenosine is known to metabolize differently in different species and it is not clear whether the effect was due to the ultra-rapid metabolism of adenosine or the model not being sensitive enough.

Summary

There was a clear cardiovascular effect of diltiazem, flecainide, and a probable effect of esmolol and dofetilide when given by intratracheal instillation. These drugs comprise four divergent classes of chemical and pharmacological agents. Although a clear response was not observed with adenosine, it is still considered worthy of evaluation in other animal models. The responses mimicked qualtitatively those of the IV route and known physiological effects of all test articles for diltiazem, flecainide, and esmolol. There may be some physical or physicochemical property of adenosine that precludes absorption from the tracheal route in this animal model. Additionally, administration into a single small airway would not be expected to produce the same exposure as administration by inhalation where the surface for diffusion would be many orders of magnitude greater.

These studies confirm the physiological effects of divergent chemicals on cardiovascular function. The intratracheal route of administration possesses 3 potential advantages. (1) It is the shortest route from point of administration to the target organ—the heart. (2) There is less dilution therefore a higher concentration to the target organ would be expected. (3) There would be a reduction in metabolism (i.e., first pass effect) since there is no organ (e.g., liver) for metabolizing between site of administration and target organ.

Example 3

Preliminary Evaluation of Solubility and Taste of Antiarrhythmic Pharmaceutical Agents when Administered as an Aerosol Objective:

To evaluate the solubilities of flecainide acetate and diltiazem hydrochloride in water and to evaluate the acceptability of taste and aftertaste of these two drugs for administration as liquid aerosols.

Experiment and Observations

Preformulation Studies

Diltiazem's solubility was >90 mg/mL at room temperature. The pH of a 3.5 mg/mL solution of diltiazem in water was 6.7. At 50 mg/mL, a diltiazem in water solution was about 80% to isotonic.

Flecainide's solubility was about 30 mg/mL at room temperature. The pH of a 2.6 mg/mL solution of flecainide in water was 5.0. At 30 mg/mL, a flecainide in water solution was about 50% to isotonic.

The following solution strengths were prepared for taste evaluation: (1) diltiazem hydrochloride—50 mg/ml solution in distilled water; and (2) flecainide acetate—30 mg/ml solution in distilled water. The solutions were clear with no visible particulate matter.

Inhalation Device:

The Aeroneb® GO device was used because it is a simple-to-use device developed specifically for patients who require respiratory therapy in and away from the home. The device can be used by patients of all ages (infant through adult) and aerosolizes solutions intended for inhalation. Aeroneb® Go works with either an AC wall controller or a battery pack, and can be cleaned with soap and water.

Inhalation Procedure:

Volunteers:

Number of subjects: 2 healthy male volunteers

Volunteer-1: age—48

Volunteer-2: age—63

Nebulizer Testing:

Water was poured into the nebulizer cup, and the nebulizer was turned on. The visible cloud of aerosol generated when the nebulizer was turned on was treated as a qualitative aerosol standard.

Flecainide Acetate:

About 1 ml of the 30 mg/ml solution was poured into the cup of the nebulizer. The nebulizer was turned on and the resulting aerosol was similar to but not as dense as the aerosol formed with the water alone.

The nebulizer was then placed in the mouth and switched on. Deep lung inhalation was performed through the nebulizer. About 40 µl (~1.2 mg of flecainide acetate) of the test solution was inhaled. The inhaled dose was sub-therapeutic in nature as it was much less than the regular 100 mg administered as tablets. Flecainide acetate is also available as an IV injection in Europe as 10 mg/ml strength in 15 ml ampoules.

Diltiazem Hydrochloride:

About 1 ml of the 50 mg/ml solution was poured into the cup of the nebulizer. The nebulizer was turned on and the resulting aerosol was similar to but not as dense as the aerosol formed with the water alone.

The nebulizer was then placed in the mouth and a switched on. Deep lung inhalation was performed through the nebulizer. About 40 µl (~2 mg of diltiazem hydrochloride) of the test solution was inhaled. The inhaled dose was sub-therapeutic in nature as it was much less than the IV injection marketed in the U.S. as 5 mg/ml in 5 ml vials.

Conclusions and Observations

1. The visible aerosol characteristics test solutions were similar to each other but not as dense as the water.
2. Flecainide acetate: The taste feedback from both volunteers was very similar.
   a. Taste: Mildly bitter taste felt in the back of the tongue
   b. Aftertaste: There was none to little aftertaste 5 minutes after the inhalation maneuver.
3. Diltiazem hydrochloride: Water was inhaled to wash out any of the flecainide residues.
   The taste feedback from both volunteers was very similar.
   a. Taste: Mildly bitter taste felt in the back of the tongue
   b. Aftertaste: There was none to little aftertaste 5 minutes after the inhalation maneuver.
4. Other observations:
   a. No burning sensations was felt in the mouth, throat, or lungs
   b. No visible adverse events were observed. Both volunteers rested for 60 minutes after dosing.

Example 4

A Single Ascending Dose Study of Flecainide Acetate Inhalation Solution to Assess the Safety, Tolerability, Pharmacokinetics and Pharmacodynamics of the Drug A Phase 1 study was performed in normal healthy volunteers to assess the safety, tolerability, pharmacokinetics (PK) and pharmacodynamics (PD) of oral inhaled flecainide and to compare the PK/PD relationship of inhaled flecainide acetate solution to intravenous (IV) flecainide acetate. The Phase 1 clinical study (FLE-001) was a single center study conducted at CMAX in Adelaide, Australia, comprised of two parts (sub-studies), Part A and Part B. The 1) pharmacokinetics (PK), 2) pharmacodynamics (PD), and 3) safety and tolerability of single ascending doses (SADs) of inhaled flecainide acetate compared to placebo in healthy volunteers were evaluated.

Figure 21:
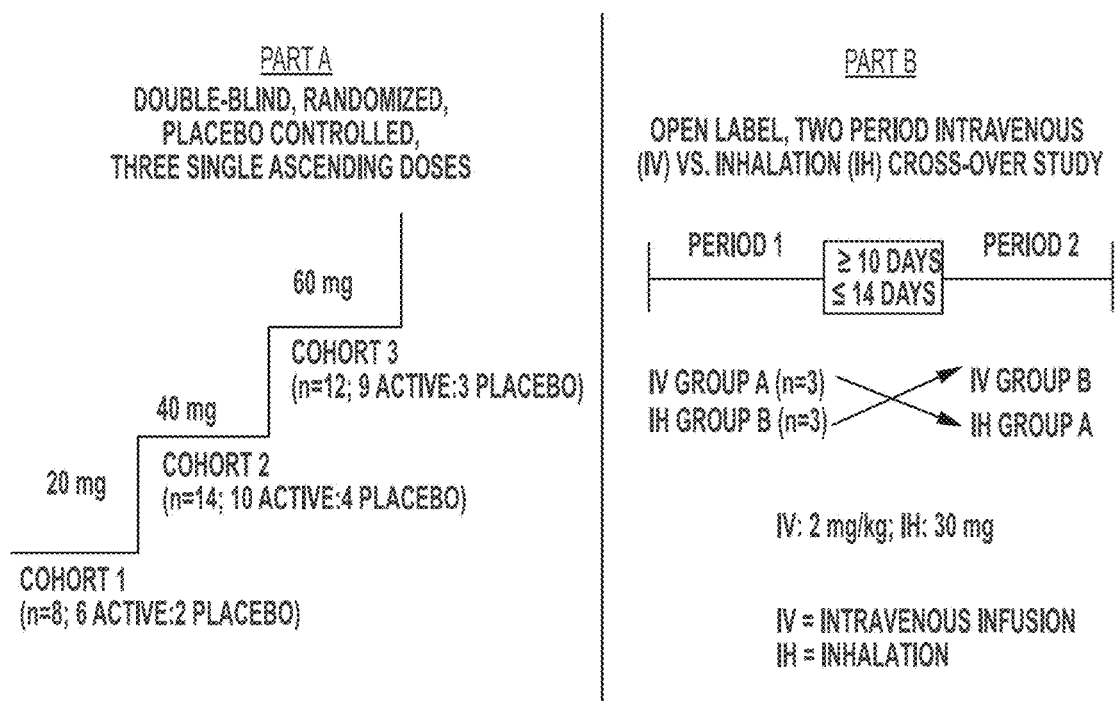
FIG. 21 shows the design for the Phase 1 clinical study.

Study Design:

This was a single-center study comprising two parts, A and B. The study design schematic is shown in FIG. 21.

Part A was a double-blind, randomized, placebo-controlled design consisting of SADs of flecainide acetate inhalation solution (estimated total lung doses [eTLD] of 20 mg, 40 mg, or 60 mg) or matching placebo inhalation solution administered using a hand-held inhaler device (AeroEclipse® II Breath Actuated Nebulizer (BAN)) to healthy adult males and females. Subjects were randomized to receive a single inhalation of either flecainide acetate inhalation solution or placebo inhalation solution in double-blind fashion. 3 cohorts of subjects, in total 34 healthy adult volunteers, were recruited for Part A study.

Figure 87A:
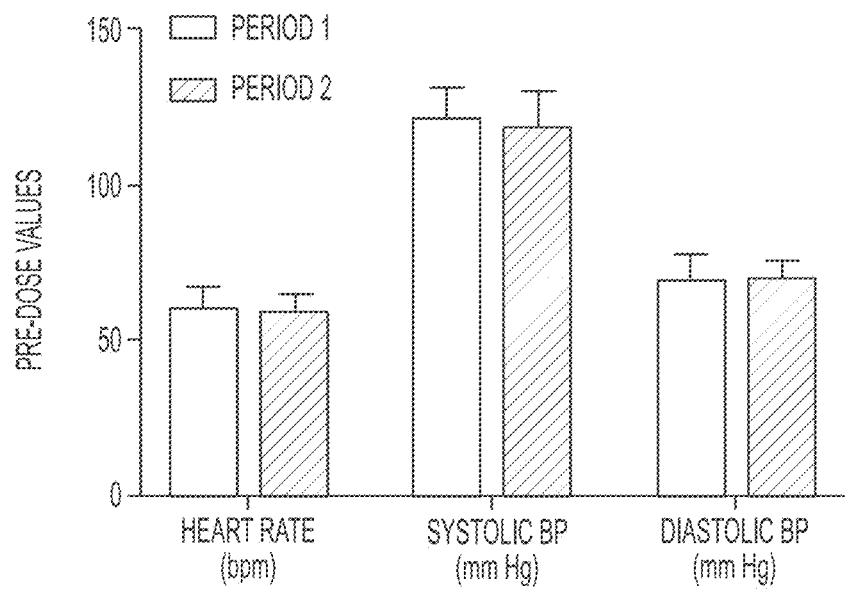
FIG. 87A shows baseline (pre-dose) values of heart rate, systolic blood pressure (BP), and diastolic BP in Periods 1 and 2 of 6 subjects in Part B study.
Figure 87B:
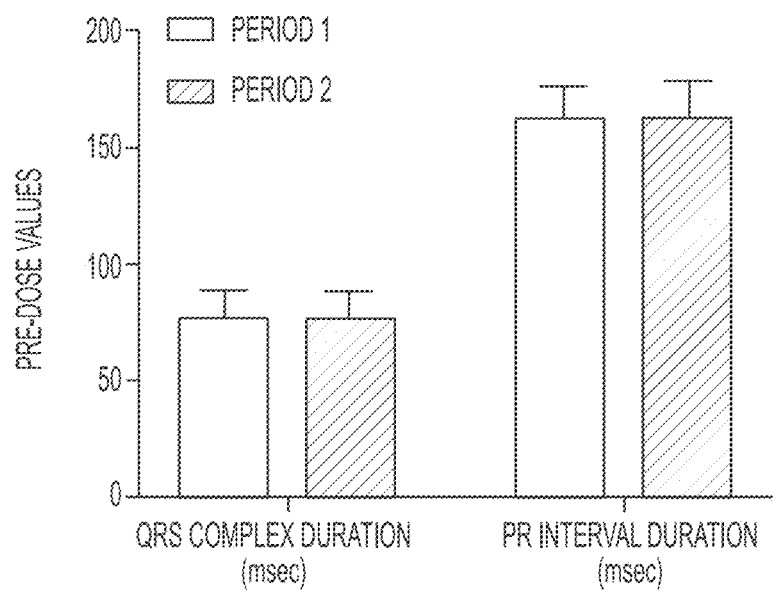

Part B was an open label non-randomized crossover in a cohort of 6 evaluable healthy adult volunteers. This part of the study consisted of two periods with each subject receiving a total of 2 doses of flecainide, one dose in each period. In Period 1, 3 subjects received flecainide acetate solution by inhalation at the dose level of 30 mg eTLD, and 3 subjects received a single dose of 2 mg/kg (or 150 mg, whichever is less) via a 10 min intravenous (IV) infusion of flecainide (Tambocor™ Injection; approved and used in clinical practice in Australia). In Period 2, the subjects who received flecainide inhalation solution in Period 1 now received a single dose of IV flecainide (2 mg/kg or 150 mg, whichever is less, via a 10 min infusion), while the subjects who received IV flecainide in Period 1 now received flecainide inhalation solution (30 mg eTLD). Shown in FIGS. 87A and 87B are the baseline (pre-dose) values of HR, Systolic BP and Diastolic BP (FIG. 87A) and, PR and QRS interval durations (FIG. 87B) for Period 1 and Period 2 in the 6 subjects studied (prior to administration of flecainide, either via IV infusion or oral inhalation. The finding that the baseline values for Period 1 and Period 2 prior to dosing are near identical is consistent with the expectation from a cross-over design study. The interpretation that there was no carry over effect of treatment or other changes in the subjects' vital signs and ECG intervals between the two periods.

Chronologically, experiments involving Cohorts 1, 2, and 5 started in early stage of this clinical study, while experiments involving subjects in Cohort 3 started later. As a result, some of the data analyses presented below are based on data from Cohorts 1, 2, and/or 5 without data from Cohorts 3.

Study Population:

In Cohorts 1 and 2, all 22 volunteer subjects were healthy male Caucasians, except for one Asian.

In Cohort 3, all 12 volunteer subjects were male Caucasians.

In Cohort 5, 7 volunteer subjects were enrolled, among which 6 completed the study. All subjects were male. Of the 6 volunteer subjects who completed the study, 5 were Caucasians and one Asian.

Doses:

Subjects in Cohort 1 (n=8) inhaled placebo (n=2) or 20 mg eTLD of a flecainide acetate solution (n=6). Subjects in Cohort 2 (n=14) inhaled placebo (n=4) or 40 mg eTLD of a flecainide acetate solution (n=10). Subjects in Cohort 3 (n=12) inhaled placebo (n=3) or 60 mg eTLD of a flecainide acetate solution (n=9). Subjects in Cohort 5 first inhaled 30 mg eTLD of a flecainide acetate solution and later received 2 mg/kg of flecainide by IV infusion (n=3), or subjects in Cohort 5 initially received 2 mg/kg of flecainide by IV infusion and subsequently inhaled 30 mg eTLD of a flecainide acetate solution (n=3).

In this study, for inhalation delivery of flecainide, the estimated total lung doses (eTLDs) were calculated to account for losses of flecainide in the inhalation device and losses of flecainide in subjects' mouth and throat. eTLD was thereby used to denote the dose that actually reached the lungs of the subjects. By design, in all nebulizers there can be a residual volume or mass of drug solution that stays in the nebulizer, and there can also be a percentage of the aerosol caught by subject's throat and mouth. For instance, in this study, it was estimated that 30% of the aerosol was lost in subject's throat and mouth. Therefore the eTLD would be:

eTLD=(100−30)%*amount of aerosolized drug that left nebulizer=70%*(amount of drug placed in nebulizer−amount of drug staying in nebulizer).

The percentage of aerosol that is caught by subject's throat and mouth can depend on the aerosol particle size, for example, the fraction of the aerosol that is above approximately 5 microns. The amount that passes the throat and gets to the lungs can be termed "Fine Particle Fraction (FPF)."

The amount of drug that stays in the nebulizer can depend on the design of the nebulizer and how it is operated. For example, for some jet nebulizers, this can be about 0.5 to 2 mL of solution. For some vibrating mesh nebulizers, it can be 0.05 to 0.3 mL. For Dry Powder Inhalers, it can be 10% to 50% of the dose, etc.

Safety:

Heart rate and systolic and diastolic blood pressure were measured pre-dose, immediately following oral inhalation or IV infusion of placebo or flecainide, and up to 360 minutes after oral inhalation or IV infusion of placebo or flecainide to evaluate cardiovascular safety.

Pulmonary safety was assessed by performing lung spirometry tests and measuring peripheral oxygen saturation ($SpO_{2\%}$) prior to dosing and at various times after completion of the inhalation. Lung spirometry tests evaluated all lung function parameters, including forced vital capacity (FVC), forced expiratory volume in 1 second (FEV1), peak expiratory flow (PEF), and forced expiratory flow at 25% and 75% intervals (FEF25-75). Auscultation and respiration rate were also measured prior to dosing and at various times after inhalation. Chest x-rays were performed on subjects before and after flecainide inhalation.

Adverse events were monitored and recorded.

PK:

Venous plasma concentration of flecainide was measured following oral inhalation or IV infusion (10 min) of flecainide.

The following PK parameters were calculated: the maximum venous plasma concentration of flecainide observed ($C_{max}$), the time at which the $C_{max}$ was observed ($T_{max}$), the area under the concentration-time curve up to the last measurable concentration ($AUC_{Last}$), the time at which flecainide plasma levels decreased to half of what they were at equilibrium due to distribution to tissues throughout the body (distribution $t_{1/2}$), and the time at which flecainide plasma levels decreased to half of what they were at equilibrium due to metabolism and elimination (elimination $t_{1/2}$).

PD:

Intensive electrocardiographic (ECG) monitoring was performed in all subjects during the study to assess the pharmacodynamic activity (e.g., QRS intervals) of inhaled or IV administered flecainide. The ECG recordings included: 1) Continuous real-time ECG telemetry for observation of patient safety starting at 12 hours pre-dose and continuing for 12 hours post-dose, 2) 12-lead ECGs for immediate review by medical staff to ascertain the safety of the procedures and drug administration were recorded at pre-specified (or any time as needed) before dosing (pre-dose) and after dosing (post-dose), and 3) continuous 12-lead ECG (cECG, iCardiac Holter monitoring) was recorded for 24 hours, starting 1 hour prior to dosing and up to 24 hours post dosing.

Results:

Safety Evaluations:

The changes in heart rate (HR), arterial systemic blood pressure (BP), and pulmonary function test parameters associated with administration of flecainide or placebo were assessed. In addition, the effects of changing posture from semi-recumbent to seated upright, vice-versa and during inhalation on HR and BP were assessed (Cohort 5).

Transient increases (between 1 and 3 minutes) in both HR and systolic and diastolic BPs were observed in subjects administered inhaled flecainide and placebo. These changes can be attributed to the sympathetic reflex (unloading of baroreceptors) responses to postural changes (from semi-recumbent to seated) and likely to the oral inhalation procedure, e.g., the relatively prolonged and deep respiratory breath, akin to ~2 seconds of breath-holding at the end of inspiratory phase of the inhalation.

Figure 22:
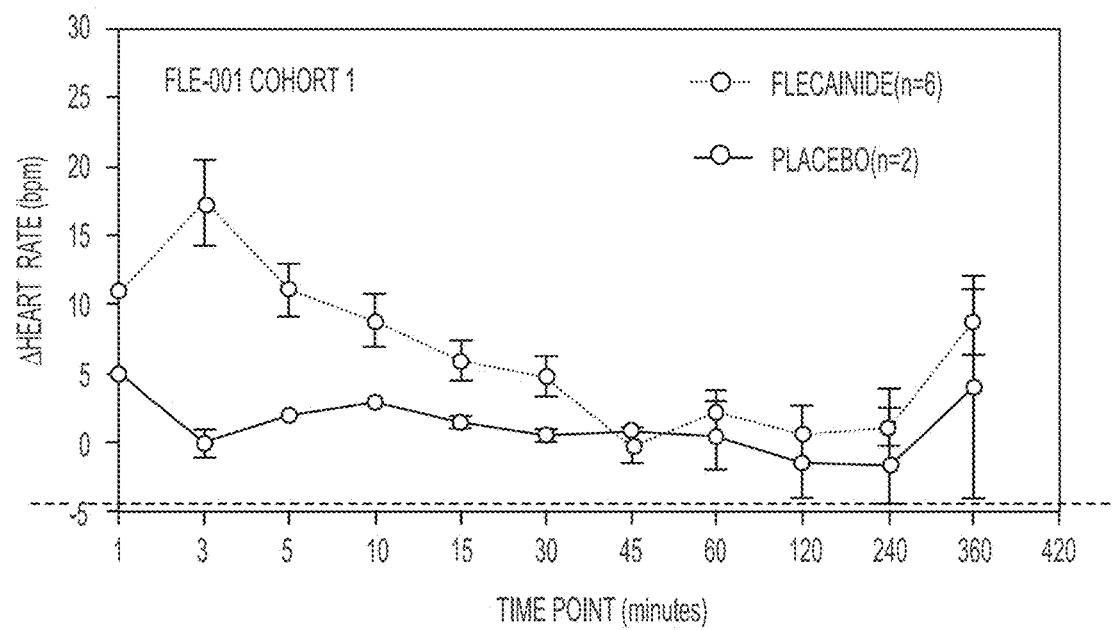
FIG. 22 shows the time course of the changes in the heart rate (AHR) relative to the baseline (pre-dose) following oral inhalation of 20 mg eTLD (estimated Total Lung Dose) of flecainide acetate solution and placebo in subjects of Cohort 1. Values are the mean±standard error of the mean (SEM).

Heart Rate Measurements:

The magnitude of the increases in HR was variable, not dose-dependent (e.g., greater increases in the 20 mg eTLD than in the 30, 40 and 60 mg eTLD groups). The baseline HR in beats per minute (bpm) was within the expected range for the population of healthy subjects in Cohort 1. Immediately, at the end of inhalation of 20 mg eTLD of flecainide acetate, there was an initial increase in HR from baseline with mean change-from-baseline heart rate (ΔHR) of ~12 bpm at 1 and 3 minutes, with subsequently smaller increases at later time points. Fifteen and 30 minutes after the end of inhalation, mean ΔHR was ~4 bpm (FIG. 22).

Figure 23:
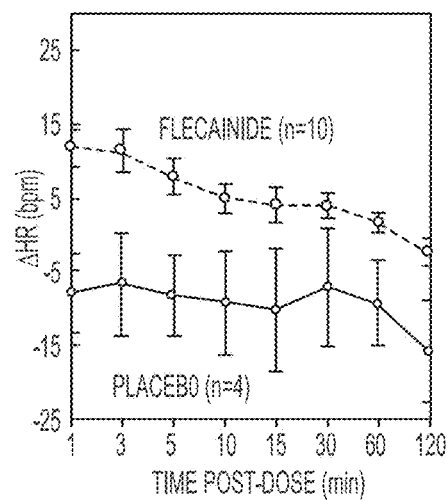
FIG. 23 shows the changes in heart rate (AHR) following inhalation of 40 mg eTLD of flecainide acetate and placebo solutions in subjects of Cohort 2 relative to pre-dose values. Values are the mean±SEM.

In subjects of Cohort 2, there was an initial transient increase in the HR of 12 to 8 bpm at 1 to 3 minutes, respectively, after completion of inhalation of 40 mg eTLD of flecainide. Thereafter, the HR quickly decreased toward the pre-dose; at 10 minutes, post-dosing ΔHR was +5 bpm (FIG. 23).

Figure 72:
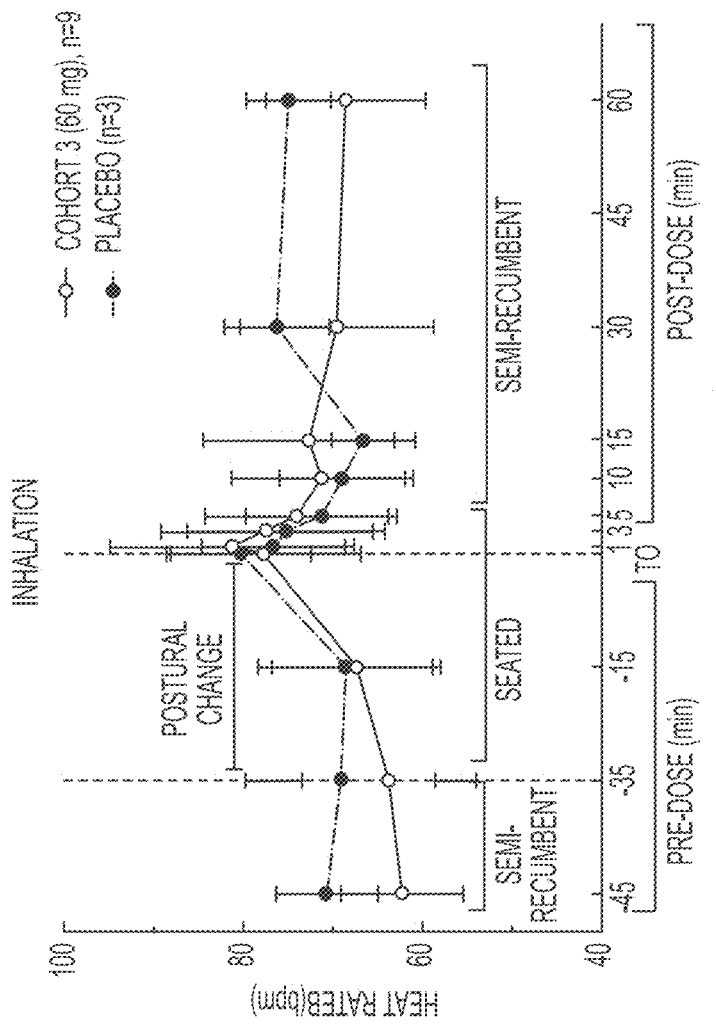

The time course of the changes in HR in subjects of Cohort 3 that were given either flecainide (eTLD of 60 mg) or placebo inhalation solutions are shown in FIG. 72. For 60 mg eTLD (FIG. 72) the changes in heart rate (HR) were comparable to those observed in the placebo group.

Figure 24:
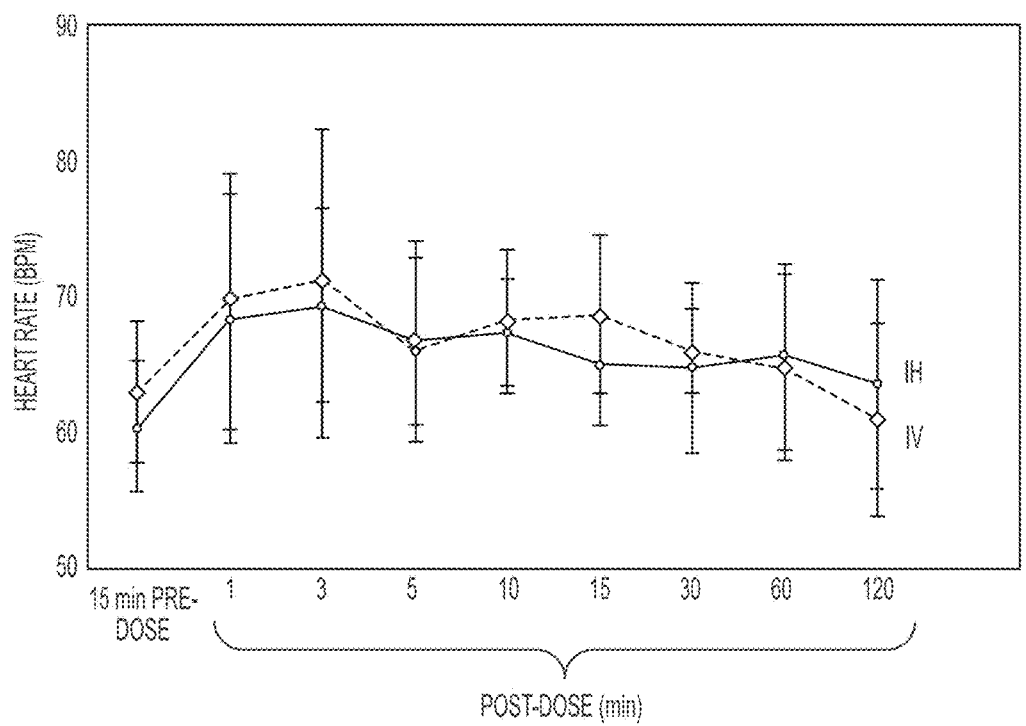
FIG. 24 shows the heart rate (bpm) of subjects in Cohort 5 following oral inhalation (IH) of flecainide acetate solution (30 mg eTLD) and administration of flecainide acetate solution by IV (2 mg/kg). Values are the mean±standard deviation (SD).

An increase in HR was observed in subjects of Cohort 5 following single dose administration of inhaled flecainide (30 mg eTLD) and IV flecainide (2 mg/kg) (FIG. 24).

There was no change in HR following the inhalation of the placebo solution.

Figure 25A:
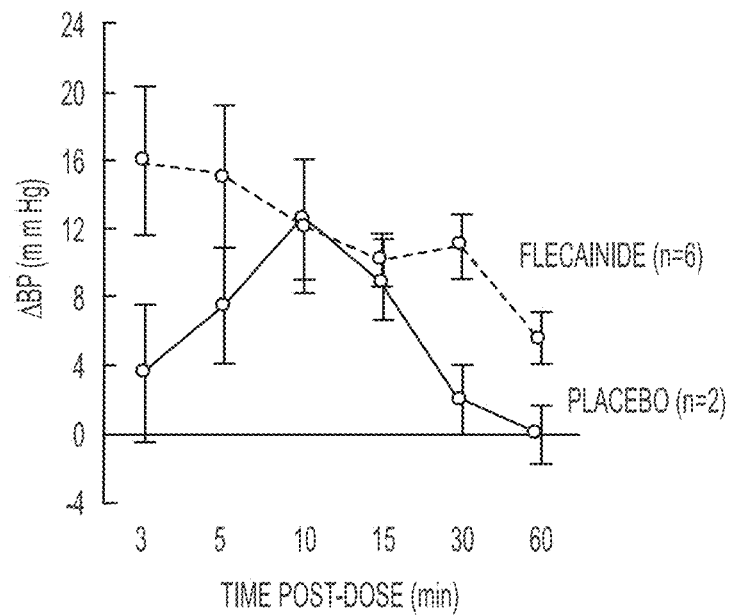
FIG. 25A shows changes in systolic blood pressure (BP) from subjects of Cohort 1 following inhalation of 20 mg eTLD of flecainide acetate and placebo solutions.
Figure 25B:
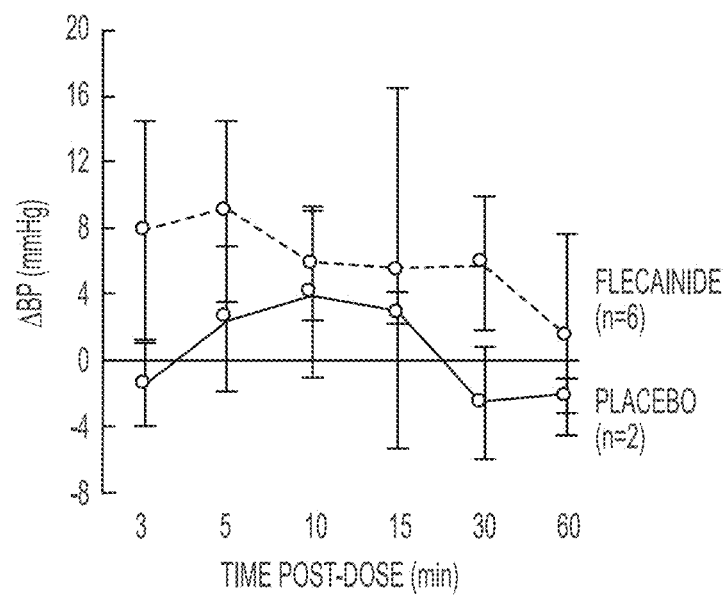
FIG. 25B shows changes in diastolic BP from subjects of Cohort 1 following inhalation of 20 mg eTLD of flecainide acetate and placebo solutions.

Systolic and Diastolic Blood Pressure Measurements:

During inhalation of either flecainide acetate or placebo solutions, both systolic and diastolic blood pressure (BP) of subjects in Cohort 1 increased during the first 15 minutes (placebo) to 30 minutes (flecainide) after completion of the inhalation. Thereafter, they declined toward the pre-dose pressures (FIGS. 25A and B).

Figure 26A:
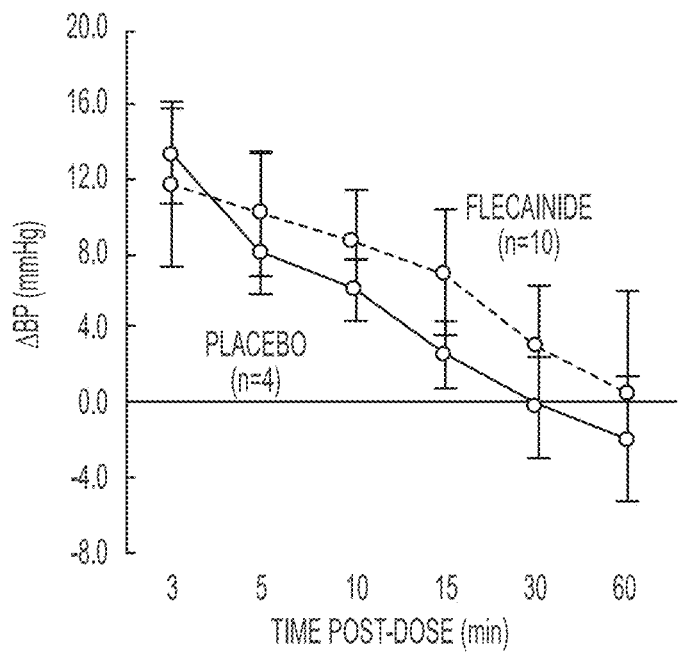
FIG. 26A shows changes in systolic BP from subjects of Cohort 2 following inhalation of 40 mg eTLD of flecainide acetate and placebo solutions.
Figure 26B:
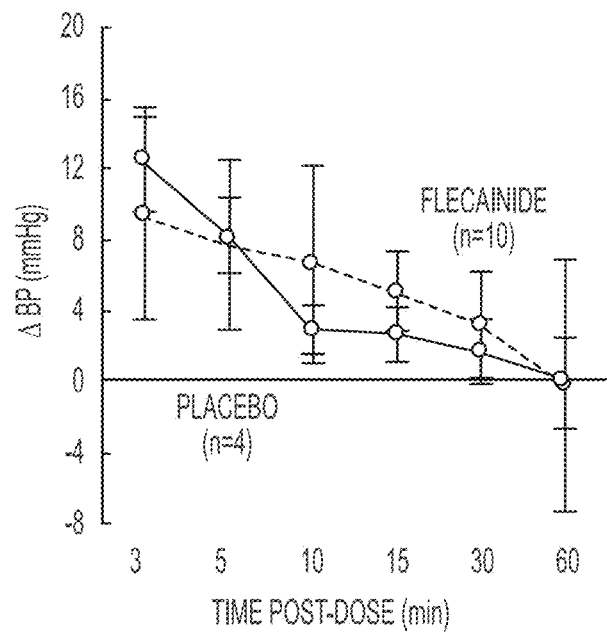
FIG. 26B shows changes in diastolic BP from subjects of Cohort 2 following inhalation of 40 mg eTLD of flecainide acetate and placebo solutions.

During inhalation of either flecainide (40 mg eTLD) or placebo, both systolic and diastolic pressures in subjects of Cohort 2 rose transiently during the initial 1 to 3 minutes and declined toward pre-dose values within the following 10 to 15 minutes after completion of the inhalation (FIGS. 26A and B).

In the subjects of cohort 3, those that inhaled the highest eTLD of 60 mg, the increases in systolic and diastolic BP at or near the time ($T_{max}$) of maximal (peak) concentration ($C_{max}$) of flecainide achieved, were 5 and 4 mmHg, respectively; whereas for subjects that inhaled the placebo solution, the increases were 3 and 2 mmHg, respectively.

Considering the overlapping standard deviations of the mean values, the magnitude of the changes in blood pressure (systolic and diastolic), for subjects receiving either inhaled flecainide or placebo, were similar for all doses tested.

Figure 27A:
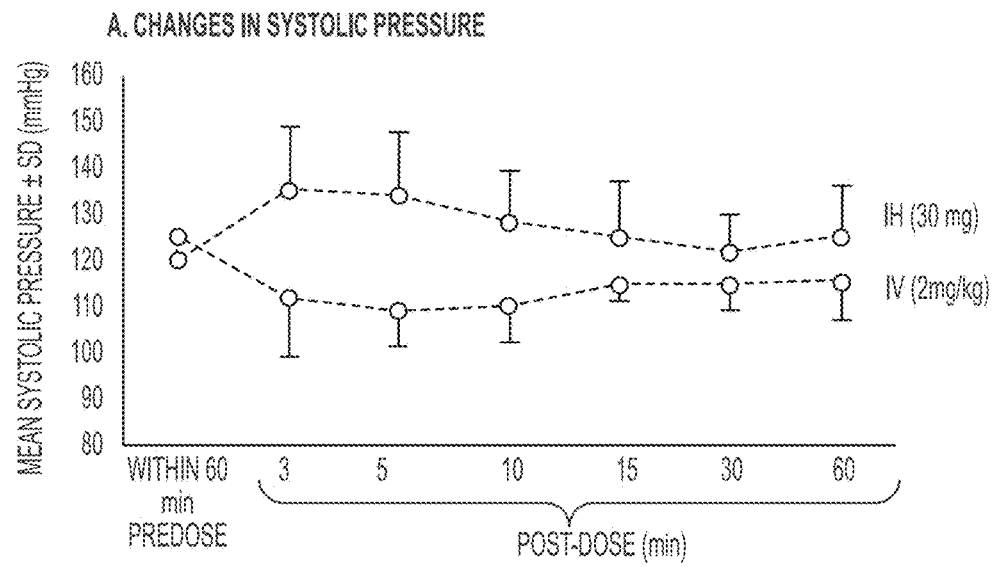
FIG. 27A shows changes in systolic BP from subjects of Cohort 5 following single dose administration of inhaled (IH) flecainide (30 mg eTLD) and IV flecainide (2 mg/kg). Values are the mean±SD.
Figure 27B:
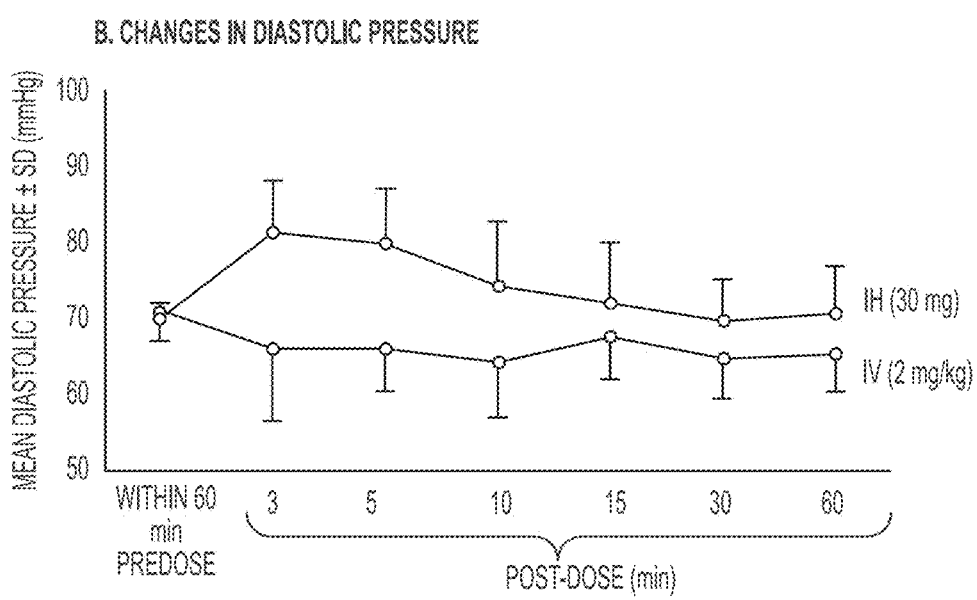
FIG. 27B shows changes in diastolic BP from subjects of Cohort 5 following single dose administration of inhaled (IH) flecainide (30 mg eTLD) and IV flecainide (2 mg/kg). Values are the mean±SD.

Increases in systolic and diastolic BP were observed in subjects of Cohort 5 following single dose administration of inhaled flecainide (30 mg eTLD; FIGS. 27A and B). Decreases in systolic and diastolic BP were observed following IV flecainide administration (2 mg/kg; FIGS. 27A and B).

Figure 73:
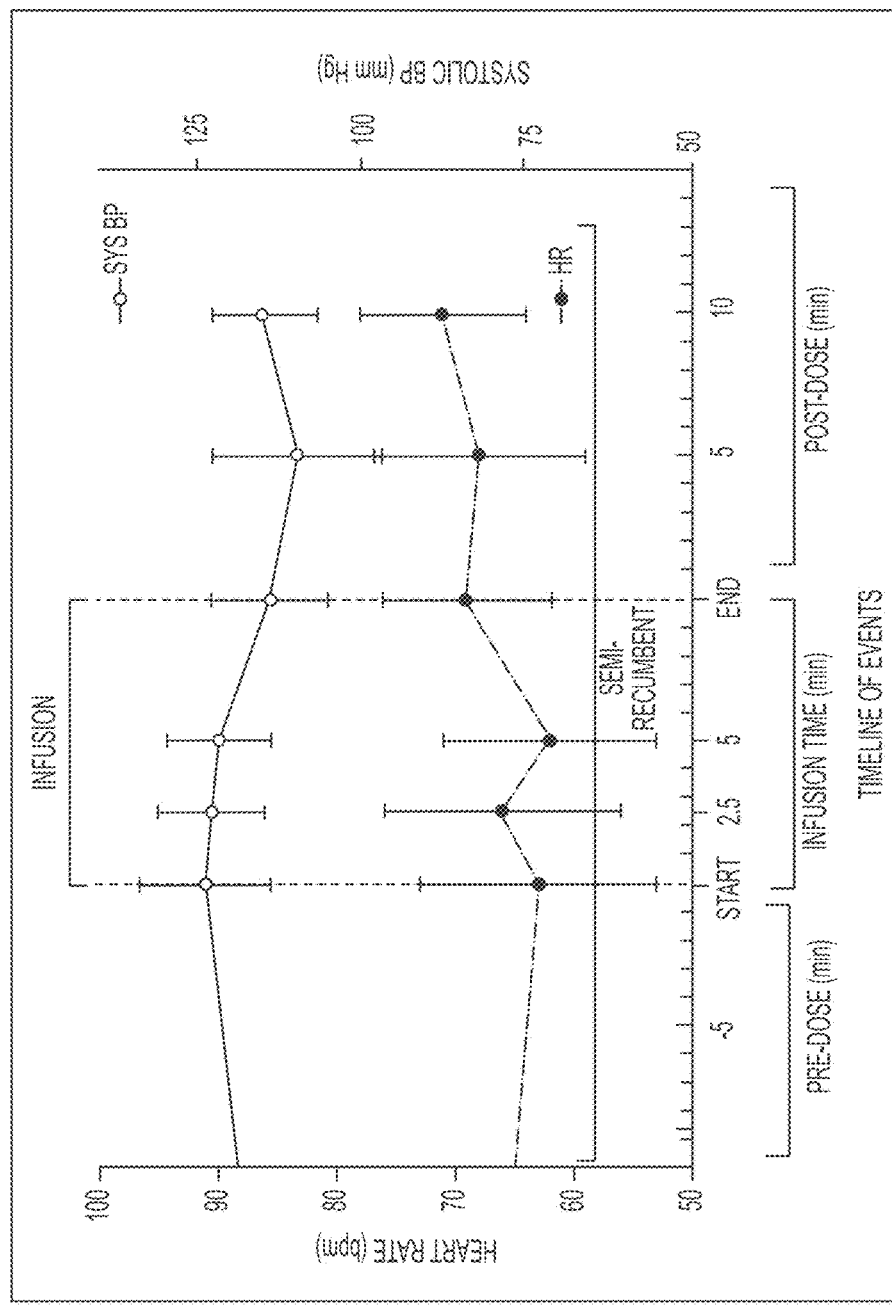
Figure 74:
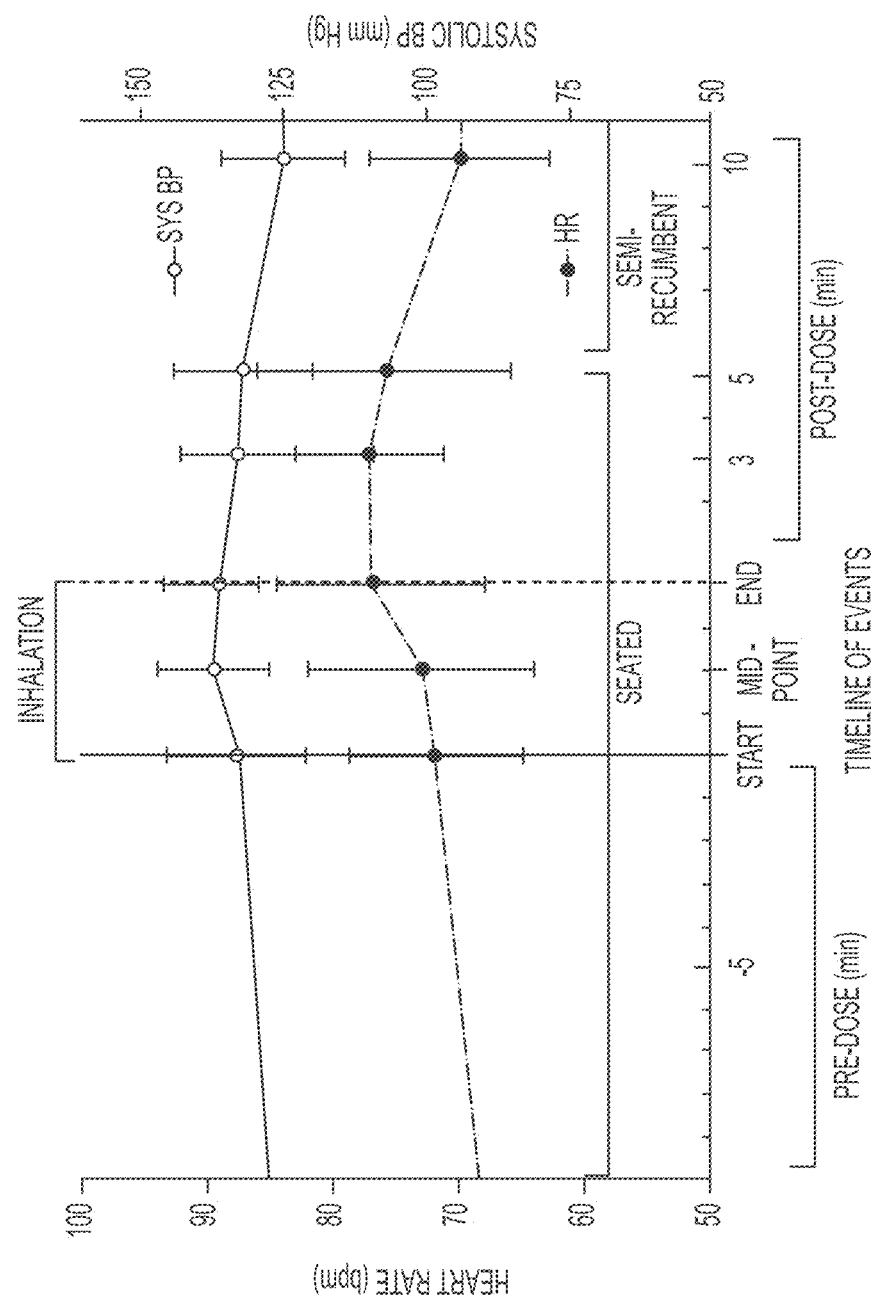
Figure 75A:
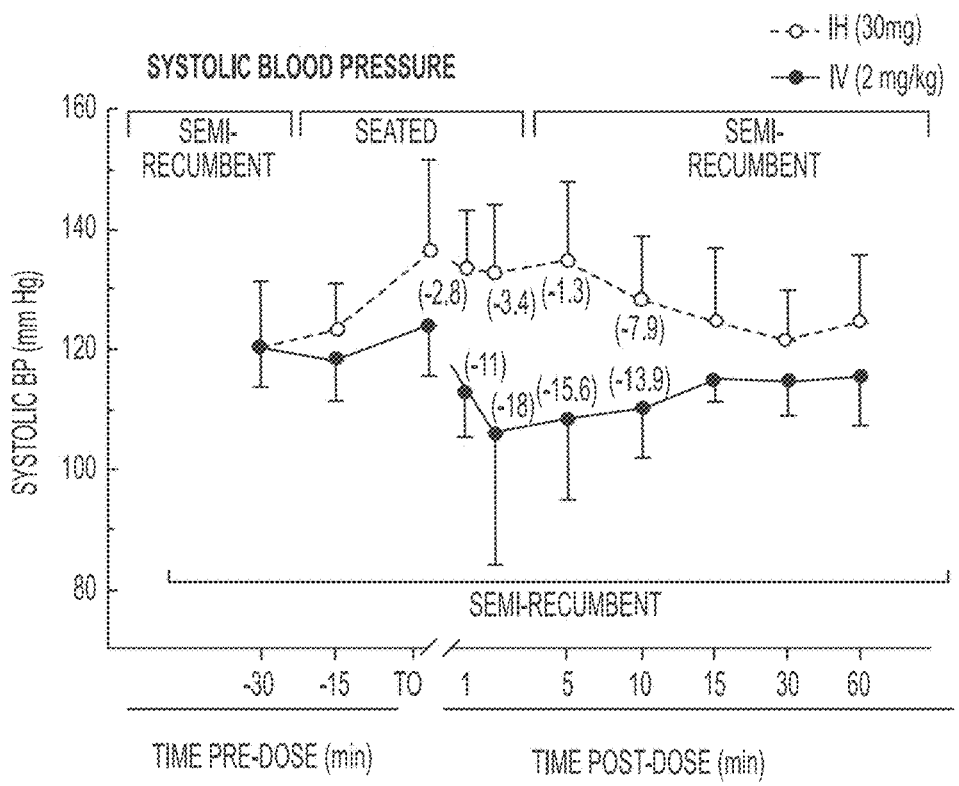
FIG. 75A shows systolic and diastolic blood pressures following flecainide intravenous delivery in 6 subjects.
Figure 75B:
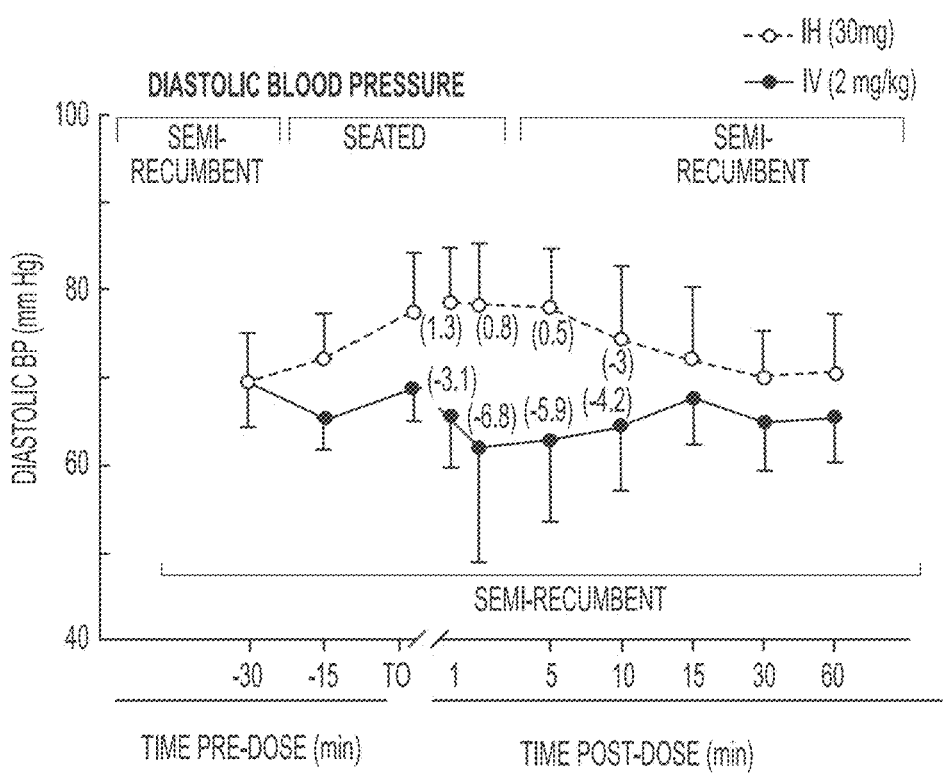
FIG. 75B shows systolic and diastolic blood pressures following flecainide inhalation (IH) administration in 6 subjects.

Further analyses are shown in FIG. 73 with regards to changes in HR and blood pressures after IV flecainide or inhaled flecainide. The maximal increase in HR with administration of IV infusion of flecainide was 7 bpm, at the end of infusion (FIG. 73). The increases in HR during and following the IV infusion of flecainide were accompanied by a transient decrease in systolic pressure of 9 mmHg at the end of infusion (FIG. 73) and as much as 18 mmHg at 3 minutes post-dosing (FIG. 75A). Diastolic pressure decreased by ~2 mmHg at the end of infusion (not shown) and by as much as 7 mmHg at 3 minutes post-dosing (FIG. 75B). The maximal increase in HR with administration of inhaled flecainide was 5 bpm, at the end of inhalation (FIG. 74). During oral inhalation of flecainide, the HR at 1 minute after completion of inhalation (duration of inhalation ~4.5 minutes) increased by 2 bpm (FIG. 74). Not shown at mid-point (1.5 minutes) into the inhalation, the HR, which was highly variable among subjects, increased from 68±12 to 77±17 bpm (data not available for 4 of 6 subjects). The changes in systolic (FIGS. 74 and 75A) and diastolic (FIG. 75B) pressures were rather small, in the range of −3 to +1 mmHg. For the administration via inhalation, the changes, increases or decreases, in HR and BP can be attributed, in part, to the change in posture and/or inhalation procedure (FIGS. 72, 75A and 75B). For the IV infusion, the transient decrease in BP can be attributed to the negative ionotropic effects of flecainide, whereas the increase in HR is due to the baroreceptor reflex triggered by the fall in BP. FIGS. 75A and 75B summarize the changes in systolic (FIG. 75A) and diastolic blood (FIG. 75B) pressures following administration of IV infusion or oral inhalation of flecainide, and it shows a lack of negative hemodynamic effects of inhaled flecainide at an eTLD of 30 mg compared to the −5-fold higher dose (~150 mg) of flecainide given via IV infusion.

Lung Spirometry Measurements:

For all the subjects in Cohorts 1, 2, 3, and 5, all standard lung spirometry measurements (e.g., FEV1, PEF, FVC and FEF 25-75) and peripheral 02 saturation values were normal before and after flecainide or placebo. Likewise, there were minimal or no changes in respiratory rate. There were no differences among cohorts or between randomized treatment assignment.

The results of the lung spirometry tests performed in subjects of Cohort 1 are summarized in Table 1 below.

TABLE 1

Changes in pulmonary function parameters of subjects from Cohort 1 prior to and following oral inhalation of flecainide acetate (20 mg eTLD) and placebo solutions.

| Time Point | Test | Unit | Flecainide (n = 6) | | | Placebo (n = 2) | | |
| --- | --- | --- | --- | --- | --- | --- | --- | --- |
| | | | Mean | Std. Dev | SEM | Mean | Std. Dev | SEM |
| 12 hours Pre-dose | FVC | L | 6.02 | 0.25 | 0.11 | 6.17 | 1.12 | 0.80 |
| | FEV1 | L | 5.26 | 1.25 | 0.51 | 5.19 | 0.95 | 0.67 |
| | PEF | L/s | 11.30 | 1.86 | 0.76 | 9.52 | 0.15 | 0.11 |
| | FEF 25-75 | L/s | 5.38 | 2.13 | 0.87 | 5.67 | 1.05 | 0.75 |
| 3 hours Post-dose | FVC | L | 6.42 | 0.96 | 0.39 | 6.10 | 1.44 | 1.02 |
| | FEV1 | L | 5.27 | 1.22 | 0.50 | 5.14 | 1.11 | 0.78 |
| | PEF | L/s | 10.87 | 1.88 | 0.77 | 10.37 | 2.34 | 1.66 |
| | FEF 25-75 | L/s | 5.48 | 1.99 | 0.81 | 5.48 | 0.99 | 0.70 |
| 24 hours Post-dose | FVC | L | 6.36 | 0.98 | 0.40 | 6.18 | 1.31 | 0.93 |
| | FEV1 | L | 5.18 | 1.27 | 0.52 | 5.25 | 1.03 | 0.73 |
| | PEF | L/s | 11.09 | 2.01 | 0.82 | 10.70 | 2.14 | 1.52 |
| | FEF 25-75 | L/s | 5.40 | 2.73 | 1.12 | 5.69 | 0.84 | 0.59 |

Abbreviations:
FVC = forced vital capacity;
FEV1 = forced expiratory volume in 1 second;
PEF = peak expiratory flow;
FEF25-75 = forced expiratory flow at 25% and 75% intervals The results of the lung spirometry tests performed in subjects of Cohort 2 are summarized in Table 2 below.

TABLE 2

Changes in pulmonary function parameters of subjects from Cohort 2 prior to and following oral inhalation of flecainide acetate (40 mg eTLD) and placebo solutions

| Time Point | Test | Units | Flecainide (n = 10) | | | Placebo (n = 4) | | |
|---|---|---|---|---|---|---|---|---|
| | | | Mean | Std. Dev | SEM | Mean | Std. Dev | SEM |
| 12 hours Pre-dose | FVC | L | 6.18 | 0.96 | 0.32 | 5.56 | 0.53 | 0.26 |
| | FEV1 | L | 5.04 | 0.74 | 0.25 | 4.67 | 0.56 | 0.28 |
| | PEF | L/s | 10.83 | 1.73 | 0.55 | 9.71 | 0.91 | 0.45 |
| | FEF25-75 | L/s | 5.00 | 0.91 | 0.29 | 4.61 | 0.95 | 0.48 |
| 3 hours Post-dose | FVC | L | 6.19 | 0.72 | 0.23 | 5.64 | 0.56 | 0.28 |
| | FEV1 | L | 4.96 | 0.57 | 0.18 | 4.58 | 0.36 | 0.18 |
| | PEF | L/s | 10.66 | 1.94 | 0.61 | 9.59 | 1.28 | 0.54 |
| | FEF25-75 | L/s | 4.34 | 0.77 | 0.24 | 4.51 | 0.54 | 0.27 |
| 24 hours Post-dose | FVC | L | 6.39 | 0.68 | 0.22 | 5.68 | 0.80 | 0.40 |
| | FEV1 | L | 5.08 | 0.51 | 0.16 | 4.60 | 0.66 | 0.33 |
| | PEF | L/s | 11.14 | 1.96 | 0.62 | 9.60 | 1.54 | 0.77 |
| | FEF25-75 | L/s | 4.80 | 0.73 | 0.23 | 4.60 | 0.82 | 0.41 |

The pre-dose and post-dose for all lung function parameters (e.g., FVC, FEV1, PEF, and FEF25-75) were within the normal range for the population studied, and not different from each other. There were no differences between either cohorts (1 vs 2) or groups (placebo vs flecainide) within each cohort (Table 1 and Table 2).

Peripheral oxygen saturation measurements: peripheral oxygen saturation levels measured in subjects of Cohort 1 are summarized in Table 3.

Peripheral oxygen saturation levels measured in subjects of Cohort 2 are summarized in Table 4.

The pre-dose and post-dose values for $SpO_2$ were within the normal range (97-98%) and not different from each other. There were minimal or no differences in $SpO_2\%$ between groups (flecainide vs placebo) and Cohorts (1 vs 2).

Auscultation was normal in all subjects before and after inhalation of flecainide (20 mg eTLD, 30 mg eTLD, 40 mg eTLD) and placebo solutions.

No changes in respiration rate were measured before and after inhalation of flecainide (20 mg eTLD, 30 mg eTLD, 40 mg eTLD) and placebo solutions.

Chest x-rays were normal and showed no changes in subjects before and after inhalation of flecainide (20 mg eTLD, 30 mg eTLD, 40 mg eTLD) and placebo solutions.

TABLE 3

Summary of data on peripheral oxygen saturation ($SpO_2\%$) for subjects of Cohort 1 measured prior to and at various times following inhalation of flecainide acetate solution (20 mg eTLD) or placebo.

| | Time Point | Oxygen Saturation ($SpO2\%$) | | |
|---|---|---|---|---|
| | | Mean | Std. Dev | SEM |
| Flecainide (n = 6) | Predose | 98 | 0.82 | 0.33 |
| | 15 min Postdose | 97 | 1.21 | 0.49 |
| | 30 min Postdose | 97 | 1.60 | 0.65 |
| | 45 min Postdose | 97 | 1.21 | 0.49 |
| | 60 min Postdose | 97 | 0.75 | 0.31 |
| | 75 min Postdose | 98 | 0.84 | 0.34 |
| | 90 min Postdose | 98 | 0.52 | 0.21 |
| | 105 min Postdose | 97 | 0.89 | 0.37 |
| | 120 min Postdose | 98 | 0.55 | 0.22 |
| Placebo (n = 2) | Predose | 98 | 0.71 | 0.50 |
| | 15 min Postdose | 97 | 0.00 | 0.00 |
| | 30 min Postdose | 97 | 1.41 | 1.00 |
| | 45 min Postdose | 97 | 0.71 | 0.50 |
| | 60 min Postdose | 97 | 0.00 | 0.00 |
| | 75 min Postdose | 98 | 0.71 | 0.50 |
| | 90 min Postdose | 98 | 0.71 | 0.50 |
| | 105 min Postdose | 98 | 0.71 | 0.50 |
| | 120 min Postdose | 98 | 0.71 | 0.50 |

TABLE 4

Summary of data on peripheral oxygen saturation ($SpO_2\%$) for subjects of Cohort 2 measured prior to and at various times following inhalation of flecainide acetate solution (40 mg eTLD) or placebo.

| | Time | Oxygen Saturation ($SpO2\%$) | | |
|---|---|---|---|---|
| | | Mean | Std. Dev | SEM |
| Flecainide (n = 10) | Predose | 97 | 0.79 | 0.25 |
| | 15 min Postdose | 96 | 1.81 | 0.57 |
| | 30 min Postdose | 97 | 0.85 | 0.27 |
| | 45 min Postdose | 96 | 0.82 | 0.26 |
| | 60 min Postdose | 96 | 0.92 | 0.29 |
| | 75 min Postdose | 97 | 1.16 | 0.37 |
| | 90 min Postdose | 97 | 0.63 | 0.20 |
| | 105 min Postdose | 97 | 0.88 | 0.28 |
| | 120 min Postdose | 97 | 0.52 | 0.16 |
| Placebo (n = 4) | Predose | 98 | 0.50 | 0.25 |
| | 15 min Postdose | 98 | 0.82 | 0.41 |
| | 30 min Postdose | 98 | 0.50 | 0.25 |
| | 45 min Postdose | 98 | 0.58 | 0.29 |
| | 60 min Postdose | 98 | 0.00 | 0.00 |
| | 75 min Postdose | 98 | 0.58 | 0.29 |
| | 90 min Postdose | 98 | 0.96 | 0.48 |
| | 105 min Postdose | 98 | 0.50 | 0.25 |
| | 120 min Postdose | 98 | 0.50 | 0.25 |

Adverse Events:

In part A of the study, out of 34 subjects studied, 25 were given a flecainide solution via oral inhalation and 9 subjects were given a placebo solution. There was a total of 66 treatment-emergent adverse events (TEAEs) in 28 out of 34 subjects (82%). All adverse events were mild and required no treatment.

In study involving Cohorts 1 and 2, the majority of adverse events lasted between 15-90 minutes. Flecainide was well tolerated, and no subject interrupted the inhalation. Table 5 below summarizes the most common adverse events reported by subjects in Cohorts 1 and 2.

TABLE 5

Summary of the most common adverse events in subjects following inhalation of a flecainide acetate solution or placebo solution

|  | Cohort 1 (n = 8) | | Cohort 2 (n = 14) | |
|---|---|---|---|---|
| Adverse Event | Placebo (n = 2) | Flecainide (n = 6) | Placebo (n = 4) | Flecainide (n = 10) |
| Throat Discomfort/ Irritation | 0 | 2 | 1 | 5 |
| Lightheadedness | 1 | 1 | 0 | 1 |
| Cough | 0 | 1 | 1 | 1 |

A summary of the study-drug related AEs and the assessment of their intensity is summarized in Table 6. From all 34 subjects studied, 24 (71%) had a total of 47 TEAEs that were considered study-drug related. Only 2 (6%) subjects had a total of 3 moderate or severe TEAEs; 1 subject (3%) had 2 TEAEs that were considered study-drug related. No serious adverse events were reported, and no subject had to interrupt the inhalation of the flecainide acetate or placebo solutions.

TABLE 6

Summary of Treatment-Emergent Adverse Events by Treatment by Cohort/Inhaled Flecainide Dose Level and Treatment Type: Part A (Safety Population)

|  | IH Flecainide | | | Total | |
|---|---|---|---|---|---|
|  | 20 mg (N = 6) n (%) | 40 mg (N = 10) n (%) | 60 mg (N = 9) n (%) | Flecainide (N = 25) n (%) | Placebo (N = 9) n (%) |
| Subjects with at least one: |  |  |  |  |  |
| TEAE | 4 (67) | 10 (100) | 8 (89) | 22 (88) | 6 (67) |
| Study Drug Related[1,3] | 2 (33) | 10 (100) | 8 (89) | 22 (80) | 4 (44) |
| Moderate or Severe[2] | 1 (17) | 1 (10) |  | 2 (8) |  |

TABLE 6-continued

Summary of Treatment-Emergent Adverse Events by Treatment by Cohort/Inhaled Flecainide Dose Level and Treatment Type: Part A (Safety Population)

|  | IH Flecainide | | | Total | |
|---|---|---|---|---|---|
|  | 20 mg (N = 6) n (%) | 40 mg (N = 10) n (%) | 60 mg (N = 9) n (%) | Flecainide (N = 25) n (%) | Placebo (N = 9) n (%) |
| Study Drug Related, Moderate or Severe[1,2,3] SAEs |  | 1 (10) |  | 1 (4) |  |
| Number of: |  |  |  |  |  |
| TEAEs | 12 | 24 | 23 | 59 | 7 |
| Study Drug Related[1,2] | 7 | 19 | 17 | 43 | 4 |
| Moderate or Severe[3] | 1 | 2 |  | 3 |  |
| Study Drug Related, Moderate or Severe[1,2,3] SAEs |  | 2 |  | 2 |  |

Abbreviations: N = number of subjects; SAE = serious adverse event; TEAE = treatment-emergent adverse event;
[1]Related TEAE = Probable and Possible Related TEAEs;
[2]Subjects reporting more than one TEAE were counted only once using the strongest study drug relationship category;
[3]subjects reporting more than one TEAE were counted only once using the highest severity grade.

The majority of TEAEs occur in 1 or 2 subjects each; those occurring in >2 subjects across all cohorts and receiving either flecainide or placebo inhalation solution are summarized in Table 7.

The AEs that occurred more frequently in subjects receiving flecainide were oropharyngeal discomfort, shortness of breath (dyspnoea), cough and dry mouth. However, the incidence of AEs reported by the subjects that received flecainide appears not to be dose-dependent. These AEs were considered mild in intensity and required no treatment. Two moderate adverse events (AEs) were reported by one subject from Cohort #2 (40 mg eTLD); lightheadedness and oropharyngeal discomfort.

Of the 43 total TEAEs in the combined flecainide dose groups, 38 (in $19/25$ subjects, 76%) and 5 events in 1 subject (4%) were considered to be probably and possibly study-drug related, respectively. The most frequent events in the total flecainide group were (events, subjects and percentage): Oropharyngeal discomfort: 10 events in $10/25$ subjects (40%); Dyspnoea (shortness of breath): 4 events in $4/25$ subjects (16%); Dizziness: 3 events in $3/25$ subjects (12%); Cough: 3 events in $3/25$ subjects (12%); Dry mouth: 3 events in $3/25$ subjects (12%); Headache: 3 events in $2/25$ subjects (8%); Dysgeusia: 2 events in $2/25$ subjects (8%).

TABLE 7

Summary of Treatment-Emergent Adverse Events in ≥2 Subjects in the Total Flecainide or Placebo Groups by MedDRA System Organ Class, Preferred Term, Cohort/Inhaled Flecainide Dose Level and Treatment Type: Part A (Safety Population)

|  | IH Flecainide Dose Group | | | Total | |
|---|---|---|---|---|---|
| System Organ Class, Preferred Term | 20 mg (N = 6) n (%) [events] | 40 mg (N = 10) n (%) [events] | 60 mg (N = 9) n (%) [events] | IH Flecainide (N = 25) n (%) [events] | Placebo (N = 9) n (%) [events] |
| Nervous system disorders | 2 (33) [4] | 3 (30) [4] | 3 (33) [3] | 8 (32) [11] | 1 (11) [1] |
| Dizziness | 1 (17) [1] | 1 (10) [1] | 1 (11) [1] | 3 (12) [3] | 1 (11) [1] |
| Dysgeusia |  | 2 (20) [2] |  | 2 (8) [2] |  |
| Headache | 2 (33) [3] |  | 2 (22) [2] | 4 (16) [5] |  |
| Respiratory, thoracic, and mediastinal disorders | 3 (50) [5] | 8 (80) [11] | 6 (67) [9] | 17 (68) [25] | 3 (33) [4] |

TABLE 7-continued

Summary of Treatment-Emergent Adverse Events in ≥2 Subjects in the Total Flecainide
or Placebo Groups by MedDRA System Organ Class, Preferred Term, Cohort/Inhaled
Flecainide Dose Level and Treatment Type: Part A (Safety Population)

|  | IH Flecainide Dose Group | | | Total | |
| --- | --- | --- | --- | --- | --- |
| System Organ Class, Preferred Term | 20 mg (N = 6) n (%) [events] | 40 mg (N = 10) n (%) [events] | 60 mg (N = 9) n (%) [events] | IH Flecainide (N = 25) n (%) [events] | Placebo (N = 9) n (%) [events] |
| Cough | 1 (17) [2] | 1 (10) [1] | 1 (11) [1] | 3 (12) [4] | |
| Dyspnoea | 1 (17) [1] | 3 (30) [3] | 2 (22) [2] | 6 (24) [6] | |
| Oropharyngeal discomfort | 2 (33) [2] | 5 (50) [5] | 4 (44) [4] | 11 (44) [11] | 1 (11) [1] |
| Gastrointestinal disorders | | 3 (30) [3] | 5 (56) [8] | 8 (32) [11] | 2 (22) [2] |
| Diarrhoea | | | 2 (22) [2] | 2 (8) [2] | |
| Dry mouth | | 1 (10) [1] | 2 (22) [2] | 3 (12) [3] | 1 (11) [1] |
| General disorders and administration site conditions | | 2 (20) [2] | 1 (11) [2] | 3 (12) [4] | |
| Catheter site pain | | 1 (10) [1] | 1 (11) [1] | 2 (8) [2] | |

Abbreviations: N = number of subjects; SAE = serious adverse event; TEAE = treatment-emergent adverse event;
Note:
If a subject had more than one AE coded to the same MedDRA term, the subject was counted only once.

In the pooled placebo group, there were 4 events in 4/9 subjects (44%) deemed possibly or probably related to study-drug; they were the following: oropharyngeal discomfort, respiratory tract irritation, abdominal discomfort, and dry mouth. No TEAEs related to the study device were reported.

In Part B of the study, all six subjects had a total of 12 and 49 TEAEs during inhaltion (IH) and 10 min IV infusion of flecainide, respectively, that is 4-fold fewer TEAEs with IH than IV (Table 8). All subjects had at least 1 study-drug-related TEAE. All TEAEs reported by subjects following inhalation were mild in intensity whereas following IV infusion, 4 of these in 2 subjects (29%) were considered moderate or severe (Table 8). There were 1 severe and 2 moderate intensity AEs, probably related to the study drug, reported by the same 6 subjects when they received IV infusion of flecainide. The serious AE occurred in a subject in which the IV infusion had to be interrupted for hypotension (systolic BP<65 mmHg) and reported severe lightheadedness (dizziness). There were no SAEs reported with either IH or IV flecainide administration (Table 8).

TABLE 8

Overall Summary of Treatment-Emergent Adverse Events by Flecainide
Dosing Route (IH and IV): Part B (Safety Population)

|  | IH (N = 6) n (%) | IV (N = 7) n (%) |
| --- | --- | --- |
| Number of Subjects with at least one: | | |
| TEAE | 6 (100) | 7 (100) |
| Related TEAEs1 | 6 (100) | 7 (100) |
| Moderate or Severe TEAEs[3] | 0 | 2 (29) |
| Related, Moderate or Severe TEAEs[1,2,3] | 0 | 2 (29) |
| SAE | 0 | 0 |
| Number of | | |
| Treatment-Emergent Adverse Events | 12 | 49 |
| Related TEAEs[1] | 0 | 35 |
| Moderate or Severe TEAEs | 0 | 4 |
| Related, Moderate or Severe TEAEs[1] | 0 | 4 |
| SAEs | 0 | 0 |

Abbreviations: IH = inhaled (30 mg eTLD inhaled flecainide); IV = intravenous (2 mg/kg intravenous flecainide [Tambacor] to a maximum dose of 150 mg); N = number of subjects; SAE = serious adverse event; TEAE = treatment emergent adverse event;
[1]Related TEAE = Probable and Possible Related TEAEs;
[2]Subjects reporting more than one TEAE were counted only once using the strongest study drug relationship category;
[3]Subjects reporting more than one TEAE were counted only once using the highest severity grade.

The majority of the TEAEs occurred in 1 or 2 subjects each; those occurring in ≥2 however, as already pointed out, there were 4-fold fewer TEAEs associated with IH administration compared with IV: 12 events in 6 subjects (average of 2 events per subject), versus 49 events in 7 subjects (average of 7 events per subject), respectively.

The most frequent TEAEs associated with IV infusion of flecainide were the following: dizziness (6 events in 6/7 subjects, 86%) and headache (6 events in 5/7 subjects, 71%). Also, oral paraesthesia, occurred only in conjunction with IV infusion in 3 subjects (43%). Three events of peripheral coldness and chest discomfort in 2 and 1 subject each, and 2 events in 2 subjects each of application site coldness, catheter site pain, chest discomfort, and fatigue were also associated with IV infusion.

TABLE 9

Summary of Treatment-Emergent Adverse Events in ≥2 Total
Subjects by MedDRA System Organ Class, Preferred Term, and
Flecainide Dosing Route (IH and IV) (Part B) Safety Population

| System Organ Class, Preferred Term | IH (N = 6) n (%) [events] | IV (N = 7) n (%) [events] |
| --- | --- | --- |
| Nervous system disorders | | 7 (100) [13] |
| Dizziness | | 6 (86) [6] |

TABLE 9-continued

Summary of Treatment-Emergent Adverse Events in ≥2 Total Subjects by MedDRA System Organ Class, Preferred Term, and Flecainide Dosing Route (IH and IV) (Part B) Safety Population

| System Organ Class, Preferred Term | IH (N = 6) n (%) [events] | IV (N = 7) n (%) [events] |
|---|---|---|
| Headache | | 5 (71) [6] |
| Vascular disorders | | 3 (43) [4] |
| Peripheral coldness | | 2 (29) [3] |
| Respiratory, thoracic and mediastinal disorders | 5 (83) [7] | 2 (29) [3] |
| Oropharyngeal discomfort | 4 (67) [4] | |
| Gastrointestinal disorders | 1 (17) [1] | 5 (71) [6] |
| Hypoaesthesia oral | 1 (17) [1] | 1 (14) [1] |
| Paraethesia oral | | 3 (43) [3] |
| General disorders and administration site conditions | 2 (33) [2] | 4 (57) [13] |
| Application site coldness | | 2 (29) [2] |
| Catheter site pain | | 2 (29) [2] |
| Chest discomfort | 2 (33) [2] | 1 (14) [3] |
| Fatigue | | 2 (29) [2] |

Abbreviations: IH = inhaled (30 mg eTLD inhaled flecainide); IV = intravenous (2 mg/kg intravenous flecainide [Tambacor] to a maximum dose of 150 mg); N = number of subjects; TEAE = treatment-emergent adverse event;
Note:
If a subject had more than one AE coded to the same MedDRA term, the subject was counted only once.

With IH administration of flecainide, oropharyngeal discomfort was the most frequent TEAE occurring in 4 of $\frac{4}{6}$ subjects (67%). The only other TEAE associated with IH administration that occurred in more than 1 subject was chest discomfort, in 2 of $\frac{2}{6}$ subjects (33%). However, 3 such events also occurred in 1 subject in conjunction with IV infusion of flecainide.

Among the TEAEs associated with both IH and IV infusion, 9 such events from a total of 12, and 35 events from a total of 49, respectively were considered study-drug related. The type of study-drug related events associated with IV infusion of flecainide were the following: dizziness (6 events in 6 subjects), and headache (5 events in 5 subjects), and paresthesia oral (3 events in 3 subjects). Other study-drug related events associated with IV flecainide administration were: peripheral coldness, palpitations, and chest discomfort, each occurring 2 times 1 subject, and 2 occurrences in 2 subjects of application site coldness.

There were 4 probably study-drug related events associated with IH administration of flecainide; oropharyngeal discomfort in 4 subjects, the remaining 5 study-drug related events for the IH administration route all occurred once in 1 subject each. They were cough, dysphonia, dyspnoea, oral hypoesthesia and chest discomfort. No TEAEs were considered to be related to study device.

Figure 28:
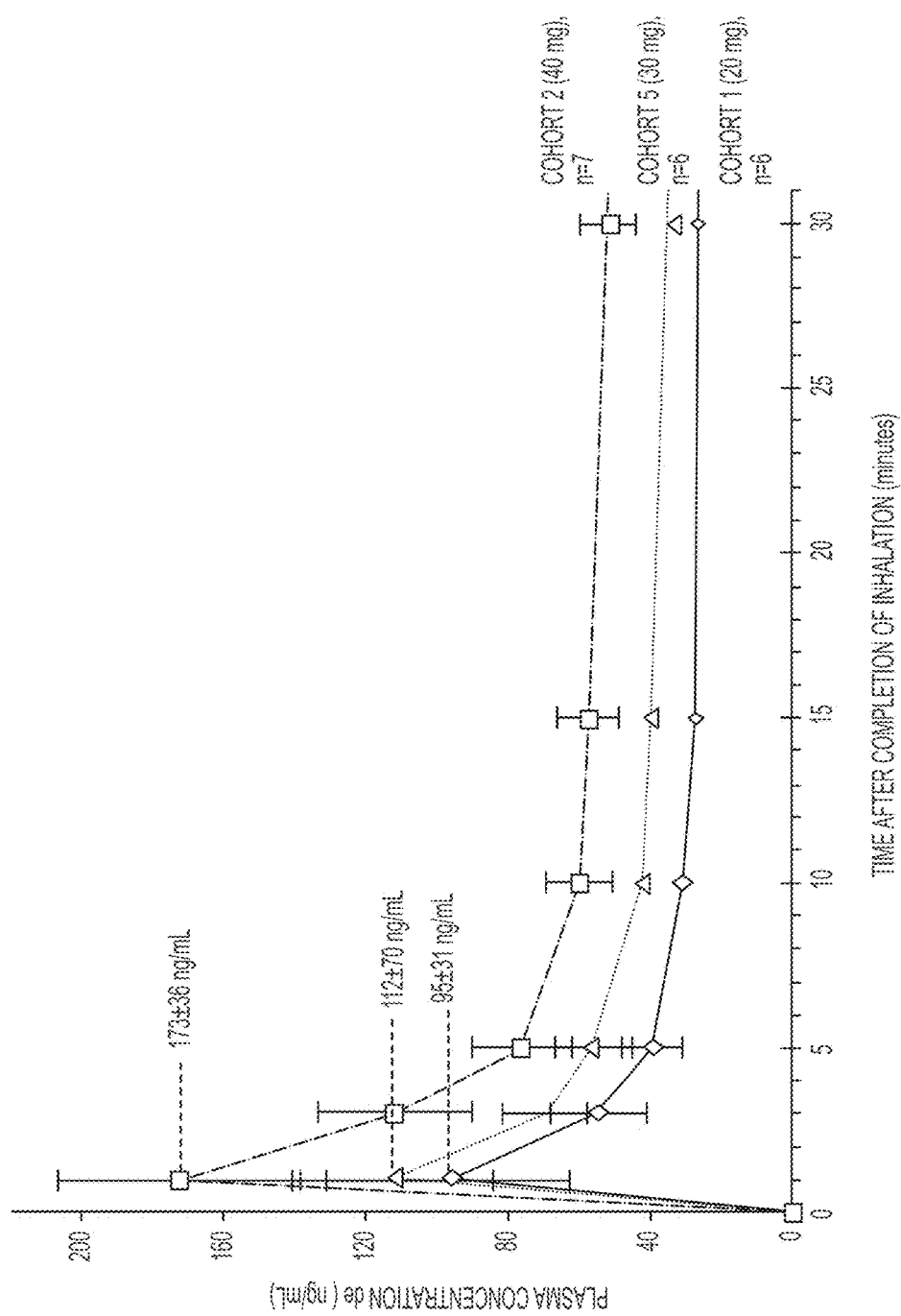
FIG. 28 shows mean venous plasma concentration-time curves following inhalation of 20 mg eTLD, 30 mg eTLD, and 40 mg eTLD of flecainide acetate solution.

Pk Results:

Initial analyses demonstrated that oral inhalation of flecainide acetate solution (20 mg eTLD, 30 mg eTLD, or 40 mg eTLD) resulted in venous plasma concentrations of drug that exhibited near dose proportionality (FIG. 28).

Figure 76A:
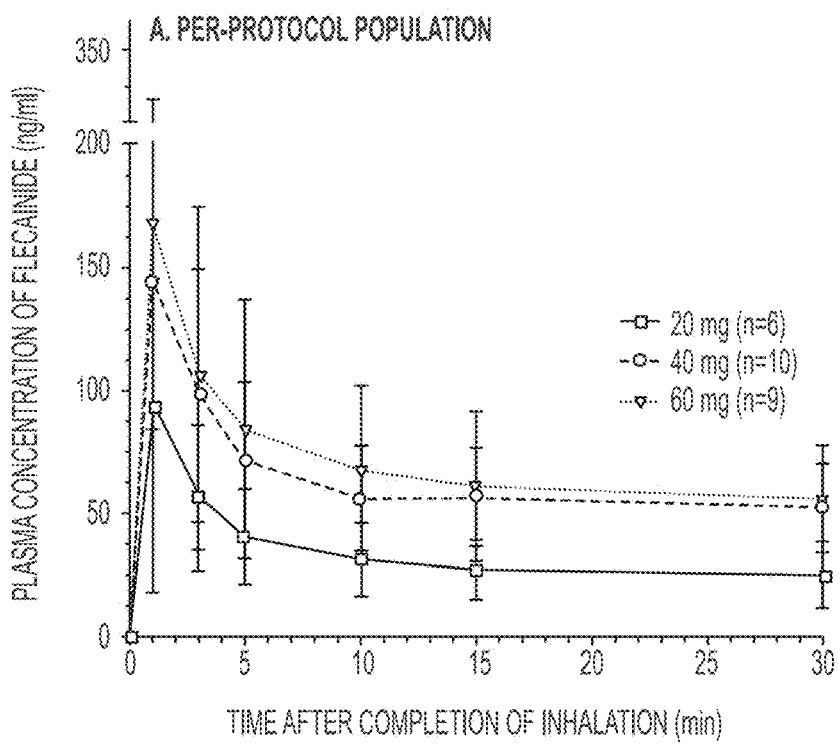
FIGS. 76A and 76B show venous plasma concentration-time curves of the per-protocol population and post-hoc population following oral inhalation of 20, 40, and 60 mg eTLD flecainide, respectively.
Figure 76B:
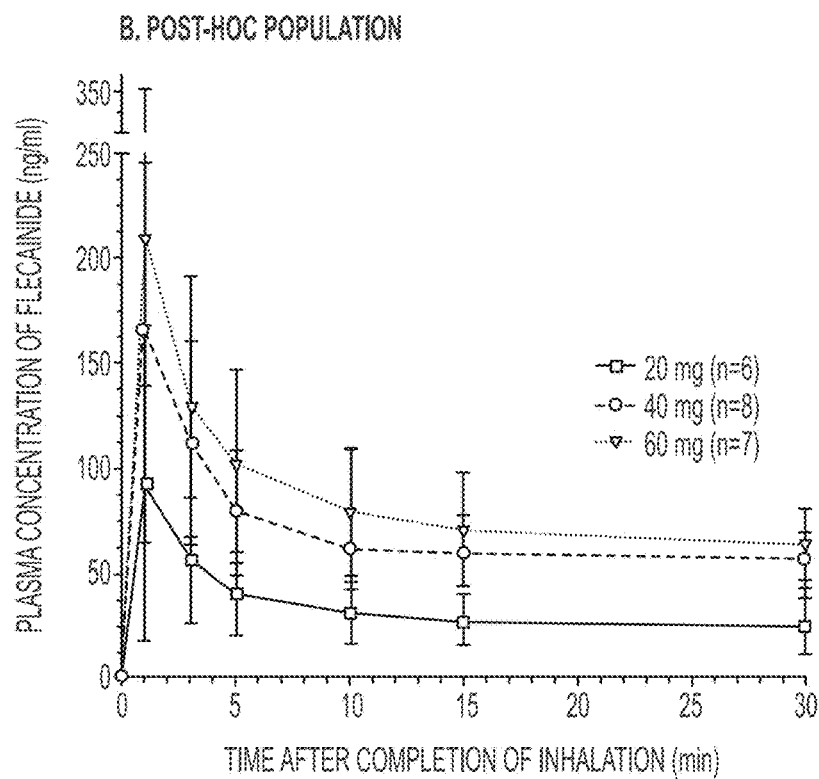

FIGS. 76A and 76B show plots of the mean plasma flecainide concentration versus time for the eTLDs of 20, 40 and 60 mg eTLD oral inhalation doses generated per protocol (FIG. 76A) and from post-hoc (FIG. 76B) datasets. In the majority of the subjects (21 of 25 subjects, 84%), following completion of oral inhalation (IH) of flecainide acetate solution, the venous plasma concentration of drug rose rapidly, within 1 to 3 minutes after completion of inhalation, and quickly declined. In two subjects, each in the 40 and 60 mg eTLD cohorts, the Tax values (e.g., time to occurrence of the maximum plasma concentration) were greater than 15 minutes, (e.g., ranged from 20 min to 4 hours) after the end of inhalation, and, in addition, the $C_{max}$ (e.g., maximum plasma concentration) values were 3-fold lower (see below) than the other 21 subjects. Removal of all data from these four subjects from the main analysis (e.g., per-protocol) dataset had minimal effect on the range and distribution of all pharmacokinetic parameter values. However, the $C_{max}$ of the two subjects (70.9 and 43.5 ng/ml) from the 40 mg eTLD cohort were 3.0-fold lower and for the two subjects (82.3 and 51.3 ng/ml) from the 60 mg eTLD cohort were 3.4-fold lower than the mean $C_{max}$ values of the remaining subjects of the respective cohorts. Inclusion of $C_{max}$ data from these subjects markedly increased the range of $C_{max}$ values and consequently, the PD data from these subjects were also excluded from subsequent analyses. The dataset that excludes these four subjects is referred to as post-hoc dataset (FIG. 76B). The data described in the text, presented in the tables and figures, hereinafter, are from the post-hoc population, which does not include data from the four subjects mentioned above.

Table 10 summarizes the estimates of the pharmacokinetic (PK) parameters of flecainide administered via oral inhalation with a rapid distribution phase lasting ~10-15 minutes (estimated $t_{1/2\alpha}$ of 3.5-4.2 minutes) and elimination $t_{1/2\beta}$ of 9-12 hours. The distribution phase and elimination half-life were independent of the doses of flecainide. The $C_{max}$ and $AUC_{Last}$ were dose-dependent. It is noteworthy that the venous plasma concentration-time curves for flecainide (eTLDs of 20, 40, or 60 mg eTLD) administered via oral inhalation or via IV infusion are similar (see FIGS. 84A and 84B). The great similarity in the concentration-time profile curves between flecainide delivered via oral inhalation and IV infusion (shown in FIGS. 84A and 84B) indicates comparable pharmacokinetics by these two routes of administration. This finding is relevant because the IV route of administration of 2 mg/kg (or maximum 150 mg) of flecainide has been established to be safe and highly efficacious in converting recent onset symptomatic AF into NSR.

Figure 29A:
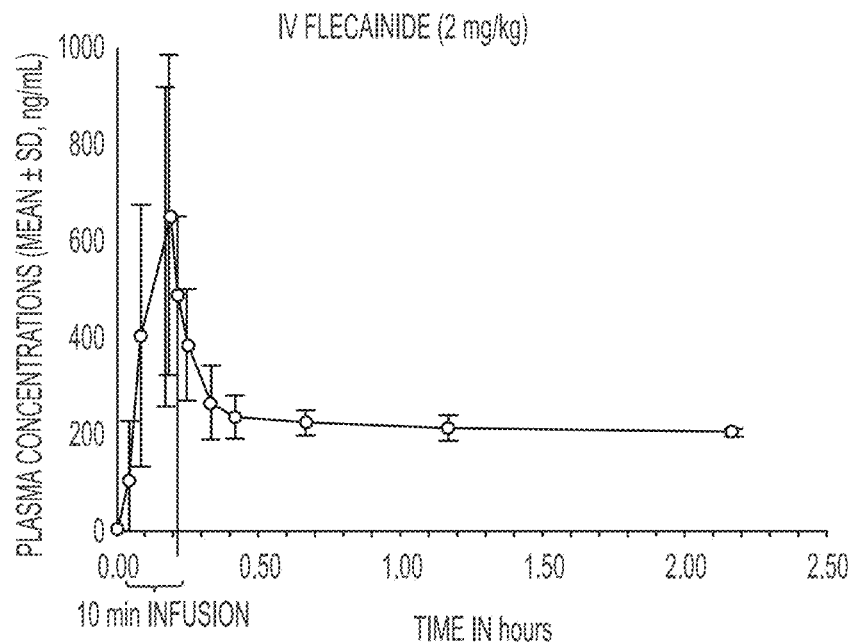
FIG. 29A shows the mean venous plasma concentration-time curve following administration of flecainide acetate solution by IV (2 mg/kg). Data points represent the mean±SD.
Figure 77A:
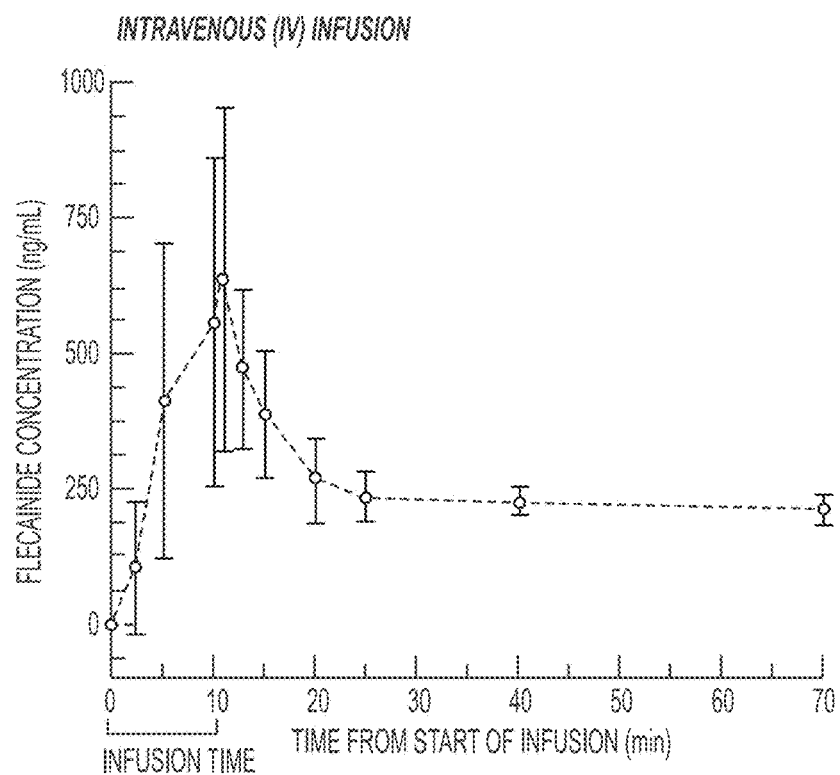
FIGS. 77A and 77B show venous plasma concentration-time curves following intravenous infusion and inhalation of flecainide, respectively.
Figure 77B:
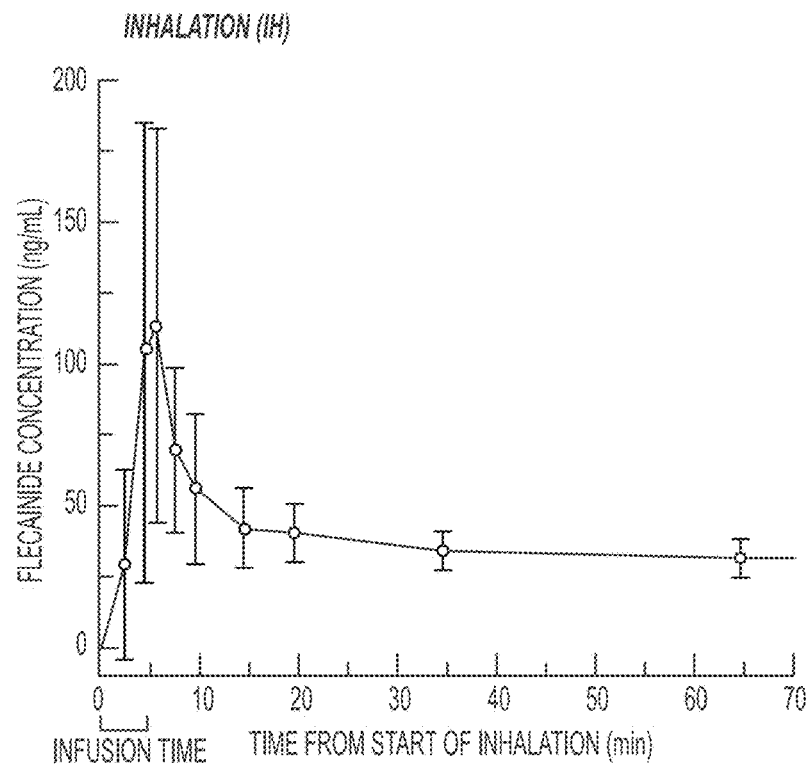

Part B study provided comparison of PK profiles between IV flecainide and inhaled flecainide. In subjects of Cohort 5, the venous plasma concentration-time curves for inhaled flecainide (30 mg eTLD) were similar to those for flecainide administered via IV infusion (2 mg/kg; FIGS. 29A and B). The peripheral venous plasma concentration-time curves for flecainide delivered via IV infusion (2 mg/kg over 10 min; total dose of 149±17 mg) or inhalation (eTLD of 30 mg) are also replotted on a different time scale in FIGS. 77A and 77B. Peak plasma concentrations of flecainide ($C_{max}$) following intravenous administration and inhalation were 749±308 and 120±70 ng/ml, respectively. The time to $C_{max}$ ($T_{max}$) for intravenous infusion was between 1 and 60 minutes after the end of 10 min infusion, and ≤1 min post-inhalation (Table 11). The mean time to complete the inhalation of 30 mg eTLD of flecainide in the six subjects was 4.5 min. The summary of the pharmacokinetic parameters ($C_{max}$, Distribution ($t_{1/2\alpha}$) and Elimination ($t_{1/2\beta}$) half-lives) are presented in Table 11. Distribution phase and elimination half-life were nearly identical for intravenous infusion and inhalation: 4.7±01.4 min and 10.0±1.8 hrs, respectively, for intravenous, and 4.3±1.5 min and 10.1±2.0 hrs, respectively, for inhalation. Furthermore, the distribution and elimination half-lives following intravenous administration in this Phase 1 study were similar to those published in the literature for intravenous flecainide.

TABLE 10

Summary of PK Values of Flecainide administered
via Oral Inhalation or IV

| Route of Administration | $T_{max}$ min | $C_{max}$ ng/mL | $AUC_{Last}$ Hr · ng/mL | Elim. $t_{1/2\beta}$ hours | Dist. $t_{1/2\alpha}$[#] min |
|---|---|---|---|---|---|
| Inhaled (20 mg) n = 6 | 1 (1, 3) | 95.1 (79) | 421 (45) | 9.87 (25) | 3.86 (34) |
| Inhaled (40 mg) n = 8* | 1 (0, 1) | 173 (47) | 685 (26) | 9.0 (24) | 4.19 (39) |
| Inhaled (60 mg) n = 7* | 1 (0, 3) | 232 (78) | 946 (22) | 12.0 (14) | 3.47 (17) |

All values for inhaled flecainide are arithmetic mean (CV %) except $T_{max}$ values (measured from end of inhalation) which are median (min, max).
*Based on PK cut-off criteria of $T_{max} \geq 15$ min, data from 2 subjects were excluded.
[#]Data from 1 subject from 20 and 40 mg eTLD cohorts and 3 subjects from the 60 mg eTLD cohort could not be estimated.

Figure 29B:
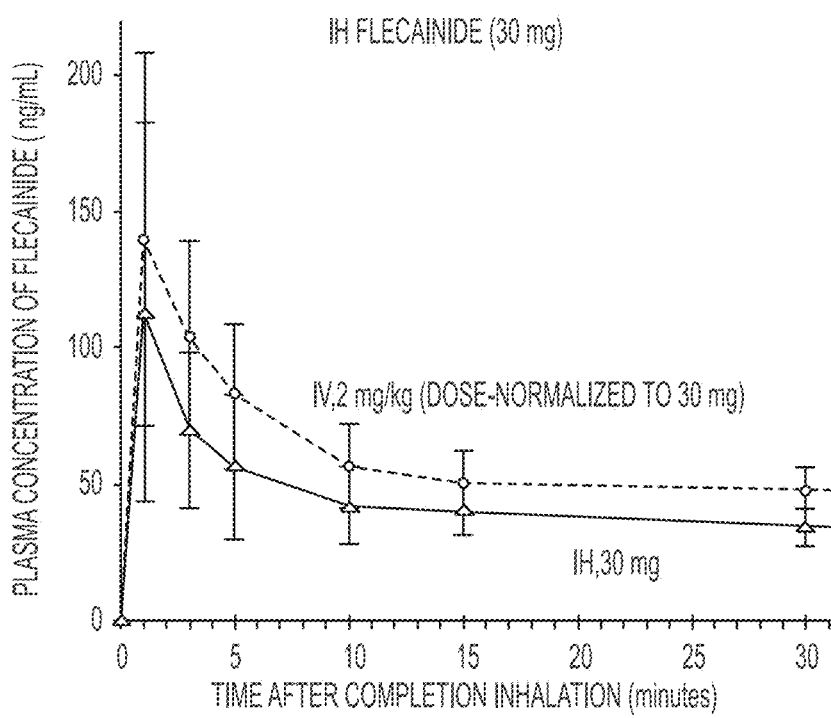
FIG. 29B shows mean venous plasma concentration-time curves following administration of flecainide acetate solution by inhalation (IH; 30 mg eTLD) or IV (2 mg/kg). Data points represent the mean±SD.
Figure 78:
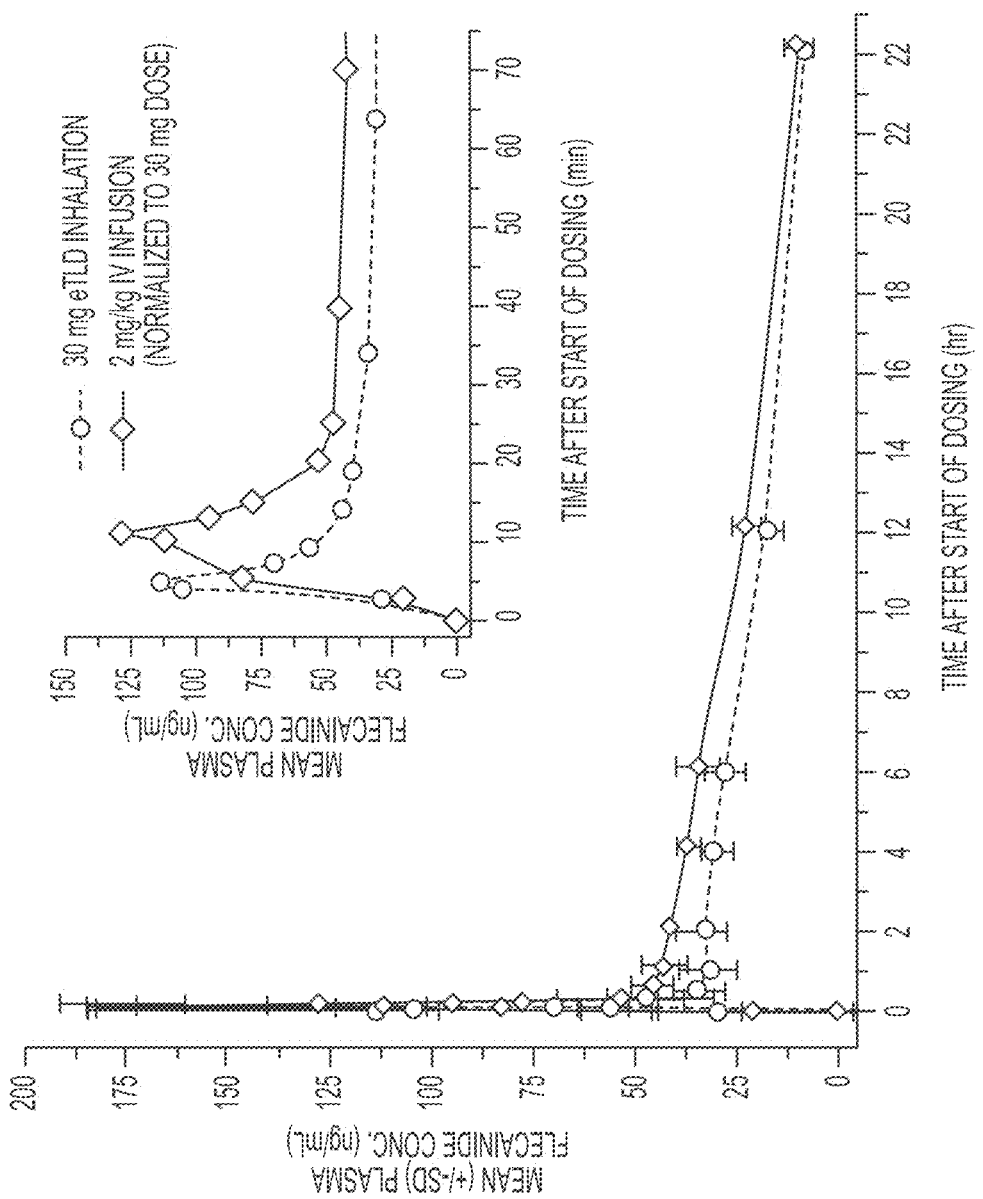

To directly compare the PK profiles of flecainide given via IV infusion and oral inhalation, the mean±/−SD plasma flecainide concentration vs time for the IV dose was normalized to 30 mg in order to match the 30 mg eTLD oral inhalation dose. FIG. 29B and FIG. 78 show the comparison between the normalized plasma flecainide concentration of IV infusion and plasma flecainide concentration of inhalation on different time scales, respectively. The resulting concentration-time profile curves are near-identical, indicating comparable pharmacokinetics by these two routes of administration.

TABLE 11

Summary of PK values of Flecainide Administered
via IH or IV and from Literature (shaded)

| Route of administration | $T_{max}$ (min after EOI) | $C_{max}$ (ng/mL) | $AUC_{last}$ (hr*ng/mL) | Dist. $t_{1/2}$ (min) | Elim. $t_{1/2}$ (hr) |
|---|---|---|---|---|---|
| IV (2 mg/Kg) Cohort 5, n = 6 | 1 (0, 60) | 749 (41) | 3051 (11) | 4.28[#] (36) | 10.0 (18) |
| Inhaled (30 mg) Cohort 5, n = 6 | 0.5 (0, 1) | 120 (59) | 487 (20) | 4.67[#] (30) | 10.1 (20) |
| IV (2 mg/Kg)* n = 3 (Mean ± SEM) | 10.0 | 1644 ± 534 | 4211 ± 456 | 2.6 ± 0.7 | 9.3 ± 0.1 |

EOI = end of inhalation or infusion
All values (from Part B of study, shown in rows 1-2) are arithmetic mean (CV %) except $T_{max}$ values which are median (min, max)
[#]Data from 1 subject in the IH arm and 2 subjects in the IV arm could not be estimated
*Tambacor package insert, 2012, Eisai Co. Ltd.

Figure 31:
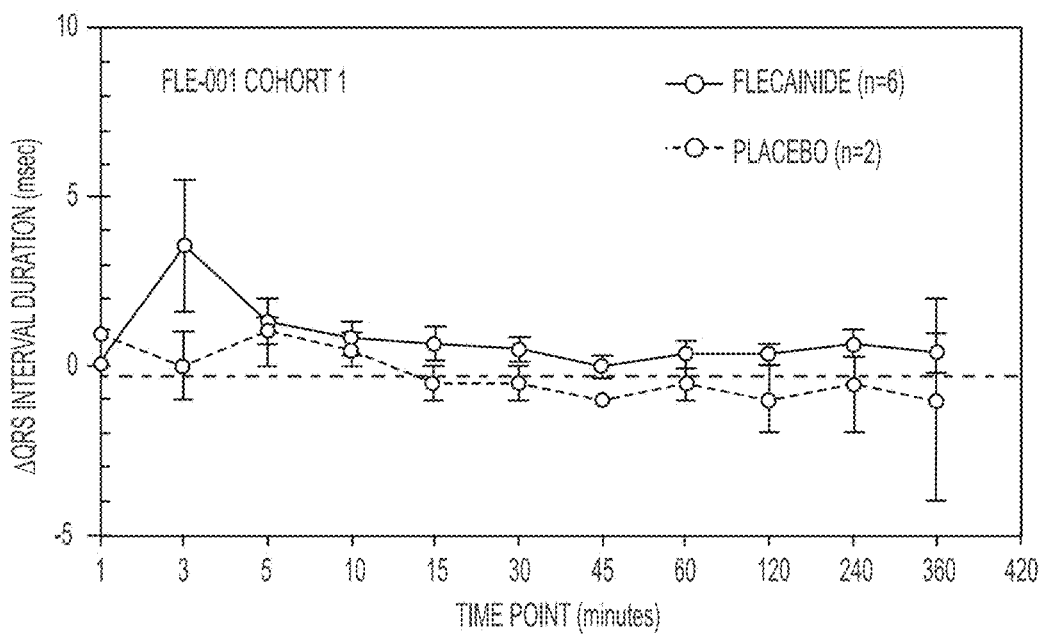
FIG. 31 shows the time course of the changes in QRS interval duration (ΔQRS) relative to the baseline (pre-dose) following oral inhalation of 20 mg eTLD of flecainide acetate solution and placebo. Values are the mean±SEM; n=6 (flecainide), n=2 (placebo).

Pd Results:
QRS Interval Duration:

There was a small increase of mean ΔQRS (mean change from baseline, pre-dose QRS interval duration) between 1 and 3 minutes after the end of flecainide inhalation in subjects of Cohort 1. FIG. 31 shows the time course of the changes in QRS interval duration (ΔQRS) in 6 subjects following the inhalation of 20 mg eTLD of flecainide and in 2 subjects following the inhalation of placebo.

Figure 32:
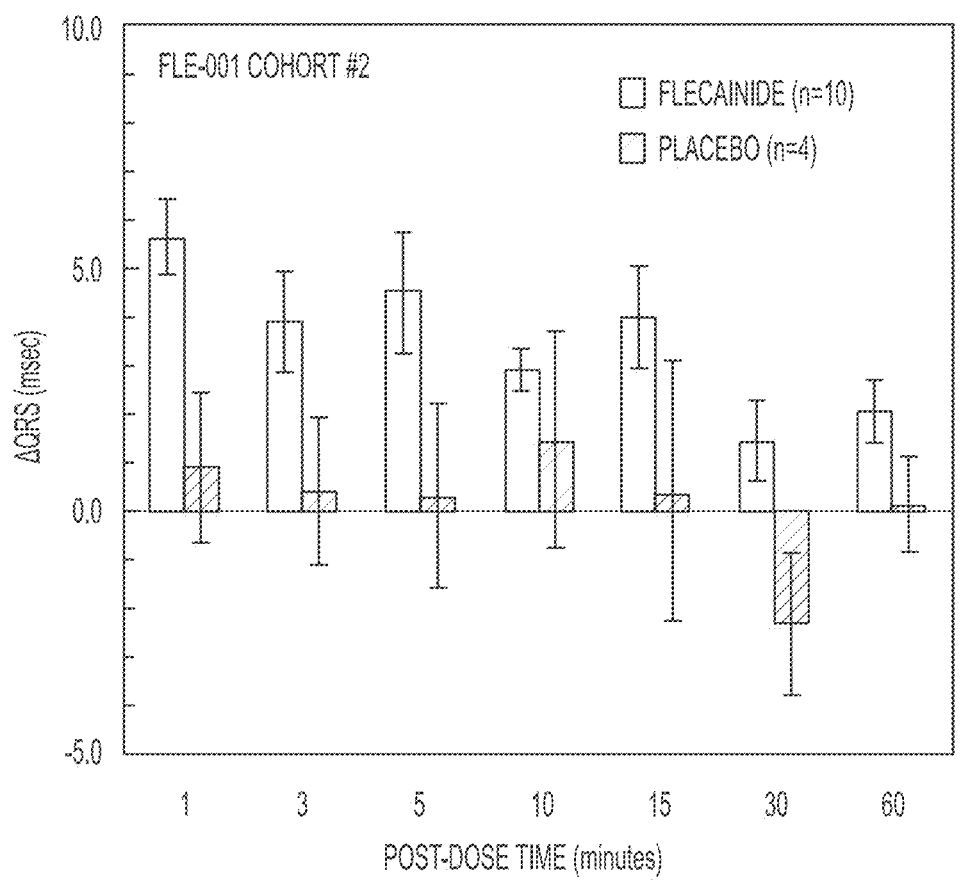
FIG. 32 shows the time course of the changes in QRS interval duration (ΔQRS) relative to the baseline (pre-dose) following oral inhalation of 40 mg eTLD of flecainide acetate solution and placebo. Values are the mean±SEM; n=10 (flecainide), n=4 (placebo).

There was a transient increase between 1 and 3 minutes post-dosing in the QRS duration in subjects of Cohort 2 (40 mg eTLD flecainide); in the majority of subjects, the maximal increase in the QRS interval duration (ΔQRS) was observed at 1 minute post-dosing. The changes in QRS interval duration for the 10 subjects of Cohort 2 that were exposed to inhaled flecainide are depicted in FIG. 32.

Figure 33A:
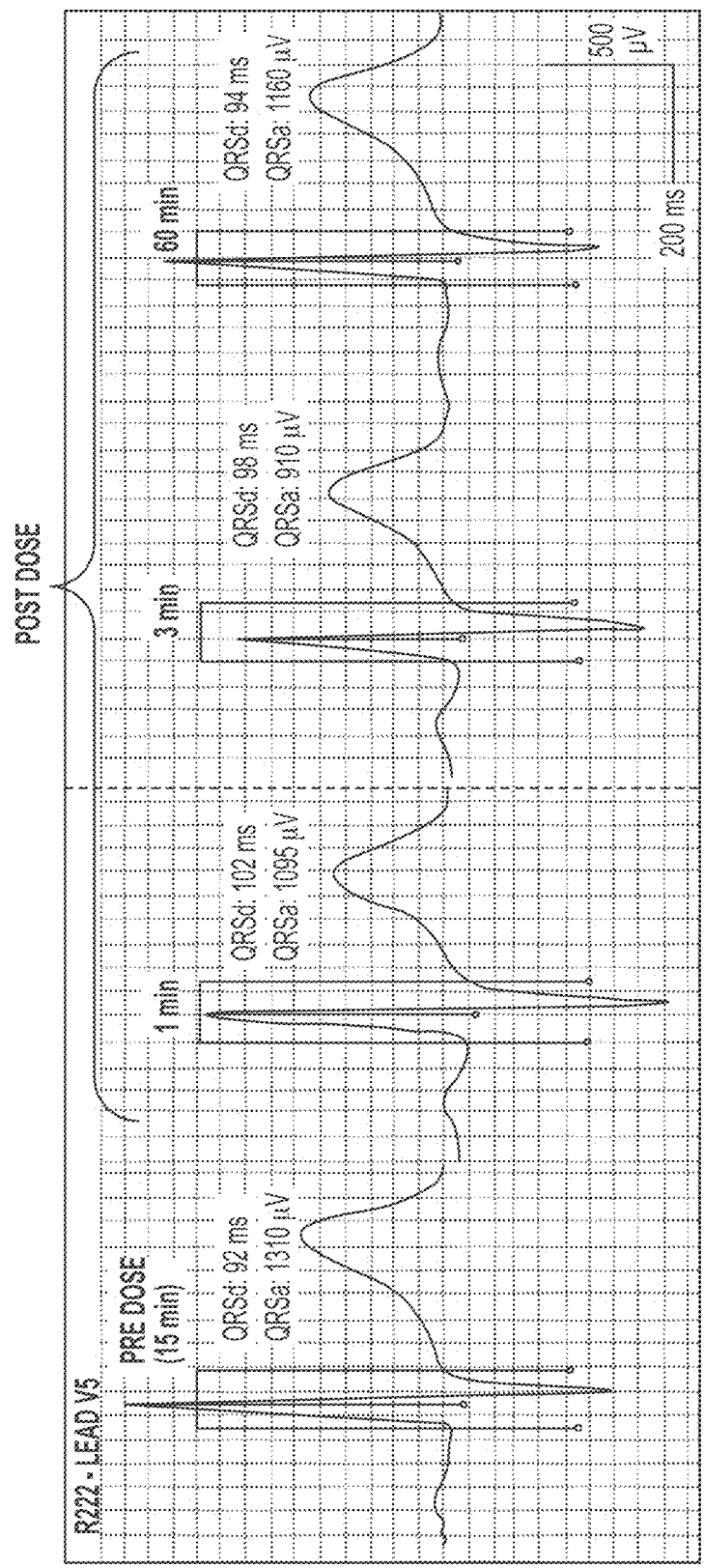
FIG. 33A shows selected digitized electrocardiographic (ECG) tracings from lead V5 depicting the P-, QRS- and T-wave complexes recorded prior to (pre-dose) and at various times after (post-dose) completion of inhalation of 40 mg eTLD of flecainide. Denoted in each panel are the values of the QRS interval duration in milliseconds (QRSd, ms) and R-wave amplitude in microvolts (QRSa, µV).
Figure 33B:
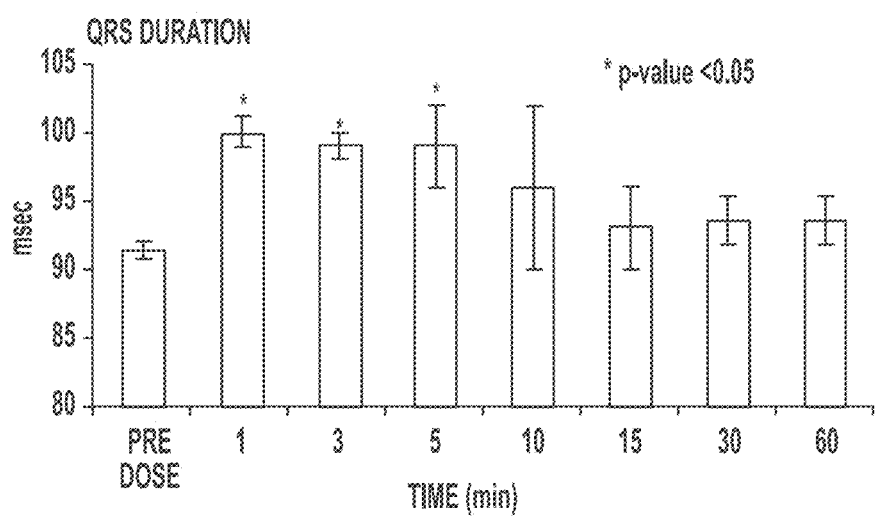
FIG. 33B shows bar graphs summarizing the time course of changes in QRS interval duration measured from ECGs at the respective times and obtained from the same subject in FIG. 13A. *p<0.05.
Figure 33C:
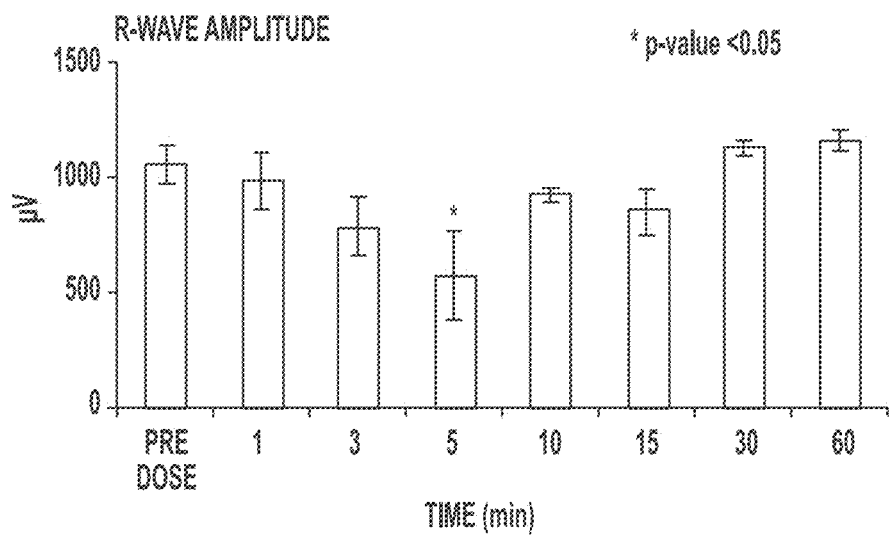
FIG. 33C shows bar graphs summarizing the time course of changes in R-wave amplitude measured from ECGs at the respective times and obtained from the same subject in FIG. 13A. *p<0.05.

Representative ECG tracings from an individual subject (R222) in Cohort 2 who was exposed to inhaled flecainide (40 mg eTLD) acetate solution are shown in FIG. 33A. The ECG tracings show that the QRS duration (QRSd) increased by 10 msec at 1 minute post-dosing, whereas the amplitude of the R-wave (QRSa) decreased by 400 μV at 3 min post-dosing. The bar graphs summarize the average changes in QRS interval duration (FIG. 33B) and R-wave amplitude (FIG. 33C) of subject R222 recorded from several tracings of ECGs for each time point. The maximal increase in duration (~9 msec) and decrease in amplitude (~480 μV) of the QRS interval complexes were transient and statistically significant (p<0.05).

Figure 79:
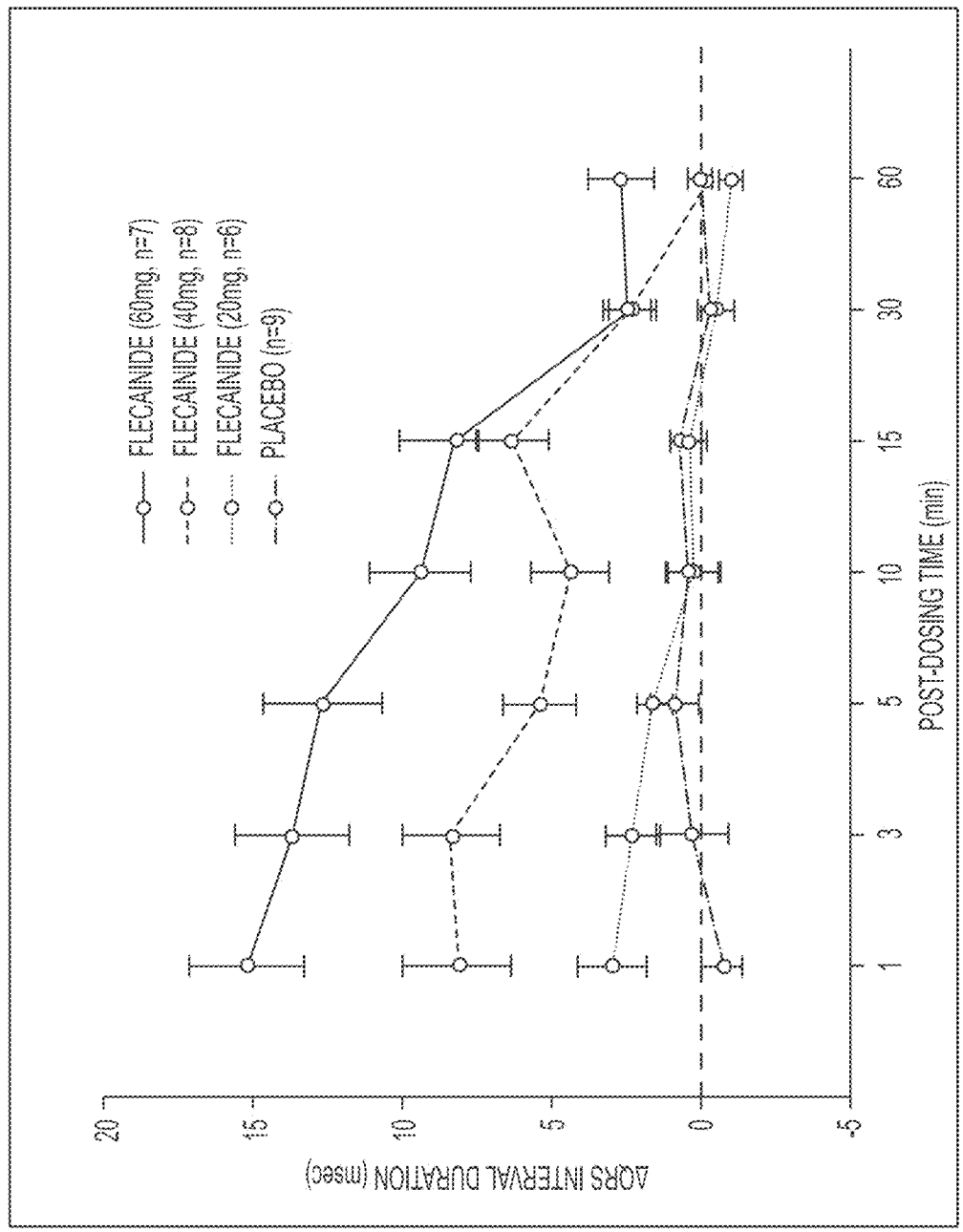

The time course of changes in the QRS interval duration in Cohorts 1, 2, and 3 were all plotted following after completion of inhalation either inhalation of flecainide acetate or placebo solutions (FIG. 79; only data for post-hoc population). The magnitude of QRS prolongation at 1 min post-inhalation dosing was minimal (3.0 msec) with the eTLD of 20 mg eTLD, intermediate (8.2 msec) with the 40 mg dose and attained a maximum of 16 msec with the 60 mg eTLD. The magnitude of the maximal QRS widening achieved following the administration of the three doses were 2.9-fold between 20 mg eTLD and 40 mg eTLD, and 4.5-fold between 20 mg eTLD and 60 mg eTLD. Once the maximal QRS interval prolongation was achieved (1 to 3 minutes, in general), the QRS interval duration decreased as a function of time; at 30 min after completion of inhalation, the QRS interval duration returned to near pre-dose levels. At 2, 4, 6, 8 and 24 hours post-inhalation dosing, the QRS interval durations, for all subjects of the 3 cohorts, remained unchanged at near the pre-dose (baseline) values (range 80 to 90 msec). Subjects who received placebo had minimal changes in QRS interval, at any timepoint.

Figure 34:
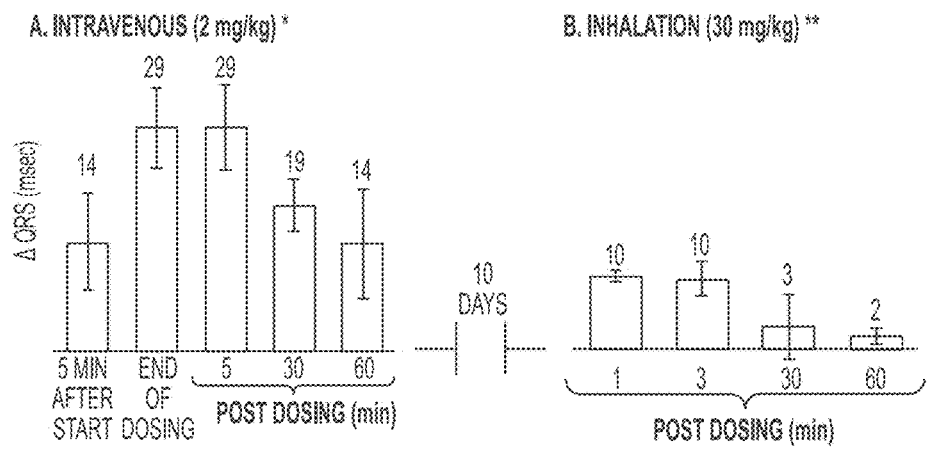
FIG. 34 shows the changes in QRS interval duration (ΔQRS) relative to the baseline (pre-dose) in subjects of Cohort 5 (IV-inhalation crossover) following A) administration of flecainide acetate solution by IV (2 mg/kg; *10 min infusion, intraventricular conduction delay lasted 5-10 min) and B) oral inhalation of 30 mg eTLD of flecainide acetate solution (**4 min inhalation).
Figure 80A:
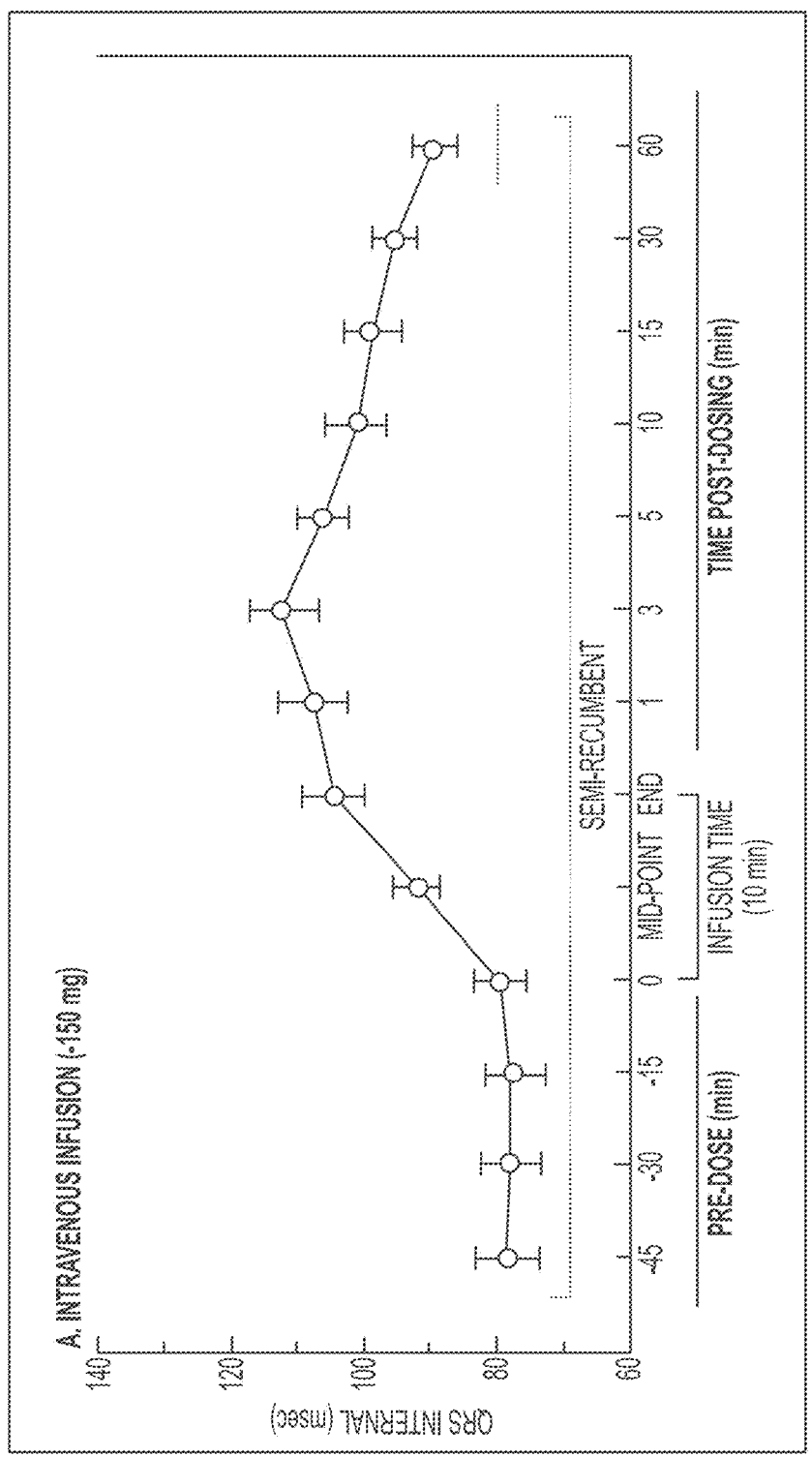
FIGS. 80A and 80B show time courses of changes in QRS interval duration following flecainide via IV infusion and oral inhalation, respectively.
Figure 80B:
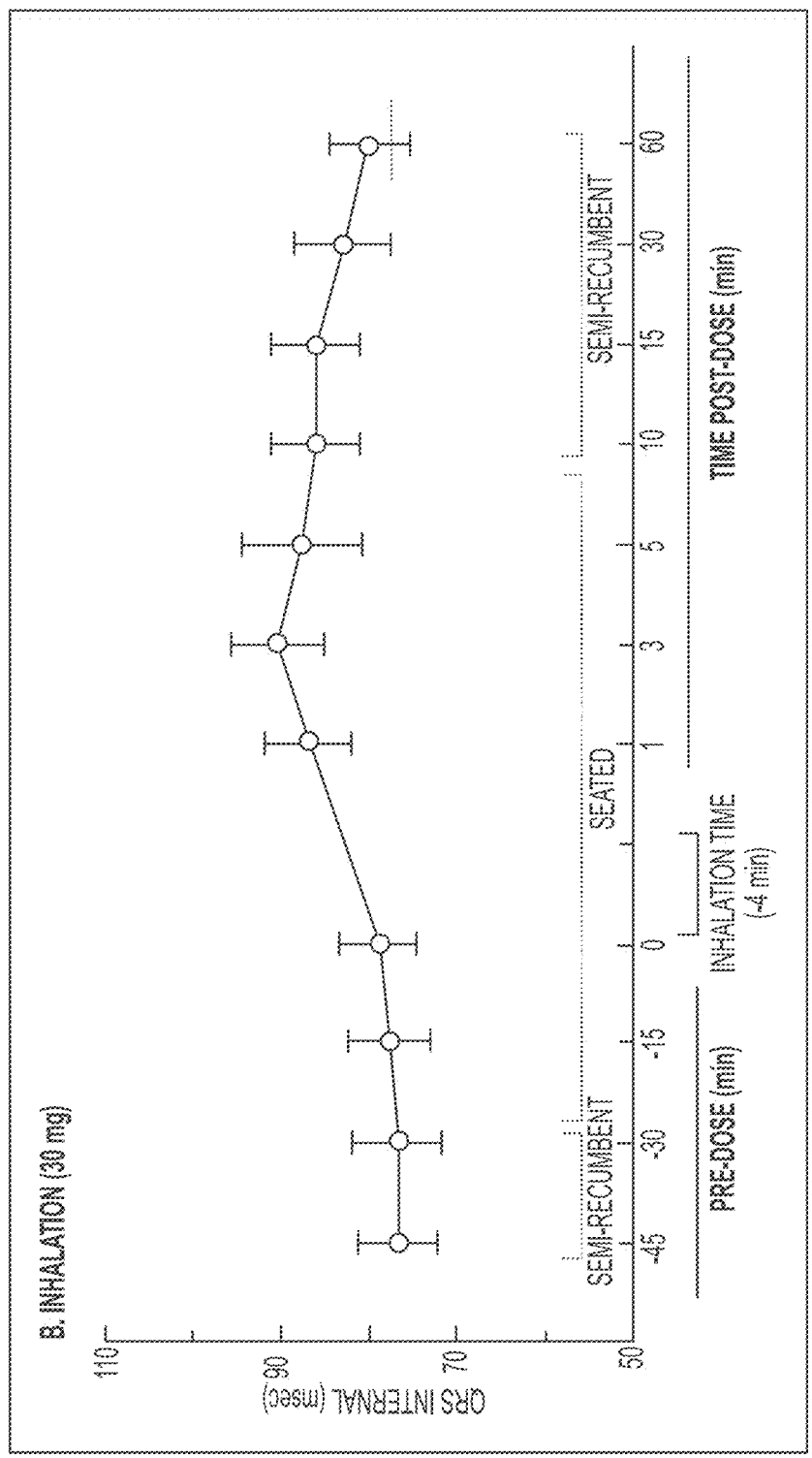

In Part B study, the time course of the changes in QRS interval duration measured from 12-lead ECGs were obtained in the six subjects prior to, during and following flecainide IV infusion (2 mg/kg, administered over 10 mins) and inhalation (30 mg eTLD, mean time 4 min). Subjects in Cohort 5 demonstrated a marked prolongation of the QRS interval after IV infusion of flecainide (2 mg/kg) and showed a transient increase in the QRS interval duration between 1 and 3 minutes post-inhalation of 30 mg eTLD of flecainide acetate solution (FIG. 34). QRS interval duration data from Cohort 5 are also shown in FIGS. 80A and 80B. The mean (±SEM) of the maximal increase in QRS interval duration following IV infusion was 34.2±2.4 msec and following inhalation was 12.4±2.6 msec. The widening of the QRS interval duration was transient in both cases but lasted much longer following intravenous (>60 min) compared to inhalation (15-30 min). At 2 hours following the IV infusion the QRs interval duration was still 12.5 msec longer than baseline (pre-dose value of 78±2 msec), and then steadily shortened at 4, 6 and 8 hours post-dosing. At 24 hours, prior to discharge, the QRS interval duration was still ~7 msec longer than the pre-drug baseline value. In 3 of 6 subjects the IV infusion of flecainide caused a non-specific intraventricular conduction delay, indicative of excessive prolongation of the QRS interval duration. In contrast, these changes were not observed in any of the same subjects when flecainide (eTLD of 30 mg) was given via oral inhalation. From 2 to 24 hours, post-inhalation of the eTLD of 30 mg, the QRS interval duration differed by <2 msec from the pre-dose baseline value of 78±2 msec.

Pr Interval:

PR interval measurements were also obtained as flecainide is known to prolong the PR interval in a dose-dependent manner.

Figure 30:
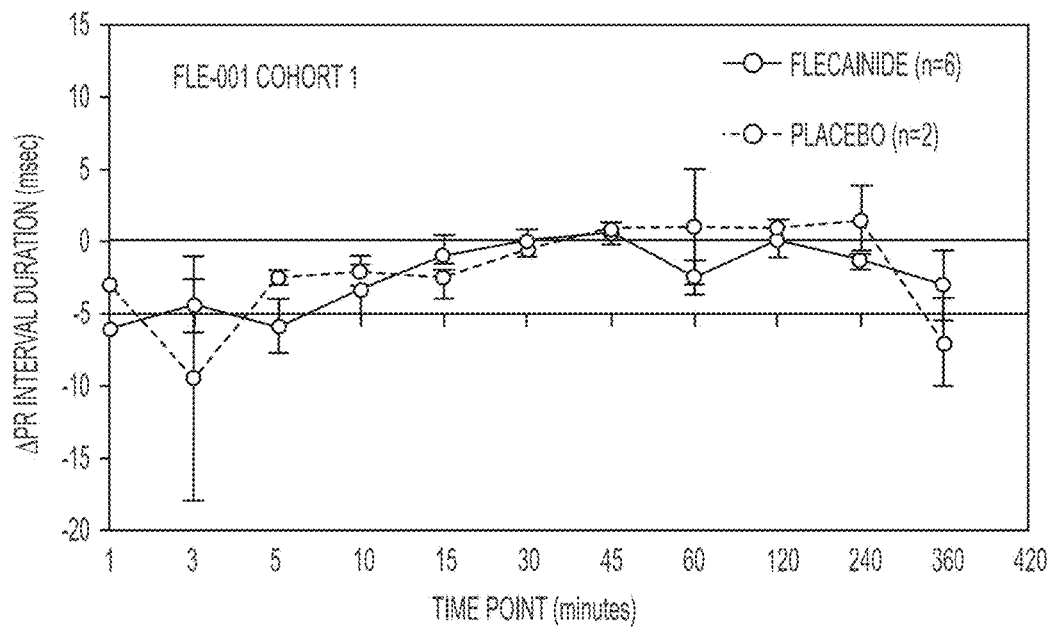
FIG. 30 shows the time course of the changes in PR interval duration (APR) relative to the baseline (pre-dose) following oral inhalation of 20 mg eTLD of flecainide acetate solution and acetate buffer (placebo). Values are the mean±SEM; n=6 (flecainide), n=2 (placebo).

In subjects of Cohort 1, the PR interval (time elapsed from onset of atrial depolarization and onset of ventricular depolarization) was shortened at early time points with mean ΔPR of −6 msec and −4.5 msec at 1 and 3 minutes post-dosing, and values smaller than −3.0 msec from 10 minutes to 4 hours after dosing (FIG. 30).

Figure 81:
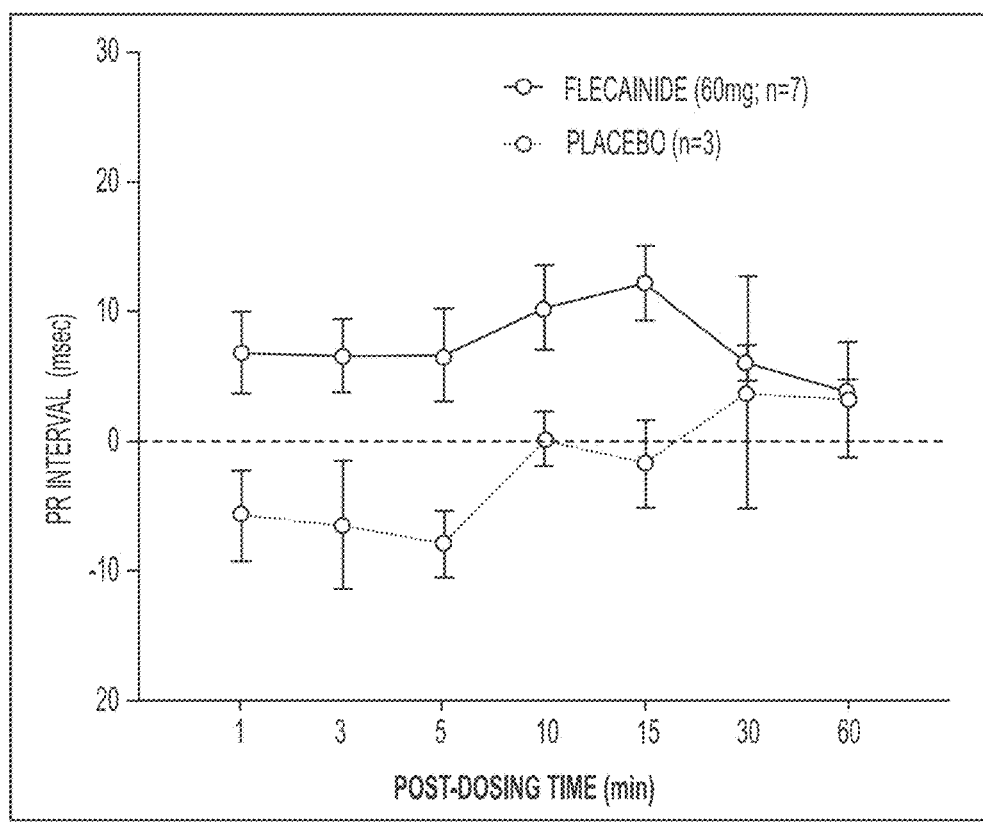

Data for Cohort 3 subjects inhaling 60 mg eTLD of flecainide or placebo solution are shown in FIG. 81. There was a ~5 msec prolongation in the PR interval duration at the early time points (1 to 5 min), and up to 12 msec at 10 and 15 minutes following administration of flecainide. In contrast, following the inhalation of placebo solution, there was a ~5 msec shortening in the PR interval duration for the first 5 min, and thereafter it returned towards the pre-dose values. Minimal or no changes of the PR interval duration were seen in subjects that inhaled 20 or 40 mg eTLD of flecainide. The PR interval durations at 2, 4, 6, 8 and 24 hours post-inhalation dosing, from the subjects of all 3 cohorts, were near identical to the baseline (pre-dose) values, that is, in the range of 140 to 150 msec. In all subjects that inhaled the placebo solution (combined cohorts), the PR interval shortened. The relatively small or no changes in PR interval observed prior to, during and after (up to 5-10 minutes post-dosing) can be attributed to the confounding effects of postural changes and the inhalation procedure itself. The protocol required a seated posture during inhalation of flecainide or placebo solution. The postural changes from semi-recumbent (before inhalation) to seated (during inhalation) position triggers a sympathetic reflex that leads to a shortening of the PR interval. The sympathetic reflex-driven PR interval shortening with seated posture is evident in the placebo curve of FIG. 81. Therefore, the PR interval shortening associated with upright posture likely negated most of the expected lengthening of the PR interval in subjects receiving flecainide.

Figure 82A:
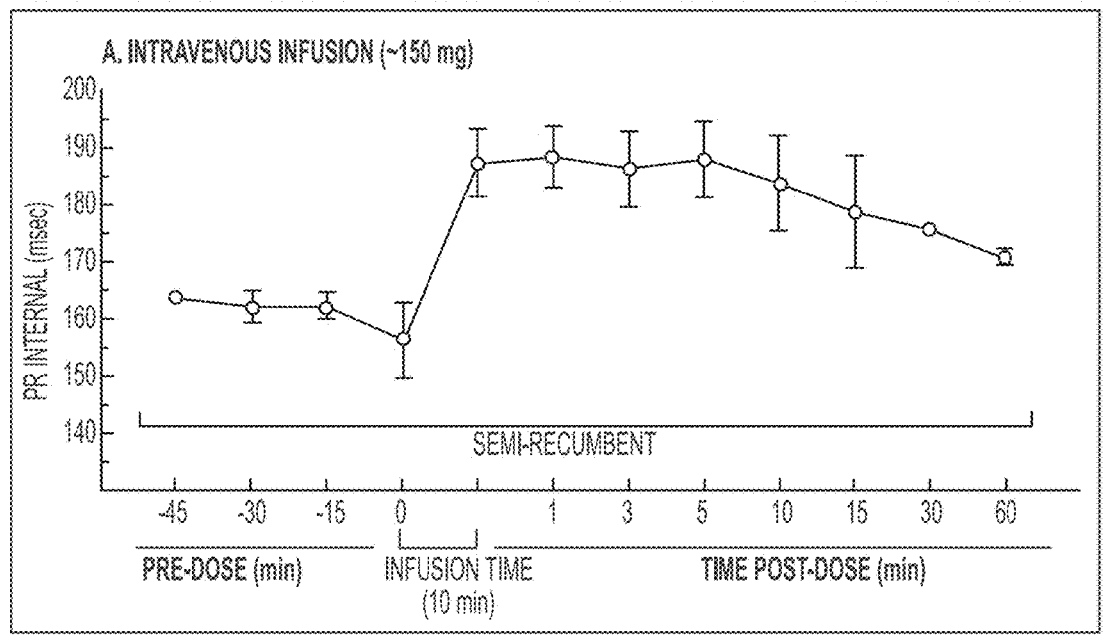
FIGS. 82A and 82B show time courses of changes in PR interval following flecainide IV infusion and oral inhalation, respectively.
Figure 82B:
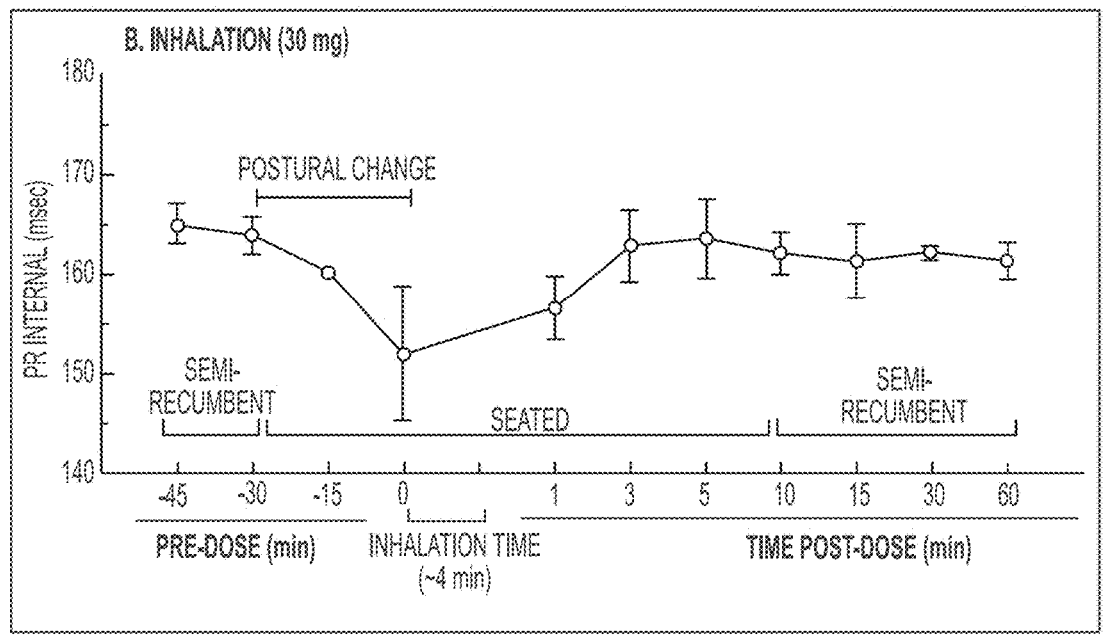

The results of Part B of the Phase 1 study, in which interval measurements were obtained before, during, and after seated position, clearly shows the re-lengthening of the PR interval following inhalation of flecainide after being shortened during the change in subject's position from semi-recumbent to seated upright posture of the subjects. FIGS. 82A and 82B show the changes in PR interval duration measured from 12-lead ECGs in the six subjects prior to, during and following IV infusion. Forty-five min prior to administration of flecainide the PR interval durations were similar being 164±1 msec with IV infusion and 165±2.0 msec with inhalation. At the end of the IV infusion of flecainide (FIG. 82A), the PR interval prolonged to 187±6 and remained prolonged at 60 min post-IV infusion. At 2 hours post-IV infusion, the PR interval was still ~12 msec longer than the pre-drug baseline value of 161±3 msec, and thereafter returned toward baseline; at 8 and 24 hours the PR interval had fully returned to pre-drug baseline. The ECG changes in PR interval duration with inhalation were more complex because of the effects of postural changes. As shown in FIG. 82B, when the subjects changed position from semi-recumbent to seated, the PR interval duration shortened by 13 msec from the pre-dose value measured at −45 min. Subsequently, from the start to the end of the inhalation, the PR interval duration prolonged by 12 msec at 5 min after completion of inhalation and then decreased toward the pre-dose values. The shortening of the PR interval duration following the postural change (from semi-recumbent to seated) can be attributed to an increase in sympathetic tone and was consistent with the observed increases in heart rate (FIG. 72) and systolic blood pressure. The PR interval at 2 hours and beyond (4, 6, 8 and 24 hours) post-oral IH flecainide was (160 msec), approximately 2 msec longer than the 158.5 msec of the pre-drug baseline value. In summary, IV infusion and oral inhalation of flecainide were associated with maximal PR interval prolongations of 25 msec and 12 msec, respectively.

Figure 35:
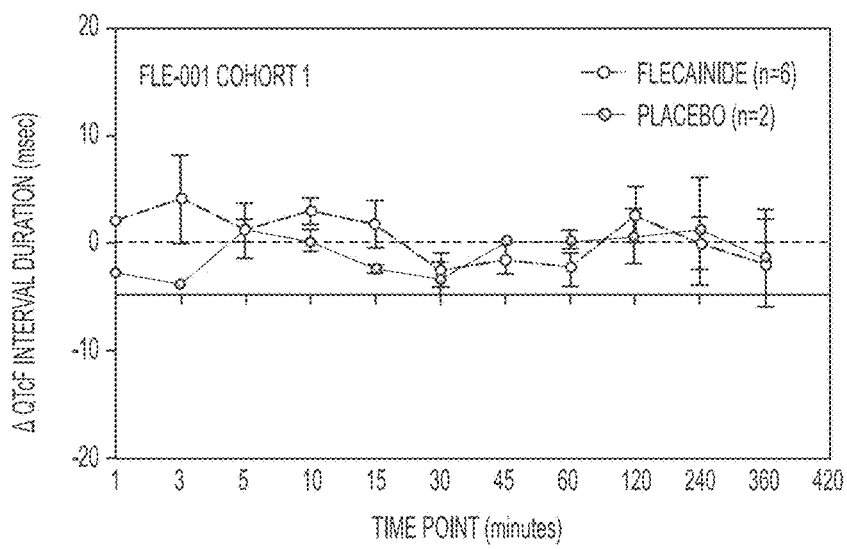
FIG. 35 shows the time course of the changes in the QTcF interval duration (ΔQTcF) relative to the baseline (pre-dose) following oral inhalation of 20 mg eTLD of flecainide acetate solution and placebo. Values are the mean±SEM; n=6 (flecainide), n=2 (placebo).

Fridericia HR Corrected QT (QTcF) Interval:

The QTcF interval changed little in subjects of Cohort 1 following inhalation of 20 mg eTLD of flecainide, with small mean changes across post-inhalation time points that varied between +4.0 msec and −2.7 msec during the first 6 hours (FIG. 35).

In subjects of Cohorts 2 and 5, ΔQTcF post-inhalation time points varied ±4 msec for 40 mg eTLD and 30 mg eTLD inhaled flecainide, respectively.

T-Wave Morphology:

No changes in T-wave morphology were observed following inhalation of flecainide acetate solution (20 mg eTLD, 30 mg eTLD, and 40 mg eTLD).

Figure 36:
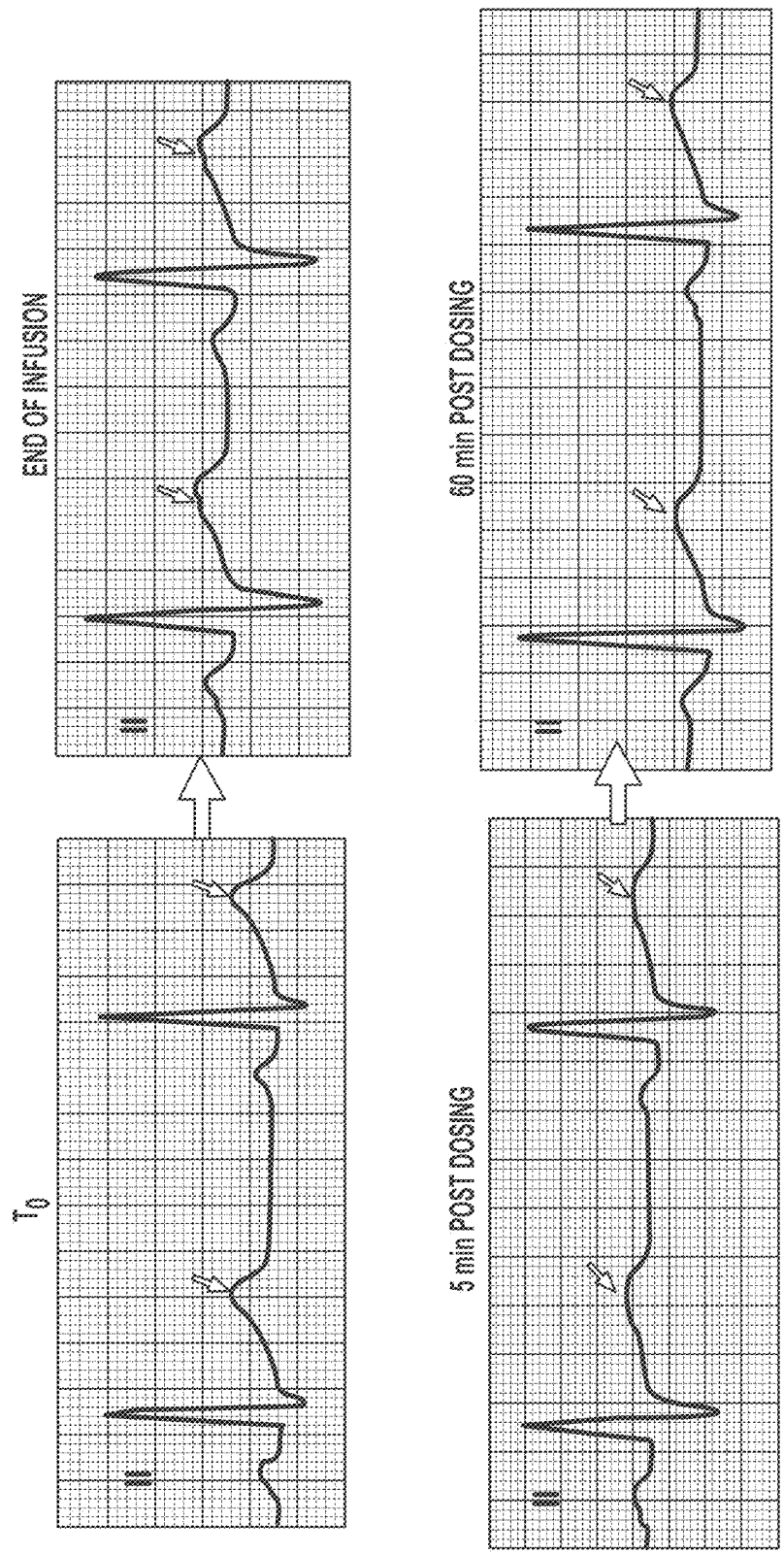
FIG. 36 shows ECG tracings recorded from a subject administered flecainide (2 mg/kg) by IV. Small arrows on the electrogram indicate the T-wave.
Figure 37:
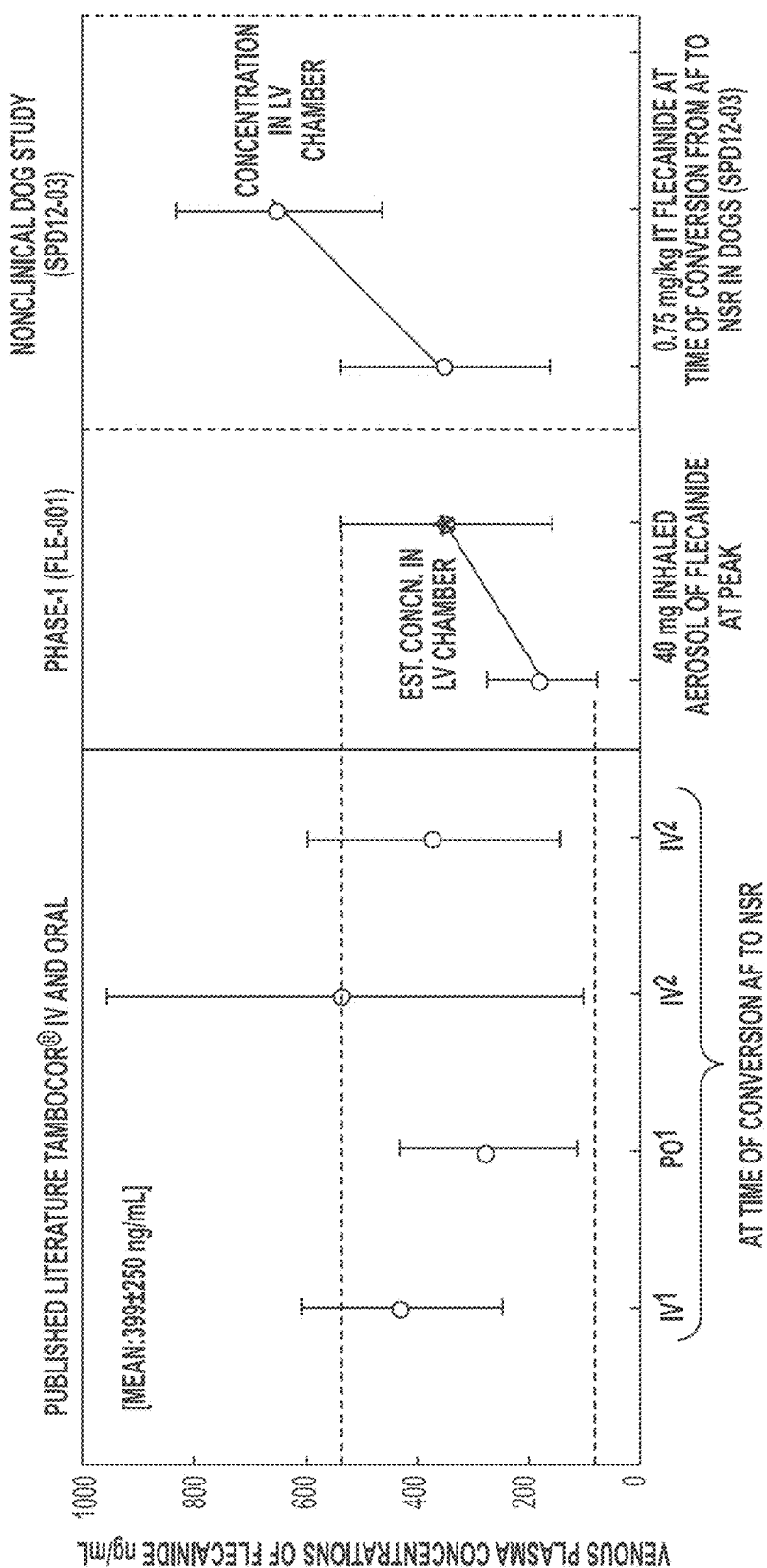
FIG. 37 shows venous plasma concentrations of flecainide administered IV or orally at the time of cardioversion of atrial fibrillation (AF) in patients with recent onset AF (left panel), following oral inhalation of 40 mg eTLD of flecainide acetate solution by healthy volunteers (center panel), and at the time of conversion of AF to NSR in dogs following intratracheal (IT) instillation of 0.75 mg/kg of flecainide (right panel). LV=Left Ventricle; *Mean+SD of plasma concentration (×1.96-fold) extrapolated from animal studies in dogs at time of cardioversion.
Figure 38:
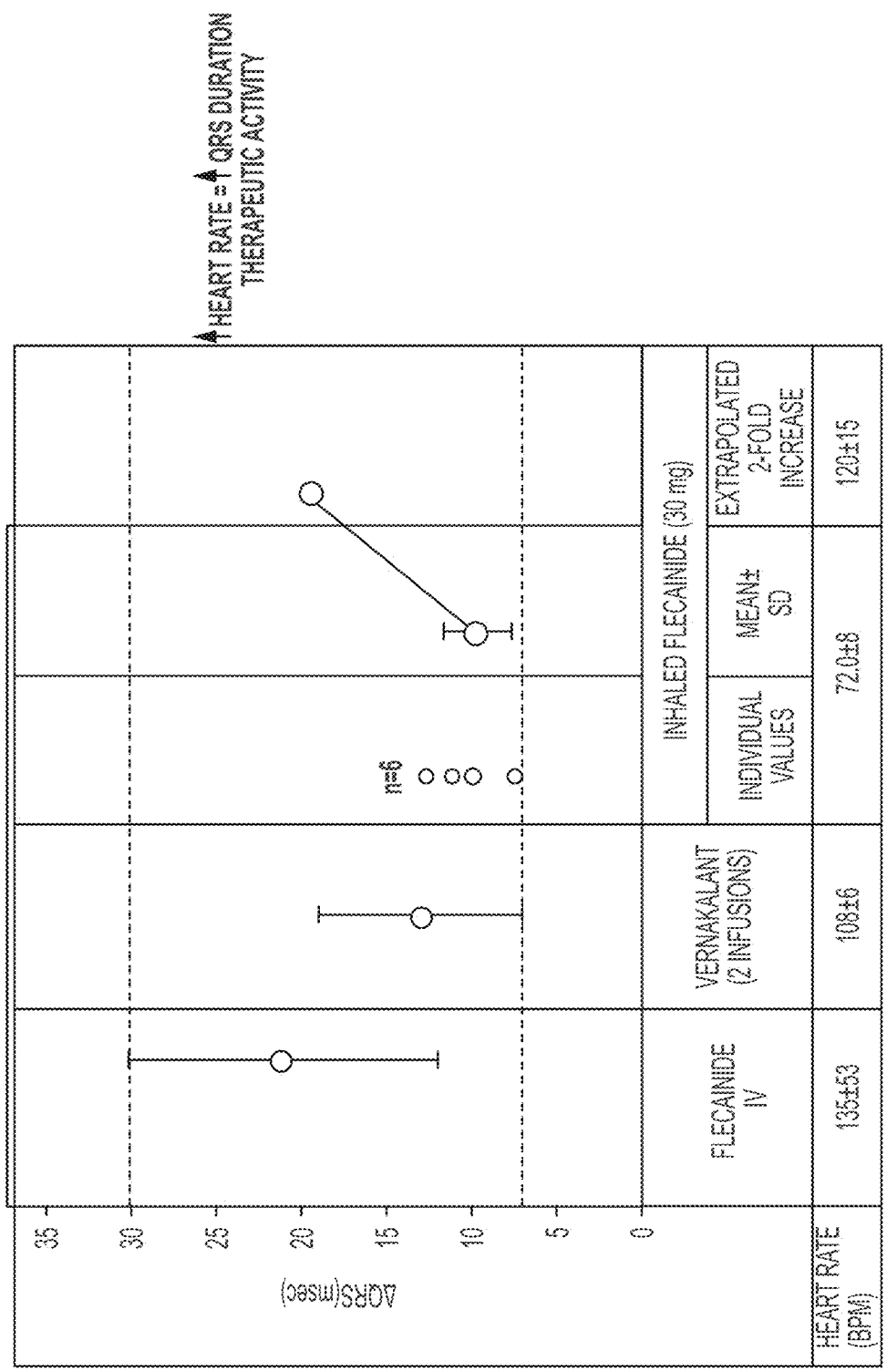
FIG. 38 shows comparative ΔQRS interval prolongation (msec) associated with the administration of flecainide or vernakalant at the time of cardioversion of AF in patients with recent onset AF and following oral inhalation of 30 mg eTLD of flecainide acetate solution by healthy volunteers.

T-wave notching, which is an abnormality in T-wave morphology, has been observed following IV infusion of flecainide (2 mg/kg; FIG. 36).

Figure 83:
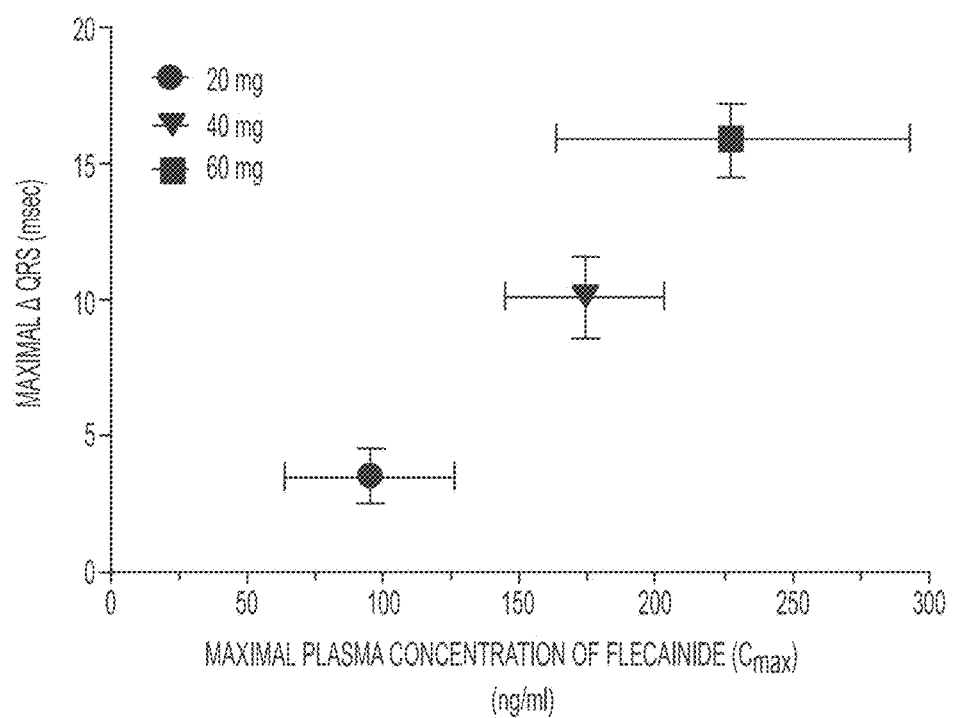

PK-PD Relationship:

The antiarrhythmic efficacy of flecainide can be strongly correlated with the widening of the QRS interval. FIG. 83 shows the dose-concentration response relationship, for the post-hoc population in Cohorts 1, 2, and 3, of the effects of inhalation of flecainide on the prolongation of the QRS interval duration. The PK-PD relationship shown below is based on the non-steady state, peak plasma levels of flecainide and maximal changes in QRS interval durations post-inhalation. The maximal QRS interval prolongations were 3.5±1.0, 10±1.5, 16±1.4 for the eTLDs of 20, 40 and 60 mg eTLD, respectively.

In Part B of the present study (FLE-001), flecainide was administered in single doses via either IV infusion (over 10 minutes) and via oral inhalation (~4.5 min) in the same subjects. Thus, steady-state plasma levels of flecainide given either via IV or oral inhalation were not achieved. Consequently, the PK-PD relationship described below are based on the non-steady state, rapidly changing plasma levels of flecainide ($[Flec]_{plasma}$) and changes in QRS interval durations (ΔQRS) measured at specific times. As expected from non-steady state conditions, and shown in FIGS. 84A and 84B, a temporal dissociation is observed between ($[Flec]_{plasma}$) and ΔQRS. During both the rapid rise and decline (distribution phase) of the plasma concentration of flecainide, the changes in QRS interval duration lag those of the peripheral venous concentrations of flecainide. The hysteresis between concentrations and responses (QRS) applies for both routes of administration, IV and inhalation.

According to results of the early PK studies of flecainide by Conard et al (1984), peripheral venous plasma levels of flecainide "reflect cardiac tissue concentrations of unchanged flecainide". Hence, as a corollary, the prolongation of the QRS interval duration caused by flecainide can reflect the ventricular myocardium (primarily left) concentrations of flecainide.

Figure 84A:
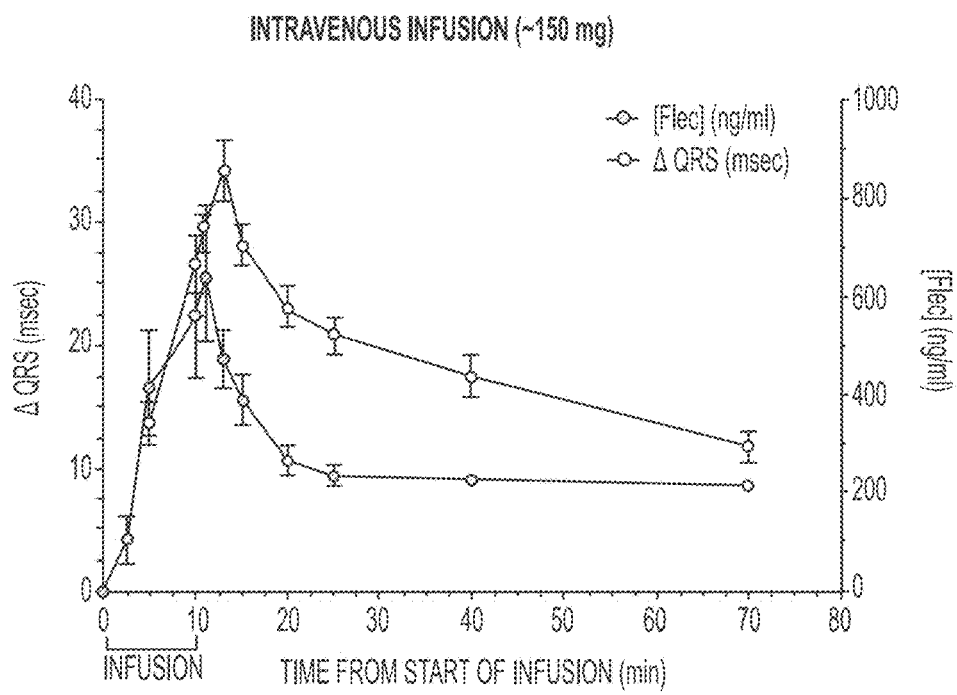
FIGS. 84A and 84B show time courses of changes in plasma concentrations of flecainide and QRS duration with flecainide IV infusion and oral inhalation, respectively.
Figure 84B:
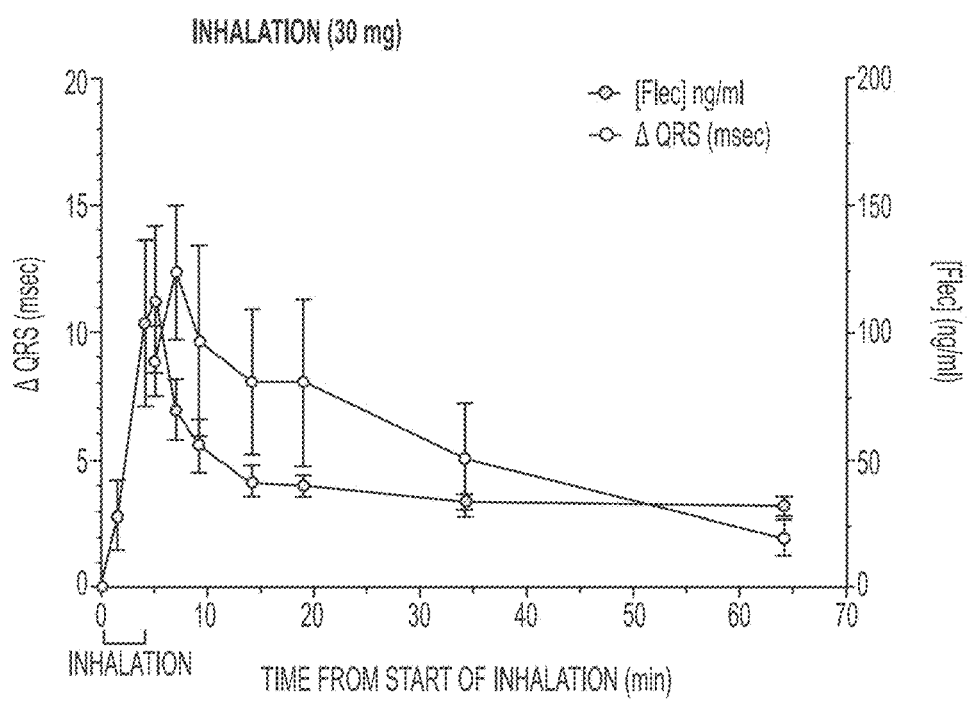
Figure 85:
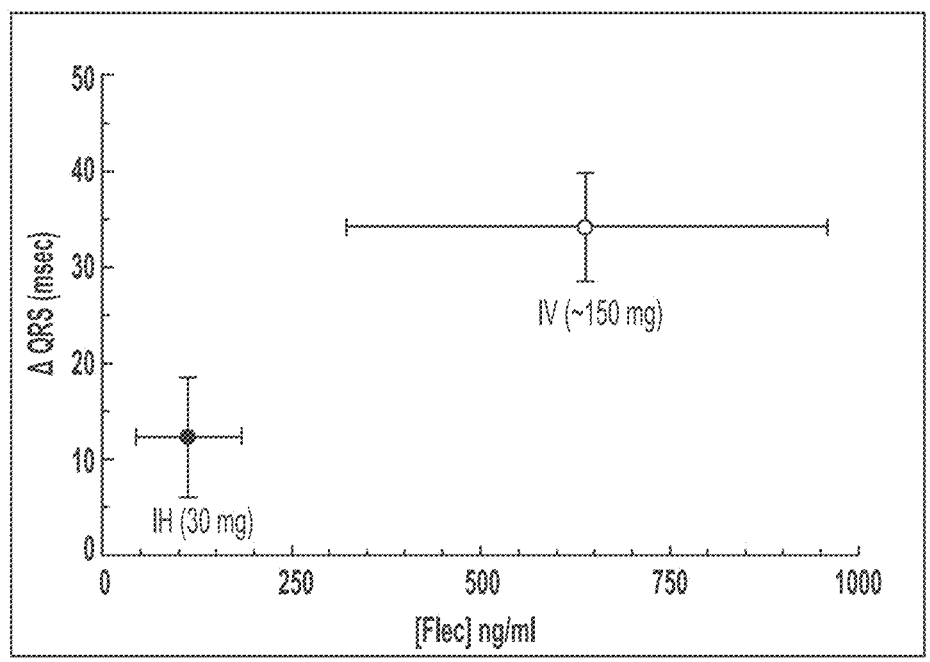

Based on the findings shown in FIGS. 84A and 84B, it was sought to determine the relationship between peak plasma levels of flecainide ($C_{max}$) and the maximal ΔQRS instead of using the time-matched values of both variables. The results of this analysis are shown in FIG. 85.

Figure 86:
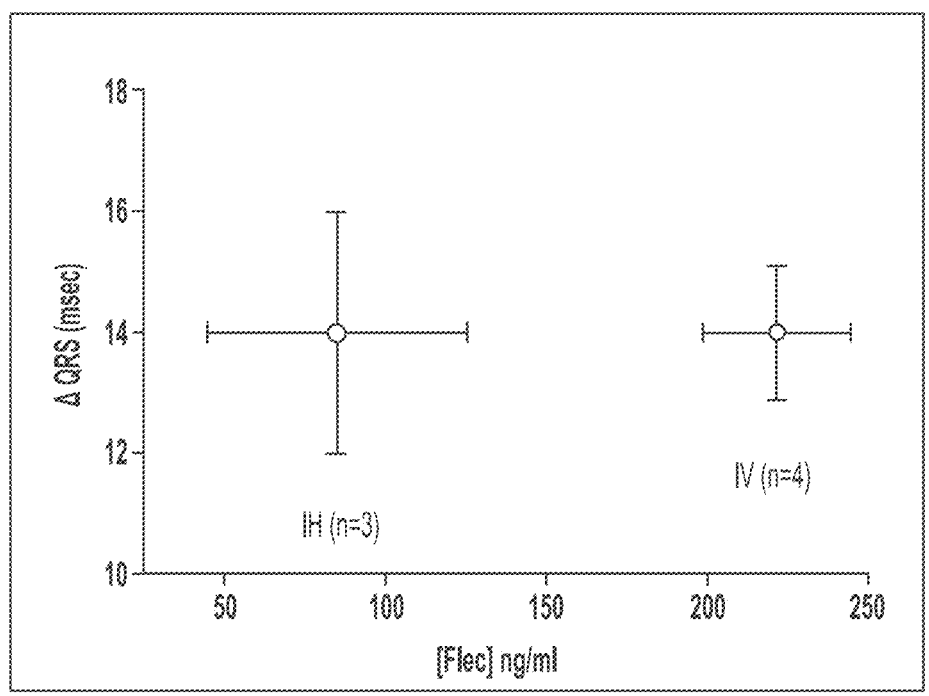

The lower dose of flecainide delivered via oral inhalation (eTLD of 30 mg) resulted in lower (6.2-fold) maximal plasma levels of flecainide when compared to the higher dose delivered via IV infusion (~150 mg). Likewise, the pharmacodynamic activity of flecainide, reflected by changes in the QRS interval duration, were accordingly smaller (2.7-fold) following inhalation than IV infusion. Thus, it appears that a 2.3-fold (6.2/2.7) lower plasma concentration of flecainide given by inhalation can cause prolongation of QRS interval duration of magnitudes achieved following a 10 min IV infusion. In keeping with this interpretation, as depicted in FIG. 86, a direct comparison of data from the subjects with near-equal ΔQRS (12.0 to 16 msec) following either IV infusion or oral inhalation, yielded plasma concentrations of 222±23 and 85±40.3 ng/ml, respectively. Thus, a 2.6-fold lower plasma level of flecainide achieved following inhalation results in a ΔQRS of 14 msec, a QRS interval widening similar to that achieved at 5 min into the IV infusion of flecainide; equivalent to 1 mg/kg, that is, half of the dose administered (FIGS. 84A and 84B).

Summary:

The results of this Phase 1 study demonstrated that inhalation doses of flecainide, in the range of 30 to 60 mg eTLD, are safe, well-tolerated and deliver flecainide into the systemic circulation, within 1 to 3 minutes after the completion of inhalation, in sufficient amounts to elicit the expected electrophysiological effects of flecainide, such as prolongation of QRS interval. In Part B of the study, head-to-head comparisons were made between the PK, PD, safety and tolerability of an eTLD of 30 mg of flecainide given via oral inhalation and that of a 10-minute IV infusion dose of 2 mg/kg of flecainide (~150 mg). Inhaled flecainide was compared with IV flecainide because flecainide given via IV at the approved dose of 2 mg/kg is an established agent for acute pharmacological cardioversion of recent onset atrial fibrillation. Relevant to the potential effectiveness of inhaled flecainide to cardiovert AF is the observation that at the time of conversion of atrial fibrillation to sinus rhythm by flecainide IV, the venous plasma flecainide concentrations are in the range of 114 to 742 ng/ml and the increases in QRS interval duration are in the range of 12 to 30 msec (Crijns H et al, 1988; Suttorp M J et al, 1990; Donovan K D et al, 1995). Inhaled flecainide at eTLD≥30 mg was found to yield venous plasma flecainide concentrations and cause QRS interval prolongation within the same range reported above for IV, albeit in the lower end of the range reported to convert atrial fibrillation to sinus rhythm by IV flecainide. Therefore, based on the pharmacokinetics and pharmacodynamics of flecainide reported in the literature, inhaled flecainide at eTLDs≥30 mg could be effective in converting recent-onset atrial fibrillation to sinus rhythm within minutes of administration. Compared to the approved IV flecainide dose, the lower doses of inhaled flecainide are likely to be better tolerated and safer.

Example 5

Pharmacokinetic and Pharmacodynamic Effects of Intratracheal Instillation of Flecainide Acetate with Comparison to Intravenous Administration in Anesthetized Pigs The PK and PD responses to intratracheal (IT) instillation were compared with IV delivery of flecainide in an intact porcine model that has been previously shown to be clinically relevant (Kumar et al 2009).

Experimental Design:

The studies were carried out in male Yorkshire pigs (n=9) weighing 36±1.0 kg (mean±SEM). The pigs were pre-anesthetized with telazol (4.7 mg/kg, intramuscular) and subsequently further anesthetized using alpha-chloralose (80 mg/kg, IV bolus, followed by 24 mg/kg/h continuous IV infusion). The animals were intubated and ventilated at a constant rate of 12 breaths/min and tidal volume of 400 ml per stroke.

All catheters were positioned under fluoroscopic guidance. An Orbiter electrode catheter was placed in the right atrium for recording local atrial electrograms. Ventricular electrograms were obtained using a decapolar electrode catheter positioned in the left ventricle (LV). Arterial blood pressure was continuously monitored from a femoral arterial sheath. Simultaneous blood samples were drawn from the pigtail catheter positioned in the LV and from a catheter in the jugular vein. Electrograms were monitored using a Prucka CardioLab workstation (GE Medical Systems, Milwaukee, Wis.) from atrial and ventricular sites. For IT instillation of flecainide acetate solution, a 5Fr angioplasty catheter that was 1 cm longer than the endotracheal tube was introduced into the trachea via the endotracheal tube and its tip was positioned under fluoroscopy at the tracheal carina level.

In the IV infusion experiments, flecainide (2 mg/kg, IV bolus over 2 min) was infused via a 7Fr sheath inserted into the right femoral vein. The RR, PR, QTc, and JTc intervals and QRS duration were measured in six sequential beats, recorded seconds before each time point.

In the IT instillation experiments, flecainide (2 mL of 0.75 mg/kg or 1.5 mg/kg concentrations, IT) was administered in a single "push" of 2 to 3 sec via the angioplasty catheter positioned in the endotracheal tube. For example, for a 36 kg pig, a dose of 27 mg/2 mL (0.75 mg/kg) or 54 mg/2 mL (1.5 mg/kg) of flecainide solution can be used. The QT interval was corrected using Bazett's formula (QTc=QT/√RR) and is presented in this report as the QTc interval.

When more than one dose was tested in a single experiment, a washout period of 30 to 60 min was allowed in order to keep residual levels of flecainide to a minimum before testing the new dose.

For the experiments on the effects of IT instillation of flecainide on duration of AF, the arrhythmia was induced using intrapericardial administration of acetylcholine (ACh) (1 mL at a concentration of 15 mg/mL) followed by burst pacing for 1 min. Flecainide (1.5 mg/kg, IT) was given after 2 min of successful AF induction.

Blood samples were collected from venous circulation and through the LV pigtail catheter in sodium heparin tubes at 0, 2, 5, 10, 15 and 30 min after the start of IV or IT flecainide. The samples were centrifuged and frozen at −80°

C. until drug level determination was performed using a bioanalytical assay method developed by Climax Laboratories, Inc.

Data are reported as means+ SEM. Statistical analyses were performed using the SAS system (9.4) to apply ANOVA with a post-hoc Dunnett's test. Statistical significance was assumed at p<0.05.

Figure 39:
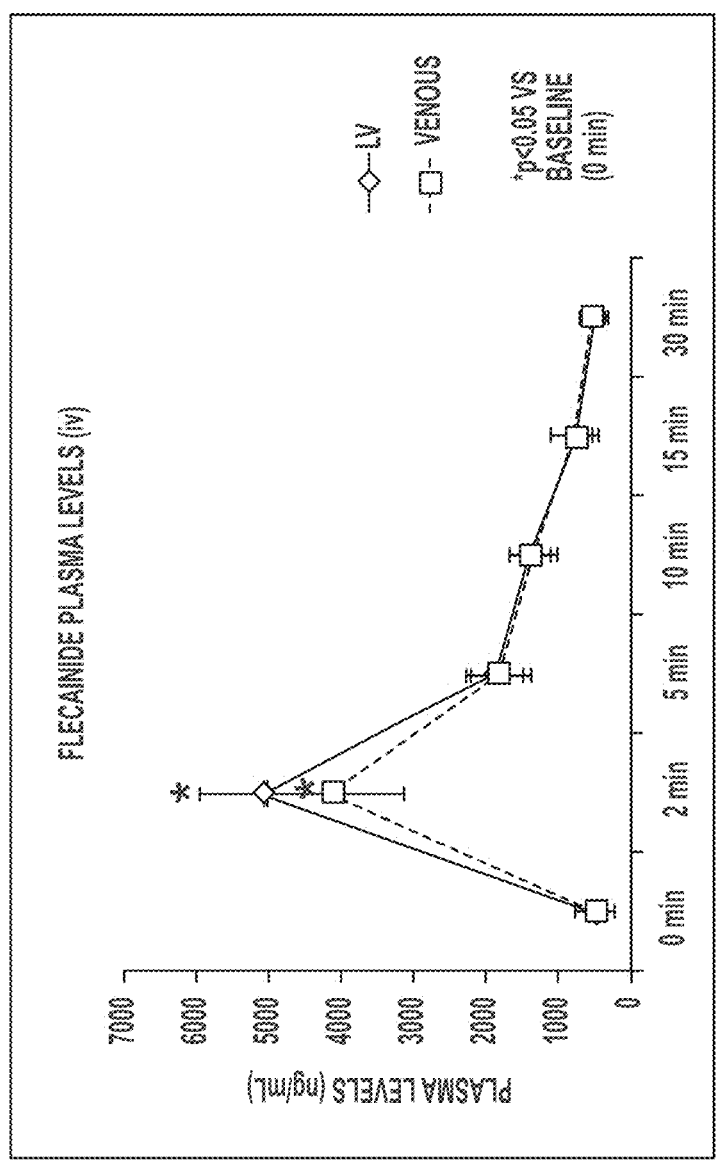

Results:

Pk Responses:

IV Infusion:

Following IV infusion of flecainide (2 mg/kg over 2 min), both LV and venous plasma levels peaked at 2 min (LV: 5127±849.4 ng/mL, p<0.05; Venous: 4151±1030.0 ng/mL, p<0.05) and progressively declined throughout the experiment to lower levels at 30 min (LV: 497±189.5 ng/mL; Venous: 519±195.6 ng/mL) (FIG. 39).

Figure 40:
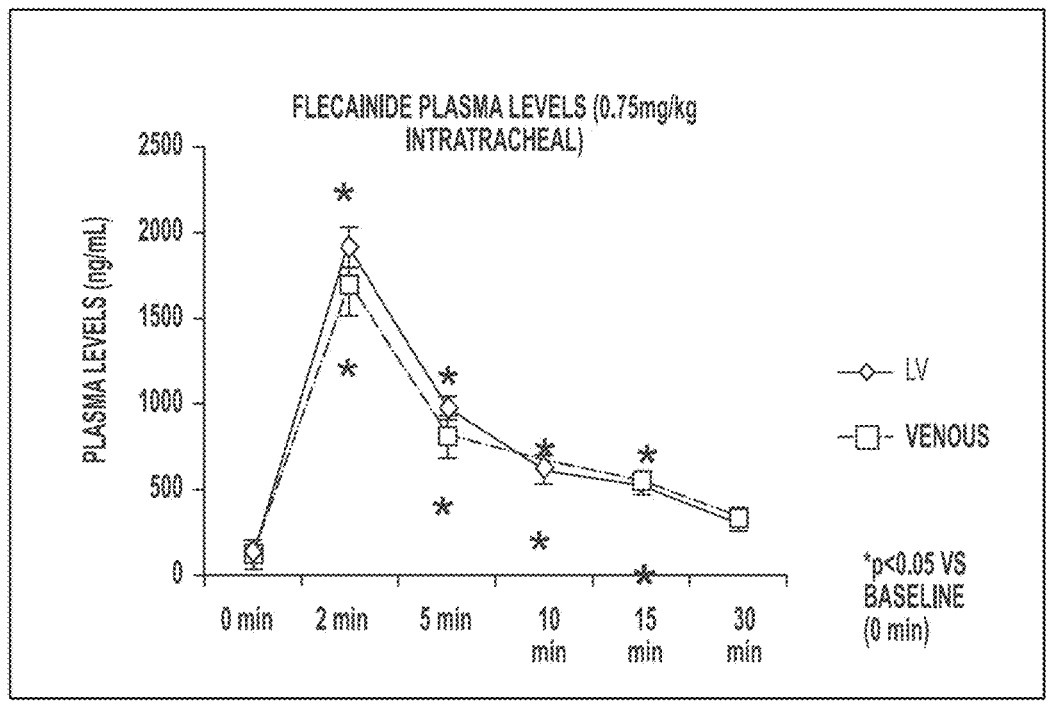

IT Instillation of 0.75 mg/kg:

Following IT instillation of the lower dose of flecainide (0.75 mg/kg), both LV and venous plasma levels peaked at 2 min (LV: 1916±122.2 ng/mL, p<0.05; Venous: 1688±176.7 ng/mL, p<0.05) and remained significantly elevated compared to baseline at 5, 10, and 15 min before progressively declining throughout the experiment to lower levels at 30 min (LV: 299±28.6 ng/mL; Venous: 341±54.6 ng/mL) (FIG. 40).

Figure 41:
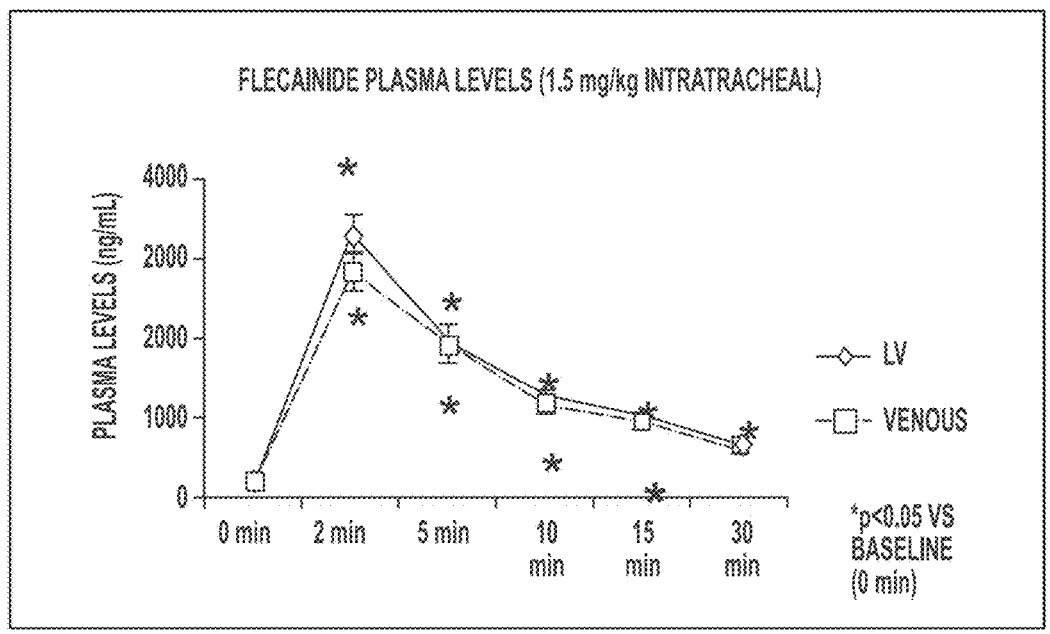

IT Instillation of 1.5 mg/kg:

Following IT instillation of the higher dose of flecainide (1.5 mg/kg) both LV and venous plasma levels peaked at 2 min (LV: 3308±247.5 ng/mL, p<0.05; Venous: 2808±216.5 ng/mL, p<0.05) and remained significantly elevated compared to baseline at 5, 10, and 15 min. Venous plasma remained significantly elevated compared to baseline at 30 min (Venous: 676±79.7 ng/mL, p<0.05) while left ventricular chamber plasma did not (LV: 637±69.5 ng/mL) (FIG. 41).

Figure 42:
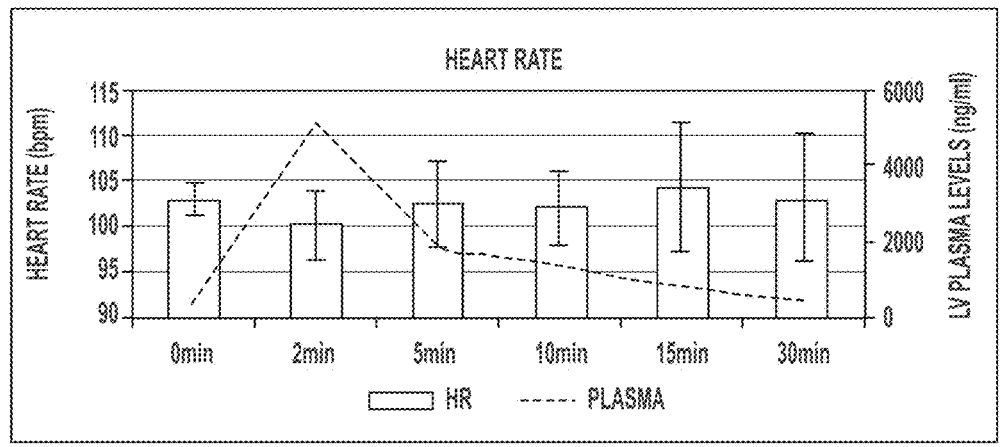

Pd Responses:

IV Infusion:

Heart Rate:

Prior to IV infusion of flecainide (2 mg/kg, IV bolus over 2 min), heart rate was 103±1.9 bpm. After IV flecainide infusion, ANOVA revealed that heart rate was not significantly altered across 30 min (p=0.9936) (FIG. 42).

Figure 43:
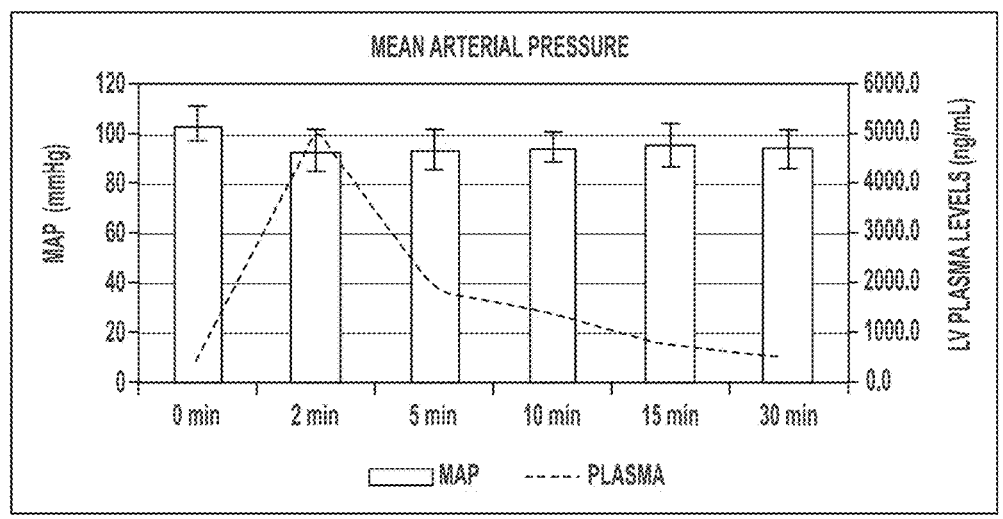

Arterial Blood Pressure:

Prior to IV infusion of flecainide (2 mg/kg, IV bolus over 2 min), mean arterial blood pressure was 105±6.7 mmHg. After IV flecainide infusion, ANOVA analysis revealed that mean arterial pressure was not significantly altered across 30 min (p=0.8852) (FIG. 43).

Figure 44:
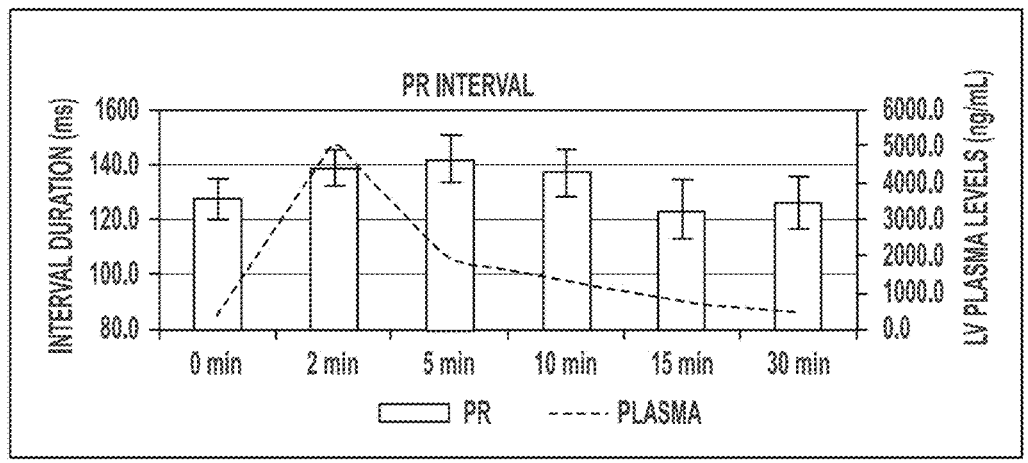

Pr Interval:

Prior to IV infusion of flecainide (2 mg/kg, IV bolus over 2 min), the PR interval was 127±7.8 ms. After IV flecainide administration, ANOVA revealed that the PR interval was not significantly changed across 30 min (p=0.5161; FIG. 44).

Figure 45:
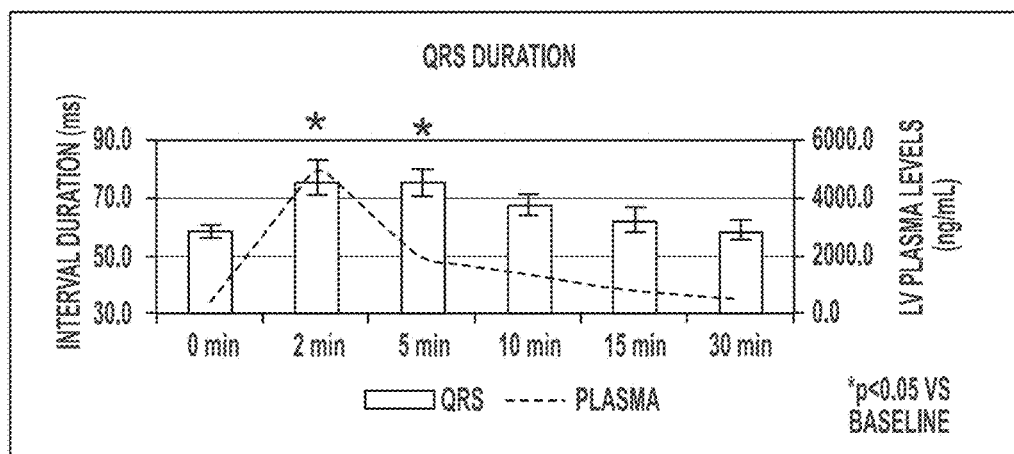

Qrs Duration:

Prior to IV infusion of flecainide (2 mg/kg bolus over 2 min), QRS duration was 58±1.9 ms. After IV flecainide administration, QRS duration significantly increased to 77±6.2 ms and 76±4.8 ms coincident with peak plasma levels of the drug at 2 min and 5 min, respectively (p<0.05). Thereafter, QRS duration progressively decreased toward the baseline levels (59±3.0 ms) at 30 min (FIG. 45).

Figure 46:
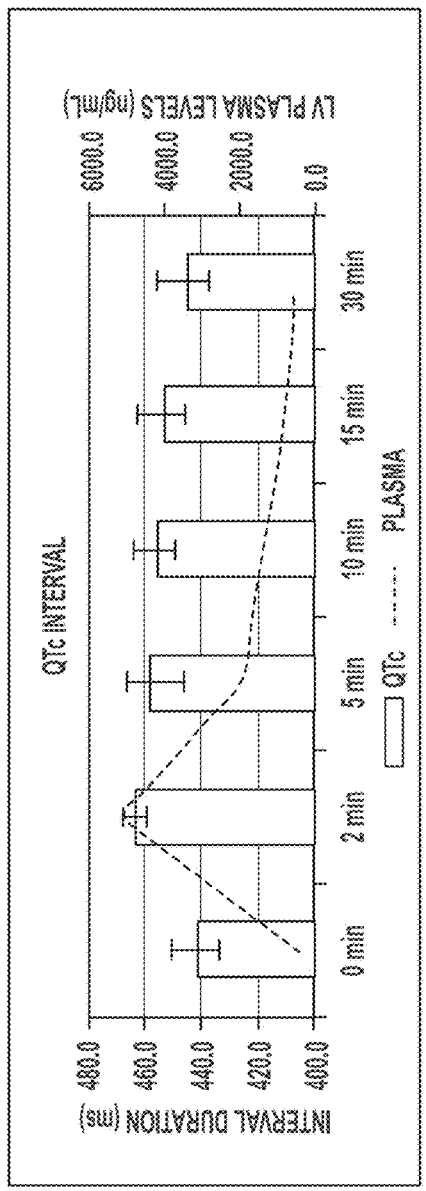

Qtc Interval:

Prior to IV infusion of flecainide (2 mg/kg bolus over 2 min), the QTc interval was 442±7.9 ms. After IV flecainide administration, ANOVA revealed that the QTc interval was not significantly changed across 30 min (p=0.35; FIG. 46).

Figure 47:
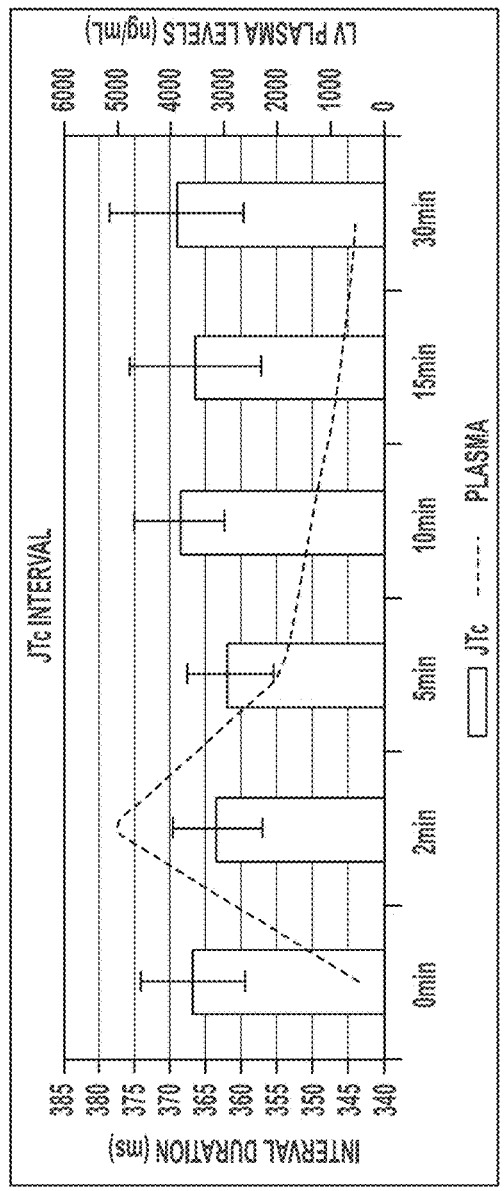

Jtc Interval:

Prior to IV infusion of flecainide (2 mg/kg bolus over 2 min), the duration of the JTc interval was 367±7.4 ms. After IV flecainide administration, ANOVA revealed that the JTc interval was not significantly changed across 30 min (p=0.9686; FIG. 47).

Figure 48:
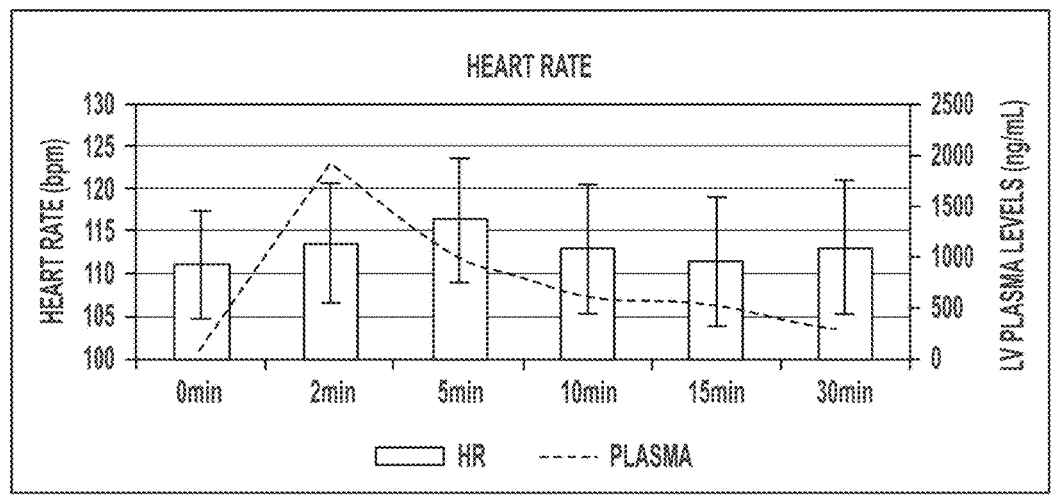

IT Instillation of 0.75 mg/kg:

Heart Rate:

Prior to IT instillation of the lower dose of flecainide (0.75 mg/kg), heart rate was 111±6.4 bpm. After IT infusion, ANOVA revealed that heart rate was not significantly altered across 30 min (p=0.9970; FIG. 48).

Figure 49:
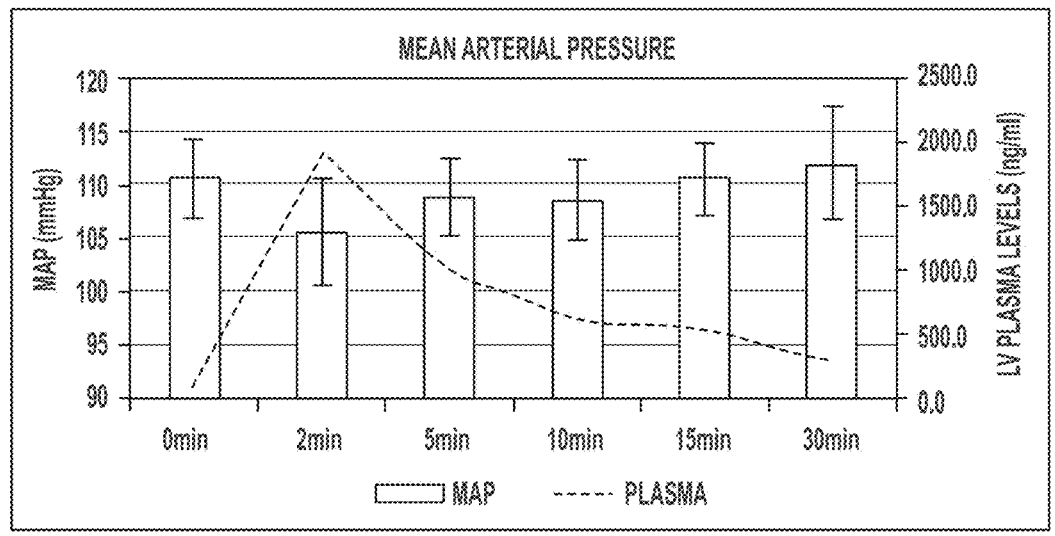

Arterial Blood Pressure:

Prior to the IT instillation of the lower dose of flecainide (2 mL of 0.75 mg/kg), mean arterial blood pressure was 111±3.6 mmHg. After IV flecainide infusion, ANOVA analysis revealed that mean arterial pressure was not significantly altered across 30 min (p=0.9112; FIG. 49).

Figure 50:
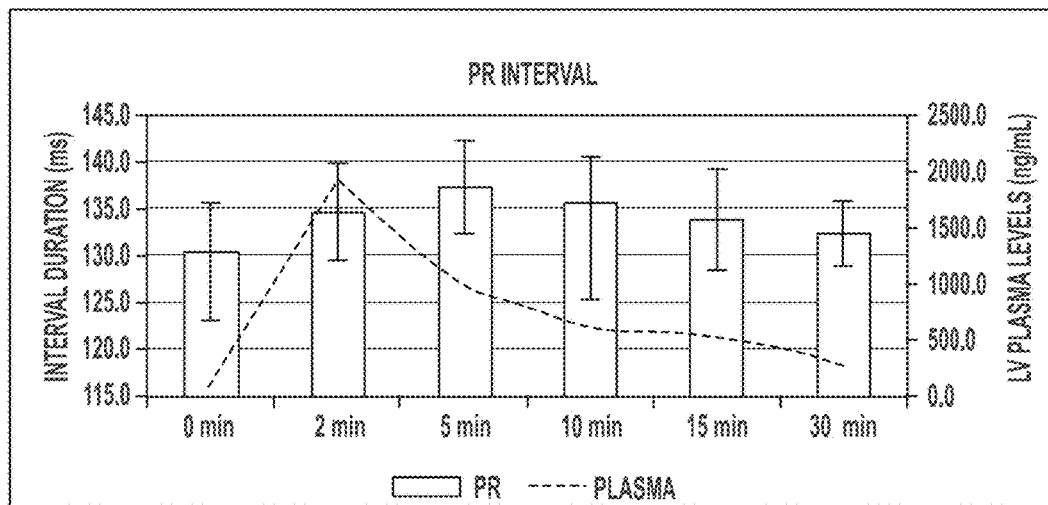

Pr Interval:

Prior to the IT instillation of the lower dose of flecainide (2 mL of 0.75 mg/kg), the PR interval was 130±5.3 ms. After IT flecainide instillation, ANOVA revealed that the PR interval was not significantly changed across 30 min (p=0.9351; FIG. 50).

Figure 51:
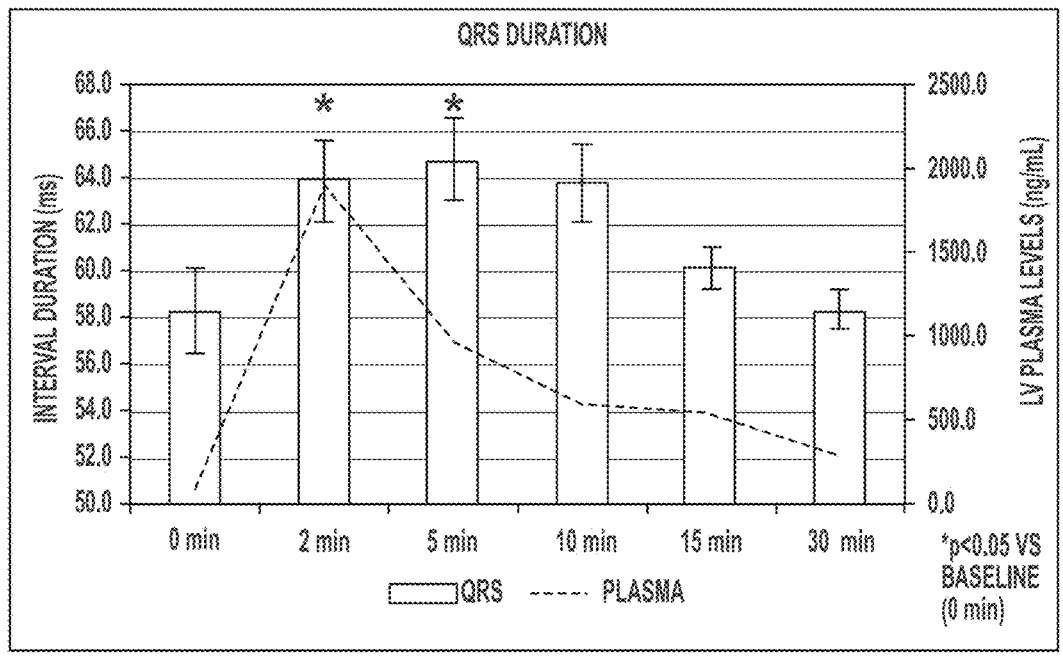

Qrs Duration:

Prior to the IT instillation of the lower dose of flecainide (2 mL of 0.75 mg/kg), QRS duration was 58±1.8 ms. After instillation, QRS duration significantly increased to 64±1.6 ms and 65±1.7 ms (p<0.05) coincident with peak plasma levels of the drug at 2 and 5 min, respectively. Thereafter, QRS duration progressively decreased toward the baseline levels (58±0.9 ms) at 30 min (FIG. 51).

Figure 52:
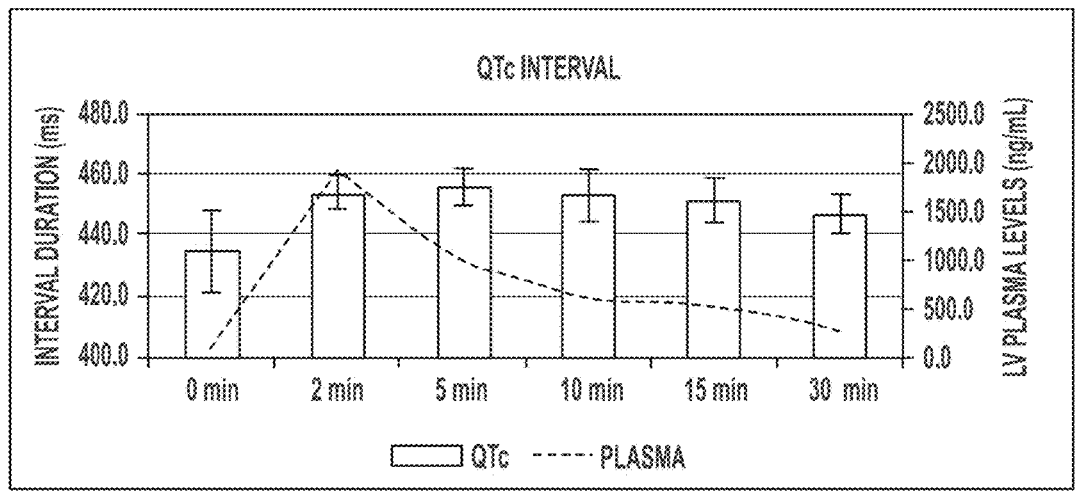

Qtc Interval:

Prior to the IT instillation of the lower dose of flecainide (2 mL of 0.75 mg/kg), the QTc interval was 435±12.9 ms. After instillation, ANOVA revealed that QTc was not significantly changed across 30 min (p=0.5505; FIG. 52).

Figure 53:
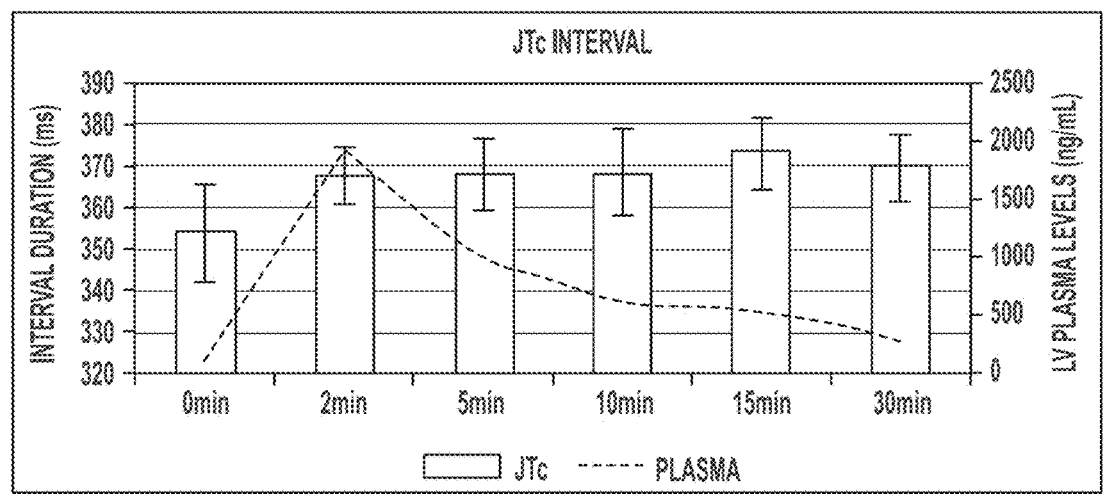

Jtc Interval:

Prior to the IT instillation of the lower dose of flecainide (2 mL of 0.75 mg/kg), the JTc interval was 354±12.0 ms. After IT flecainide administration, ANOVA revealed that the JTc interval was not significantly changed across 30 min (p=0.7605; FIG. 53).

Figure 54:
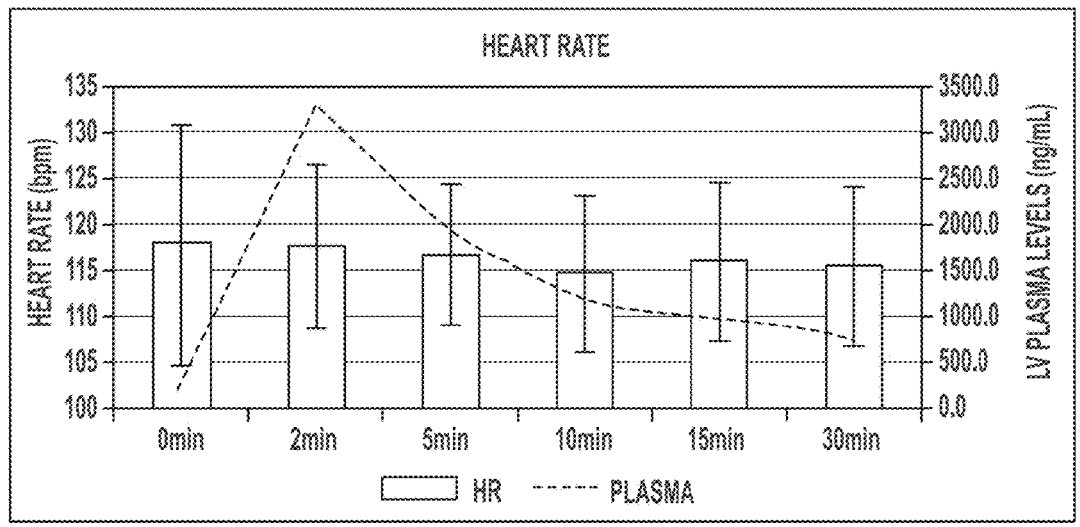

IT Instillation of 1.5 mg/kg:

Heart Rate:

Prior to IT instillation of the higher dose of flecainide (1.5 mg/kg), heart rate was 118±13.2 bpm. After IT infusion, ANOVA revealed that heart rate was not significantly altered across 30 min (p=0.9999; FIG. 54).

Figure 55:
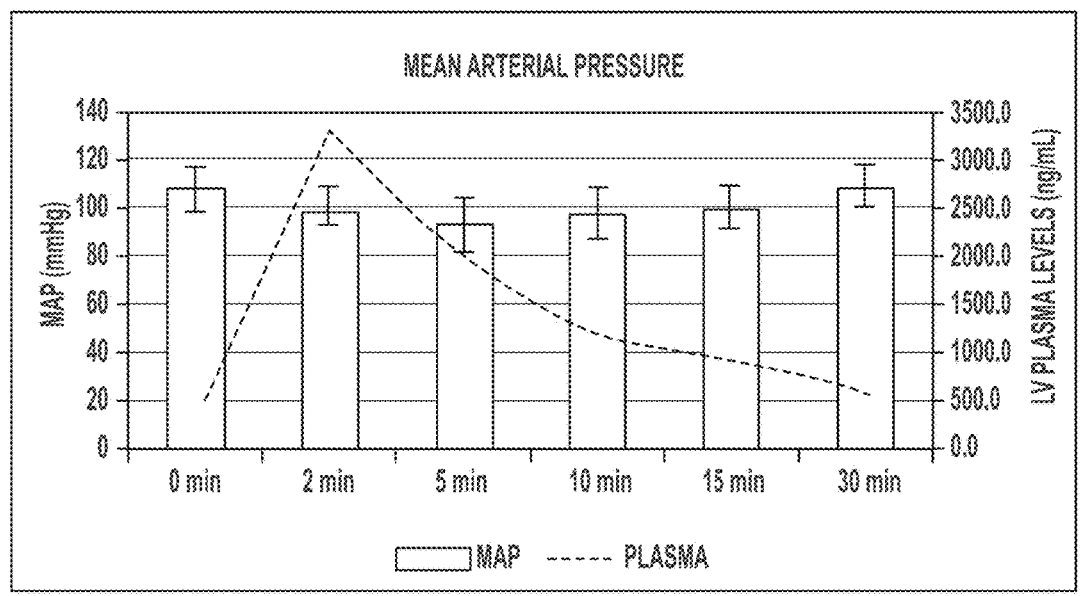

Arterial Blood Pressure:

Prior to IT instillation of the higher dose of flecainide (1.5 mg/kg), mean arterial blood pressure was 108±9.4 mmHg. After IT infusion, ANOVA analysis revealed that mean arterial pressure was not significantly altered across 30 min (p=0.9894; FIG. 55).

Figure 56:
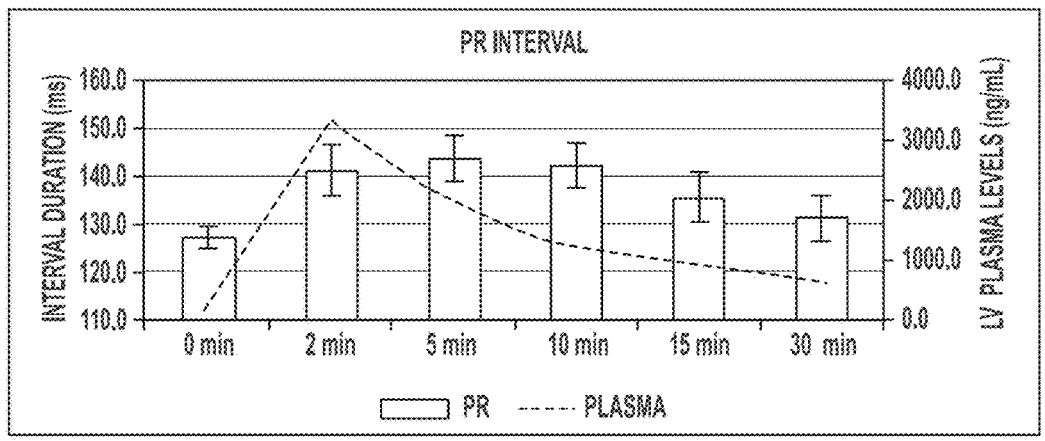

Pr Interval:

Prior to the IT instillation of the higher dose of flecainide (2 mL of 1.5 mg/kg), the PR interval was 127±2.3 ms. After instillation, ANOVA revealed that the PR interval was not significantly changed across 30 min (p=0.0819; FIG. 56).

Qrs Duration:

Prior to the intratracheal instillation of the higher dose of flecainide (2 mL of 1.5 mg/kg), QRS duration was 57±0.4 ms. Following IT instillation of the higher dose of flecainide (1.5 mg/kg), QRS duration significantly increased to 68±1.9 ms, 69±2.2 ms, 67±1.7 ms, and 64±1.3 ms (p<0.05), coincident with the increase in the plasma level of the drug at 2

Figure 57:
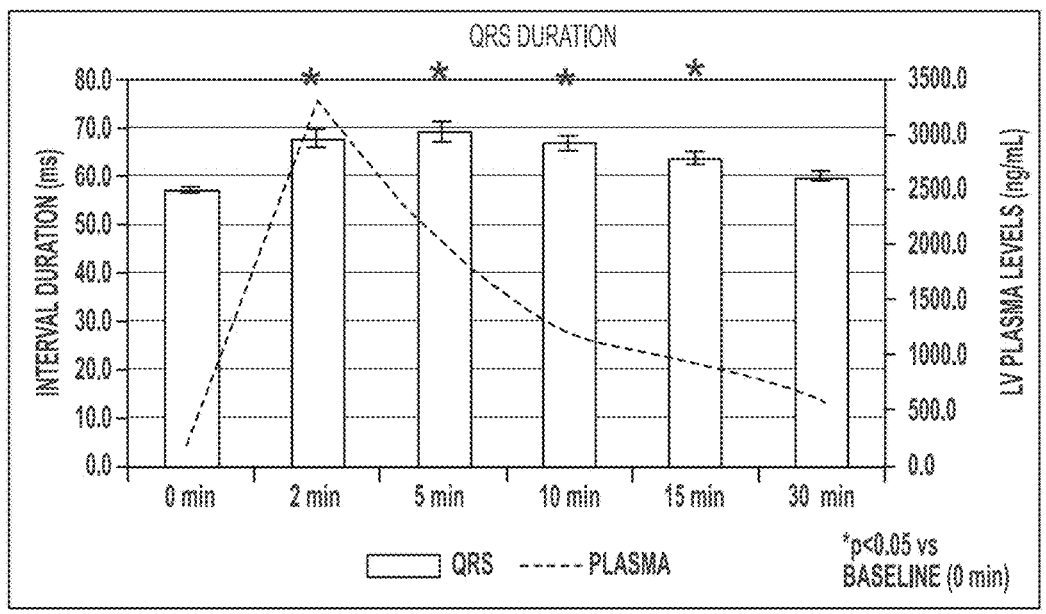

(peak plasma level), 5, 10, and 15 min, respectively. Thereafter, QRS duration progressively decreased toward the baseline levels (60±0.9 ms) at 30 min (FIG. 57).

Figure 58:
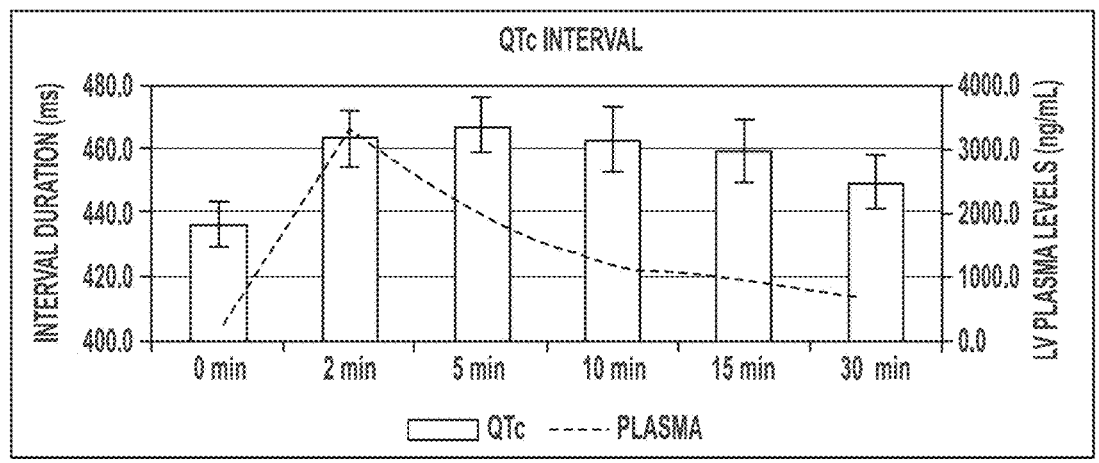

Qtc Interval:

Prior to the IT instillation of the higher dose of flecainide (2 mL of 1.5 mg/kg), the QTc interval was 436±7.1 ms. After instillation, ANOVA revealed that the QTc interval was not significantly changed across 30 min (p=0.1510; FIG. 58).

Figure 59:
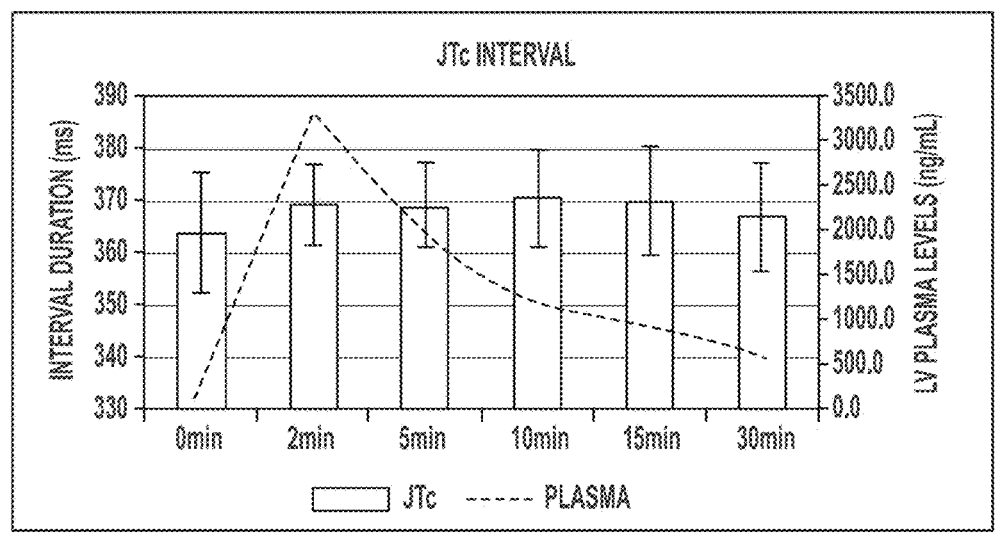

Jtc Interval:

Prior to the IT instillation of the higher dose of flecainide (2 mL of 1.5 mg/kg), the JTc interval was 364±11.5 ms. After instillation, ANOVA revealed that the JTc interval was not significantly changed across 30 min (p=0.9968; FIG. 59).

Figure 60:
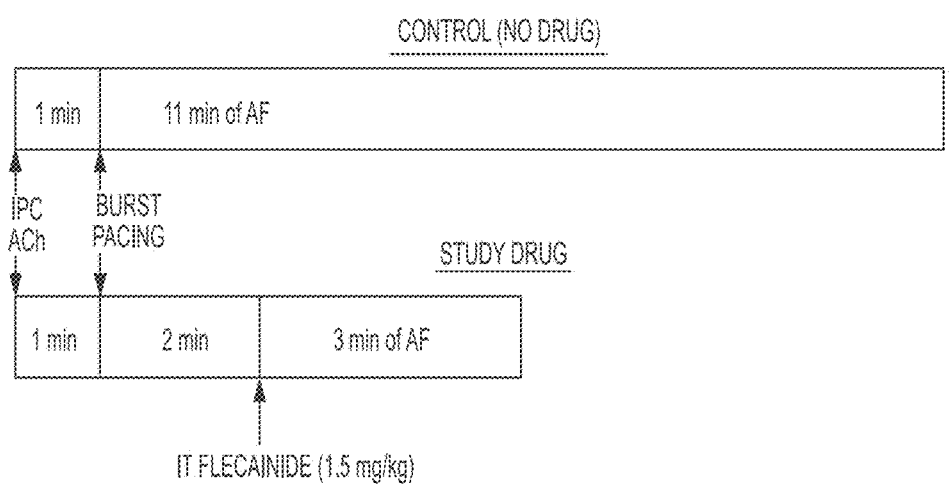

Duration of Atrial Fibrillation:

At one min after intrapericardial administration of ACh (1 ml of 100 mM), burst pacing was performed to initiate AF in the control cohort (FIG. 60).

In the absence of flecainide, AF persisted for 11±0.6 min before spontaneous conversion to sinus rhythm. The data are shown in Table 12 below.

TABLE 12

Effects of intratracheal instillation of flecainide (1.5 mg/kg) on AF duration.

| Pig #s | AF duration | |
|---|---|---|
| | No drug | Flecainide |
| 239 | 12 | 3 |
| 236 | 10 | 4 |
| 238 | 12 | 3 |
| Mean | 11 | 3 |
| SEM | 0.6 | 0.2 |
| p value | | 0.008992 |

Figure 61:
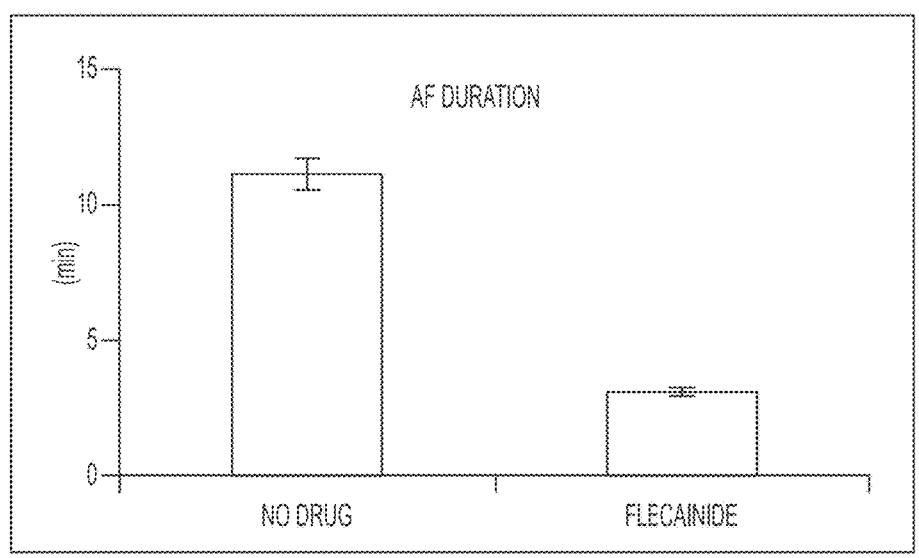

In the experimental cohort, after ACh and burst-pacing-induced AF, a stable period of 2 min of AF was allowed (FIG. 60). Then, IT instillation of the higher dose of flecainide (2 mL of 1.5 mg/kg) was performed. AF was converted to sinus rhythm at 3±0.2 min, a reduction of 73% in AF duration from the untreated condition (p<0.009; Table 12; FIG. 61). Importantly, once sinus rhythm was restored by flecainide, no recurrence of AF occurred within the 30-min window of observation.

Figure 62A:
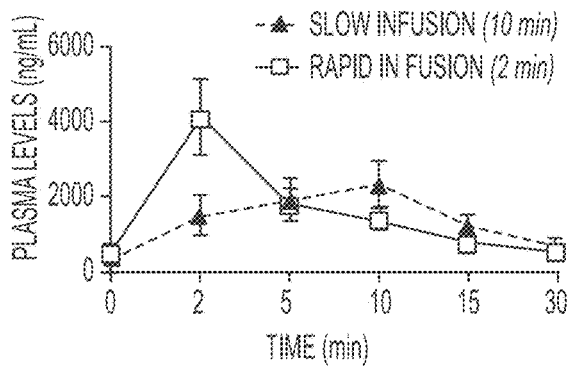
FIG. 62A shows the effects of slow versus rapid infusion of IV administered flecainide on the venous plasma levels of flecainide.
Figure 62B:
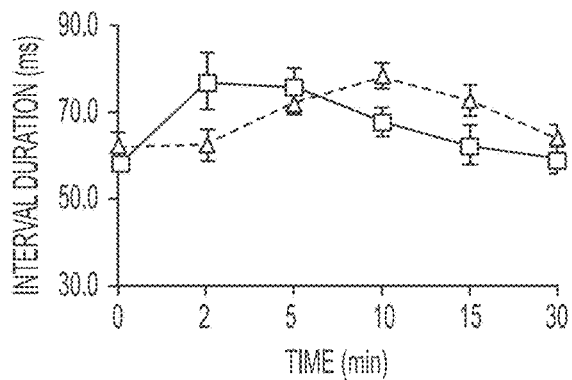
FIG. 62B shows the effects of slow versus rapid infusion of IV administered flecainide on the QRS interval duration.

In a separate study using a porcine model, the effect of the delivery rate (i.e., slow versus rapid infusion) of IV administered flecainide on the PK and PD was evaluated. Venous plasma concentrations (FIG. 62A) and the QRS interval duration (FIG. 62B) varied in response to slow infusion (10 min) compared with rapid infusion (2 min) of IV flecainide.

Figure 62C:
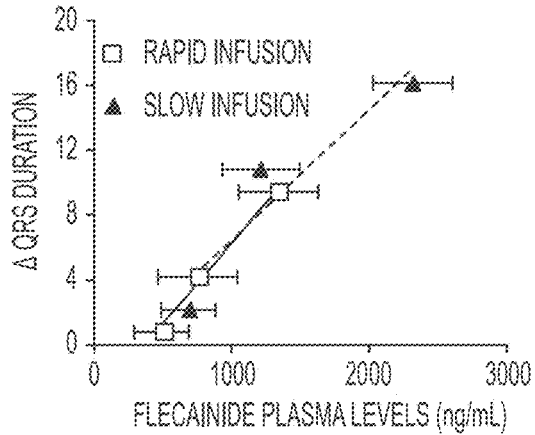
FIG. 62C shows the correlation between venous plasma levels of slowly versus rapidly infused, IV administered flecainide and QRS widening.

As shown in FIG. 62C, venous plasma levels of flecainide were positively correlated with QRS duration.

Summary:

IT instillation of the antiarrhythmic agent flecainide generated a pharmacokinetic profile that was similar to IV infusion of flecainide.

In addition, IT instillation of flecainide altered electrocardiographic parameters in a manner consistent with its pharmacological activity and conducive to conversion of recent-onset AF to sinus rhythm.

Example 6

Accelerated Cardioversion of Atrial Fibrillation to Normal Sinus Rhythm by Intratracheal Delivery of Flecainide Acetate in an Intact Porcine Model The study tested the efficacy of intratracheal (IT) flecainide to convert atrial fibrillation (AF) to normal sinus rhythm in a large animal model that reproducibly induces AF.

Figure 63:
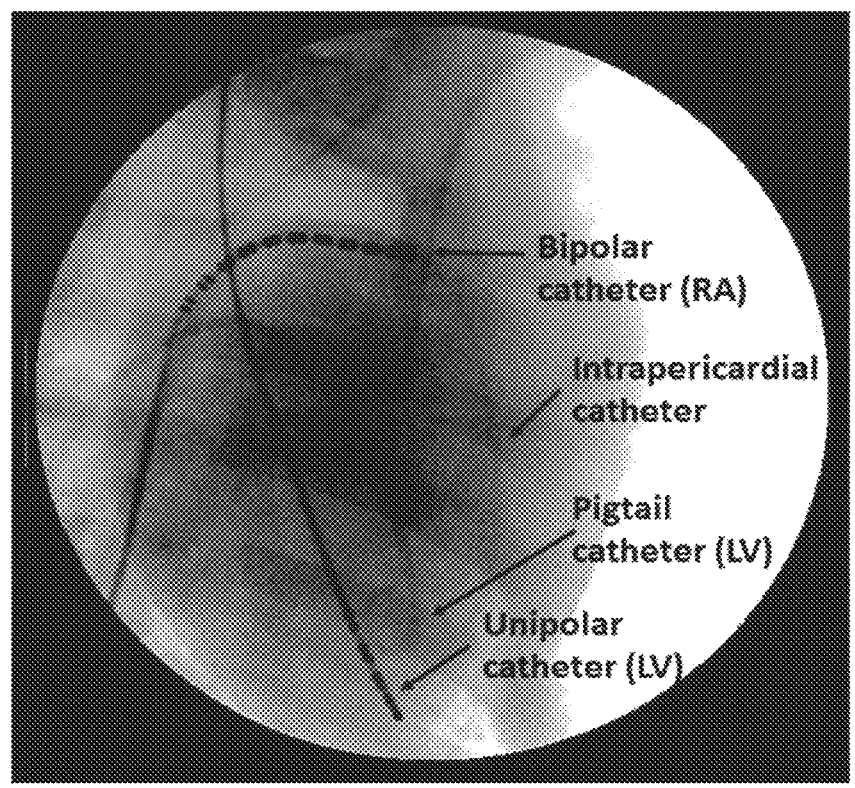

Experimental Design:

In closed-chest anesthetized Yorkshire pigs, intrapericardial (IPC) acetylcholine (ACh) (1 mL of 102.5 mM solution) followed by burst pacing reproducibly induced AF (n=6). Catheter placement is shown in FIG. 63.

At 2 min after AF induction in all 6 animals, IT flecainide (1.5 or 0.75 mg/kg) or no drug was randomly administered. After 30-min recovery, the alternate intervention was tested. Times for conversion to normal sinus rhythm were compared.

Figure 64:
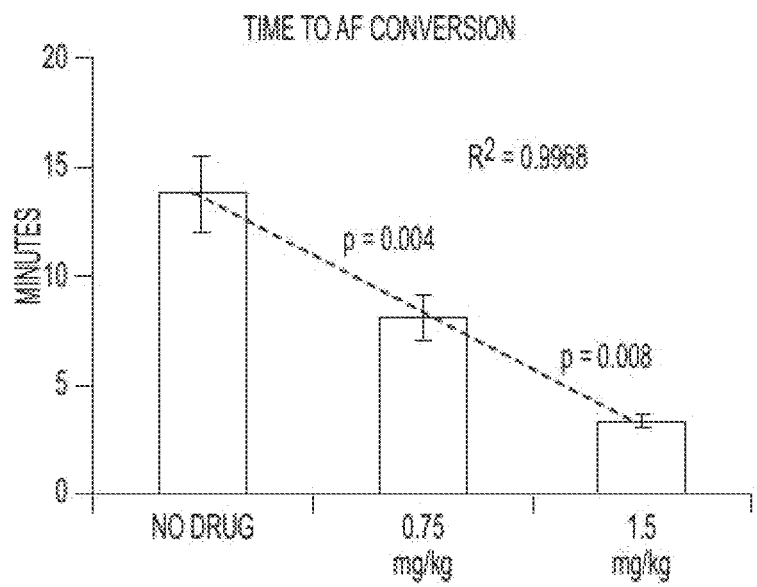

Results:

Both IT flecainide doses used accelerated conversion of AF to normal sinus rhythm. As shown in FIG. 64, AF duration correlated with flecainide dose. IT instillation of flecainide (1.5 mg/kg; n=5) accelerated conversion of AF to normal sinus rhythm in 3.4±0.3 min (mean±SEM) compared to 12.3±1.9 min following no drug (p=0.008), a shortening in AF duration of 72%. The lower IT dose of flecainide (0.75 mg/kg; n=3) converted AF to normal sinus rhythm in 8.1±1.0 min, reducing AF duration by 50% vs. no-drug (16.2±0.9; p=0.003).

Figure 65:
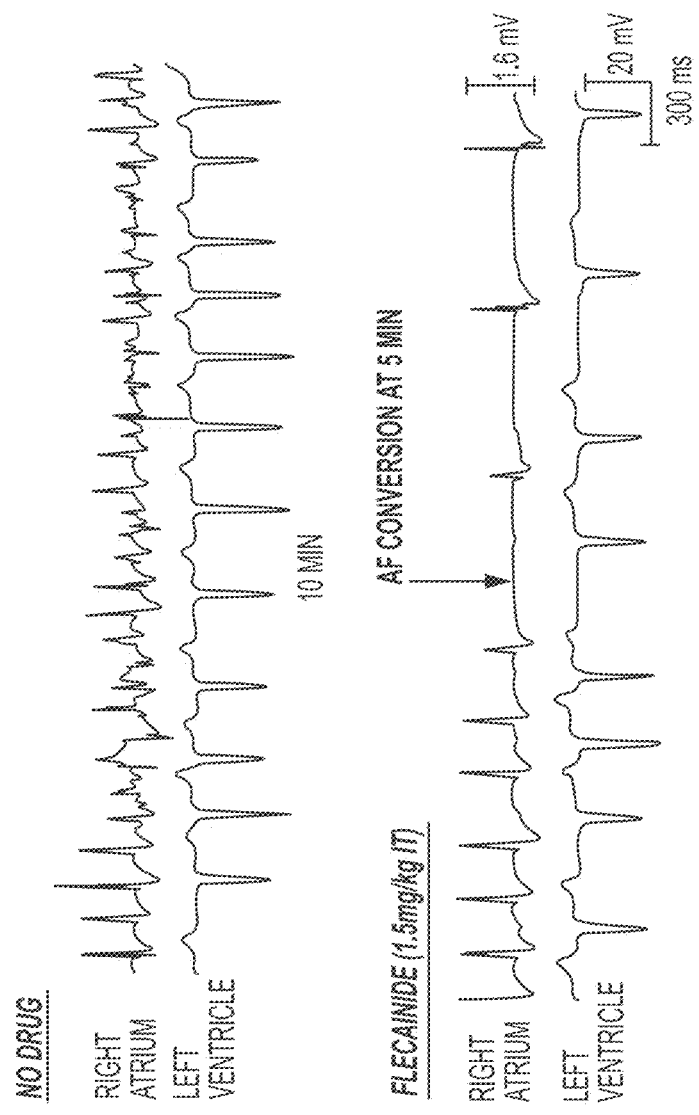

FIG. 65 shows representative electrograms demonstrating AF conversion at 5 min after IT flecainide (1.5 mg/kg) compared to no conversion by 10 min after no drug.

Figure 66A:
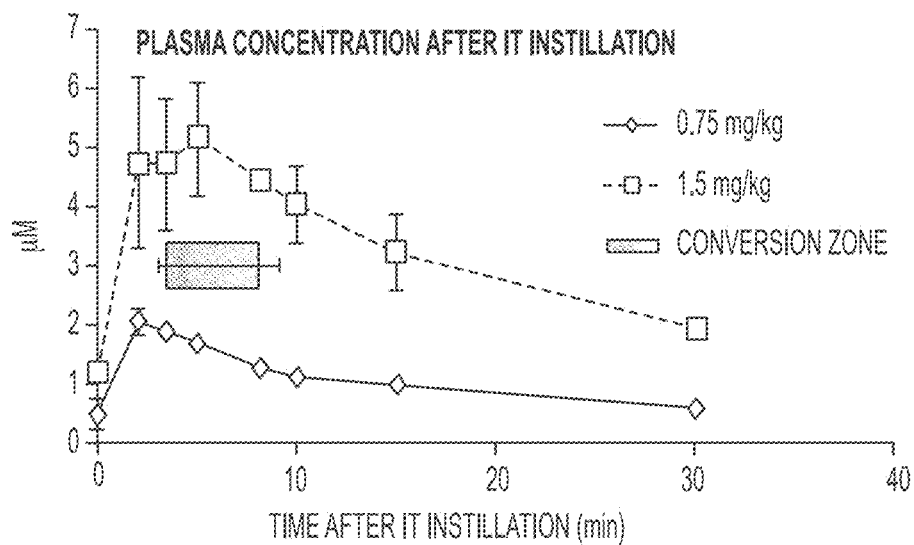
FIG. 66A shows the plasma concentration of flecainide reached levels required for conversion of AF to NSR within 10 min after IT flecainide (0.75 mg/kg and 1.5 mg/kg).

FIG. 66A illustrates that the plasma concentration of flecainide reached levels required for conversion within 10 min after IT flecainide (0.75 mg/kg and 1.5 mg/kg).

Figure 66B:
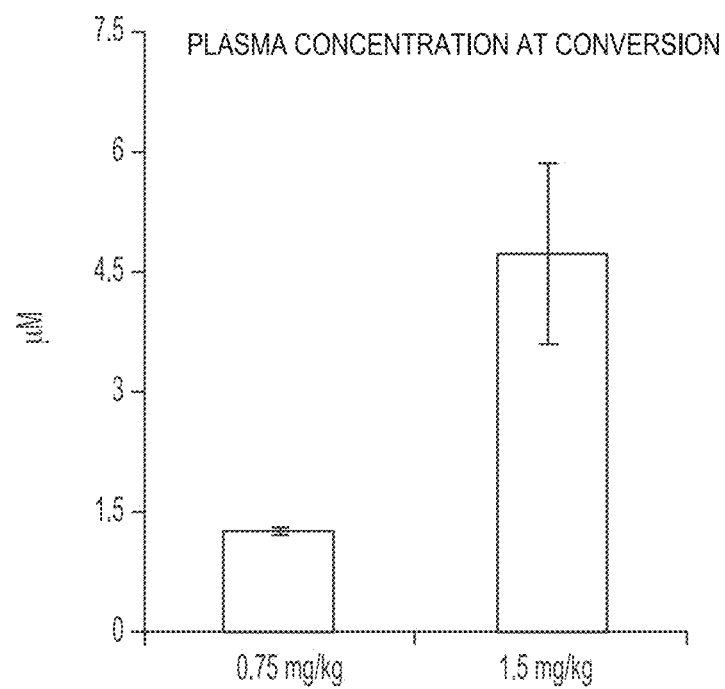
FIG. 66B shows the plasma concentrations of flecainide at the time of conversion of AF to NSR following IT instillation of flecainide (0.75 mg/kg and 1.5 mg/kg).

FIG. 66B depicts the plasma concentrations of flecainide at the time of conversion of AF to NSR following IT instillation of flecainide (0.75 mg/kg and 1.5 mg/kg).

Figure 67:
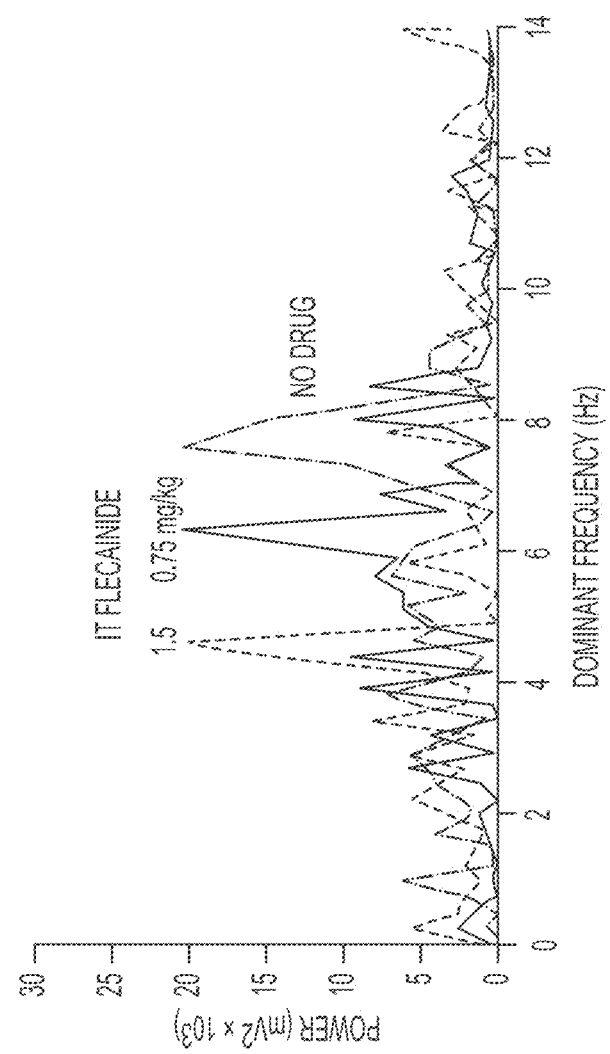
Figure 68A:
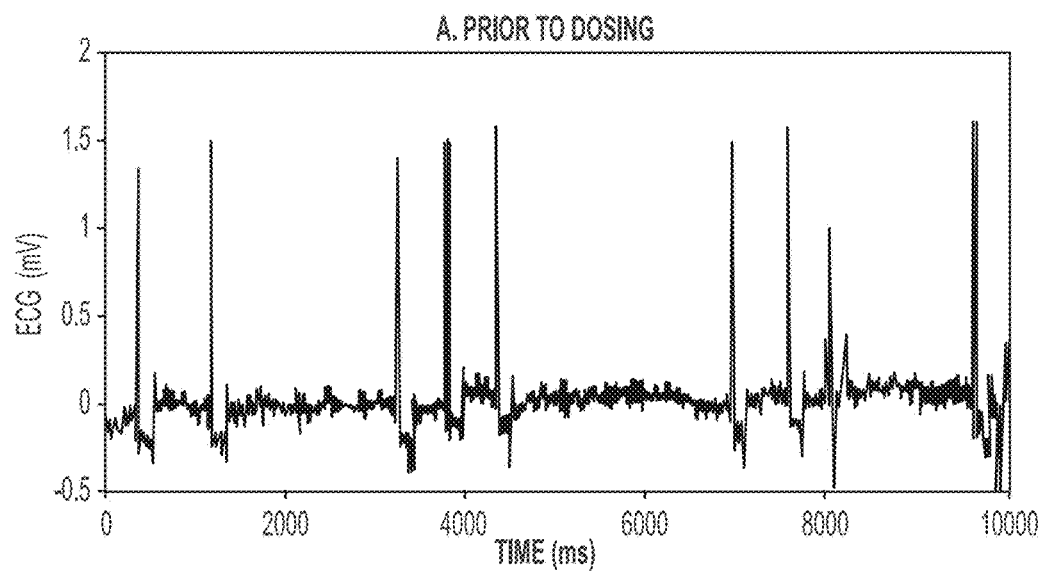
Figure 68B:
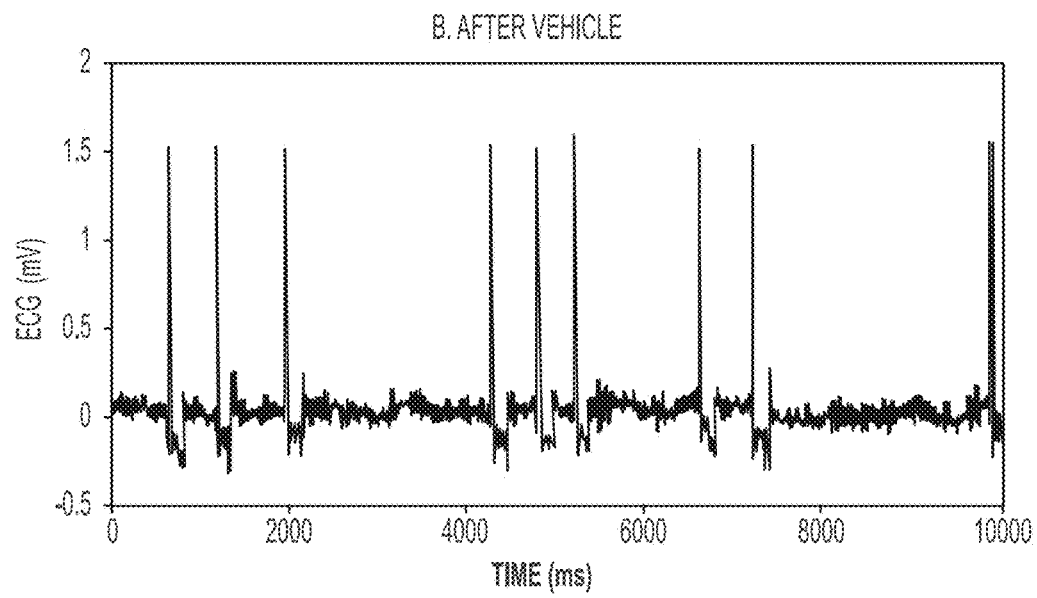
FIG. 68B shows a representative ECG demonstrating persistence of AF after IT instillation of vehicle.
Figure 68C:
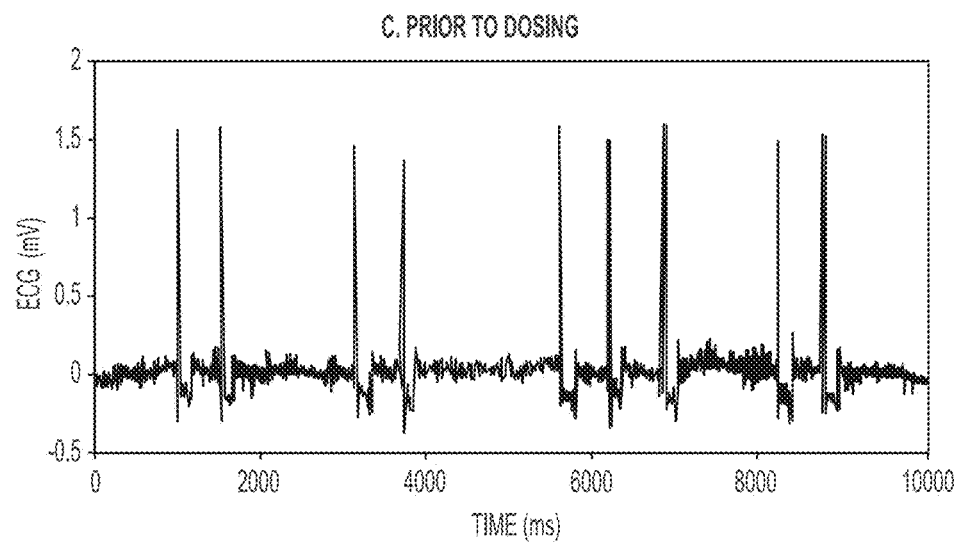
FIG. 68C shows a representative ECG demonstrating AF prior to dosing.
Figure 68D:
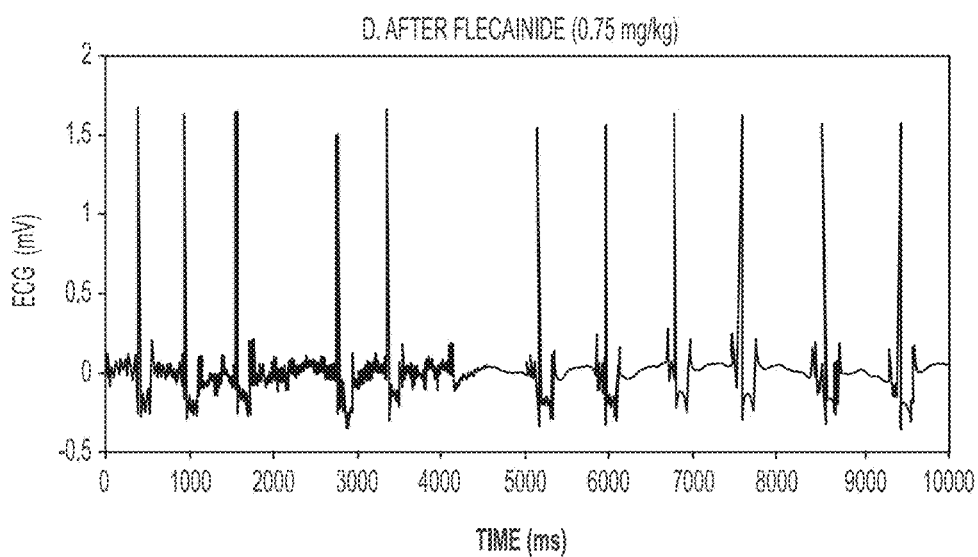
FIG. 68D shows a representative ECG demonstrating conversion of AF to NSR following IT flecainide (0.75 mg/kg).

FIG. 67 demonstrates that IT flecainide reduced the dominant frequency of AF.

Summary:

IT flecainide instillation (1.5 mg/kg or 0.75 mg/kg) was 100% effective in rapidly converting AF to normal sinus rhythm and restored MAP and ventricular rate to baseline values.

The basis for this efficacy is likely rapid absorption of the drug through the lungs and delivery as a first-pass bolus to the left atrium via pulmonary veins.

If the present findings can be confirmed in human subjects, flecainide delivered via inhalation could provide a potential option for therapy of new-onset paroxysmal AF.

Example 7

Rapid Cardioversion of Recent-Onset Atrial Fibrillation with Pulmonary Delivery of Flecainide in Anesthetized Dogs The study tested the hypothesis that pulmonary delivery of flecainide via IT instillation can, within seconds/few minutes of administration, convert AF into normal sinus rhythm in a dog model of stable AF.

Experimental Design:

The study was carried out in anesthetized healthy adult beagle dogs with induced AF. Acute AF was induced using the combination of phenylephrine (2-10 mg/kg), to increase heterogeneity of atrial refractory periods via increased loading and through a baroreceptor-mediated increase in parasympathetic efferent activity, and right atrial burst pacing (40-50 Hz for ~15 min). The AF induced using this method was, in general, stable for more than 30 mins.

After induction of AF, animals were first given vehicle (0.9% NaCl, volume-matched) via IT installation. Later flecainide, at 2 mg/mL bolus was given (<20 sec) via IT at single or cumulative doses of 0.25 to 0.75 mg/kg. For comparison purposes, two dogs were given flecainide via intravenous bolus injection (<20 sec) at single or cumulative doses of 0.25 to 0.75 mg/kg.

The cardiac rhythm was monitored prior to, during AF, and up to 10 min post-dosing and/or until conversion to NSR.

Plasma concentrations of flecainide were measured in the LV and femoral vein at the time of conversion. In some dogs, plasma levels of flecainide were also measured in the pulmonary artery (PA).

Results:

No conversion of AF to NSR was observed in vehicle treated dogs (0/6).

As shown in Table 13 below, IT-delivered flecainide converted AF to NSR in 63±18 sec at a mean dose of 0.79±0.04 mg/kg in 6/6 dogs. At the time of conversion of AF to NSR, plasma levels of flecainide were ~2-fold higher in the LV than in the systemic venous circulation. In 2/2 dogs, IV bolus of flecainide converted AF to NSR in 29 seconds.

TABLE 13

Effects of IT flecainide in the setting of AF on conversion times to NSR, and systemic and LV plasma concentration at the time of conversion.

| Route | Animal # | Dose[1] (mg/kg) | Time to NSR (sec) | Plasma Concentration[2] (ng/mL) | |
|---|---|---|---|---|---|
| | | | | LV | Venous |
| IT | 001 | 0.75 (0.25 + 0.5) | 147 | 538 | 421 |
| | 002 | 0.75 (0.25 + 0.5) | 52 | 1140 | 533 |
| | 003* | 0.75 | 12 | 3105 | 1670 |
| | 004 | 0.75 | 23 | 700 | 219 |
| | 005 | 0.75 | 62 | 351 | 109 |
| | 006 | 1.0 (0.75 + 0.25) | 83 | 1000 | 717 |
| | Mean ± SEM | 0.79 ± 0.04 | 63 ± 18 | 1139 ± 380 | 611 ± 213 |

[1]Cumulative dose of flecainide with individual doses shown in parenthesis.
[2]Measured at the time of conversion (±1 min).
*This animal had a time to NSR (12 seconds) that was 2- to 10-fold faster than in the other dogs. Likewise, in this dog, the LV and venous plasma levels (ng/mL) were 10- to 2.7-fold and 15- and 2-fold higher, respectively than that observed in other does.

FIGS. 68A-D show a representative ECG demonstrating conversion of AF to NSR by IT flecainide, but not by vehicle.

Figure 69:
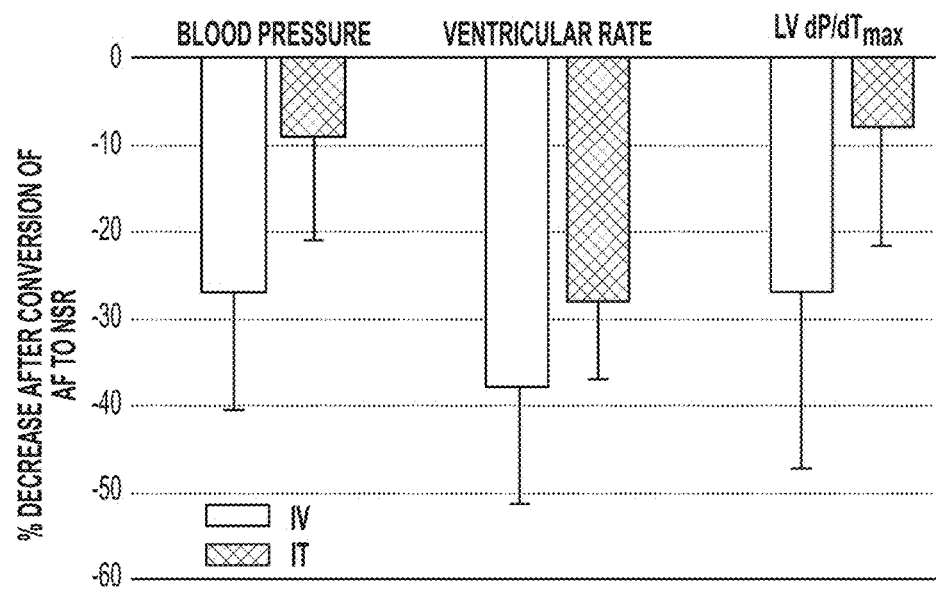

FIG. 69 summarizes the changes in blood pressure (BP), ventricular rate (VR), and LV dP/dtmax (the maximal rate of rise of LV pressure) upon conversion of AF to NSR following administration of flecainide via IV or IT. Flecainide given IV caused greater effects in BP, VR and LV dP/dtmax upon conversion of AF to NSR compared with IT administration.

Figure 70:
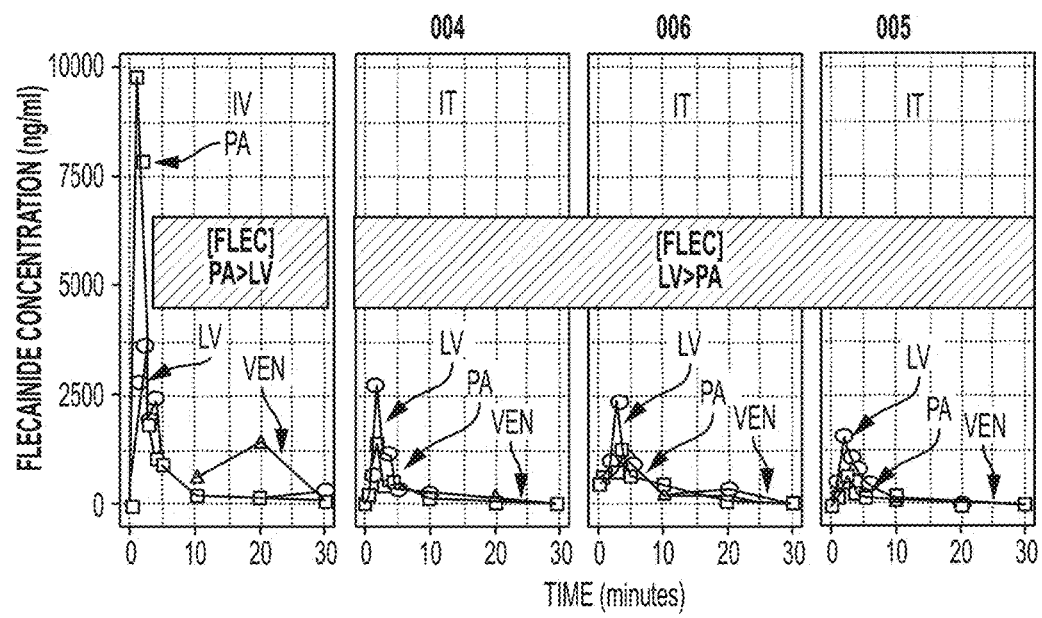

The plasma concentrations of flecainide in the pulmonary artery (PA) and left ventricular chamber (LV) were dependent on the route of delivery (IT and IV) of flecainide (FIG. 70). Following IV infusion, the concentrations of flecainide in the PA were transiently higher (2.1- to 3.5-fold) than those in the LV chamber. Conversely, after IT instillation of flecainide, its concentrations were transiently higher (1.4- to 3.2-fold) in the LV chamber than in the PA.

Figure 71:
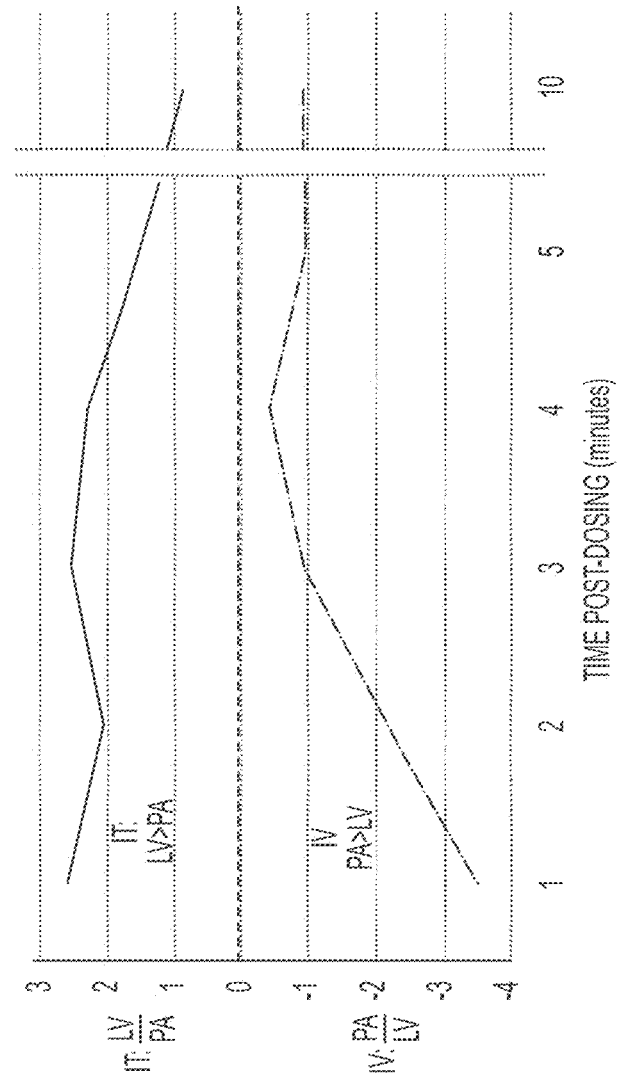

The ratios of the plasma concentrations of flecainide between LV and PA (and vice versa PA and LV) for IT were reversed to those for IV delivery (FIG. 71).

Summary:

LV (left atrium) levels of flecainide achieved following pulmonary delivery of flecainide were sufficient to rapidly terminate AF.

The plasma concentrations of flecainide when delivered via IT were transiently higher (~2.5 fold) in the LV than in the PA. Conversely, following IV infusion, flecainide plasma concentrations were transiently higher (~3.5 fold) in the PA than in the LV. At about 4-10 mins after the administration of flecainide (IV or IT), the LV and PA concentrations were nearly equal.

Direct delivery of flecainide to the left atrium using oral inhalation may prove to be more efficacious, faster, and safer than either the IV or oral delivery alternatives.

The foregoing embodiments and advantages are merely exemplary and are not to be construed as limiting the present invention. The description of the present invention is intended to be illustrative, and not to limit the scope of the claims. Many alternatives, modifications, and variations will be apparent to those skilled in the art.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. An inhalation pharmaceutical composition comprising a unit dose of an antiarrhythmic agent in a liquid solution that is therapeutically effective for treating atrial arrhythmia in a human subject in need thereof, wherein said antiarrhythmic agent is selected from the group consisting of: flecainide, a salt thereof, and a solvate thereof, wherein said unit dose of said antiarrhythmic agent is about 50 mg to about 350 mg, wherein a concentration of said antiarrhythmic agent in said unit dose is about 35 to about 60 mg/mL, and wherein said pharmaceutical composition is formulated for administration via inhalation.

2. The inhalation pharmaceutical composition of claim 1, wherein said unit dose of said antiarrhythmic agent, when administered to a healthy subject via inhalation, has a maximum ΔQRS of from about 1 to about 100 msec as measured by electrocardiography in a human pharmacokinetics/pharmacodynamics study.

3. The inhalation pharmaceutical composition of claim 2, wherein said maximum ΔQRS is from about 3 to about 20 msec.

4. The inhalation pharmaceutical composition of claim 1, wherein said unit dose of said antiarrhythmic agent, when administered to a healthy subject via inhalation, has a maximum ΔQRS same as or greater than a maximum ΔQRS achieved by a second amount of said antiarrhythmic agent when administered intravenously to said subject as measured by electrocardiography in a human pharmacokinetics/pharmacodynamics study, wherein said unit dose is less than half of said second amount.

5. The inhalation pharmaceutical composition of claim 1, wherein said concentration of said antiarrhythmic agent is about 35 to about 50 mg/mL.

6. The inhalation pharmaceutical composition of claim 1, wherein said concentration of said antiarrhythmic agent is about 45 mg/mL.

7. The inhalation pharmaceutical composition of claim 1, wherein said concentration of said antiarrhythmic agent is 45 mg/mL.

8. The inhalation pharmaceutical composition of claim 1, comprising about 60 to about 130 mg of said antiarrhythmic agent.

9. The inhalation pharmaceutical composition of claim 1, comprising about 50 to about 90 mg of said antiarrhythmic agent.

10. The inhalation pharmaceutical composition of claim 1, wherein a volume of said liquid solution in said unit dose is about 1 mL to about 6 mL.

11. The inhalation pharmaceutical composition of claim 1, wherein said antiarrhythmic agent comprises flecainide acetate.

12. The inhalation pharmaceutical composition of claim 1, further comprising a pH buffer prepared from acetic acid.

13. The inhalation pharmaceutical composition of claim 1, wherein a pH of said inhalation pharmaceutical composition is from 5.0 to 6.5.

14. The inhalation pharmaceutical composition of claim 1, wherein said inhalation pharmaceutical composition has physiological isotonicity.

15. The inhalation pharmaceutical composition of claim 1, wherein said unit dose of said antiarrhythmic agent, when administered to a healthy subject via inhalation, has a $T_{max}$ of from about 0.2 to about 5 minutes as measured in a human pharmacokinetics/pharmacodynamics study.

16. The inhalation pharmaceutical composition of claim 1, wherein said unit dose of said antiarrhythmic agent, when administered to a healthy subject via inhalation, has a $C_{max}$ of from about 100 to about 250 ng/mL as measured in a human pharmacokinetics/pharmacodynamics study.

17. The inhalation pharmaceutical composition of claim 1, wherein said unit dose of said antiarrhythmic agent, when administered to a healthy subject via inhalation, has a $AUC_{Last}$ of from about 100 to about 10000 hr*ng/mL as measured in a human pharmacokinetics/pharmacodynamics study.

18. The inhalation pharmaceutical composition of claim 17, wherein said $AUC_{Last}$ is from about 200 to about 2000 hr*ng/mL.

19. The inhalation pharmaceutical composition of claim 1, wherein said unit dose of said antiarrhythmic agent, when administered to a healthy subject via inhalation, has a distribution $t_{1/2}$ of from about 0.1 to about 15 minutes as measured in a human pharmacokinetics/pharmacodynamics study.

20. The inhalation pharmaceutical composition of claim 19, wherein said distribution $t_{1/2}$ is from about 3 to about 5 minutes.

21. The inhalation pharmaceutical composition of claim 1, wherein said unit dose of said antiarrhythmic agent, when administered to a healthy subject via inhalation, has an elimination $t_{in}$, of from about 1 to about 25 hours as measured in a human pharmacokinetics/pharmacodynamics study.

22. The inhalation pharmaceutical composition of claim 21, wherein said elimination $t_{1/2}$ is from about 8.5 to about 10.5 hours.

23. A kit comprising the inhalation pharmaceutical composition of claim 1 and an aerosolization device.

* * * * *